US009877965B2

(12) United States Patent
Leamon et al.

(10) Patent No.: US 9,877,965 B2
(45) Date of Patent: Jan. 30, 2018

(54) VITAMIN RECEPTOR DRUG DELIVERY CONJUGATES FOR TREATING INFLAMMATION

(71) Applicant: Endocyte, Inc., West Lafayette, IN (US)

(72) Inventors: Christopher Paul Leamon, West Lafayette, IN (US); Iontcho Radoslavov Vlahov, West Lafayette, IN (US); Yingjuan June Lu, West Lafayette, IN (US); Kevin Yu Wang, Zionsville, IN (US); Fei Yu, West Lafayette, IN (US); Paul Joseph Kleindl, Lebanon, IN (US); Hari Krishna R. Santhapuram, West Lafayette, IN (US)

(73) Assignee: Endocyte, Inc., West Lafayette, IN (US)

( * ) Notice: Subject to any disclaimer, the term of this patent is extended or adjusted under 35 U.S.C. 154(b) by 0 days.

(21) Appl. No.: 14/671,790

(22) Filed: Mar. 27, 2015

(65) Prior Publication Data

US 2015/0314015 A1 Nov. 5, 2015
US 2017/0319585 A9 Nov. 9, 2017

Related U.S. Application Data

(63) Continuation-in-part of application No. 13/518,291, filed as application No. PCT/US2010/061897 on Dec. 22, 2010, now abandoned, application No. 14/671,790, which is a continuation-in-part of application No. 12/666,712, filed as application No. PCT/US2008/068093 on Jun. 25, 2008, now Pat. No. 9,138,484.

(60) Provisional application No. 61/289,952, filed on Dec. 23, 2009, provisional application No. 61/291,103, filed on Dec. 30, 2009, provisional application No. 61/351,032, filed on Jun. 3, 2010, provisional application No. 61/374,830, filed on Aug. 18, 2010, provisional application No. 61/386,785, filed on Sep. 27, 2010, provisional application No. 61/391,230, filed on Oct. 8, 2010, provisional application No. 61/036,186, filed on Mar. 13, 2008, provisional application No. 60/946,092, filed on Jun. 25, 2007.

(51) Int. Cl.
| | |
|---|---|
| *A61K 38/00* | (2006.01) |
| *A61P 9/10* | (2006.01) |
| *C07K 14/47* | (2006.01) |
| *A61K 31/519* | (2006.01) |
| *A61K 47/48* | (2006.01) |
| *C07K 7/06* | (2006.01) |
| *A61K 31/436* | (2006.01) |

(52) U.S. Cl.
CPC .......... *A61K 31/519* (2013.01); *A61K 31/436* (2013.01); *A61K 47/481* (2013.01); *A61K 47/48061* (2013.01); *A61K 47/48107* (2013.01); *A61K 47/48338* (2013.01); *C07K 7/06* (2013.01)

(58) Field of Classification Search
CPC ............ A61K 47/48061; A61K 47/481; A61K 31/436
See application file for complete search history.

(56) References Cited

U.S. PATENT DOCUMENTS

| | | |
|---|---|---|
| 2,515,483 A | 7/1950 | Wolf et al. |
| 2,816,110 A | 12/1957 | Sletzinger et al. |
| 3,387,001 A | 6/1968 | Hargrove et al. |
| 3,392,173 A | 7/1968 | Hargrove et al. |
| 3,632,622 A | 1/1972 | Moore et al. |
| 3,641,109 A | 2/1972 | Emerson et al. |
| 4,166,810 A | 9/1979 | Cullinan et al. |
| 4,203,898 A | 5/1980 | Cullinan et al. |
| 4,316,885 A | 2/1982 | Rakhit |
| 4,337,339 A | 6/1982 | Farina et al. |
| 4,639,456 A | 1/1987 | Trouet et al. |
| 4,650,803 A | 3/1987 | Stella et al. |
| 4,691,024 A | 9/1987 | Shirahata |
| 4,713,249 A | 12/1987 | Schroder |
| 4,801,688 A | 1/1989 | Laguzza et al. |
| 4,866,180 A | 9/1989 | Vyas et al. |
| 4,870,162 A | 9/1989 | Trouet et al. |
| 5,006,652 A | 4/1991 | Cullinan et al. |
| 5,094,849 A | 3/1992 | Cullinan et al. |
| 5,100,883 A | 3/1992 | Schiehser |
| 5,108,921 A | 4/1992 | Low et al. |
| 5,118,677 A | 6/1992 | Caufield |
| 5,118,678 A | 6/1992 | Kao et al. |
| 5,120,842 A | 6/1992 | Failli et al. |
| 5,130,307 A | 7/1992 | Failli et al. |

(Continued)

FOREIGN PATENT DOCUMENTS

| | | |
|---|---|---|
| CA | 2372841 | 11/2000 |
| CA | 2376175 | 12/2000 |

(Continued)

OTHER PUBLICATIONS

Attur et al., Inflamm. Res., 2000, 49, 020-026.*
Agoston E.S. et al., "Vitamin D Analogs as Anti-Carcinogenic Agents," *Anti-Cancer Agents in Medicinal Chemistry*, 2006; 6(1): 53-71.
Anderson et al., "Potocytosis: Sequestration and transport of small molecules by caveolae," *Science*, 1992; 255: 410-411.
Antony A.C., "Folate receptors," *Annu Rev Nutr*, 1996; 16: 501-21.
Antony A.C., "The biological chemistry of folate receptors," *Blood*, 1992; 79(11):2807-2820.

(Continued)

*Primary Examiner* — Kaipeen Yang
(74) *Attorney, Agent, or Firm* — Barnes & Thornburg LLP

(57) ABSTRACT

Described herein are compositions, methods, compounds, conjugates, and kits for use in targeted drug delivery using drug delivery conjugates containing hydrophilic spacer linkers for use in treating disease states caused by pathogenic cell populations, such as inflammatory cells.

16 Claims, 81 Drawing Sheets

(56) References Cited

U.S. PATENT DOCUMENTS

| | | |
|---|---|---|
| 5,138,051 A | 8/1992 | Hughes et al. |
| 5,140,104 A | 8/1992 | Coughlin et al. |
| 5,151,413 A | 9/1992 | Caufield et al. |
| 5,169,851 A | 12/1992 | Hughes et al. |
| 5,194,447 A | 3/1993 | Kao |
| 5,221,670 A | 6/1993 | Caufield |
| 5,233,036 A | 8/1993 | Hughes |
| 5,258,389 A | 11/1993 | Goulet et al. |
| 5,260,300 A | 11/1993 | Hu |
| 5,266,333 A | 11/1993 | Cady |
| 5,302,584 A | 4/1994 | Kao et al. |
| 5,362,718 A | 11/1994 | Skotnicki et al. |
| 5,378,696 A | 1/1995 | Caufield |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,416,016 A | 5/1995 | Low et al. |
| 5,417,982 A | 5/1995 | Modi |
| 5,463,048 A | 10/1995 | Skotnicki et al. |
| 5,491,231 A | 2/1996 | Nelson et al. |
| 5,547,668 A | 8/1996 | Kranz et al. |
| 5,552,545 A | 9/1996 | Pearce et al. |
| 5,562,907 A | 10/1996 | Arnon |
| 5,583,020 A | 12/1996 | Sullivan |
| 5,627,165 A | 5/1997 | Glazier |
| 5,635,382 A | 6/1997 | Low et al. |
| 5,672,486 A | 9/1997 | Soulillou |
| 5,688,488 A | 11/1997 | Low et al. |
| 5,998,603 A | 12/1999 | Cook |
| 6,004,555 A | 12/1999 | Thorpe et al. |
| 6,030,941 A | 2/2000 | Summerton et al. |
| 6,056,973 A | 5/2000 | Allen |
| 6,077,499 A | 6/2000 | Griffiths |
| 6,093,382 A | 7/2000 | Wedeking et al. |
| 6,171,614 B1 | 1/2001 | Chaikof et al. |
| 6,171,859 B1 | 1/2001 | Herrnstadt et al. |
| 6,177,404 B1 | 1/2001 | DeFeo-Jones et al. |
| 6,184,042 B1 | 2/2001 | Neumann et al. |
| 6,207,157 B1 | 3/2001 | Gu et al. |
| 6,290,929 B1 | 9/2001 | Camden et al. |
| 6,291,673 B1 | 9/2001 | Fuchs et al. |
| 6,291,684 B1 | 9/2001 | Borzilleri et al. |
| 6,315,978 B1 | 11/2001 | Grissom et al. |
| 6,335,434 B1 | 1/2002 | Guzaev et al. |
| 6,340,701 B1 | 1/2002 | Chari et al. |
| 6,342,244 B1 | 1/2002 | Zalipski et al. |
| 6,365,179 B1 | 4/2002 | Zalipsky et al. |
| 6,399,625 B1 | 6/2002 | Zhu |
| 6,399,626 B1 | 6/2002 | Zhu et al. |
| 6,399,638 B1 | 6/2002 | Vite et al. |
| 6,432,973 B1 | 8/2002 | Zhu et al. |
| 6,440,991 B1 | 8/2002 | Zhu et al. |
| 6,511,986 B2 | 1/2003 | Zhang et al. |
| 6,541,612 B2 | 4/2003 | Mulnar-Kimber et al. |
| 6,548,505 B1 | 4/2003 | Martin et al. |
| 6,596,757 B1 | 7/2003 | Chari et al. |
| 6,617,333 B2 | 9/2003 | Raibindran et al. |
| 6,670,355 B2 | 12/2003 | Azrulan et al. |
| 6,677,357 B2 | 1/2004 | Zhu et al. |
| 6,680,330 B2 | 1/2004 | Zhu et al. |
| 6,713,607 B2 | 3/2004 | Caggiano et al. |
| 6,800,653 B2 | 10/2004 | Regueiro-Ren et al. |
| 6,821,731 B2 | 11/2004 | Gillis et al. |
| 6,915,855 B2 | 7/2005 | Steele et al. |
| 6,958,153 B1 | 10/2005 | Ormerod et al. |
| 7,019,014 B2 | 3/2006 | Bernan et al. |
| 7,029,674 B2 | 4/2006 | Carreno et al. |
| 7,033,594 B2 | 4/2006 | Low et al. |
| 7,060,709 B2 | 6/2006 | Cooperstone et al. |
| 7,060,797 B2 | 6/2006 | O'Toole et al. |
| 7,067,111 B1 | 6/2006 | Yang et al. |
| 7,074,804 B2 | 7/2006 | Zhu et al. |
| 7,105,328 B2 | 9/2006 | Wood et al. |
| 7,122,361 B2 | 10/2006 | Liu et al. |
| 7,128,893 B2 | 10/2006 | Leamon et al. |
| 7,153,957 B2 | 12/2006 | Chew et al. |
| 7,238,368 B2 | 7/2007 | Zalipsky et al. |
| 7,279,562 B2 | 10/2007 | Molnar-Kimber et al. |
| 7,582,744 B2 | 9/2009 | Manoharan et al. |
| 7,601,332 B2 | 10/2009 | Vlahov et al. |
| 7,754,885 B2 | 7/2010 | Hoefle et al. |
| 7,776,814 B2 | 8/2010 | Dömling et al. |
| 7,816,377 B2 | 10/2010 | Dömling et al. |
| 7,875,612 B2 | 1/2011 | Green et al. |
| 7,910,594 B2 | 3/2011 | Vlahov et al. |
| 8,044,200 B2 | 10/2011 | Xu et al. |
| 8,105,568 B2 | 1/2012 | Vlahov et al. |
| 8,288,557 B2 | 10/2012 | Vlahov et al. |
| 8,349,901 B2 | 1/2013 | Satyam |
| 8,383,122 B2 | 2/2013 | Dai et al. |
| 8,394,922 B2 | 3/2013 | Cheng et al. |
| 8,465,724 B2 | 6/2013 | Vlahov et al. |
| 8,470,822 B2 | 6/2013 | Green et al. |
| 8,476,451 B2 | 7/2013 | Ellman et al. |
| 8,497,365 B2 | 7/2013 | Davis et al. |
| 8,765,096 B2 | 7/2014 | Leamon |
| 8,802,632 B2 | 8/2014 | Cheng et al. |
| 8,889,880 B2 | 11/2014 | Vlahov et al. |
| 9,061,995 B2 | 6/2015 | Chari et al. |
| 9,090,563 B2 | 7/2015 | Vlahov et al. |
| 2001/0031252 A1 | 10/2001 | Low et al. |
| 2002/0151088 A1 | 10/2002 | Molnar-Kimber et al. |
| 2003/0022831 A1 | 1/2003 | Rothbard |
| 2003/0086900 A1 | 5/2003 | Low et al. |
| 2003/0162234 A1 | 8/2003 | Jallad |
| 2003/0194409 A1 | 10/2003 | Rothman et al. |
| 2004/0018203 A1 | 1/2004 | Pastan et al. |
| 2004/0033195 A1 | 2/2004 | Leamon et al. |
| 2004/0047917 A1 | 3/2004 | Wilson et al. |
| 2005/0004010 A1 | 1/2005 | Collins et al. |
| 2005/0026068 A1 | 2/2005 | Gogolides et al. |
| 2005/0107325 A1 | 5/2005 | Manoharan et al. |
| 2005/0227985 A9 | 10/2005 | Green et al. |
| 2005/0239713 A1 | 10/2005 | Domling et al. |
| 2005/0239739 A1 | 10/2005 | Matulic-Adamic et al. |
| 2005/0249740 A1 | 11/2005 | Doemling |
| 2006/0019911 A1 | 1/2006 | Papisov |
| 2006/0058266 A1 | 3/2006 | Manoharan et al. |
| 2006/0105975 A1 | 5/2006 | Pendergrast et al. |
| 2006/0128754 A1 | 6/2006 | Hoefle et al. |
| 2006/0217360 A1 | 9/2006 | Hoefle et al. |
| 2006/0222653 A1 | 10/2006 | Abel et al. |
| 2007/0009434 A1 | 1/2007 | Low et al. |
| 2007/0134332 A1 | 6/2007 | Turnell et al. |
| 2007/0275904 A1 | 11/2007 | Vite et al. |
| 2008/0096893 A1 | 4/2008 | Zebala |
| 2008/0280937 A1 | 11/2008 | Leamon et al. |
| 2009/0247614 A1 | 10/2009 | Manoharan et al. |
| 2010/0004276 A1 | 1/2010 | Vlahov et al. |
| 2010/0040669 A1 | 2/2010 | Higuchi |
| 2010/0048490 A1 | 2/2010 | Vlahov et al. |
| 2010/0074863 A1 | 3/2010 | Or et al. |
| 2010/0104626 A1 | 4/2010 | Leamon et al. |
| 2010/0129314 A1 | 5/2010 | Singh et al. |
| 2010/0144647 A1 | 6/2010 | Kratz et al. |
| 2010/0240701 A1 | 9/2010 | Vlahov et al. |
| 2010/0323973 A1 | 12/2010 | Leamon et al. |
| 2011/0027274 A1 | 2/2011 | Cheng et al. |
| 2011/0166319 A1 | 7/2011 | Dai et al. |
| 2011/0172254 A1 | 7/2011 | Leamon et al. |
| 2011/0245295 A1 | 10/2011 | Chai et al. |
| 2012/0022245 A1 | 1/2012 | Low et al. |
| 2012/0065149 A1 | 3/2012 | Vlahov et al. |
| 2012/0129779 A1 | 5/2012 | Richter |
| 2012/0252738 A1 | 10/2012 | Richter |
| 2012/0252739 A1 | 10/2012 | Richter |
| 2012/0258905 A1 | 10/2012 | Leamon et al. |
| 2013/0116195 A1 | 5/2013 | Leamon et al. |
| 2013/0184435 A1 | 7/2013 | Vlahov et al. |
| 2013/0203680 A1 | 8/2013 | Leamon et al. |
| 2013/0217638 A1 | 8/2013 | Wessjohann et al. |
| 2013/0281678 A1 | 10/2013 | Dai et al. |

(56) References Cited

U.S. PATENT DOCUMENTS

| | | |
|---|---|---|
| 2014/0058063 A1 | 2/2014 | Vlahov et al. |
| 2014/0058064 A1 | 2/2014 | Vlahov et al. |
| 2014/0066594 A1 | 3/2014 | Vlahov et al. |
| 2014/0073761 A1 | 3/2014 | Leamon et al. |
| 2014/0073763 A1 | 3/2014 | Low et al. |
| 2014/0080175 A1 | 3/2014 | Vlahov et al. |
| 2014/0107316 A1 | 4/2014 | Vlahov et al. |
| 2014/0249315 A1 | 9/2014 | Vlahov et al. |
| 2014/0323690 A1 | 10/2014 | Cheng et al. |

FOREIGN PATENT DOCUMENTS

| | | |
|---|---|---|
| EP | 0 116 208 A1 | 8/1984 |
| EP | 0 163 550 A2 | 12/1985 |
| EP | 0 247 792 | 12/1987 |
| EP | 0 280 741 A1 | 9/1988 |
| EP | 0 354 728 | 2/1990 |
| JP | 59-175493 | 10/1984 |
| JP | 60-255789 | 12/1985 |
| WO | WO85/05554 | 12/1985 |
| WO | WO 88/01622 | 3/1988 |
| WO | WO 90/12096 | 10/1990 |
| WO | WO 91/07418 | 5/1991 |
| WO | WO95/15335 | 6/1995 |
| WO | WO96/36367 | 11/1996 |
| WO | WO 98/08382 | 3/1998 |
| WO | WO 98/08859 | 3/1998 |
| WO | WO 98/10651 | 3/1998 |
| WO | WO 99/20626 | 4/1999 |
| WO | WO 99/61055 | 12/1999 |
| WO | WO 00/35422 | 6/2000 |
| WO | WO 00/66091 | 11/2000 |
| WO | WO 00/74721 | 12/2000 |
| WO | WO01/13957 | 3/2001 |
| WO | WO 01/28592 | 4/2001 |
| WO | WO 01/74382 | 10/2001 |
| WO | WO02/059272 | 8/2002 |
| WO | WO 02/085908 | 10/2002 |
| WO | WO 02/087424 | 11/2002 |
| WO | WO 02/098868 | 12/2002 |
| WO | WO03/050295 | 6/2003 |
| WO | WO03/092742 | 11/2003 |
| WO | WO 03/097647 | 11/2003 |
| WO | WO 2004/005326 | 1/2004 |
| WO | WO 2004/005327 | 1/2004 |
| WO | WO 2004/012735 | 2/2004 |
| WO | WO2004/022099 | 3/2004 |
| WO | WO2004/037210 | 5/2004 |
| WO | WO 2004/046170 | 6/2004 |
| WO | WO 2004/054622 | 7/2004 |
| WO | WO 2004/069159 | 8/2004 |
| WO | WO 2005/074901 | 8/2005 |
| WO | WO 2005/112919 | 12/2005 |
| WO | WO2005/115912 | 12/2005 |
| WO | WO 2006/012527 | 2/2006 |
| WO | WO 2006/042146 | 4/2006 |
| WO | WO2006/089007 | 8/2006 |
| WO | WO 2006/101845 | 9/2006 |
| WO | WO2006/105141 | 10/2006 |
| WO | WO2007/002222 | 1/2007 |
| WO | WO 2007/022493 | 2/2007 |
| WO | WO 2007/022494 | 2/2007 |
| WO | WO2007/022512 | 2/2007 |
| WO | WO2007/140298 | 12/2007 |
| WO | WO 2008/057437 | 5/2008 |
| WO | WO 2008/101231 | 8/2008 |
| WO | WO 2008/112873 | 9/2008 |
| WO | WO 2009/002993 | 12/2008 |
| WO | WO 2009/055562 | 4/2009 |
| WO | WO 2010/045598 | 4/2010 |
| WO | WO 2010/033733 | 5/2010 |
| WO | WO 2011/069116 | 6/2011 |
| WO | WO2011/106639 | 9/2011 |
| WO | WO 2011/130598 | 10/2011 |
| WO | WO2012/019123 | 2/2012 |
| WO | WO 2012/047525 | 4/2012 |
| WO | WO2013/149185 | 10/2013 |
| WO | WO 2014/062697 | 4/2014 |
| WO | WO2014/078484 | 5/2014 |
| WO | WO 2015/106599 | 7/2015 |

OTHER PUBLICATIONS

Antony A.C. et al., "Studies of the Role of a Particulate Folate-binding Protein in the Uptake of 5-Methyltetrahydrofolate by Cultured Human KB Cells," *J. Biological Chem.*, 1985; 260(28):14911-7.

Archer M.C. et al., "Separation of Folic Acid Derivatives and Pterins by High-Performance Liquid Chromatography," *Methods in Enzymology*, 1980; 66: pp. 452-459.

Arya et al., "Design and Synthesis of Analogs of Vitamin E: Antiproliferative Activity Against Human Breast Adenocarcinoma Cells," *Bioorganic & Medicinal Chemistry Letters*, 1998; vol. 8, pp. 2433-2438.

Ayers W.A., "Effect of Vitamin B12 and Analogs on the Respiration of a Marine Bacterium," *Archives of Biochemistry and Biophysics*, 1962, vol. 96, pp. 210-215.

Barnett C.J. et al., "Structure-Activity Relationships of Dimeric Catharanthus Alkaloids. 1. Deacetylvinblastine Amide (Vindesine) Sulfate," *J. Med. Chem.* 21: 88-96 (1978).

Bavetsias, V. et al., "Design and synthesis of Cyclopenta[g]quinazoline-based antifolates as inhibitors of thymidylate synthase and potential antitumor agents," J Med Chem, 2000; 43(10): 1910-1926.

Bavetsias, V., et al., "The design and synthesis of water-soluble analogues of CB30865, a quinazolin-4-one-based antitumor agent," J Med Chem, 2002; 45(17): 3692-3702.

Birinberg E. M. et al., "Synthesis and antimetabolic activity of pyrimidine analogs of folic and pteroic acids," *Pharmaceutical Chemistry Journal*, 1969; 3(6): pp. 331-333.

Bock et al., "Sulfonamide structure-activity relationships in a cell-free system. 2. Proof for the formation of a sulfonamide-containing folate analog," *Journal of Medical Chemistry*, 17: 23-28 (1974).

Boger, D.L. et al., "An improved synthesis of 1,2,9,9a-tetrahydrocyclopropa[c]benz[e]indol-4-one (CBI): a simplified analog of the CC-1065 alkylation subunit," *J. Org. Chem.*, 1992; 57: 2873-2876.

Campbell et al., "Folate-binding protein is a marker for ovarian cancer," *Cancer Res.*, 1991; 51: 5329-5338.

Cho et al., "Single-chain Fv/folate conjugates mediate efficient lysis of folate-receptor-positive tumor cells," *Bioconjug. Chem.* 8(3): 338-346 (1997).

Christensen et al., "Membrane receptors for endocytosis in the renal proximal tubule," *Int. Rev. Cytol.*, 1998; 180: 237-284.

Churlaud C. et al., "Novel 4-(Trimethylsilyl)aminoalkanes and 4-(Trimethylsilyl)aminoalk-2-enes, via a 1,5-Hydride Shift, in the Reaction of α-Unsaturated Silanes with Aminomethylbenzotriazoles," *Organomettalics*, 1999; 18(21): 4270-4274.

Citro G. et al., "Inhibition of leukemia cell proliferation by folic acid—polylysine-mediated introduction of c-myb antisense oligodeoxynucelotides into HL-60 cells," *Br. J. Cancer*, 1994; 69: 463-467.

Cope A.C. et al., "Thermal Rearrangement of Allyl-type Sulfoxides, Sulfones and Sulfinates," *J. Am. Chem. Soc.*, 1950; 72; 59-67.

Cosulich D.B. et al., "Analogs of Pteroylglutamic Acid. I. N10-Alkylpteroic Acid and Derivatives," *JACS*, 1948, 70 (5), pp. 1922-1926.

DeVita, Jr., Vincent et al (eds); *Biologic Therapy of Cancer*, 2nd ed., J.B. Lippincott Company; 1995.

Domling A. et al., "Myxobacterial Epothilones and Tubulysins as Promising Anticancer Agents," *Molecular Diversity*, 2005; 9: 141-147.

Douglas J.T. et al., "Targeted Gene Delivery by Tropism-Modified Adenoviral Vectors," *Nat. Biotechnol.*, 1996, vol. 14, pp. 1574-1578.

(56) References Cited

OTHER PUBLICATIONS

Eichman, J.D. et al., "The Use of PAMAM Dendrimers in the Efficient Transfer of Genetic Material Into Cells", Jul. 2000, *PSTT*, vol. 3, No. 7, pp. 232-245.

Foong, L.Y. et al., "Development of a Novel Thiol Reagent for Probing Ion Channel Structure: Studies in a Model System," Biochemistry, 1997, vol. 36, pp. 1343-1348.

Frankel AE., "Immunotoxin therapy of cancer," *Oncology*, 1993; 7(5): 69-78.

Shealy Y.F., "Synthesis and Evaluation of Some New Retinoids for Cancer Chemoprevention," *Preventive Medicine*, 1989, vol. 18, pp. 624-645.

Gangjee et al., "The effect of 5-alkyl modification on the biological activity of pyrrolo[2,3-d]pyrimidine containing classical and non-classical antifolates as inhibitors of dihydrofolate reductase and as antitumor and/or antiopportunistic infection agents," *J Med Chem.*, 2008; 51(15):4589-4600.

Garin-Chesa et al., "Trophoblast and ovarian cancer antigen LK26. Sensitivity and specificity in immunopathology and molecular identification as a folate-binding protein," *Am. J. Pathol.* 142(2): 557-562 (1993).

GE Healthcare, Instructions 71-7104-00 AD (1993).

Gibbs, DD et al., "BGC 945, a novel tumor-selective thymidylate synthase inhibitor targeted to alpha-folate receptor-overexpressing tumors," Cancer Res, 2005; 65(24): 11721-11728.

Gottschalk S. et al., "Folate receptor mediated DNA delivery into tumor cells: potosomal disruption results in enhanced gene expression," *Gene Therapy*, 1994; 1(3): 185-191.

Greene T.E. et al., "Protective Groups in Organic Synthesis," 2d edition, John Wiley & Sons, Inc. New York (1991).

Hanck A.B. et al., "Dexpanthenol (Ro 01-4709) in the treatment of constipation," *Acta Vitaminol Enzymol*, 1982; vol. 4 (1-2), pp. 87-97 (abstract only).

Harvison, P.J. et al., "Synthesis and Biological Activity of Novel Folic Acid Analogues: Pteroyl-S-alkylhomocysteine Sulfoximines," *Journal of Medicinal Chemistry*, 1992, vol. 35, pp. 1227-1233.

U.S. Appl. No. 60/946,092, filed Jun. 25, 2007, Vlahov et al.
U.S. Appl. No. 60/982,595, filed Nov. 25, 2007, Vlahov et al.
U.S. Appl. No. 61/036,176, filed Mar. 13, 2008, Vlahov et al.
U.S. Appl. No. 61/036,186, filed Mar. 13, 2008, Vlahov et al.

Henderson, E.A. et al., Targeting the alpha-folate receptor with cyclopenta[g]quinazoline-based inhibitors of thymidylate synthase, Bioorg Med Chem, 2006; 14(14): 5020-5042.

Ho R. I. et al., "A simple radioassay for dihydrofolate synthetase activity in *Escherichia coli* and its application to an inhibition study of new pteroate analogs," *Anal. Biochem.*, 1976, 73(2), pp. 493-500.

Hofland et al., "Folate-targeted gene transfer in vivo," *Mol Ther* 5(6): 739-744 (2002).

Hofle, G. et al., "Semisynthesis and Degradation of the Tubulin Inhibitors Epothilone and Tubulysin", 2003, *Pure Appl. Chem.*, vol. 75, Nos. 2-3, pp. 167-178.

Holladay et al., "Riboflavin-mediated delivery of a macromolecule into cultured human cells," *Biochim Biophys Acta*, 1426(1): 195-204 (1999).

Holm, J. et al., "Folate receptors in malignant and benign tissues of human female genital tract," *BioSci. Rep.*, 17(4): 415-427 (1997).

Holm, J. et al., "High-affinity folate binding in human choroid plexus. Characterization of radioligand binding, immunoreactivity, molecular heterogeneity and hydrophobic domain of the binding protein," *Biochem J.*, 280(1): 267-271 (1991).

Hosomi A. et al., "Affinity for a-tocopherol transfer protein as a determinant of the biological activities of vitamin E analogs," *Federation of European Biochemical Societies Letters*, 1997, vol. 409, pp. 105-108.

Houlihan, C. M. et al., "Preparation and Purification of Pteroic Acid from Folic Acid," *Analytical Biochemistry*, 1972, vol. 46, pp. 1-6.

Hynes et al., "Quinazolines as inhibitors of dihydrofolate reductase. 4. Classical analogues of folic and isofolic acids", *Journal of Medical Chemistry*, 1977; 20: 588-591.

Jackman, A. L. et al., "Antifolates targeted specifically to the folate receptor," Adv Drug Deliv Rev, 2004; 56(8): 1111-1125.

Jones T.R. et al., "A potent antitumour quinazoline inhibitor of thymidylate synthetase: synthesis, biological properties and therapeutic results in mice," *Eur J Cancer*, 1981; 17(1):11-9.

Jones T.R. et al., "Quinazoline antifolates inhibiting thymidylate synthase: variation of the amino acid," *J Med Chem*, 1986; 29(6):1114-8.

Jung K.H. et al., "Intramolecular o-glycoside bond formation," *Chem. Rev.*, 2000, 100, 4423-42.

Kagechika H et al., "Synthetic Retinoids: Recent Developments Concerning Structure and Clinical Utility," *Journal of Medicinal Chemistry*, 2005; vol. 48, No. 19, pp. 5875-5883.

Kamen et al., "Delivery of folates to the cytoplasm fo MA104 cells is mediated by a surface receptor that recycles," *J. Biol. Chem.*, 263: 13602-13609 (1988).

Kamen et al., "The folate receptor works in tandem with a probenecid-sensitive carrier in MA104 cells in vitro," *J. Clin. Invest.*, 87(4): 1442-1449 (1991).

Kamen, B. A. et al., "Receptor-mediated folate accumulation is regulated by the cellular folate content," *Proc. Natl. Acad. Sci. USA*, 83: 5983-5987 (1986).

Kandiko C.T. et al., "Inhibition of Rat Brain Pyruvate Dehydrogenase by Thiamine Analogs," *Biochemical Pharmacology*, 1988; vol. 37, No. 22, pp. 4375-4380.

Kane et al., "The influence of extracellular folate concentration on methotrexate uptake by human KB cells. Partial characterization of a membrane-associated methotrexate binding protein," *J. Biol. Chem.*, 261: 44-49 (1986).

Kim et al., "Synthesis and biological activity of 10-thia-10-deaza analogs of folic acid, pteroic acid, and related compounds", *Journal of Medical Chemistry*, 18: 776-780 (1975).

Kranz et al., "Conjugates of folate and anti-T-cell-receptor antibodies specifically target folate-receptor-positive tumor cells for lysis," *Proc. Natl. Acad. Sci. USA*, 1995; 92(20), pp. 9057-9061.

Kumar H.P. et al., "Folate transport in Lactobacillus salivarius. Characterization of the transport mechanism and purification and properties of the binding component," *J. Biol. Chem.*. 1987; 262(15):7171-7179.

Ladino et al., "Folate-maytansinoids: target-selective drugs of low molecular weight," *Int. J. Cancer*, 73(6): 859 864 (1997).

Lambooy J. P., "Riboflavin Analogs Utilized for Metabolism by a Lactobacillus Casei Mutant," *Int. J. Biochem.*, vol. 16, No. 2, 1984, pp. 231-234.

Landuer W. et al., "The Interaction in Teratogenic Activity of the Two Niacin Analogs 3-acetylpyridine and 6-aminonicotinamide," *J Exp Zool*, 151(3):253-258 (1962).

Langone, J.J., et al., "Radioimmunoassays for the Vinca Alkaloids, Vinblastine and Vincristine", 1979, *Analytical Biochemistry*, No. 95, pp. 214-221.

Larock R.C., "Comprehensive Organic Transformations, a guide to functional group preparations," VCH Publishers, Inc. New York (1989).

Leamon CP et al, "Cytotoxicity of folate-Pseudomonas exotoxin conjugates toward tumor cells. Contribution of translocation domain," *J. Biol. Chem.* 268(33): 24847-24854 (1993).

Leamon CP et al., "Comparative Preclinical Activity of the Folate-targeted Vinca Alkaloid Conjugates EC140 and EC145," *Int J Cancer*, 2007; 121(7):1585-92.

Leamon CP et al., "Cytotoxicity of momordin-folate conjugates in cultured human cells," *J. Biol. Chem.*, 1992; 267(35): 24966-24971.

Leamon CP et al., "Delivery of macromolecules into living cells: a method that exploits folate receptor endocytosis," *Proc. Natl. Acad. Sci. USA* 88(13): 5572-5573 (1991).

Leamon CP et al., "Folate-mediated targeting: from diagnostics to drug and gene delivery," *Drug Discovery Today* 6: 44-51 (2001).

Leamon CP et al., "Folate-targeted chemotherapy," Adv Drug Deliv Rev, 2004;56(8): 1127-41.

Leamon CP et al., "Membrane folate-binding proteins are responsible for folate-protein conjugate endocytosis into cultured cells," *Biochem. J.* 291: 855-860 (1993).

Leamon CP et al., "Selective targeting of malignant cells with cytotoxin-folate conjugates," *J. Drug Target.* 2(2): 101-112 (1994).

(56) References Cited

OTHER PUBLICATIONS

U.S. Appl. No. 60/590,580, filed Jul. 23, 2004, Vlahov et al.
Leamon CP et al., "Synthesis and biological evaluation of EC140: A novel folate-targeted vinca alkaloid conjugate," *Bioconjug Chem*, 2006;17(5):1226-32.
Leamon CP et al., "Synthesis and Biological Evaluation of EC20: A New Folate-Derived, (99m)Tc-Based Radiopharmaceutical," *Bioconjug. Chem.* 13(6): 1200-1210 (2002).
Leamon CP et al., "Synthesis and biological evaluation of EC72: a new folate-targeted chemotherapeutic," *Bioconjug Chem.*, 2005;16(4):803-11.
Leamon et al., "Folate-mediated drug delivery: effect of alternative conjugation chemistry," *J. Drug Target* 7(3): 157-169 (1999).
Lee et al, "Measurement of Endosome pH Following Folate Receptor-Mediated Endocytosis," *Biochim. Biophys. Acta* 1312(3): 237-242 (1996).
Lee W.W. et al., "Folic acid antagonists. Methotrexate analogs containing spurious amino acids. Dichlorohomofolic acid," *Journal of Medical Chemistry*, 17: 326-330 (1974).
Lee et al., "Synthesis and evaluation of taxol-folic acid conjugates as targeted antineoplastics," *Bioorg Med Chem*. 10(7): 2397-2414, (2002).
Lee, Francis Y. F., et al., "BMS-247550: A Novel Epothilone Analog With a Mode of Action Similar to Paclitaxel But Possessing Superior Antitumor Efficacy," *Clin Cancer Res*, 2001, No. 7, pp. 1429-1437.
Lee, R. J. and Huang, L., "Folate-Targeted, Anionic Liposome-Entrapped Polylysine-Condensed Dna For Tumor Cell-Specific Gene Transfer," *J. Biol. Chem*. 271(14): 8481-8487 (1996).
Lee, R. J. and Low, P. S, "Delivery of liposomes into cultured KB cells via folate receptor-mediated endocytosis," *J. Biol. Chem*. 269(5): 3198-3204 (1994).
Lee, R. J. and Low, P. S., "Folate-mediated tumor cell targeting of liposome-entrapped doxorubicin in vitro," *Biochim. Biophys. Acta* 1233: 134-144 (1995).
Lemon, Julia, et al., "Conversion of Pterolyglutamic Acid to Pteroic Acid by Bacterial Degradation," *Archives of Biochemistry*, 1948; vol. 19, pp. 311-316.
Levy, Carl C., et al. "The Enzymatic Hydrolysis of Methotrexate and Folic Acid", 1967, *The Journal Of Biological Chemistry*, vol. 242, No. 12, pp. 2933-2938.
Lewis et al., "Receptor-mediated folate uptake is positively regulated by disruption of actin cytoskeleton," *Cancer Res*. 58(14): 2952-2956 (1998).
Li et al, "Targeted delivery of antisense oligodeoxynucleotides by LPDII," *J. Liposome Res*. 7(1): 63 (1997).
Liu et al., "Targeted Drug Delivery to Chemoresistant Cells: Folic Acid Derivatization of FdUMP[10] Enhances Cytotoxicity Toward 5-FU-Resistant Human Colorectal Tumor Cells," *J. Org. Chem*. 66: 5655-5663 (2001).
Lonsdale D, "A Review of the Biochemistry, Metabolism and Clinical Benefits of Thiamin(e) and Its Derivatives," publication, Advance Access Publication, vol. 3, Feb. 2006, pp. 49-59.
Lopes et al., "Acyloxymethyl as a drug protecting group. Part 5.1 Kinetics and mechanism of the hydrolysis of tertiary N-acyloxymethylsulfonamides," *J. Chem. Soc.*, Perkin Trans. 2 pp. 431-439 (1999).
Low P.S. et al., "Folate Receptor-Targeted Drugs for Cancer and Inflammatory Diseases," *Adv Drug Deliv Rev*, 2004;56(8):1055-1058.
Lu et al., "Folate-targeted enzyme prodrug cancer therapy utilizing penicillin-V amidase and a doxorubicin prodrug," *J. Drug Target*, 7(1): 43-53 (1999).
Lu, J. Y. and Low, P. S., "Folate targeting of haptens to cancer cell surfaces mediates immunotherapy of syngeneic murine tumors," *Cancer Immunol Immunother*, 51: 153-162 (2002).
Lu, J. Y. and Low, P. S., "Folate-mediated delivery of macromolecular anticancer therapeutic agents," *Adv. Drug Del Rev*, 2002; 54(5): 675-693.

Luo et al., "Efficient syntheses of pyrofolic acid and pteroyl azide, reagents for the production of carboxyl-differentiated derivatives of folic acid," *J. Am. Chem. Soc.*, 119: 10004-10013 (1997).
Mack D.O. et al., "The Carboxylation Activity of Vitamin K Analogs with Substitutions at Position 2, 3, or 5," *Journal of Biological Chemistry*, 1979; vol. 254, pp. 2656-2664.
Mancuso A.J. et al., "Activated Dimethyl Sulfoxide: Useful Reagents for Synthesis," Synthesis, 1981, pp. 165-184.
March, Advanced Organic Chemistry, 1992, John Wiley & Sons, 4th Ed., pp. 362-363, 816, 885, 896.
Mathais et al., "Receptor-mediated targeting of 67Ga-deferoxamine-folate to folate-receptor-positive human KB tumor xenografts," *Nucl Med Biol*, 26(1): 23-25 (1999).
Mathais et al., "Synthesis of [(99m)Tc]DTPA-folate and its evaluation as a folate-receptor-targeted radiopharmaceutical," *Bioconjug Chem*, 11(2): 253-257 (2000).
Mathias et al., "Indium-111-DTPA-Folate as a potential folate-receptor-targeted radiopharmaceutical," *J. Nucl. Med.*, 39(9): 1579-1585 (1998).
Mathias et al., "Tumor-Selective Radiopharmaceutical Targeting Via Receptor-Mediated Endocytosis of Gallium-67-Deferoxamine-Folate," *J. Nucl. Med*, 37(6): 1003-1008 (1996).
Mathias, C. J., "A kit formulation for preparation of [(111)in]In-DTPA-folate, a folate-receptor-targeted radiopharmaceutical," *Nucl. Med. Biol.*, 25(6): 585-587 (1998).
Matsui et al., "Studies on mitomycins. III. The synthesis and properties of mitomycin derivatives," *J Antibiot*, 21: 189-198 (1968).
Kamao M. et al., "Determination of Plasma Vitamin K by High Performance Liquid Chromatography with Fluorescence Detection Using Vitamin K Analogs as Internal Standards," *Journal of Chromatography B*, 2005; vol. 816, pp. 41-48.
McAlinden TP et al., "Synthesis and Biological Evaluation of a Fluorescent Analogue of Folic Acid," *Biochemistry*, 1991; 30: 5674-81.
McHugh M et al., "Demonstration of a High Affinity Folate Binder in Human Cell Membranes and Its Characterization in Cultured Human KB Cells," *J Biol Chem*, 1979; 254(22):11312-8.
Melani et al., "Targeting of interleukin 2 to human ovarian carcinoma by fusion with a single-chain Fv of antifolate receptor antibody," *Cancer Res*. 58(18): 4146-4154 (1998).
U.S. Appl. No. 60/808,367, filed May 25, 2006, Vite et al.
Melby, E.L. et al, "Entry of Protein Toxins in Polarized Epithelial Cells"; *Cancer Research*, 1993; 53: 1755-1760.
Mislick et al., "Transfection of folate-polylysine DNA complexes: evidence for lysosomal delivery," *Bioconjug. Chem.*, 6(5): 512-515 (1995).
Mock D.M. et al., "Urinary Biotin Analogs Increase in Humans During Chronic Supplementation: the Analogs are Biotin Metabolites," *Am J Physiol Endocrinol Metab*, 1997; 272: E83-E85.
Morshed et al., "Folate transport proteins mediate the bidirectional transport of 5-methyltetrahydrofolate in cultured human proximal tubule cells," *J. Nutr.*, 127(6): 1137-1147 (1997).
Nair et al., "Folate analogs altered in the C9—N10 bridge region. 14. 11-Oxahomofolic acid, a potential antitumor agent", *Journal of Medical Chemistry*, 23: 59-65 (1980).
Nair et al., "Folate analogs altered in the C9—N10 bridge region. 18. Synthesis and antitumor evaluation of 11-oxahomoaminopterin and related compounds," *Journal of Medical Chemistry*, 24: 1068-1073 (1981).
Nair et al., "Folate analogs altered in the C9—N10 bridge region: N10-tosylisohomofolic acid and N10-tosylisohomoaminopterin," *Journal of Medical Chemistry*, 21: 673-677 (1978).
Nair et al., "Folate analogs altered in the C9—N10 bridge region: 11-thiohomofolic acid," *Journal of Medical Chemistry*, 22: 850-855 (1979).
Nair et al., "Folate analogs. 20. Synthesis and antifolate activity of 1',2',3',4',5',6'-hexahydrohomofolic acid," *Journal of Medical Chemistry*, 26: 135-140 (1983).
Nair et al., "Folate analogs. 21. Synthesis and antifolate and antitumor activities of N10-(cyanomethyl)-5,8-dideazafolic acid," *Journal of Medical Chemistry*, 26: 605-607 (1983).

(56) References Cited

OTHER PUBLICATIONS

Nair et al., "Folate analogs. 22. Synthesis and biological evaluation of two analogs of dihydrofolic acid possessing a 7,8-dihydro-8-oxapterin ring system," *Journal of Medical Chemistry*, 26: 1164-1168 (1983).

Nair et al., "Folate analogues altered in the C9—N10 bridge region. 10-Oxafolic acid and 10-oxaaminopterin," *Journal of Medical Chemistry*, 19: 825-829 (1976).

Neuss, N. et al., "Vinca Alkaloids. XXX (1). Chemistry of the Deoxyvinblastines (Deoxy-VLB), Leurosine (VLR), and Pleurosine, Dimeric Alkaloids From Vinca," *Tetrahedron Letters*, No. 7, pp. 783-787 (1968).

Neuzil J. et al., "Vitamin E Analogs: A New Class of Multiple Action Agents with Anti-Neoplastic and Anti-Atherogenic Activity," *Apoptosis*, 2002; vol. 7, pp. 179-187.

Nielsen P. et al., "Phosphates of Riboflavin and Riboflavin Analogs: A Reinvestigation by High-Performance Liquid Chromatography," Analytical Biochemistry, vol. 130, 1983, pp. 359-368.

Nimmo-Smith R.H. et al., "Some Effects of 2-deaminopteroylglutamic Acid upon Bacterial Growth," *J. Gen. Microbial.*, 1953; 9: 536-544.

Nishikawa, Yuji et al., "Growth Inhibition of Hepatoma Cells Induced by Vitamin K and Its Analogs," *Journal of Biological Chemistry*, 1995; vol. 270, No. 47, pp. 28304-28310.

Nomura, Makoto et al., "Development of an Efficient Intermediate a-[2-(Trimethylsilyl)ethoxy]-2-N-[2-(trimethylsilyl)ethoxycarbonyl]folic Acid, for the Synthesis of Folate (y)-Conjugates, and Its Application to the Synthesis of Folate-Nucleoside Conjugates," *Journal of Organic Chemistry*, 2000, vol. 65, pp. 5016-5021.

Nosaka K.et al., "Separate Determination of Anticoccidial Thiamine Analogs by High-performance Liquid Chromatography," *ActaA Vitaminol. Et Enzymol*, 1984, vol. 6 (2), pp. 137-142.

Oatis et al., "Synthesis of quinazoline analogues of folic acid modified at position 10," *Journal of Medical Chemistry*, 20: 1393-1396 (1977).

Olsnes S. et al., "Immunotoxins—entry into cells and mechanisms of action," *Immunology Today*, 1989; vol. 10, No. 9, pp. 291-295.

Patrick et al., "Folate Receptors as Potential Therapeutic Targets in Choroid Plexus Tumors of Sv40 Transgenic Mice," *J. Neurooncol,.* 32(2): 111-123 (1997).

Patrick et al., "Intracerebral bispecific ligand-antibody conjugate increases survival of animals bearing endogenously arising brain tumors," *Int. J. Cancer*, 78(4): 470-79 (1998).

Peltier, Hillary M., et al., "The Total Synthesis of Tubulysin D," 2006, *J. Am. Chem. Soc.*, No. 128, pp. 16018-16019.

Pizzorno G., et al., "Intracellular metabolism of 5,10-dideazatetrahydrofolic acid in human leukemia cell lines," *Molecular Pharmacology*, 1991, 39 (1), pp. 85-89.

Plante et al., "Polyglutamyl and polylysyl derivatives of the lysine analogues of folic acid and homofolic acid," *Journal of Medical Chemistry*, 19: 1295-1299 (1976).

Politis I. et al., "The Effect of Various Vitamin E Derivatives on the Urokinase-Plasminogen Activator System of Ovine Macrophages and Neutrophils," *British Journal of Nutrition*, vol. 89, 2003, pp. 259-265.

Prabhu V. et al., "Arabidopsis dihydropteroate synthase: general properties and inhibition by reaction product and sulfonamides," *Phytochem.*, 1997; 45(1): 23-27.

Prasad et al., "Functional coupling between a bafilomycin A1-sensitive proton pump and a probenecid-sensitive folate transporter in human placental choriocarcinoma cells," *Biochim. Biophys. Acta*, 1994; 1222(2): 309.

Pratt, A.G. et al. "The Hydrolysis of Mono-, Di, and Triglutamate Derivatives Of Folic Acid With Bacterial Enzymes," *The Journal Of Biological Chemistry*, 1968, vol. 243, No. 24, pp. 6367-6372.

Punj, V. et al., "Effect of Vitamin D Analog (1α Hydroxy D5) Immunoconjugated to Her-2 Antibody on Breast Cancer," *Int. J. Cancer*, 2004; 108: 922-929.

Raghavan B et al., "Cytotoxic Simplified Tubulysin Analogues," *J. Med. Chem.*, 2008; 51(6), pp. 1530-1533.

Ranasinghe, M. G. et al.; "A Facile Synthesis of Unsymmetrical Thiolsulfonates via Sulfonylation of Mercaptans," *Synthetic Communications*, 1988; 18(3), pp. 227-232.

Reddy et al., "Optimization of folate-conjugated liposomal vectors for folate receptor-mediated gene therapy," *J. Pharm. Sci*, 88(11): 1112-1118 (1999).

Reddy et al., "Preclinical evaluation of EC145, a folate-vinca alkaloid conjugate," *Cancer Res.*, 2007; 67:4434-42.

Reddy et al., "Retargeting of viral vectors to the folate receptor endocytic pathway," *J Control Release*, 74(1-3): 77-82 (2001).

Reddy, J. A., Low, P. S., "Folate-Mediated Targeting of Therapeutic and Imaging Agents to Cancers," *Crit. Rev. Ther. Drug Carrier Syst.*, vol. 15, No. 6, 1998, pp. 587-627.

Remington: The Science & Practice of Pharmacy, 21th Edition (Lippincott Williams & Wilkins, 2005).

Renz P. et al., "Synthesis of 4-Aza-5, 6-diethylbenzimidazole and Biosynthetic Preparation of 4- and 7-Aza-5, 6-dimethylbenzimidazolylcobamide," *Z. Naturforsch*, 1997, vol. 52c, pp. 287-291.

Rijnboutt et al., "Endocytosis of GPI-linked membrane folate receptor-alpha," *J. Cell Biol.*, 132(1-2): 35-47 (1996).

Roberts et al., "Folic acid analogs. Modifications in the benzene-ring region. 3. Neohomofolic and neobishomofolic acids. An improved synthesis of folic acid and its analogs," *Journal of Medical Chemistry*, 16: 697-699 (1973).

Roberts et al., "Folic acid analogs. Modifications in the benzene-ring region. 2. Thiazole analogs," *Journal of Medical Chemistry*, 15: 1310-1312 (1972).

Roberts et al., "Folic acid analogs. Modifications in the benzene-ring region. 1. 2'- and 3'-Azafolic acids," *Journal of Medical Chemistry*, 14: 125-130 (1971).

Roberts et al., "Folic acid analogs. Modifications in the benzene-ring region. 4. 3'-Ethyl- and 3'-isopropylfolic acids," *Journal of Medical Chemistry*, 17: 219-222 (1974).

Rose W.C., "Taxol-Based Combination Chemotherapy and Other In Vivo Preclinical Antitumor Studies," *J Natl Cancer Inst Monogr*, 1993, No. 15, pp. 47-53.

Ross et al., "Differential regulation of folate receptor isoforms in normal and malignant tissues in vivo and in established cell lines. Physiologic and clinical implications," *Cancer*, 73(9): 2432-2443, (1994).

Rothberg et al, "Cholesterol controls the clustering of the glycophospholipid-anchored membrane receptor for 5-methyltetrahydrofolate," *J. Cell Biol.*, 111(6): 2931-2938 (1990).

Rothberg et al., "The glycophospholipid-linked folate receptor internalizes folate without entering the clathrin-coated pit endocytic pathway," *J. Cell Biol.*, 110(3): 637-649 (1990).

Roy et al., "Targeting T cells against brain tumors with a bispecific ligand-antibody conjugate," *Int. J. Cancer* 76(5): 761-66 (1998).

Sadasivan et al., "The complete amino acid sequence of a human folate binding protein from KB cells determined from the cDNA," *J. Biol. Chem.*, 1989; 264: 5806-5811.

Sargent D.R. et al., "Antimetabolites of Pantothenic Acid, Ureido- and Carbamoyl-Derivatives," *Texas Reports on Biology and Medicine*, 1975, vol. 33, No. 3, pp. 433-443.

Sasse F. et al., "Tubulysins, New Cytostatic Peptides from Myxobacteria Acting on Microtubuli Production, Isolation, Physico-Chemical and Biological Properties," *The Journal of Antibiotics*, 2000; vol. 53, No. 9, pp. 879-885.

Scott J.M, "Preparation and Purification of Pteroic Acid from Pteroylglutamic Acid (Folic Acid)," *Methods In Enzymology*, 1980, vol. 66, pp. 657-660.

Search Report for Taiwan Patent Application No. 093101735, dated Jul. 14, 2007, 1 page.

Semb J. et al., "Pteroic Acid Derivatives. V. Pteroyl-α-glutamyl-α-glutamylglutamic Acid, Pteroyl-γ-glutamyl-α-glutamylglutamic Acid, Pteroyl-α-glutamyl-γ-glutamylglutamic Acid," *JACS*, 1949; 71 (7): 2310-2315.

Senter et al., "Development of a Drug-Release Strategy Based on the Reductive Fragmentation of Benzyl Carbamate Disulfides," *J. Org. Chem.*, 55: 2975-2978 (1990).

(56) References Cited

OTHER PUBLICATIONS

Shimizu M. et al., "Synthesis and biological activities of new 1alpha, 25-dihydroxy-19-norvitamin D3 analogs with modifications in both the A-ring and the side chain," *Bioorganic & Medicinal Chemistry*, 2006; 14(12): 4277-94.

Shimizu, Kazui, et al., "Novel vitamin D3 antipsoriatic antedrugs: 16-En-22-oxa-1a,25-(OH)2D3 analogs," *Bioorganic & Medicinal Chemistry*, 2006;14: 1838-1850.

Shoup T.M. et al., "Synthesis of Fluorine-18-Labeled Biotin Derivatives: Biodistribution and Infection Localization," *J. Nucl. Med.*, 1994; 35: 1685-1690.

Skinner W.A. et al., "Structure-Activity Relations in the Vitamin E Series. II. Derivatives of α-Tocopherol Substituted at the 5-Methyl Group," *J. Med. Chem.*, 1969; 12 (1): 64-66.

Smart et al., "Clustered folate receptors deliver 5-methyltetrahydrofolate to cytoplasm of MA104 cells," *J. Cell Biol.*, 134(5): 1169-1177 (1996).

Smart et al., "Protein kinase C activators inhibit receptor-mediated potocytosis by preventing internalization of caveolae," *J. Cell Biol.*, 124(3): 307-313 (1994).

Spry C. et al., "A Class of Pantothenic Acid Analogs Inhibits Plasmodium Falciparum Pantothenate Kinase and Represses the Proliferation of Malaria Parasites," *Antimicrobial Agents and Chemotherapy*, 2005; 49(11): 4649-4657.

Steinberg, G. et al., "Synthesis and Evaluation of Pteroic Acid-Conjugated Nitroheterocyclic Phosphoramidates as Folate Receptor-Targeted Alkylating Agents," *J. Med. Chem.* 44: 69-73 (2001).

Steinmetz, H. et al., "Isolation, Crystal and Solution Structure Determination, and Biosynthesis of Tubulysins—Powerful Inhibitors of Tubulin Polymerization from Microbacteria", *Angew. Chem. Int. Ed.*, 2004, No. 43, pp. 4888-4892.

Takahata Y. et al., "Synthesis, Properties and Microbiological Activity of Hydrophobic Derivatives of Vitamin B12," *J. Nutr. Sci. Vitaminol.*, 1995, vol. 41, pp. 515-526.

Takasu, H. et al., "c-Fos protein as a target of anti-osteoclastogenic action of vitamin D, and synthesis of new analogs," *The Journal of Clinical Investigation*, 2006; vol. 116, No. 2, pp. 528-535.

Takeda, K. et al., "A Synthesis of a New Type of Alkoxycarbonylating Reagents from 1,1-Bis[6-(trifluoromethyl)benzotriazolyl] Carbonate (BTBC) and Their Reactions," *Sythesis*, 1987; 6: 557-560.

Temple et al., "Synthesis of pseudo cofactor analogs as potential inhibitors of the folate enzymes," *Journal of Medical Chemistry*, 25: 161-166 (1982).

Toffoli et al., "Overexpression of folate binding protein in ovarian cancers," *Int. J. Cancer* 74(2): 193-198 (1997).

Toraya T. et al., "Immobilized Derivatives of Vitamin B12 Coenzyme and Its Analogs," *Methods in Enzymology*, vol. 67, pp. 57-66, 1980.

Toraya T. et al., "The Synthesis of Several Immobilized Derivatives of Vitamin B12 Coenzyme and Their Use as Affinity Adsorbents for a Study of Interactions of Diol Dehydrase with the Coenzyme," *The Journal of Biological Chemistry*, 1990; vol. 255, No. 8, pp. 3520-3525.

Trachewsky D., "Antihypertensive Effect of Riboflavin Analogs in Rats with Mineralocorticoid-Induced Hypertension," *Hypertension*, 1981; vol. 3, No. 1, pp. 75-80.

Truneh A. et al., "Temperature-sensitive differential affinity of TRAIL for its receptors. DR5 is the highest affinity receptor," *J Biol Chem*, 2000; 275(30):23319-25.

Turek et al., "Endocytosis of folate-protein conjugates: ultrastructural localization in KB cells," *J. Cell Sci.* 106: 423-430 (1993).

Turk et al., "Characterization of a novel pH-sensitive peptide that enhances drug release from folate-targeted liposomes at endosomal pHs," *Biochim Biophys Acta*, 1559(1): 56-68 (2002).

Ueda M. et al., "Effect of Vitamin B12 Derivatives on Urinary Excretion of Methylmalonic Acid in Liver Diseases," *Acta Med. Okayama*, 1970; vol. 24, pp. 365-372.

Varma, R. et al., "GPI-anchored proteins are organized in submicron domains at the surface," *Nature*, 394(6695): 798-801 (1998).

Verwey, J., "Mitomycin C-Induced Renal Toxicity, a Dose-Dependent Side Effect?," *Eur J Cancer Clin Onco*, 1987; vol. 23, No. 2, pp. 195-199.

Vesely D.L. et al., "Biotin Analogs Activate Guanylate Cyclase," *Molecular and Cellular Biochemistry*, 1984; vol. 60, pp. 109-114.

Vlahov I.R. et al., "Design and regioselective synthesis of a new generation of targeted chemotherapeutics. Part 1: EC145, a folic acid conjugate of desacetylvinblastine monohydrazide," *Bioorg Med Chem Lett*, 2006; 16(19):5093-6.

Vogel et al., "Peptide-Mediated Release of Folate-Targeted Liposome Contents From Endosomal Compartments," *J. Am. Chem. Soc.*, 1996; 118(7): 1581-1586.

Vyas D. et al., "A practical synthesis of mitomycin A and its analogs," *J Org Chem*, 1986; 31:4307-4309.

Wang et al., "Delivery of antisense oligodeoxyribonucleotides against the human epidermal growth factor receptor into cultured KB cells with liposomes conjugated to folate via polyethylene glycol," *Proc. Natl, Acad. Sci. USA*, 92(8): 3318-3322 (1995).

Wang et al., "Design and synthesis of [111In]DTPA-folate for use as a tumor-targeted radiopharmaceutical," *Bioconjug Chem.*, 8(5): 673-679 (1997).

Wang et al., "Synthesis, purification, and tumor cell uptake of 67Ga-deferoxamine-folate, a potential radiopharmaceutical for tumor imaging," *Bioconj. Chem.*, 1996; 7(1): 56-62.

Wang S. et al., "Folate-mediated targeting of antineoplastic drugs, imaging agents, and nucleic acids to cancer cells," *J. Control Rel*, 1998; 53(1-3): 39-48.

Weinstock et al., "Folic acid analogs. II. p-{[(2,6-Diaminno-8-purinyl)methyl]amino}-benzoyl-L-glutamic acid and related compounds," *Journal of Medical Chemistry*, 13: 995-997 (1970).

Weitman et al., "Cellular localization of the folate receptor: potential role in drug toxicity and folate homeostasis," *Cancer Res.*, 1992; 52(23): 6708-6711.

Weitman et al., "Distribution of the folate receptor GP38 in normal and malignant cell lines and tissues," *Cancer Res.*, 1992; 52(12): 3396-3401.

Westerhof G.R. et al., "Carrier- and Receptor-Mediated Transport of Folate Antagonists Targeting Folate-Dependent Enzymes: Correlates of Molecular-Structure and Biological Activity," *Molecular Pharmacology*, 1995, 48, pp. 459-471.

Westerhof GR et al., "A photoaffinity analogue of folic acid as a probe for the identification and function of a membrane folate binding protein (mFBP) in human CCRF-CEM leukemia cells," *Proccedings of the American Association for Cancer Research*, 1991; 32:328.

Wiener et al., "Targeting dendrimer-chelates to tumors and tumor cells expressing the high-affinity folate receptor," *Invest. Radiol.* 32(12): 748-54 (1997).

Wu M. et al., "Clustering of GPI-anchored folate receptor independent of both cross-linking and association with caveolin," *J. Membr. Biol.* 159(2): 137-147 (1997).

Wang, Xiu-Fang et al., "Vitamin E Analogs Trigger Apoptosis in HER2/erbB2-Overexpressing Breast Cancer Cells by Signaling Via the Mitochondrial Pathway," *Biochemical and Biophysical Research Communication*, 2005; vol. 326, pp. 282-289.

Zimmer H. et al., "Potential anticancer agents V., Synthesis of folic acid and pteroic acid analogs derived of caffeine and theophylline," *Arzneimittelforschung*, 1966, 16(4), pp. 541-545.

Zimmerman, J., "Folic acid transport in organ-cultured mucosa of human intestine. Evidence for distinct carriers," *Gastroenterol.* 99(4): 964-972 (1990).

Angier, R. B., et al., "Pteroic Acid Analogs Containing Arsenic," J. American Chem. Soc., vol. 76, 1954, pp. 902-904.

Boothe, J. H., et al., "Pteroic Acid Derivatives. II. Pteroyl-γ-glutamylglutamic Acid and Pteroyl-γ-glutamyl-γ-glutamylglutamic Acid," J. American Chem. Soc., vol. 70, 1948, pp. 1099-1102.

Bartels R. et al., "Determination of pteroic acid by high-performance thin-layer chromatography: Contribution to the investigation of 7,8-dihydropteroate synthase," *Journal of Chromatography A*, 1994; vol. 659(1): 185-189.

Wikipedia, Derivative (Chemistry), http://en.wikipedia.org/wiki/Derivative_(chemistry), downloaded Dec. 16, 2009.

(56) References Cited

OTHER PUBLICATIONS

Wikipedia, Analog (Chemistry), http://en.wiltipedia.org/wiki/Analog_(chemistry), downloaded Dec. 16, 2009.
Wikipedia, List of Purification Methods in Chemistry, http://en.wikipedia.org/wiki/List_of_purification_methods_in_chemistry, downloaded Dec. 16, 2009.
Wikipedia, Solution, http://en.wikipedia.org/wiki/Solution, downloaded Dec. 17, 2009.
Principles of Ion Exchange Chromatography, http://www.separations.us.tosohbioscience.com/ServiceSupport/TechSupport/ResourceCenter/PrinciplesofChromatography/IonExchange, downloaded Dec. 23, 2009.
Wikipedia, Conjugate, http://en.wikipedia.org/wiki/Conjugate, downloaded Dec. 17, 2009.
Wikipedia, Complex (Chemistry), http://en.wikipedia.org/wiki/Complex_(chemistry), downloaded Dec. 23, 2009.
Leamon Christopher P., "Aspects of Folate-Mediated Drug Delivery . . . Beyond Purdue" PowerPoint Presentation presented at Purdue University on May 4, 1999, (22 pages).
Achilefu et al. "A New Method for the Synthesis of Tri-tert-butyl Diethylenetriaminepentaacetic Acid Its Derivatives" *J. Org. Chem.* 2000; 65:1562-1565.
Carl et al. "A novel connector linkage applicable in prodrug design" J. Med. Chem. 1981;24(5):479-480.
Coney et al. "Cloning of a tumor-associated antigent: MOv18 and MOv19 antibodies recognize a folate-binding protein" Cancer Res. 1991;51(22):6125-32.
Crapatureanu et al. "Molecular necklaces. Cross-linking hemoglobin with reagents containing covalently attached ligands" Bioconjugate Chemistry, 1999;10(6):1058-67. Abstract Only.
Darnell, Ed. Molecular Cell Biology W. H. Freeman, San Francisco 1990;326-333.
DeNardo, Gerald. "When is Too Much Too Much and Yet Not Enough? Alas, a Plethora of Opportunities but Where's the Beef?" J. of Nuclear Medicine 2000; 41(3):470-3.
Dorwald, F. Z., "Side Reactions in Organic Synthesis: A Guide to Successful Synthesis Design," Wiley-VCH, Weinheim, 2005, p. ix of preface.
Forgac, "Structure and function of vacuolar class of ATP-driven pumps" Physiological Rev. 1989; 69(3), 765-795.
Garrett et al. "Synthesis and characterisation of polyamine-poly-(ethylene glycol) constructs for DNA binding and gene delivery" Bioorganic & Medicinal Chemistry, 2000; 8(7):1779-1797. Abstract Only.
Henderson et al. "Mediated uptake of folate by a high-affinity binding protein in sublines of L1210 cells adapted to nanomolar concentrations of folate" J. Membrane Biol., 1988;101:247-258.
Huang et al. "Design, syntheses and sequence selective DNA cleavage of functional models of bleomycin—II. 1,2-trans-di substituted cyclopropane units as novel linkers" Bioorganic & Medicinal Chemistry, 1995;3(6):647-57. Abstract Only.
Jansen et al., "Identification of a Membrane-Associated Folate-Binding Protein in Human Leukemic CCRF-CEM Cells with Transport-Related Methotrexate Resistance" in Cancer Res., 1989, 49, 2455-2459.
Jansen, "Receptor- and Carrier-Mediated Transport Systems for Folates and Antifolates," Antifolate Drugs in Cancer Therapy, Jackman, Ed., Humana Press Inc, Totowa NJ (1999): 293-321.
Jansen et al. "The Reduced Folate/Methotrexate Carrier and a Membrane-Associated Folate Binding Protein as Transport Routes for Novel Antifolates: Structure-Activity Relationship" Chemistry and Biology of Pteridines and Folates New York, 1992;767-770.
Ke et al. "Targeting the Tumor-Associated Folate Receptor with a I" IN-DTPA Conjugate of Pteroic Acid" Abstract No. 427. 48h Annual Meeting of the Society of Nuclear Medicine Toronto, Canada, Jun. 26, 2001, available May 4, 2001; 1 pg.
Kemp et al. "New Protective Groups for Peptide Synthesis—I The Bic Group Base and Solvent Lability of the 5-B enzi soxazolymethyl eneoxycarbonyl amino function" Tet. Lett. 1975;52:4625-4628.

Kutsky RJ. Handbook of Vitamins, Minerals, and Hormones, 2nd Edition. New York: Van Nostrand Reinhold: 1981;263-277.
Li et al. "Local concentration of folate binding protein GP38 in sections of human ovarian carcinoma by concentration of in vitro quantitative autoradiography." J. Nucl. Med. 1996; 37:665-672.
Linder et al., In vitro & in vivo studies with a-and y-isomers of 99'Tc-oxa folate show uptake of both isomers in folate receipt (+) KB Cell Lines J. Nuclear Med. 2000;41(5):470 Suppl.
Lee et al. "Prolonged circulating lives of single-chain Fv proteins conjugated with polyethylene glycol: a comparison of conjugation chemistries and compounds" Bioconjugate Chemistry, 1999;10(6):973-81. Abstract Only.
Mehvar R "Dextrans for targeted and sustained delivery of therapeutic and imaging agents" [Review] Journal of Controlled Release, 2000;69(1):1-25. Abstract Only.
Mezzanzanica et al. "Human T-lymphocytes targeted against an established human ovarian carcinoma with a bispecific F(ab')2 antibody prolong host survival in a murine xenograft model" Cancer Res. 1991; 51:5716-5721.
Miotti et al., "Characterization of Human Ovarian Carcinoma-Associated Antigens Defined by Novel Monoclonal Antibodies with Tumor-Restricted Specificity" Int. J. Cancer, 1987;39:297-303.
Pastan et al, eds. "The Pathways of Endocytosis" Endocytosis, Plenum Press, New York 1985;1-40.
Peterson et al. "Enzymatic cleavage of peptide-linked radiolabels from immunoconjugates" Bioconjugate Chemistry, 1999;10(4):553-7. Abstract Only.
Pizzorno et al. "5,10-Dideazatetrahydrofolic acid (DDATHF) transport in CCRFCEM and MA104 cell lines." J. Biol, Chem., 1993; 268(2):247-258.
Rothenberg et al. "Further observations on the folate-binding factor in some leukemic cells" J. Clin. Invest. 1971; 50(3):719-726.
Selhub et al. "The folate binding protein of rat kidney. Purification, properties, and cellular distribution" J. Biol. Chem. 1984;259(10):6601-6606.
Selhub et al. "Renal folate adsorption and the kidney folate binding protein I. Urinary Clearance studies" Am. J Physiol. 252:F750-F756, 1987.
Selhub et al. "Renal folate adsorption and the kidney folate binding protein II. Microinfusion studies" Am. J. Physiol. 252:F757-F760, 1987.
Sirotnak. "Obligate genetic expression in tumor cells of a fetal membrane property mediating "Folate" transport: biological significance and implications for improved therapy of human cancer" Cancer Res., 1985;45(9):3992-4000.
Stein et al. "Normal tissue reactivity of four anti-tumor monoclonal antibodies of clinical interest" Int. J. Cancer 1991;47(2):163-169.
Tanaka et al. "Preparation and characterization of a disulfide-linked bioconjugate of annexin V with the B-chain of urokinase: an improved fibrinolytic agent targeted to phospholipid-containing thrombi" Biochemistry, 1996:35(3):922-9. Abstract Only.
Toffoli et al. "Expression of folate binding protein as a prognostic factor for response to platinum-containing chemotherapy and survival in human ovarian cancer" Int. J. Cancer (Pred. Oncol) 1998; 79:121-126.
Thaden et al. "Photoaffinity behavior of a conjugate of oligonucleoside methylphosphonate, rhodamine, and psoralen in the presence of complementary oligonucleotides" Bioconjugate Chemistry, 1993;4(5):386-94. Abstract Only.
Westerhof et al. "Membrane transport of natural folates and antifolate compounds in murine L1210 Leukemia cells: role of carrier-and receptor mediated transport systems" Cancer Res. 1991;51:5507-5513.
Williams et al. "Renal tubular transport of folic acid and methotrexate in the monkey" Am. J. Physiol 1982; 242(5):F484-490.
Weygand, et al., Chemishe. Berichte (1950) 83, 460-467.
Beevers, Christopher S., et al., "Curcumin Inhibits the Mammalian Target of Rapamycin-Mediated Signaling Pathways in Cancer Cells", 2006; *Int. Journal Cancer*; Vo. 119; pp. 757-764.
Brown, Nicole E., et al., "Delayed Cystogenesis and Increased Ciliogenesis Associated with th Re-Expression of Polaris in Tg737 Mutant Mice", 2003, *Kidney International*, vol. 63, pp. 1220-1229.

(56) References Cited

OTHER PUBLICATIONS

Bukanov Nikolay, O. et al., "Long-Lasting Arrest of Murine Polycystic Kidney Disease With CDK Inhibitor Roscovitine", Dec. 14, 2006; Nature; vol. 444; pp. 949-952.
Hay, Nissim, et al., "Upstream and Downstream of mTOR", 2004, Genes & Development, vol. 18, No. 16, pp. 1926-1945.
Kennedy, Michael D., et al., "Evaluation of Folate Conjugate Uptake and Transport by the Choroid Plexus of Mice", (May 2003), vol. 20, No. 5, pp. 714-719.
Leamon, Christopher P., et al., "Folate-Liposome-Mediated Antisense Oligodeoxynucleotide Targeting to Cancer Cells: Evaluation in Vitro and in Vivo", 2003, Bioconjugate Chemistry, vol. 14, No. 4, pp. 738-747.
Nauta, Jeroen, et al., "Renal and Biliary Abnormalities in a New Murine Model of Autosomal Recessive Polycystic Kidney Disease", 1993, Pediatr. Nephrol. No. 7, pp. 163-172.
Piontek, Klaus B., et al. "A Functional Floxed Allele of Pkd1 that Can Be Conditionally Inactivated In Vivo", J. Am. Soc. Nephrol. vol. 15, pp. 3035-3043, 2004.
Shillingford, Jonathan M., et al., "The mTOR Pathway is Regulated by Polycystin-1, and its Inhibition Reverses Renal Cystogenesis in Polycyctic Kidney Disease", Apr. 4, 2006, PNAS. vol. 103, No. 14, pp. 5466-5471.
Ke CY et al., "Folate-Receptor-Targeting of In-111 Using Pteroic Acid Conjugates of Benzyl-DTPA and Benzyl-DOTA," J. Nucl. Med., 2004; 45(5):457P.
Regueiro-Ren et al., "Synthesis and Biological Activity of Novel Epothilone Aziridines," Organic Letters, 2001; vol. 3, No. 17: 2693-96.
Kamen et al., "A review of folate receptor alpha cycling and 5-methyltetrahydrofolate accumulation with an emphasis on cell models in vitro," Advanced Drug Delivery Reviews, 2004; vol. 56:1085-97.
Elnakat et al., "Distribution, functionality and gene regulation of folate receptor isoforms: implications in targeted therapy," Advanced Drug Delivery Reviews, 2004; vol. 56:1067-84.
Sabharanjak et al., "Folate receptor endocytosis and trafficking," Advanced Drug Delivery Reviews, 2004; vol. 56: 1099-1109.
Paulos et al., "Folate receptor-mediated targeting of therapeutic and imaging agents to activated macrophages in rheumatoid arthritis," Advanced Drug Delivery Reviews, 2004; vol. 56: 1205-17.
Antony, "Folate receptors: reflections on a personal odysssey and a perspective on unfolding truth," Advanced Drug Delivery Reviews, 2004; vol. 56: 1059-66.
Lu et al., "Folate receptor-targeted immunotherapy of cancer: mechanism and therapeutic potential," Advanced Drug Delivery Reviews, 2004; vol. 56: 1161-76.
Roy et al., "Folate-mediated targeting of T cells to tumors," Advanced Drug Delivery Reviews, 2004; vol. 56: 1219-31.
Ke et al., "Folate-receptor-targeted radionuclide imaging agents," Advanced Drug Delivery Reviews, 2004; vol. 56: 1143-60.
Gabizon et al., "Tumor cell targeting of liposome-entrapped drugs with phospholipid-anchored folic acid-PEG Conjugates," Advanced Drug Delivery Reviews, 2004; vol. 56: 1177-92.
Zhao et al., "Tumor-selective targeted delivery of genes and antisense oligodeoxyribonucleotides via the folate receptor," Advanced Drug Delivery Reviews, 2004; vol. 56: 1193-1204.
Paulos CM et al., "Ligand Binding and Kinetics of Folate Receptor Recycling in Vivo: Impact on Receptor-Mediated Drug Delivery," Molecular Pharmacology, 2004; 66:1406-1414.
Griesser UJ, "The Importance of Solvents," in Polymorphism in the Pharmaceutical Industry, Hilfiker ed., 2006; p. 211-230.
Wikipedia, Structural analog, http://en.wikipedia.org/wiki/Structural_analog, downloaded Apr. 7, 2009.
Wikipedia, Functional analog, http://en.wikipedia.org/wiki/Functional_analog, downloaded Apr. 7, 2009.
Wikipedia, Folic acid, http://en.wikipedia.org/wiki/Folic_acid, downloaded Apr. 7, 2009.
Lee JW et al., "Reduction of azides to primary amines in substrates bearing labile ester functionality. Synthesis of a PEG-solubilized, "Y"-shaped iminodiacetic acid reagent for preparation of folate-tethered drugs," Organic Letters, 1999; 1(2):179-181.
Atkinson SF et al., "Conjugation of folate via gelonin carbohydrate residues retains ribosomal-inactivating properties of the toxin and permits targeting to folate receptor positive cells," Journal of Biological Chemistry, 2001; 276(30):27930-27935.
Matulic-Adamic J et al., "An efficient synthesis of the ribozyme-folate conjugate," Tetrahedron Letters, 2002; 43(25):4439-4441.
Harrison JG et al., A convenient synthetic route to oligonucleotide conjugates,: Bioorganic & Medicinal Chemistry Letters, 1997; 7(8): 1041-1046.
Dyson G., May P. "The Chemistry of Synthetic Pharmaceutical Substances", translation from English M.:—"The World", 1964, pp. 12-19.
Mashkovskiy M.D. Drugs, Moscow, New wave, 2001, vol. I, p. 11.
Robert Laplanche, et al.,"Physiologically Based Pharmacokinetic (PBPK) Modeling of Everolimus (RAD001) in Rats Involving Non-Linear Tissue Uptake," Journal of Pharmacokinetics and Pharmacodynamics, 2007, vol. 34, No. 3, 373-400.
Pathalk et al., Enzymic protecting group techniques in organic synthesis, Stereosel. Biocatal. 775-797 (2000).
Dube D et al., "Preparation and Tumor Cell Uptake of Poly(N-isopropylacrylamide) Folate Conjugates"; Bioconjugate Chem, 2002; 13: 685-692.
Evans et al., "Synthessis of biotin conjugates of the antifungal compound cymoxanil," Pest Manag Sci, 2002; 58: 392-396.
Rao et al., Journal of Medicinal Chemistry, 1985, 28:1079-1088.
Conrad et al, Journal of Medicinal Chemistry, 1979, 22(4): 391-400.
Theti, D. S. et al., "Selective delivery of CB300638, a cyclopenta[g]quinazoline-based thymidylate synthase inhibitor into human tumor cell lines overexpressing the alpha-isoform of the folate receptor," Cancer Res, 2003; 63(13): 3612-3618.
Golub, T.R., et al., "Molecular Classification of Cancer: Class Discovery and Class Prediction by Gene Expression Monitoring," Science, 1999, vol. 286, 531-537 (Oct. 15, 1999).
Speckamp, et al.; "New Developments in the Chemistry of N-Acyliminium Ions and Related Intermediates" Tetrahedron 2000 vol. 56(24) 3817-3856.
Angier et al., Science, 1946, 103: 667-669.
Wolf et al., Journal of the American Chemical Society, 1947, 69: 2753-2759.
Parker et al., "Folate receptor expression in carcinomas and normal tissues determined by a quantitative radioligand binding assay," Analytical Biochemistry, 2005; 335:284-293.
Remy et al., Proceedings of the National Academy of Sciences of the United States of America, 1999, vol. 96, No. 10, pp. 5394-5399.
Na, Wang, and Kohn, "7-N-(Mercaptoalkylmitomycins: Implications of Cyclization for Drug Function," J Am Chem Soc 124:4666-77 (2002).
Putnam et al., "Polymer conjugates with anticancer activity", Advances in Polymer Science 1995, 122, 55-123.
Umemoto et al., "Molecular design of methotrexate-antibody conjugates for targeted cancer treatment", Journal of Bioactive and Compatible Polymers, 1992, 7(2), 191-219.
Sanderson et al., "In vivo drug-linker stability of an anti-CD30 dipeptide-linked auristatin immunoconjugate," Clinical Cancer Research, 2005; 11:843-852.
Wu et al., "Enhancing the enantioselectivity of candida lipase catalyzed ester hydrolysis via noncovalent enzyme modification," Journal of American Chemical Society, 1990; 112:1990-1995.
Patterson et al., "Expedient synthesis of N-Methyl tubulysin analogues with high cytotoxicity," Journal of Organic Chemistry, 2008; 73:4365-4369.
Gabizon et al., Clin Cancer Res, 9:6551-59 (2003).
Pouvreau, Isabelle et al.: "Effect of macrophage depletion by liposomes containing dichloromethylene-diphosphonate on endotoxin induce uveitis." J. Neuroimmun. (1998) 86 p. 171-181.
Lindstedt, E.W. et al.; "Anti-tnf-alpha therapy for sight threatening uveitis." Br. J. Opthalmol. (2005) 89 p. 533-536.
Mangel, Andreas: GMP news, 2002, www.gmp-compliance.ord/eca_news_159.html, downloaded Mar. 19, 2014.

(56) References Cited

OTHER PUBLICATIONS

Definition of derivative and analog, from http://cancerweb.ncl.ac.uk/cgi-omd?query=derivative and http://cancerweb.ncl.ac.uk/cgi-bin/omd?query=analog, pp. 1-5, accessed Jul. 7, 2005.
Kaneko, Takushi, "New Hydrazone Derivatives of Adiramycin and their Immunoconjugates—A Correlation between Acid Stability and Cytotoxicity", Bioconj. Chem., vol. 2, No. 3, pp. 131-141 (May 1, 1991).
PCT International Search Report/Written Opinion prepared for PCT/US2010/061897, dated Mar. 11, 2011.
Polyak et al., "Introduction of spacer peptides N-terminal to a cleavage recognition motif in recombinant fusion proteins can improve site-specific cleavage," Protein Eng., 1997; 10(6):615-9.
University of Maryland Medical Center (UMMC), Vitamin B9 (folic acid), 2014, http://umm.edu/health/medical/altmed/supplement/vitamin-b9-folic-acid, pp. 1-10.
Cerner Multum, Inc., Drugs.com, Folic Acid, http://www.drugs.com/folic_acid.html?printable=1, 1996-2014, Version: 5.01, Revision Date Oct. 15, 2009, pp. 1-4.
PCT International Search Report/Written Opinion for PCT/US2009/061049, completed Mar. 15, 2010.
Water, from http://www.biology-ionline.org/dictionary/Water, pp. 103, accessed Apr. 24, 2014.
NIOSH List of antineoplastic and Other Hazardous Drugs in Healthcare settings 2010, pp. 1-16, published Sep. 20, 2010.
Chae et al, Recombinant Expression, Isotope labeling and purification of the Vitamin D Receptor Binding Peptide, Bull. Korean Chem Soc. 2011, 32, pp. 4337-4340.
Rudinger, peptide Hormones, JA Parsons, Ed., 1976, pp. 1-7.
Sigma, 2004, pp. 1-2.
Berendsen, A Glimpse of the Holy Grail?, Science, 1998, 282, pp. 642-643.
Voet et al, Biochemistry, John Wiley & Sons Inc., 1995, pp. 235-241.
Ngo et al, Computational Complexity, Protein Structure protection, and the Levinthal Paradox, 1994, pp. 491-497.
Bradley et al, Limits of Cooperativity in a Structurally Modular Protein: Response of the Notch Ankyrin Domain to Analogous Alanine Substitutions in Each Repeat, J. Mol. Biol, 2002, 324, pp. 373-386.
Definition of moiety, from http://dictionary.reference.com/browse/moiety, pp. 1-3, accessed Aug. 26, 2010.
Muller, Prodrug approaches for Enhancing the Bioavailability of Drugs with Low Solubility, Chemistry & Biodiversity, 2009, 6, pp. 2071-2083.
Beaumont et al, Design of ester prodrugs to enhance oral absorption of poorly permeable compounds: Challenges to the Discovery Scientist, Current Drug Metbolism, 2003, 4, 461-485.
Hyo-Kyung Han, Targeted prodrug design to optimize drug delivery, AAPS Pharmsci 2000, 2(10), article 6, p. 1-11.
Yashveer Singh et al, Recent trends in targeted anticancer prodrug and conjugate design, Curr Med Chem, 2008, 15(18): 1802-1826.
Testa B, Prodrug Research: Futile or Fertile?, Biochem Pharm, 2004, 68, pp. 2097-2106.
Ettmayer et al, Lessons learned from marketed and investigational prodrugs, J. Med Chem, 2004, 47(10), pp. 2393-2404.

Machine Translation of WO 2004/005326, Jan. 15, 2004, pp. 1-5.
European Search Report prepared for corresponding European Application Serial No. 08841521.1, dated Jul. 18, 2011.
Paranjpe, et al., "Tumor-targeted bioconjugate based delivery of camptothecin: design, synthesis and in vitro evaluation," ScienceDirect Journal of Controlled Release 100 (2004) 275-292.
Yang, et al., "Characterization of the pH of Folate Receptor-Containing Endosomes and the Rate of Hydrolysis of Internalized Acid-Labile Folate-Drug Conjugates," JPET 321: 462-468, 2007.
Henne, et al., "Synthesis and activity of a folate peptide camptothecin prodrug," ScienceDirect, Bioorganic & Medical Chemistry Letters 16 (2006) 5350-5355.
PCT International Search Report/Written Opinion for PCT/US2008/056824, completed Jul. 24, 2009.
Vlahov I. et al., "An assembly concept for the consecutive introduction of unsymmetrical disulfide bonds: synthesis of a releasable multidrug conjugate of folic acid," 2007, J. Org Chem, 72, 5968-5972.
Wang, L. et al., "Synthesis, biological, and antitumor activity of a highly potent 6-substituted pyrrolo[2,3-d]pyrimidine thienoyl antifolate inhibitor with proton-coupled folate transporter and folate receptor selectivity over the reduced folate carrier that inhibits β-glycinamide ribonucleotide formyltransferase," 2011, J. Med. Chem., 54, 7150-7164.
Vlahov I. et al., "Design and regioselective synthesis of a new generation of targeted therapeutics. Part 3: Folate conjugates of aminopterin hydrazide for the treatment of inflammation," 2011, Bioorg. Med. Chem. Lett., 21, 1202-1205.
Vlahov, I. et al., "Design and regioselective synthesis of a new generation of targeted chemotherapeutics. Part II: Folic acid conjugates of tubulysins and their hydrazides," Bioorg. Med. Chem. Lett., 2008, 18(16), 4558-4561.
Endocyte: Endocyte Enrolls First Patient in Phase 1 Study for the Small Molecule Drug Conjugate EC1456, a Folate-Targeted Tubulysin Conjugate in Advanced Solid Tumors. Dec. 2013. [Retrieved on May 6, 2015).
Leamon, et al., "Patient selection and targeted treatment in the management of platinum-resistant ovarian cancer," Pharmacogenomics and Personalized Medicine, 6:113-125 (2013).
Zaragoza, D., Side Reactions in Organic Synthesis, 2005, Wiley-VCH Verlag GmbH & Co. KGaA, Weinheim, Preface, p. 9.
Attur, M. et al., "Differential anti-inflammatory effects of immunosuppressive drugs: Cyclosporin, rapamycin and FK-506 on inducible nitric oxide synthase, nitric oxide, cyclooxygenase-2 and $PGE_2$ production," Inflamm. res. 2000, 49, 020-026.
Christoper Leamon et al., "Folate Receptor specific anti-tumor activity of EC0305, a folate-tubulysin conjugate," AACR Annual Meeting, 2007, 67, 9, (abstract only).
Beil,L. "Is your breakfast giving you cancer," Prevention, updated Mar. 29, 2010, available via internet at http://www.nbcnews.com/id/35874922/ns/health-diet_and_nutrition/t/your-breakfast-giving-you-cancer/#.V40IrflVj2l.
Adessi, C. et al., "Converting a Peptide into a Drug: Strategies to Improve Stability and Bioavailability," Current Medicinal Chemistry, 2002, 9, 963-978.
Weinstein, "Commentary: Three Decades of Folic Acid Antagonists in Dermatology," Arch Dermatol, Jun. 1983, vol. 119, 525-527.

* cited by examiner

Fig. 3

|  | TNF-α | IL-1α | IL-6 | IL-10 | MIP-1α |
|---|---|---|---|---|---|
| Unstimulated |  |  |  |  |  |
| LPS/IFN-γ |  |  |  |  |  |
| xs Folic Acid |  |  |  |  |  |
| EC0746 |  |  |  |  |  |
| EC0746/FA |  |  |  |  |  |
| Methotrexate |  |  |  |  |  |
| Aminopterin |  |  |  |  |  |

|  | EC0746 | Total free drug released | % Total free drug released |
|---|---|---|---|
| Cmax (nmol/L) | 321 | 34 | 9.6% |
| Tmax | 30 min | 1 h | - |
| $AUC_{0-t}$ (nmol*min/ml) | 32.5 | 7.3 | 18% |

**XTT Assay: 2 hr/ 72 hr "*chase*"**

**TNF-α Assay: 2 hr/ 72 hr "*chase*"**

*C = Competition only at 1000x

Untreated

XTT cell viability

TNF-α production

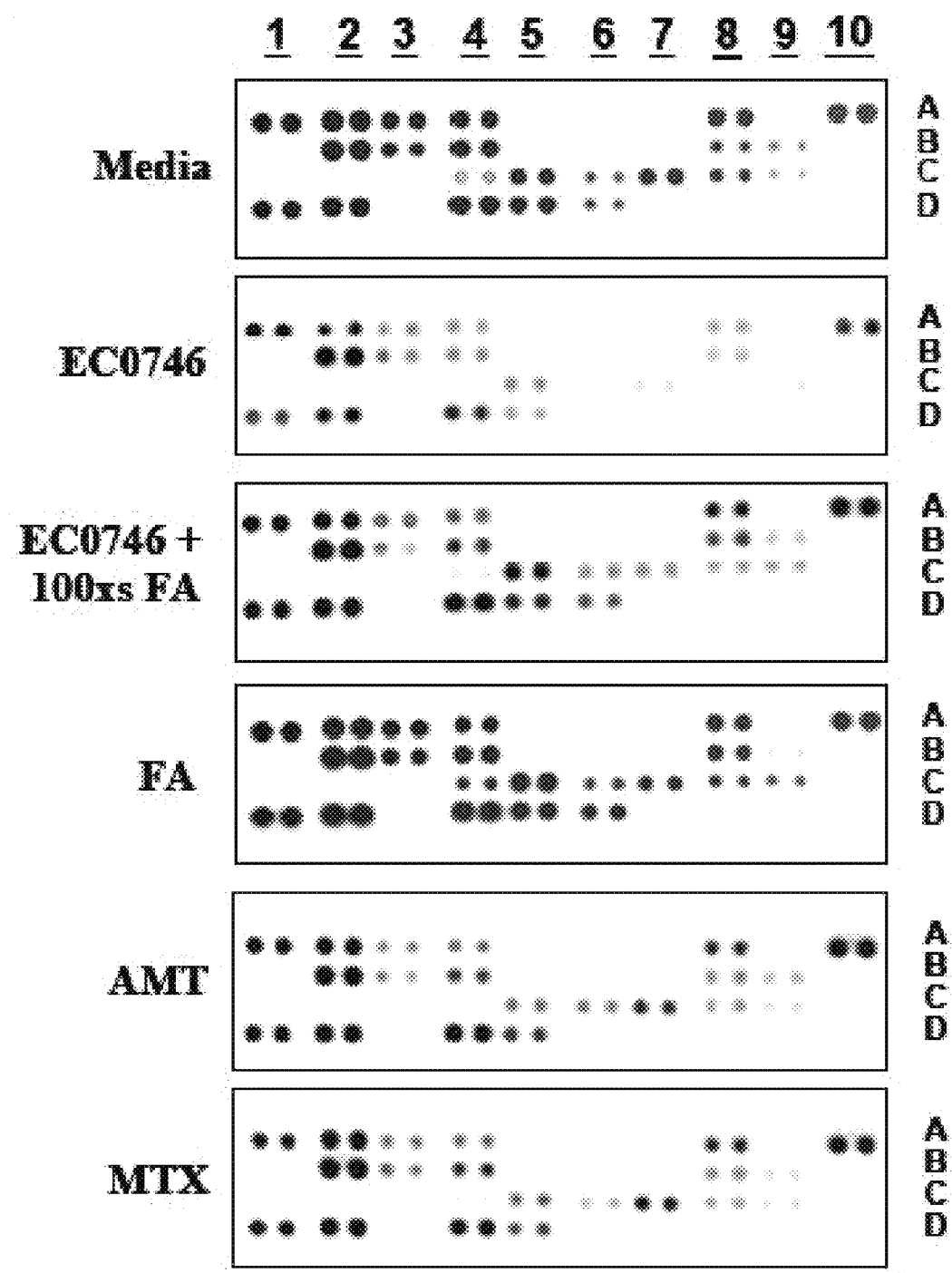

Fig. 27B

|    | A         | B      | C         | D                  |
|----|-----------|--------|-----------|--------------------|
| 1  | PC        | blank  | blank     | PC                 |
| 2  | CINC-1    | IL-1a  | IL-13     | RANTES             |
| 3  | CINC-2aß  | IL-1ß  | IL-17     | Thymus Chemokine   |
| 4  | CINC-3    | IL-1ra | IP-10     | TIMP-1             |
| 5  | CNTF      | IL-2   | LIX       | TNF-a              |
| 6  | Fractalkine | IL-3 | L-selectin| VEGF               |
| 7  | GM-CSF    | IL-4   | MIG       | Blank              |
| 8  | sICAM-1   | IL-6   | MIP-1a    | Blank              |
| 9  | IFN-γ     | IL-10  | MIP-3a    | Blank              |
| 10 | PC        | blank  | blank     | NC                 |

Fig. 33C

Pharmacokinetic analysis

| Test Compound | | EC0746 | | | AMT |
|---|---|---|---|---|---|
| Average Dose per Rat (nmoles) | | 100 | | | 100 |
| Compounds Detected in Plasma | | EC0746 | AMT hydrazide | AMT | AMT |
| Parameters | Units | Mean (n = 3) | | | |
| $AUC_{0-t}$ | nmol·min/mL | 32.5 | 2.9 | 4.4 | 61.3 |
| CL or CL_F | mL/min | 3.3 | - | - | 1.7 |
| $T_{1/2}$ (elimination) | min | 35 | 187 | 117 | 140 |
| $T_{max}$ | min | 30 | 60 | 60 | 30 |
| $C_{max}$ | nmol/L | 321 | 11 | 23 | 601 |
| $V_z$ or $V_z\_F$ | mL | 155 | - | - | 328 |

RAW264.7 cells

TG-elicited macrophages

Arthritic macrophages

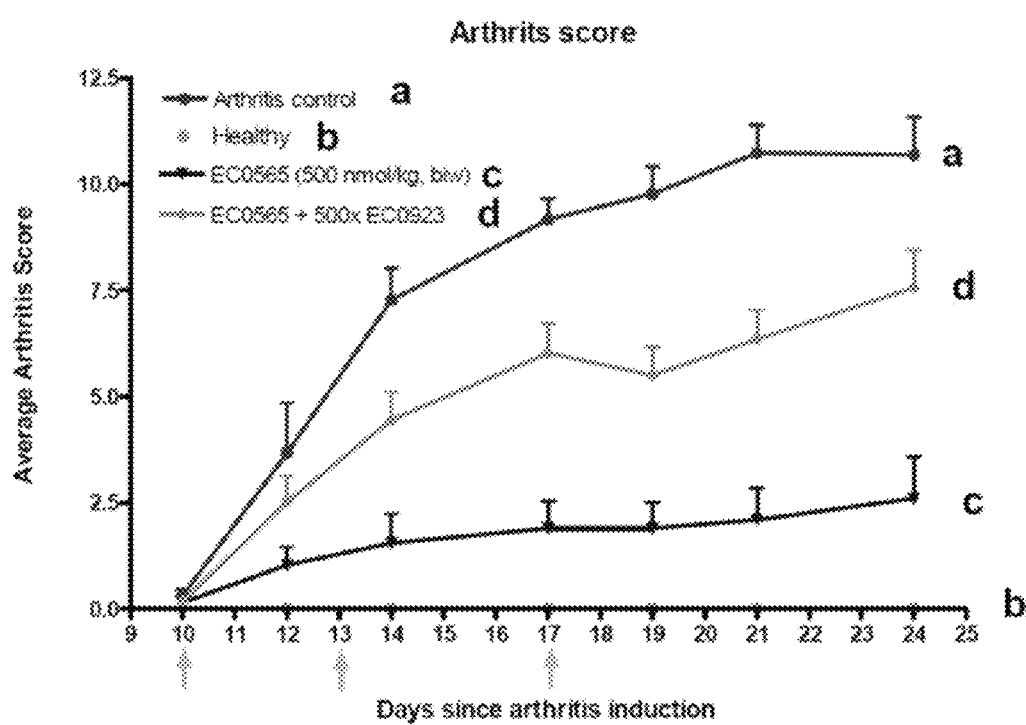

KB Cells

Percent weight change

Paw weight

VITAMIN RECEPTOR DRUG DELIVERY CONJUGATES FOR TREATING INFLAMMATION

CROSS REFERENCE TO RELATED APPLICATIONS

This application is a continuation-in part of U.S. application Ser. No. 13/518,291, filed Jun. 21, 2012, which is a U.S. national application under 35 U.S.C. §371(b) of International Application Serial No. PCT/US2010/061897 filed Dec. 22, 2010, and claims priority under 35 USC §119(e) to U.S. Provisional Application Ser. No. 61/289,952, filed on Dec. 23, 2009, U.S. Provisional Application Ser. No. 61/291,103 filed on Dec. 30, 2009, U.S. Provisional Application Ser. No. 61/351,032, filed on Jun. 3, 2010, U.S. Provisional Application Ser. No. 61/374,830, filed on Aug. 18, 2010, U.S. Provisional Application Ser. No. 61/386,785, filed on Sep. 27, 2010, and U.S. Provisional Application Ser. No. 61/391,230, filed on Oct. 8, 2010, the entire disclosures of each of which are incorporated herein by reference. This application is also a continuation-in-part of U.S. application Ser. No. 12/666,712 filed on Dec. 24, 2009, which is a U.S. national application filed under 37 C.F.R. §371(b) of International Application Serial No. PCT/US2008/068093 filed Jun. 25, 2008, which claims the benefit of priority under 35 U.S.C. §119(e) of U.S. provisional patent application Ser. Nos. 60/946,092 and 61/036,186, filed Jun. 25, 2007 and Mar. 13, 2008, respectively.

TECHNICAL FIELD

The present invention relates to compositions and methods for use in targeted drug delivery. More particularly, the invention is directed to cell-surface receptor binding drug delivery conjugates containing hydrophilic spacer linkers for use in treating disease states caused by pathogenic cell populations and to methods and pharmaceutical compositions that use and include such conjugates.

BACKGROUND

The mammalian immune system provides a means for the recognition and elimination of foreign pathogens. While the immune system normally provides a line of defense against foreign pathogens, there are many instances where the immune response itself is involved in the progression of disease. Exemplary of diseases caused or worsened by the host's own immune response are autoimmune diseases and other diseases in which the immune response contributes to pathogenesis. For example, macrophages are generally the first cells to encounter foreign pathogens, and accordingly, they play an important role in the immune response, but activated macrophages can also contribute to the pathophysiology of disease in some instances.

The folate receptor is a 38 KD GPI-anchored protein that binds the vitamin folic acid with high affinity (<1 nM). Following receptor binding, rapid endocytosis delivers the vitamin into the cell, where it is unloaded in an endosomal compartment at low pH. Importantly, covalent conjugation of small molecules, proteins, and even liposomes to folic acid does not block the vitamin's ability to bind the folate receptor, and therefore, folate-drug conjugates can readily be delivered to and can enter cells by receptor-mediated endocytosis.

Because most cells use an unrelated reduced folate carrier to acquire the necessary folic acid, expression of the folate receptor is restricted to a few cell types. With the exception of kidney, choroid plexus, and placenta, normal tissues express low or nondetectable levels of the folate receptor. It has been reported that the folate receptor β, the nonepithelial isoform of the folate receptor, is expressed on activated (but not resting) synovial macrophages. Thus, folate receptors are expressed on a subset of macrophages (i.e., activated macrophages). Folate receptors of the β isoform are also found on activated monocytes.

Accordingly, the present invention relates to the development of vitamin-targeted therapeutics, such as folate-targeted therapeutics, to treat inflammation. The folate conjugates described herein can be used to treat inflammatory diseases by targeting inflammatory cells that overexpress the folate receptor.

SUMMARY OF THE INVENTION

It has been discovered that therapeutic agents, diagnostic agents, and imaging agents may be conjugated to other compounds to control or alter their behavior, biodistribution, metabolism, and/or clearance in vivo. In one illustrative embodiment of the invention, conjugates of compounds are described that include a hydrophilic spacer linker. In one aspect, conjugates of compounds are described that include both a hydrophilic spacer linker and a targeting ligand. Illustrative of such conjugates are compounds of the following formula described herein

B-L-A wherein B is a receptor binding ligand that binds to a target cell receptor, L is a linker that comprises one or more hydrophilic spacer linkers, and A is a therapeutic agent (e.g. a drug) that is desirably delivered to the cell.

In one variation, the linker L does not include a releasable linker. In another variation, the linker L includes a releasable linker. In another embodiment, at least one of the hydrophilic spacer linkers is formed from or includes at least one carbohydrate. In one variation, the carbohydrate forms part of the linker chain connecting B and A. In another variation, the carbohydrate forms part of a side chain attached to the linker chain connecting B and A. In one variation, the linker is a polyvalent linker. In another variation, the linker is a bivalent linker.

It is appreciated that in each of the above embodiments, more than one receptor binding ligand B may be attached to the linkers described herein. It is further appreciated that more than one therapeutic agent A may be attached to the linkers described herein. Such multi-ligand and/or multi-drug conjugates are also described herein, where the linker (L) comprises a hydrophilic spacer linker.

In another embodiment, compounds are described herein that have reduced uptake by the liver and are less likely to be cleared by the liver. In one aspect, such compounds are preferentially cleared by the renal processes as compared to hepatic processes.

The therapeutic agent or therapeutic agents A include therapeutic drugs and any other compound that is desirably or advantageously delivered to a cell by targeting a cell receptor. Illustrative drugs include cytotoxic drugs, anti-inflammatory agents, and the like.

In the embodiments of compounds, compositions, and methods described herein, the cells that may be targeted with the therapeutic agents A include cells that cause inflammation, such as activated monocytes, activated macrophages, and other inflammatory cells. The targeting of the cell is accomplished by the appropriate selection of a receptor binding ligand B. It is appreciated that selective or specific targeting of a cell in vivo may be accomplished by selecting a receptor that is preferentially expressed or overexpressed by the target cell. Illustratively, the target cell preferentially expresses or overexpresses a vitamin receptor, such as a folate receptor.

In another embodiment, the conjugates described herein are included in pharmaceutical compositions in amounts effective to treat disease states associated with pathogenic populations of cells, such as cells associated with inflammation.

In another embodiment, the conjugates described herein, and pharmaceutical compositions containing them are used in methods for treating diseases and disease states associated with pathogenic populations of cells, such as cells associated with inflammation.

In another embodiment, a method for treating a patient with an inflammatory disease, the method comprising the step of administering to the patient a composition comprising a drug delivery conjugate of the formula $$BL(A^1)(A^2)_m$$

or a pharmaceutically acceptable salt, isomer, mixture of isomers, crystalline form, non crystalline form, hydrate, or solvate thereof; wherein
 m is 0 or 1;
 B is a folate;
 L is a linker that comprises one or more hydrophilic spacer linkers;
 $A^1$ is an antifolate; and
 $A^2$ has the formula

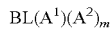

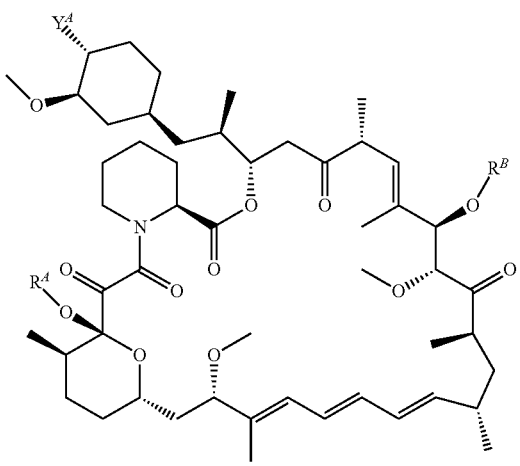

wherein
 $Y^A$ is $OR^C$ or $OCH_2CH_2OR^C$;
 one of $R^A$, $R^B$, or $R^C$ is a bond connected to L; and
 the other two of $R^A$, $R^B$, and $R^C$ are independently selected in each case from the group consisting of hydrogen, optionally substituted heteroalkyl, prodrug foming group, and $C(O)R^D$, where $R^D$ is in each instance independently selected from the group consisting of hydrogen, and alkyl, alkenyl, heteroalkyl, cycloalkyl, cycloheteroalkyl, aryl, arylalkyl, heteroaryl, and heteroarylalkyl, each of which is optionally substituted is described.

In another embodiment, a pharmaceutical composition comprising a drug delivery conjugate of the formula $$BL(A^1)(A^2)_m$$

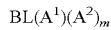

or a pharmaceutically acceptable salt, isomer, mixture of isomers, crystalline form, non crystalline form, hydrate, or solvate thereof; wherein
 m, B, L, $A^1$, $A^2$, $Y^A$, $R^A$, $R^B$, $R^C$, and $R^D$ are as described herein.

In any of the preceding embodiments, the antifolate can be aminopterin, or an analog, derivative, or conjugate thereof.

In another embodiment, a method for treating a patient with an inflammatory disease, the method comprising the step of administering to the patient a composition comprising a drug delivery conjugate of the formula $$B\text{-}L\text{-}A^3$$

or a pharmaceutically acceptable salt, isomer, mixture of isomers, crystalline form, non crystalline form, hydrate, or solvate thereof; wherein
 B is a folate;
 L is a linker that comprises one or more hydrophilic spacer linkers; and
 $A^3$ has the formula

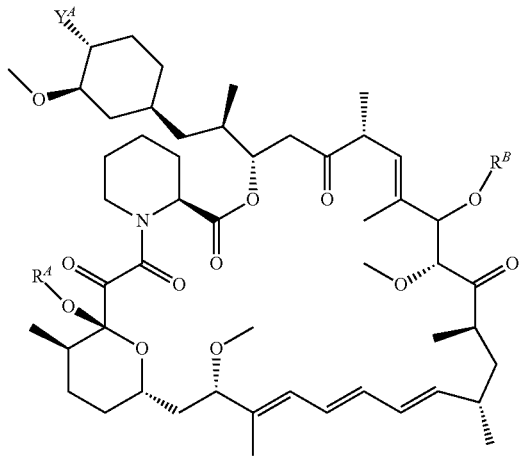

wherein
 $Y^A$ is $OR^C$ or $OCH_2CH_2OR^C$;
 one of $R^A$, $R^B$, or $R^C$ is a bond connected to L; and
 the other two of $R^A$, $R^B$, and $R^C$ are independently selected in each case from the group consisting of hydrogen, optionally substituted heteroalkyl, prodrug foming group, and $C(O)R^D$, where $R^D$ is in each instance independently selected from the group consisting of hydrogen, and alkyl, alkenyl, heteroalkyl, cycloalkyl, cycloheteroalkyl, aryl, arylalkyl, heteroaryl, and heteroarylalkyl, each of which is optionally substituted is described.

In another embodiment, a pharmaceutical composition comprising a drug delivery conjugate of the formula $$B\text{-}L\text{-}A^3$$

or a pharmaceutically acceptable salt, isomer, mixture of isomers, crystalline form, non crystalline form, hydrate, or solvate thereof; wherein
 m, B, L, $A^3$, $Y^A$, $R^A$, $R^B$, $R^C$, and $R^D$ are as described herein.

In another embodiment, a kit comprising a sterile vial, the composition of any one of the preceding embodiments, and instructions for use describing use of the composition for treating a patient with an inflammatory disease is described.

In another embodiment, is described a kit comprising a sterile vial, a composition comprising the compound as a lyophilized solid of any one of the preceding embodiments, and instructions describing use of the composition for treating a patient with an inflammatory disease, wherein the vial is an amber glass vial with a rubber stopper and an aluminum tear-off seal.

BRIEF DESCRIPTION OF THE DRAWINGS

FIG. 3 Inhibition of LPS-stimulated cytokine production (LPS (5 ug/mL), IFN-γ (100 ng/mL) for 24 hours) in thioglycolate-elicited macrophages. Compounds at 100 nM with 100xs FA (2 hour treatment followed by 72 hours in fresh medium, unstimulated cell; stimulated cells without treatment (LPS/IFN-γ), treatment with excess folic acid, treatment with EC0746 (EC0746), treatment with EC0746 and excess folic acid (EC0746/FA), treatment with methotrexate, and treatment with aminopterin. Relative folate receptor binding affinities (folic acid defined as 1.00) EC0746, 0.50; aminopterin, 0.004; and methotrexate, 0.018.

FIG. 6B—X-rays of the hind paws of a healthy control animal, an untreated animal with adjuvant induced arthritis, and an animal treated with EC0746 (500 nmol/kg).

FIG. 26H—Viability of RAW264.7 cells, measured using the XTT assay, LPS (100 ng/mL) added at 4 h before end of incubation to stimulate cytokine production, 2 hour treatment followed by 70 h "chase" in drug-free medium). Comparison of EC0746, EC0746 with excess folic acid (EC0746/FA), aminopterin (AMT), and methotrexate (MTX).

FIG. 28. Amelioration of Systemic Inflammation in Rats with Adjuvant Induced Arthritis (AIA).

FIG. 29. Anti-arthritic activity in Rats with Adjuvant Induced Arthritis (AIA).

FIG. 31. Anti-arthritic activity in Rats with Adjuvant Induced Arthritis (AIA).

FIG. 32. Effects of potential EC0746 Metabolites on RAW264.7 cells. The effects of the potential EC0746 metabolites aminopterin (AMT) and AMT hydrazide (EC0470) in 72 h incubations of RAW264.7 macrophages are shown for.

FIG. 33. Pharmacokinetics of EC0746 and potential metabolites aminopterin (AMT) and AMT hydrazide (EC0470) in Rats. FIG. 33C—Pharmacokinetic analysis of the results of FIGS. 33A,B.

FIG. 36A—A photograph of an eye from an untreated animal with experimental autoimmune uveitis (EAU). FIG. 36B—A photograph of an eye from an animal with EAU treated with EC0746 every other day starting on day 7 after EAU induction. FIG. 36C—A photograph of an eye from a healthy rat.

FIG. 44A compares the arthritis score of animals treated with biweekly injections of 500 nmol/kg of EC0565 (d) and biweekly injections of 500 nmol/kg of unconjugated everolimus (c) with healthy controls (b) and untreated animals (a).

FIG. 51B shows the average weight change for animals in treat as in FIG. 51A. a) untreated CIA animals; b) EC0565, 1000 nmol/kg/dose, tiw; and c) everolimus, 1000 nmol/kg/dose, tiw.

DETAILED DESCRIPTION

Figure 1:
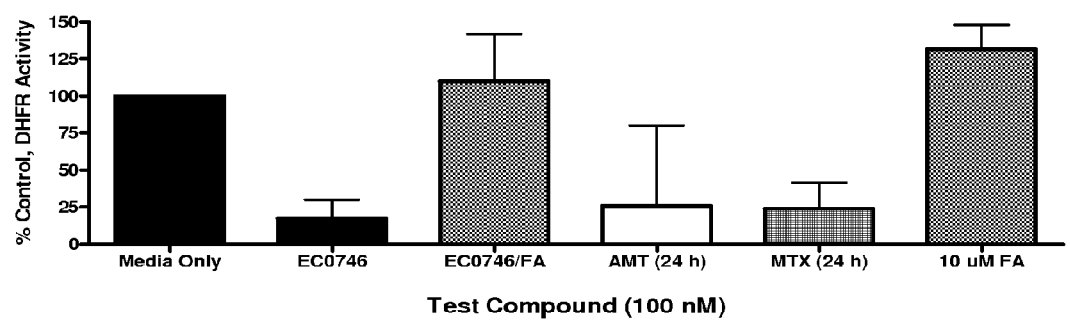
FIG. 1. Measurement of DHFR activity in the lysate of RAW264.7 cells after no treatment, treatment with EC0746 (1 hour treatment followed by 24 hours in treatment-free medium), treatment with EC0746 plus excess folic acid (EC0746/FA, 1 hour treatment followed by 24 hours in treatment-free medium), treatment with aminopterin (AMT, 24 hour treatment), treatment with methotrexate (MXT, 24 hour treatment), and treatment with folic acid (FA, 10 µM).

Drug delivery conjugates are described herein consisting of a receptor binding ligand (B), a linker (L) comprising one or more hydrophilic spacer linkers, and a therapeutic agent (A), e.g. a drug, that is desirably delivered to a cell. The receptor binding ligand (B) is covalently attached to the linker (L), and the therapeutic agent (A), or an analog or derivative thereof, is also covalently attached to the linker (L). It is to be understood that the therapeutic agent (A) includes analogs and derivatives thereof that are attached to the linker (L). The linker (L) comprises one or more spacer linkers and/or releasable linkers, and combinations thereof, in any order. In one variation, releasable linkers, and optional spacer linkers are covalently bonded to each other to form the linker. In another variation, a releasable linker is directly attached to the therapeutic agent (A), or analog or derivative thereof. In another variation, a releasable linker is directly attached to the receptor binding ligand (B). In another variation, either or both the receptor binding ligand (B) and the therapeutic agent (A), or analog or derivative thereof, is attached to a releasable linker through one or more spacer linkers. In another variation, each of the receptor binding ligand (B) and the therapeutic agent (A), or analog or derivative thereof, is attached to a releasable linker, each of which may be directly attached to each other, or covalently attached through one or more spacer linkers.

From the foregoing, it should be appreciated that the arrangement of the receptor binding ligand (B), and the therapeutic agent (A), or analog or derivative thereof, and the various releasable and optional spacer linkers may be varied widely. In one aspect, the receptor binding ligand (B), and the therapeutic agent (A), or analog or derivative thereof, and the various releasable and optional spacer linkers are attached to each other through heteroatoms, such as nitrogen, oxygen, sulfur, phosphorus, silicon, and the like. In variations, the heteroatoms, excluding oxygen, may be in various states of oxidation, such as N(OH), S(O), S(O)$_2$, P(O), P(O)$_2$, P(O)$_3$, and the like. In other variation, the heteroatoms may be grouped to form divalent radicals, such as for example hydroxylamines, hydrazines, hydrazones, sulfonates, phosphinates, phosphonates, and the like, including radicals of the formulae —(NHR$^1$NHR$^2$)—, —SO—, —(SO$_2$)—, and —N(R$^3$)O—, wherein R$^1$, R$^2$, and R$^3$ are each independently selected from hydrogen, alkyl, aryl, arylalkyl, substituted aryl, substituted arylalkyl, heteroaryl, substituted heteroaryl, and alkoxyalkyl. In one variation, the linker (L) is a polyvalent linker. In another variation, more than one receptor binding ligand (B) is attached to the polyvalent linker. In another variation, more than one therapeutic agent (A) is attached to the polyvalent linker. In another variation, more than one receptor binding ligand (B) and more than one therapeutic agent (A) is attached to the polyvalent linker.

In one embodiment, the receptor binding ligand (B) is a vitamin receptor binding ligand such as a vitamin, or an analog or a derivative thereof, capable of binding to vitamin receptors. In another embodiment, the receptor binding ligand (B) is a vitamin, or analog or derivative thereof, attached to a releasable linker which is attached to the drug through a linker (L) that is formed from one or more spacer linkers and/or releasable linkers and/or hydrophilic spacer linkers. In one variation, both the therapeutic agent (A) and the vitamin, or analog or derivative thereof, can each be attached to spacer linkers, where the spacer linkers are attached to each other through one or more releasable linkers. In addition, both the therapeutic agent (A) and the vitamin, or analog or derivative thereof, can each be attached to one or more releasable linkers, where the releasable linkers are attached to each other or through a spacer linker. Each of these radicals may be connected through existing or additional heteroatoms on the receptor binding ligand (B), therapeutic agent (A), or releasable, hydrophilic spacer, or additional spacer linker.

The binding site for the receptor binding ligand (B) can include receptors for any binding ligand (B), or a derivative or analog thereof, capable of specifically binding to a receptor wherein the receptor or other protein is uniquely expressed, overexpressed, or preferentially expressed by a population of pathogenic cells. A surface-presented protein uniquely expressed, overexpressed, or preferentially expressed by the pathogenic cells is typically a receptor that is either not present or present at lower concentrations on non-pathogenic cells providing a means for selective elimination of the pathogenic cells. The drug delivery conjugates may be capable of high affinity binding to receptors on activated macrophages, monocytes, or other inflammatory cells. The high affinity binding can be inherent to the binding ligand or the binding affinity can be enhanced by the use of a chemically modified ligand (e.g., an analog or a derivative of a vitamin).

The drug delivery conjugates described herein can be formed from, for example, a wide variety of vitamins or receptor-binding vitamin analogs/derivatives, linkers, and drugs. The drug delivery conjugates described herein are capable of selectively targeting a population of pathogenic cells in the host animal due to preferential expression of a receptor for the binding ligand, such as a vitamin, accessible for ligand binding, on the pathogenic cells. Illustrative vitamin moieties that can be used as the receptor binding ligand (B) include carnitine, inositol, lipoic acid, pyridoxal, ascorbic acid, niacin, pantothenic acid, folic acid, riboflavin, thiamine, biotin, vitamin B$_{12}$, other water soluble vitamins, the B vitamins, and the lipid soluble vitamins A, D, E and K. These vitamins, and their receptor-binding analogs and derivatives, constitute an illustrative receptor binding ligand (B) that can be coupled with the therapeutic agent (A) drug by a linker (L) to form a drug delivery conjugate as described herein. The term vitamin is understood to include vitamin analogs and/or derivatives, unless otherwise indicated. Illustratively, pteroic acid, which is a derivative of folate, biotin analogs such as biocytin, biotin sulfoxide, oxybiotin and other biotin receptor-binding compounds, and the like, are considered to be vitamins, vitamin analogs, and vitamin derivatives. It should be appreciated that vitamin analogs or derivatives as described herein refer to vitamins that incorporate an heteroatom through which the vitamin analog or derivative is covalently bound to the linker (L).

Illustrative vitamin moieties include folic acid, biotin, riboflavin, thiamine, vitamin B$_{12}$, and receptor-binding analogs and derivatives of these vitamin molecules, and other related vitamin receptor binding molecules.

In another embodiment, the cell receptor is a folate receptor, and the receptor binding ligand (B) is a folate receptor binding ligand. In another embodiment, B is a folate, such as folic acid, or an analog or derivative of folic acid that binds to folic acid receptors. It is to be understood as used herein, that the term folate is used both individually and collectively to refer to folic acid itself, and/or to such analogs and derivatives of folic acid that are capable of binding to folate receptors.

Illustrative embodiments of folate analogs and/or derivatives include folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refer to the art-recognized analogs having a carbon atom substituted for one or two nitrogen atoms in the naturally occurring folic acid structure, or analog or derivative thereof. For example, the deaza analogs include the 1-deaza, 3-deaza, 5-deaza, 8-deaza, and 10-deaza analogs of folate. The dideaza analogs include, for example, 1,5-dideaza, 5,10-dideaza, 8,10-dideaza, and 5,8-dideaza analogs of folate. Other folates useful as complex forming ligands include the folate receptor-binding analogs aminopterin, amethopterin (methotrexate), $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroylglutamic acid (dichloromethotrexate). The foregoing folic acid analogs and/or derivatives are conventionally termed folates, reflecting their ability to bind with folate-receptors, and such ligands when conjugated with exogenous molecules are effective to enhance transmembrane transport, such as via folate-mediated endocytosis as described herein.

Additional analogs of folic acid that bind to folic acid receptors are described in U.S. Patent Application Publication Nos. 2005/0227985 and 2004/0242582, the disclosures of which are incorporated herein by reference. Illustratively, such folate analogs have the general formula:

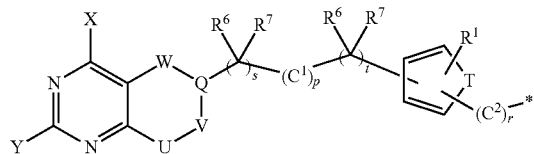

wherein X and Y are each-independently selected from the group consisting of halo, $R^2$, $OR^2$, $SR^3$, and $NR^4R^5$;

U, V, and W represent divalent moieties each independently selected from the group consisting of —$(R^{6a})C$=, —N=, —$(R^{6a})C(R^{7a})$—, and —$N(R^{4a})$—; Q is selected from the group consisting of C and CH; T is selected from the group consisting of S, O, N, and —C=C—;

$C^1$ and $C^2$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4a}$)S(O)$_2$—, —C($R^{6b}$)($R^{7b}$)—, —N(C=CH)—, —N(CH$_2$C=CH)—, $C_1$-$C_{12}$ alkylene, and $C_1$-$C_{12}$ alkyeneoxy, where Z is oxygen or sulfur;

$R^1$ is selected-from the group consisting of hydrogen, halo, $C_1$-$C_{12}$ alkyl, and $C_1$-$C_{12}$alkoxy; $R^2$; $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group; $R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group; and p, r, s, and t are each independently either 0 or 1.

As used herein, it is to be understood that the term folate refers both individually to folic acid used in forming a drug delivery conjugate, or alternatively to a folate analog or derivative thereof that is capable of binding to folate receptors.

In one aspect of such folate analogs, when s is 1, t is 0, and when s is 0, t is 1. In another aspect of such folate analogs, r is 1, and $C^2$ of the folate analog is covalently linked to a naturally occurring amino acid at its alpha-amino group through an amide bond. Illustrative amino acids include aspartic acid, glutamic acid, lysine, cysteine, and the like.

The vitamin can be a folate which includes a nitrogen, and in this embodiment, the spacer linkers can be alkylenecarbonyl, cycloalkylenecarbonyl, carbonylalkylcarbonyl, 1-alkylenesuccinimid-3-yl, 1-(carbonylalkyl)succinimid-3-yl, wherein each of the spacer linkers is optionally substituted with a substituent $X^1$, and the spacer linker is bonded to the folate nitrogen to form an imide or an alkylamide.

In the various embodiments described herein, the substituents $X^1$ can be alkyl, hydroxyalkyl, amino, aminoalkyl, alkylaminoalkyl, dialkylaminoalkyl, sulfhydrylalkyl, alkylthioalkyl, aryl, substituted aryl, arylalkyl, substituted arylalkyl, carboxy, carboxyalkyl, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides.

Illustrative embodiments of vitamin analogs and/or derivatives also include analogs and derivatives of biotin such as biocytin, biotin sulfoxide, oxybiotin and other biotin receptor-binding compounds, and the like. It is appreciated that analogs and derivatives of the other vitamins described herein are also contemplated herein. In one embodiment, vitamins that can be used as the receptor binding ligand (B) in the drug delivery conjugates described herein include those that bind to vitamin receptors expressed specifically on activated macrophages or activated monocytes, such as the folate receptor, which binds folate, or an analog or derivative thereof as described herein.

The linker L includes one or more hydrophilic spacer linkers. Illustrative hydrophilic linkers are described in WO2009/002993 and U.S. patent application Ser. No. 12/660712, the disclosure of which is incorporated by reference herein in its entirety. In addition, other optional spacer linkers and/or releasable linkers may be included in L. It is appreciated that additional spacer linkers may be included when predetermined lengths are selected for separating receptor binding ligand (B) from therapeutic agent (A). It is also appreciated that in certain configurations, releasable linkers may be included. For example, as described herein in one embodiment, the drug delivery conjugates may be used to deliver therapeutic agents (A) (e.g. drugs) for treating inflammation. In such embodiments, it is appreciated that once delivered, the therapeutic agent (A) is desirably released from the conjugate. For example, in the configuration where the receptor binding ligand (B) is folate, or an analog or derivative thereof, the conjugate may bind to a folate receptor. Once bound, the conjugate often undergoes the process of endocytosis, and the conjugate is delivered to the interior of the cell. Cellular mechanisms may biologically degrade the conjugate to release the drug "payload" and release the folate compound.

Accordingly, in other aspects, the conjugates B-L-A described herein also include the following general formulae:

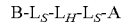

B-L$_H$-L$_R$-A

B-L$_R$-L$_H$-L$_R$-A

B-L$_S$-L$_R$-L$_H$-A

B-L$_R$-L$_H$-L$_S$-A

B-L$_R$-L$_S$-L$_H$-L$_R$-A

B-L$_H$-L$_S$-L$_H$-L$_R$-A where B, L, and A are as described herein, and L$_R$ is a releasable linker section, L$_S$ is a spacer linker section, and L$_H$ is a hydrophilic linker section of linker L. It is to be understood that the foregoing formulae are merely illustrative, and that other arrangements of the hydrophilic spacer linker sections, releasable linker sections, and spacer linker sections are to be included herein. In addition, it is to be understood that additional conjugates are contemplated that include a plurality hydrophilic spacer linkers, and/or a plurality of releasable linkers, and/or a plurality of spacer linkers.

It is appreciated that the arrangement and/or orientation of the various hydrophilic linkers may be in a linear or branched fashion, or both. For example, the hydrophilic linkers may form the backbone of the linker (L) forming the conjugate between the folate and the drug (i.e. therapeutic agent (A)). Alternatively, the hydrophilic portion of the linker (L) may be pendant to or attached to the backbone of the chain of atoms connecting the receptor binding ligand B to the therapeutic agent A. In this latter arrangement, the hydrophilic portion may be proximal or distal to the backbone chain of atoms.

In another embodiment, the linker (L) is more or less linear, and the hydrophilic groups are arranged largely in a series to form a chain-like linker in the conjugate. Said another way, the hydrophilic groups form some or all of the backbone of the linker (L) in this linear embodiment.

In another embodiment, the linker (L) is branched with hydrophilic groups. In this branched embodiment, the hydrophilic groups may be proximal to the backbone or distal to the backbone. In each of these arrangements, the linker (L) is more spherical or cylindrical in shape. In one variation, the linker (L) is shaped like a bottle-brush. In one aspect, the backbone of the linker (L) is formed by a linear series of amides, and the hydrophilic portion of the linker (L) is formed by a parallel arrangement of branching side chains, such as by connecting monosaccharides, sulfonates, and the like, and derivatives and analogs thereof.

It is understood that the linker (L) may be neutral or ionizable under certain conditions, such as physiological conditions encountered in vivo. For ionizable linkers, under the selected conditions, the linker (L) may deprotonate to form a negative ion, or alternatively become protonated to form a positive ion. It is appreciated that more than one deprotonation or protonation event may occur. In addition, it is understood that the same linker (L) may deprotonate and protonate to form inner salts or zwitterionic compounds.

In another embodiment, the hydrophilic spacer linkers are neutral, i.e. under physiological conditions, the linkers do not significantly protonate nor deprotonate. In another embodiment, the hydrophilic spacer linkers may be protonated to carry one or more positive charges. It is understood that the protonation capability is condition dependent. In one aspect, the conditions are physiological conditions, and the linker (L) is protonated in vivo. In another embodiment, the hydrophilic spacer linkers include both regions that are neutral and regions that may be protonated to carry one or more positive charges. In another embodiment, the hydrophilic spacer linkers include both regions that may be deprotonated to carry one or more negative charges and regions that may be protonated to carry one or more positive charges. It is understood that in this latter embodiment that zwitterions or inner salts may be formed.

In one aspect, the regions of the linkers (L) that may be deprotonated to carry a negative charge include carboxylic acids, such as aspartic acid, glutamic acid, and longer chain carboxylic acid groups, and sulfuric acid esters, such as alkyl esters of sulfuric acid. In another aspect, the regions of the linkers (L) that may be protonated to carry a positive charge include amino groups, such as polyaminoalkylenes including ethylene diamines, propylene diamines, butylene diamines and the like, and/or heterocycles including pyrollidines, piperidines, piperazines, and other amino groups, each of which is optionally substituted. In another embodiment, the regions of the hydrophilic spacer linkers that are neutral include poly hydroxyl groups, such as sugars, carbohydrates, saccharides, inositols, and the like, and/or polyether groups, such as polyoxyalkylene groups including polyoxyethylene, polyoxypropylene, and the like.

In one embodiment, the hydrophilic spacer linkers described herein are formed primarily from carbon, hydrogen, and oxygen, and have a carbon/oxygen ratio of about 3:1 or less, or of about 2:1 or less. In one aspect, the hydrophilic linkers described herein include a plurality of ether functional groups. In another aspect, the hydrophilic linkers described herein include a plurality of hydroxyl functional groups. Illustrative fragments that may be used to form such linkers include polyhydroxyl compounds such as carbohydrates, polyether compounds such as polyethylene glycol (PEG) units, and acid groups such as carboxyl and alkyl sulfuric acids. In one variation, oligoamide spacers, and the like may also be included in the linker (L).

Illustrative carbohydrate spacers include saccharopeptides as described herein that include both a peptide feature and sugar feature; glucuronides, which may be incorporated via [2+3] Huisgen cyclization, also known as click chemistry; β-alkyl glycosides, such as of 2-deoxyhexapyranoses (2-deoxyglucose, 2-deoxyglucuronide, and the like), and β-alkyl mannopyranosides.

In another illustrative embodiment, the hydrophilic spacer linkers described herein include a plurality of hydroxyl functional groups, such as linkers (L) that incorporate monosaccharides, oligosaccharides, polysaccharides, and the like. It is to be understood that the polyhydroxyl containing spacer linkers comprises a plurality of —(CROH)— groups, where R is hydrogen or alkyl.

In another embodiment, the hydrophilic spacer linkers include one or more of the following fragments:

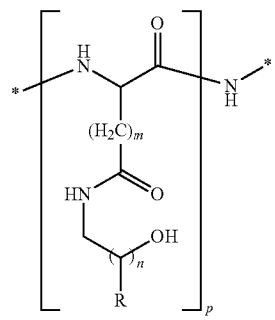

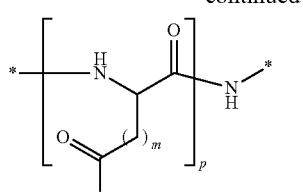
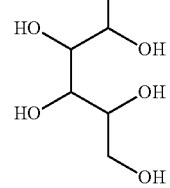
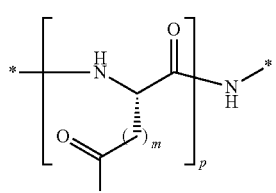
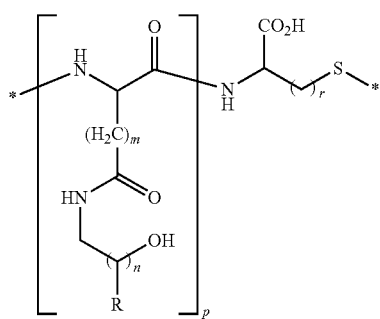
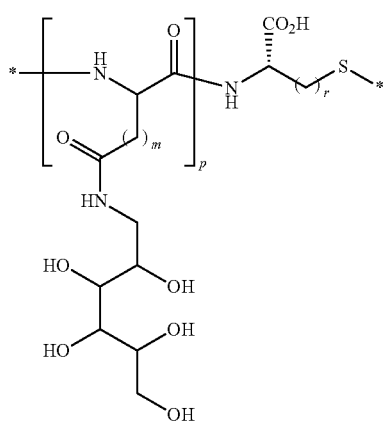
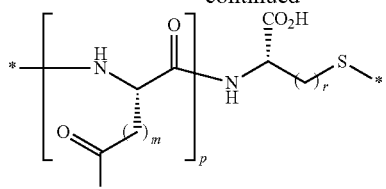
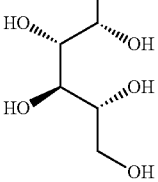
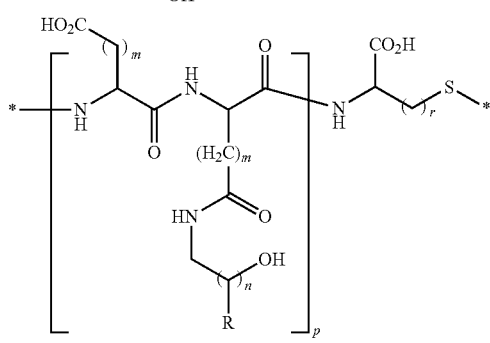
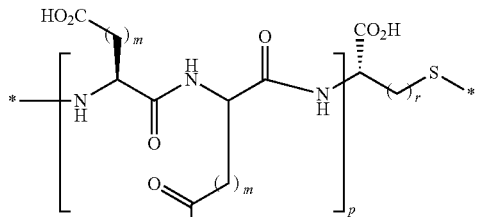
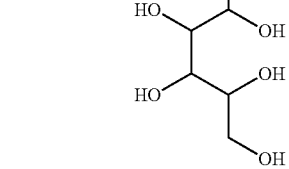
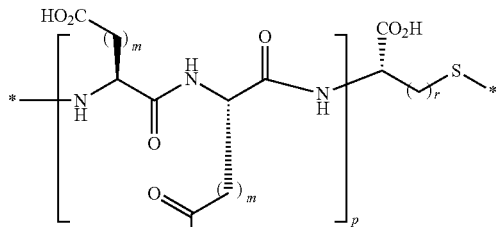
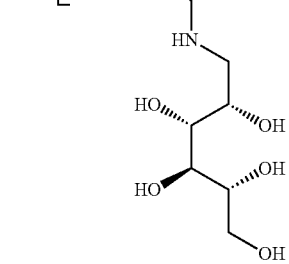

wherein R is H, alkyl, cycloalkyl, or arylalkyl; m is an independently selected integer from 1 to about 3; n is an integer from 1 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the hydrophilic spacer linkers described herein are formed primarily from carbon, hydrogen, and nitrogen, and have a carbon/nitrogen ratio of about 3:1 or less, or of about 2:1 or less. In one aspect, the hydrophilic linkers described herein include a plurality of amino functional groups.

It is understood, that in such polyhydroxyl, polyamino, carboxylic acid, sulfuric acid, and like linkers that include free hydrogens bound to heteroatoms, one or more of those free hydrogen atoms may be protected with the appropriate hydroxyl, amino, or acid protecting group, respectively, or alternatively may be blocked as the corresponding pro-drugs, the latter of which are selected for the particular use, such as pro-drugs that release the parent drug under general or specific physiological conditions.

In each of the foregoing illustrative examples of linkers L, there are also included in some cases additional spacer linkers $L_S$, and/or additional releasable linkers $L_R$. Those spacer linker and releasable linkers also may include asymmetric carbon atoms. It is to be further understood that the stereochemical configurations shown herein are merely illustrative, and other stereochemical configurations are contemplated. It is to be further understood that in the foregoing embodiments, open positions, such as (*) atoms are locations for attachment of the receptor binding ligand (B) or the therapeutic agent (A) to be delivered. In addition, it is to be understood that such attachment of either or both of B and A may be direct or through an intervening linker (L). Intervening linkers include other spacer linkers and/or releasable linkers. Illustrative additional spacer linkers and releasable linkers that are included in the conjugate described herein are described in U.S. Pat. No. 7,601,332, the disclosure of which is incorporated herein by reference.

In one embodiment, the hydrophilic spacer linker comprises one or more carbohydrate containing or polyhydroxyl group containing linkers. In another embodiment, the hydrophilic spacer linker comprises at least three carbohydrate containing or polyhydroxyl group containing linkers. In another embodiment, the hydrophilic spacer linker comprises one or more carbohydrate containing or polyhydroxyl group containing linkers, and one or more aspartic acids. In another embodiment, the hydrophilic spacer linker comprises one or more carbohydrate containing or polyhydroxyl group containing linkers, and one or more glutamic acids. In another embodiment, the hydrophilic spacer linker comprises one or more carbohydrate containing or polyhydroxyl group containing linkers, one or more glutamic acids, one or more aspartic acids, and one or more beta amino alanines. In a series of variations, in each of the foregoing embodiments, the hydrophilic spacer linker also includes one or more cysteines. In another series of variations, in each of the foregoing embodiments, the hydrophilic spacer linker also includes at least one arginine.

In another series of variations, in each of the foregoing embodiments, the hydrophilic spacer linker also includes at least one arginine.

Ilustrative spacer linkers include carbonyl, thionocarbonyl, alkylene, cycloalkylene, alkylenecycloalkyl, alkylenecarbonyl, cycloalkylenecarbonyl, carbonylalkylcarbonyl, 1-alkylenesuccinimid-3-yl, 1-(carbonylalkyl)succinimid-3-yl, alkylenesulfoxyl, sulfonylalkyl, alkylenesulfoxylalkyl, alkylenesulfonylalkyl, carbonyltetrahydro-2H-pyranyl, carbonyltetrahydrofuranyl, 1-(carbonyltetrahydro-2H-pyranyl)succinimid-3-yl, and 1-(carbonyltetrahydrofuranyl)succinimid-3-yl, wherein each of said spacer linkers is optionally substituted with one or more substituents $X^1$ as defined herein.

Illustrative releasable linkers include methylene, 1-alkoxyalkylene, 1-alkoxycycloalkylene, 1-alkoxyalkylenecarbonyl, 1-alkoxycycloalkylenecarbonyl, carbonylarylcarbonyl, carbonyl(carboxyaryl)carbonyl, carbonyl(biscarboxyaryl)carbonyl, haloalkylenecarbonyl, alkylene(dialkylsilyl), alkylene(alkylarylsilyl), alkylene(diarylsilyl), (dialkylsilyl)aryl, (alkylarylsilyl)aryl, (diarylsilyl)aryl, oxycarbonyloxy, oxycarbonyloxyalkyl, sulfonyloxy, oxysulfonylalkyl, iminoalkylidenyl, carbonylalkylideniminyl, iminocycloalkylidenyl, carbonylcycloalkylideniminyl, alkylenethio, alkylenearylthio, and carbonylalkylthio, wherein each of the releasable linkers is optionally substituted with a substituent $X^2$, as defined herein.

In any of the embodiments described herein, the substituents $X^2$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the releasable linker can include nitrogen, and the substituent $X^2$ and the releasable linker can form an heterocycle.

In any of the embodiments described herein, the substituents $X^1$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from the group consisting of an amino acid, an amino acid derivative, and a peptide, and wherein $R^6$ and $R^7$ are each independently selected from the group consisting of an amino acid, an amino acid derivative, and a peptide.

In any of the embodiments described herein, the substituents $X^1$ can be alkyl, hydroxyalkyl, amino, aminoalkyl, alkylaminoalkyl, dialkylaminoalkyl, sulfhydrylalkyl, alkylthioalkyl, aryl, substituted aryl, arylalkyl, substituted arylalkyl, carboxy, carboxyalkyl, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides.

The term cycloalkylene as used herein refers to a bivalent chain of carbon atoms, a portion of which forms a ring, such as cycloprop-1,1-diyl, cycloprop-1,2-diyl, cyclohex-1,4-diyl, 3-ethylcyclopent-1,2-diyl, 1-methylenecyclohex-4-yl, and the like.

The term aryl as used herein refers to an aromatic mono or polycyclic ring of carbon atoms, such as phenyl, naphthyl, and the like. In addition, aryl may also include heteroaryl.

The term substituted aryl as used herein refers to the replacement of one or more hydrogen atoms, generally on carbon, with a corresponding number of substituents, such as halo, hydroxy, amino, alkyl or dialkylamino, alkoxy, alkylsulfonyl, cyano, nitro, and the like.

The term heteroaryl as used herein refers to an aromatic mono or polycyclic ring of carbon atoms and at least one heteroatom selected from nitrogen, oxygen, and sulfur, such as pyridinyl, pyrimidinyl, indolyl, benzoxazolyl, and the like.

The term substituted heteroaryl as used herein refers to the replacement of one or more hydrogen atoms, generally on carbon, with a corresponding number of substituents, such as halo, hydroxy, amino, alkyl or dialkylamino, alkoxy, alkylsulfonyl, cyano, nitro, and the like.

The term optionally substituted as used herein refers to the replacement of one or more hydrogen atoms, generally on carbon, with a corresponding number of substituents, such as halo, hydroxy, amino, alkyl or dialkylamino, alkoxy, alkylsulfonyl, cyano, nitro, and the like. In addition, two hydrogens on the same carbon, on adjacent carbons, or nearby carbons may be replaced with a bivalent substituent to form the corresponding cyclic structure.

The term amino acid as used herein refers generally to aminoalkylcarboxylate, where the alkyl radical is optionally substituted, such as with alkyl, hydroxy alkyl, sulfhydrylalkyl, aminoalkyl, carboxyalkyl, and the like, including groups corresponding to the naturally occurring amino acids, such as serine, cysteine, methionine, aspartic acid, glutamic acid, and the like. It is to be understood that such amino acids may be of a single stereochemistry or a particular mixture of stereochemisties, including racemic mixtures. In addition, amino acid refers to beta, gamma, and longer amino acids, such as amino acids of the formula:

—N(R)—(CR'R")$_q$—C(O)— where R is hydrogen, alkyl, acyl, or a suitable nitrogen protecting group, R' and R" are hydrogen or a substituent, each of which is independently selected in each occurrence, and q is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornithine, threonine, and the like. In another illustrative aspect of the vitamin drug delivery conjugate intermediate described herein, the drug (i.e., therapeutic agents (A)), or an analog or a derivative thereof, includes an alkylthiol nucleophile.

As used herein the term "antifolate" refers to a compound that interferes with the metabolism of folic acid and its derivatives in cellular processes.

It is to be understood that the above-described terms can be combined to generate chemically-relevant groups, such as alkoxyalkyl referring to methyloxymethyl, ethyloxyethyl, and the like, haloalkoxyalkyl referring to trifluoromethyloxyethyl, 1,2-difluoro-2-chloroeth-1-yloxypropyl, and the like, arylalkyl referring to benzyl, phenethyl, α-methylbenzyl, and the like, and others.

The term amino acid derivative as used herein refers generally to an optionally substituted aminoalkylcarboxylate, where the amino group and/or the carboxylate group are each optionally substituted, such as with alkyl, carboxylalkyl, alkylamino, and the like, or optionally protected. In addition, the optionally substituted intervening divalent alkyl fragment may include additional groups, such as protecting groups, and the like.

The term peptide as used herein refers generally to a series of amino acids and/or amino acid analogs and derivatives covalently linked one to the other by amide bonds.

The term "releasable linker" as used herein refers to a linker (L) that includes at least one bond that can be broken under physiological conditions (e.g., a pH-labile, acid-labile, oxidatively-labile, or enzyme-labile bond). It should be appreciated that such physiological conditions resulting in bond breaking include standard chemical hydrolysis reactions that occur, for example, at physiological pH, or as a result of compartmentalization into a cellular organelle such as an endosome having a lower pH than cytosolic pH.

The cleavable bond or bonds may be present in the interior of a cleavable linker and/or at one or both ends of a cleavable linker. It is appreciated that the lability of the cleavable bond may be adjusted by including functional groups or fragments within the linker L that are able to assist or facilitate such bond breakage, also termed anchimeric assistance. In addition, it is appreciated that additional functional groups or fragments may be included within the linker L that are able to assist or facilitate additional fragmentation of the conjugates after bond breaking of the releasable linker. The lability of the cleavable bond can be adjusted by, for example, substitutional changes at or near the cleavable bond, such as including alpha branching adjacent to a cleavable disulfide bond, increasing the hydrophobicity of substituents on silicon in a moiety having a silicon-oxygen bond that may be hydrolyzed, homologating alkoxy groups that form part of a ketal or acetal that may be hydrolyzed, and the like.

It is understood that a cleavable bond can connect two adjacent atoms within the releasable linker and/or connect other linkers (L) or B and/or A, as described herein, at either or both ends of the releasable linker. In the case where a cleavable bond connects two adjacent atoms within the releasable linker, following breakage of the bond, the releasable linker is broken into two or more fragments. Alternatively, in the case where a cleavable bond is between the releasable linker and another moiety, such as an additional heteroatom, additional spacer linker, another releasable linker, the therapeutic agent A, or analog or derivative thereof, or the receptor binding ligand B, or analog or derivative thereof, following breakage of the bond, the releasable linker is separated from the other moiety.

It is understood that each of the additional spacer and releasable linkers are bivalent. It should be further understood that the connectivity between each of the various additional spacer and releasable linkers themselves, and between the various additional spacer and releasable linkers and A and/or B, as defined herein, may occur at any atom found in the various additional spacer or releasable linkers.

In another aspect, the linker (L) comprises a releasable linker, an additional spacer linker, and a releasable linker taken together to form dithioalkylcarbonylhydrazide, where the hydrazide forms a hydrazide with the therapeutic agent A, or analog or derivative thereof.

In another aspect, the linker (L) comprises a plurality of additional spacer linkers selected from the group consisting of the naturally occurring amino acids and stereoisomers thereof.

In another aspect, the linker (L) comprises a releasable linker, an additional spacer linker, and a releasable linker taken together to form 2-dithioalkyloxycarbonyl, where the carbonyl forms a carbonate with the agent A, or analog or derivative thereof.

In another aspect, the linker (L) comprises a releasable linker, an additional spacer linker, and a releasable linker taken together to form 2-dithioalkyloxycarbonylhydrazide.

In another aspect, the linker (L) comprises a releasable linker, an additional spacer linker, and a releasable linker taken together to form 2-dithioalkylaminocarbonyl, where the carbonyl forms a carbamate with the therapeutic agent A, or analog or derivative thereof.

In another aspect, the linker (L) comprises a releasable linker, an additional spacer linker, and a releasable linker taken together to form 2-dithioalkylaminocarbonyl, where the carbonyl forms a carbamate with the therapeutic agent A, or analog or derivative thereof, and the alkyl is ethyl.

In another aspect, the linker (L) comprises a releasable linker, an additional spacer linker, and a releasable linker taken together to form 2-dithioarylalkyloxycarbonyl, where the carbonyl forms a carbamate or a carbamoylaziridine with the therapeutic agent A, or analog or derivative thereof.

In one aspect, the releasable and spacer linkers may be arranged in such a way that subsequent to the cleavage of a bond in the linker (L), released functional groups chemically assist the breakage or cleavage of additional bonds, also termed anchimeric assisted cleavage or breakage.

Illustrative mechanisms for cleavage of the linkers described herein include the following 1,4 and 1,6 fragmentation mechanisms

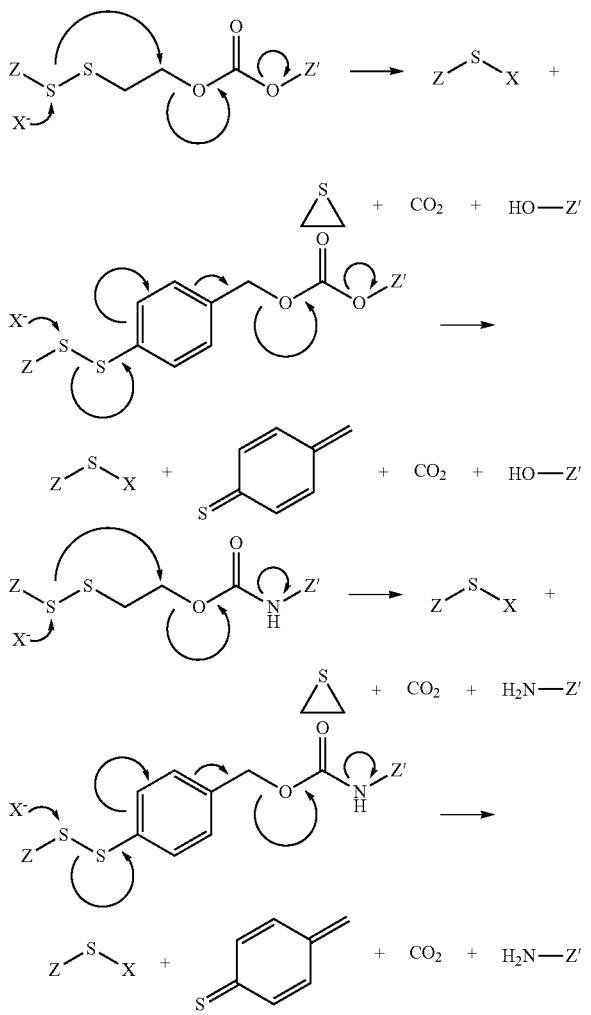

where X is an exogenous or endogenous nucleophile, glutathione, or bioreducing agent, and the like, and either of Z or Z' is the vitamin (e.g. folate), or analog or derivative thereof, or the drug, or analog or derivative thereof, or a vitamin (e.g. folate) or drug in conjunction with other portions of the linker (L). It is to be understood that although the above fragmentation mechanisms are depicted as concerted mechanisms, any number of discrete steps may take place to effect the ultimate fragmentation of the linker (L) to the final products shown. For example, it is appreciated that the bond cleavage may also occur by acid-catalyzed elimination of the carbamate moiety, which may be anchimerically assisted by the stabilization provided by either the aryl group of the beta sulfur or disulfide illustrated in the above examples. In those variations of this embodiment, the releasable linker is the carbamate moiety. Alternatively, the fragmentation may be initiated by a nucleophilic attack on the disulfide group, causing cleavage to form a thiolate. The thiolate may intermolecularly displace a carbonic acid or carbamic acid moiety and form the corresponding thiacyclopropane. In the case of the benzyl-containing linkers, following an illustrative breaking of the disulfide bond, the resulting phenyl thiolate may further fragment to release a carbonic acid or carbamic acid moiety by forming a resonance stabilized intermediate. In any of these cases, the releasable nature of the illustrative linkers described herein may be realized by whatever mechanism may be relevant to the chemical, metabolic, physiological, or biological conditions present.

It is to be understood that although the above fragmentation mechanisms are depicted as concerted mechanisms, any number of discrete steps may take place to effect the ultimate fragmentation of the linker (L) to the final products shown. Alternatively, the fragmentation may be initiated by a nucleophilic attack on the disulfide group, causing cleavage to form a thiolate. The thiolate may intermolecularly displace a carbonic acid or carbamic acid moiety and form the corresponding thiacyclopropane. In any of these cases, the releasable nature of the illustrative linkers (L) described herein may be realized by whatever mechanism may be relevant to the chemical, metabolic, physiological, or biological conditions present. Without being bound by theory, in this embodiment, acid catalysis, such as in an endosome, may also initiate the cleavage via protonation of the urethane group. In addition, acid-catalyzed elimination of the carbamate leads to the release of $CO_2$ and the nitrogen-containing moiety attached to Z, and the formation of a benzyl cation, which may be trapped by water, or any other Lewis base, as is similarly described herein.

In one embodiment, the linkers (L) described herein are compounds of the following formulae

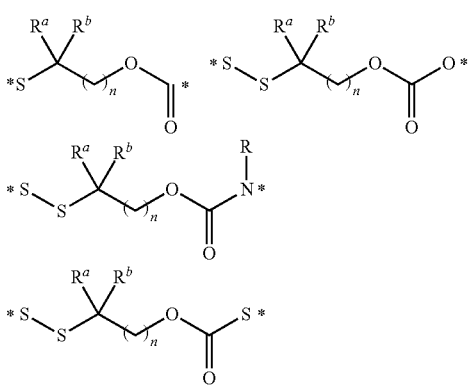

where n is an integer selected from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; R is an optionally substituted alkyl group, an optionally substituted acyl group, or a suitably selected nitrogen protecting group; and (*) indicates points of attachment for the drug, folate, other linkers (L), or other parts of the conjugate. Another illustrative mechanism involves an arrangement of the releasable and spacer linkers in such a way that subsequent to the cleavage of a bond in the linker (L), released functional groups chemically assist the breakage or cleavage of additional bonds, also termed anchimeric assisted cleavage or breakage.

In another illustrative embodiment, the linker (L) includes one or more amino acids. In one variation, the linker (L) includes a single amino acid. In another variation, the linker (L) includes a peptide having from 2 to about 50, 2 to about 30, or 2 to about 20 amino acids. In another variation, the linker (L) includes a peptide having from about 4 to about 8 amino acids. Such amino acids are illustratively selected from the naturally occurring amino acids, or stereoisomers thereof. The amino acid may also be any other amino acid, such as any amino acid having the general formula:

where R is hydrogen, alkyl, acyl, or a suitable nitrogen protecting group, R' and R" are hydrogen or a substituent, each of which is independently selected in each occurrence, and q is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornithine, threonine, and the like. In one variation, the releasable linker includes at least 2 amino acids selected from asparagine, aspartic acid, cysteine, glutamic acid, lysine, glutamine, arginine, serine, ornithine, and threonine. In another variation, the releasable linker includes between 2 and about 5 amino acids selected from asparagine, aspartic acid, cysteine, glutamic acid, lysine, glutamine, arginine, serine, ornithine, and threonine. In another variation, the releasable linker includes a tripeptide, tetrapeptide, pentapeptide, or hexapeptide consisting of amino acids selected from aspartic acid, cysteine, glutamic acid, lysine, arginine, and ornithine, and combinations thereof.

In one illustrative embodiment of the invention, a method for treating a patient with an inflammatory disease, the method comprising the step of administering to the patient a composition comprising a drug delivery conjugate of the formula

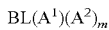

or a pharmaceutically acceptable salt, isomer, mixture of isomers, crystalline form, non crystalline form, hydrate, or solvate thereof; wherein
  m is 0 or 1;
  B is a folate;
  L is a linker that comprises one or more hydrophilic spacer linkers;
  $A^1$ is an antifolate; and
  $A^2$ has the formula

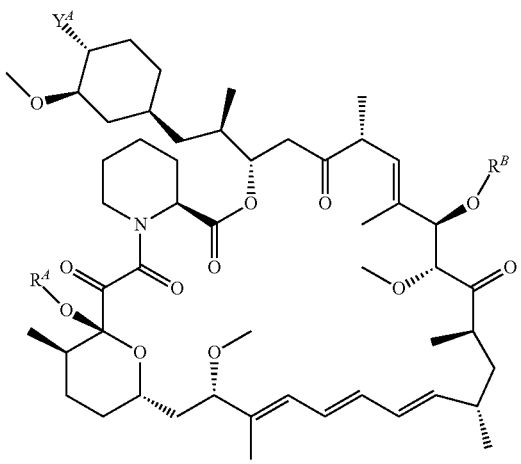

wherein
  $Y^A$ is $OR^C$ or $OCH_2CH_2OR^C$;
  one of $R^A$, $R^B$, or $R^C$ is a bond connected to L; and
  the other two of $R^A$, $R^B$, and $R^C$ are independently selected in each case from the group consisting of hydrogen, optionally substituted heteroalkyl, prodrug foming group, and $C(O)R^D$, where $R^D$ is in each instance independently selected from the group consisting of hydrogen, and alkyl, alkenyl, heteroalkyl, cycloalkyl, cycloheteroalkyl, aryl, arylalkyl, heteroaryl, and heteroarylalkyl, each of which is optionally substituted is described.

In another embodiment, a pharmaceutical composition comprising a drug delivery conjugate of the formula

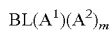

or a pharmaceutically acceptable salt, isomer, mixture of isomers, crystalline form, non crystalline form, hydrate, or solvate thereof; wherein
  m is 0 or 1;
  B is a folate;
  L is a linker that comprises one or more hydrophilic spacer linkers;
  $A^1$ is an antifolate; and
  $A^2$ has the formula

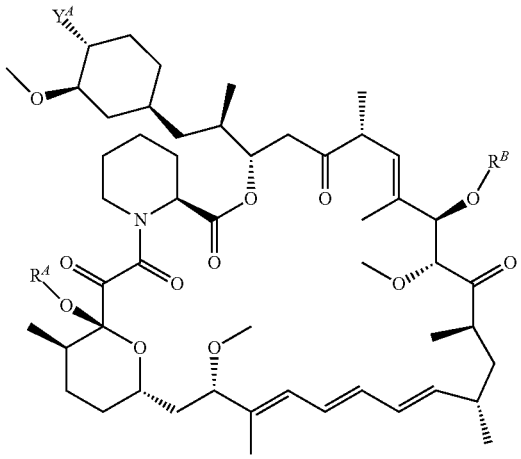

wherein

Y$^A$ is OR$^C$ or OCH$_2$CH$_2$OR$^C$;

one of R$^A$, R$^B$, or R$^C$ is a bond connected to L; and the other two of R$^A$, R$^B$, and R$^C$ are independently selected in each case from the group consisting of hydrogen, optionally substituted heteroalkyl, prodrug forming group, and C(O)R$^D$, where R$^D$ is in each instance independently selected from the group consisting of hydrogen, and alkyl, alkenyl, heteroalkyl, cycloalkyl, cycloheteroalkyl, aryl, arylalkyl, heteroaryl, and heteroarylalkyl, each of which is optionally substituted is described.

In one aspect, B, L, A$^1$, and A$^2$ in the conjugate BLA$^1$(A$^2$)$_m$ are connected as shown in the following formula:

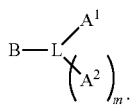

In another embodiment, the method or pharmaceutical composition of any one of the preceding embodiments wherein m is 1 and A$^1$ and A$^2$ are each covalently attached to linker L is described.

In another embodiment, the method or pharmaceutical composition of any one of the preceding embodiments wherein L is a linker of the formula

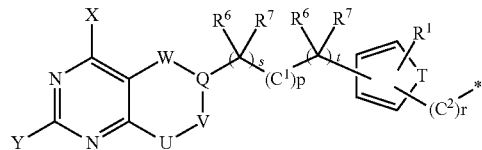

wherein * indicates the point of attachment to the linker;

X and Y are each-independently selected from the group consisting of halo, R$^2$, OR$^2$, SR$^3$, and NR$^4$R$^5$;

U, V, and W represent divalent moieties each independently selected from the group consisting of —(R$^{6a}$)C=, —N=, —(R$^{6a}$)C(R$^{7a}$)—, and —N(R$^{4a}$)—; Q is selected from the group consisting of C and CH; T is selected from the group consisting of S, O, N, and —C=C—;

C$^1$ and C$^2$ are each independently selected from the group consisting of oxygen, sulfur, —C(Z)—, —C(Z)O—, —OC(Z)—, —N(R$^{4b}$)—, —C(Z)N(R$^{4b}$)—, —N(R$^{4b}$)C(Z)—, —OC(Z)N(R$^{4b}$)—, —N(R$^{4b}$)C(Z)O—, —N(R$^{4b}$)C(Z)N(R$^{5b}$)—, —S(O)—, —S(O)$_2$—, —N(R$^{4a}$)S(O)$_2$—, —C(R$^{6b}$)(R$^{7b}$)—, —N(C=CH)—, —N(CH$_2$C=CH)—, C$_1$-C$_{12}$ alkylene, and C$_1$-C$_{12}$ alkyeneoxy, where Z is oxygen or sulfur;

R$^1$ is selected-from the group consisting of hydrogen, halo, C$_1$-C$_{12}$ alkyl, and C$_1$-C$_{12}$ alkoxy; R$^2$, R$^3$, R$^4$, R$^{4a}$, R$^{4b}$, R$^5$, R$^{5b}$, R$^{6b}$, and R$^{7b}$ are each independently selected from the group consisting of hydrogen, halo, C$_1$-C$_{12}$ alkyl, C$_1$-C$_{12}$ alkoxy, C$_1$-C$_{12}$ alkanoyl, C$_1$-C$_{12}$ alkenyl, C$_1$-C$_{12}$ alkynyl, (C$_1$-C$_{12}$ alkoxy)carbonyl, and (C$_1$-C$_{12}$ alkylamino)carbonyl;

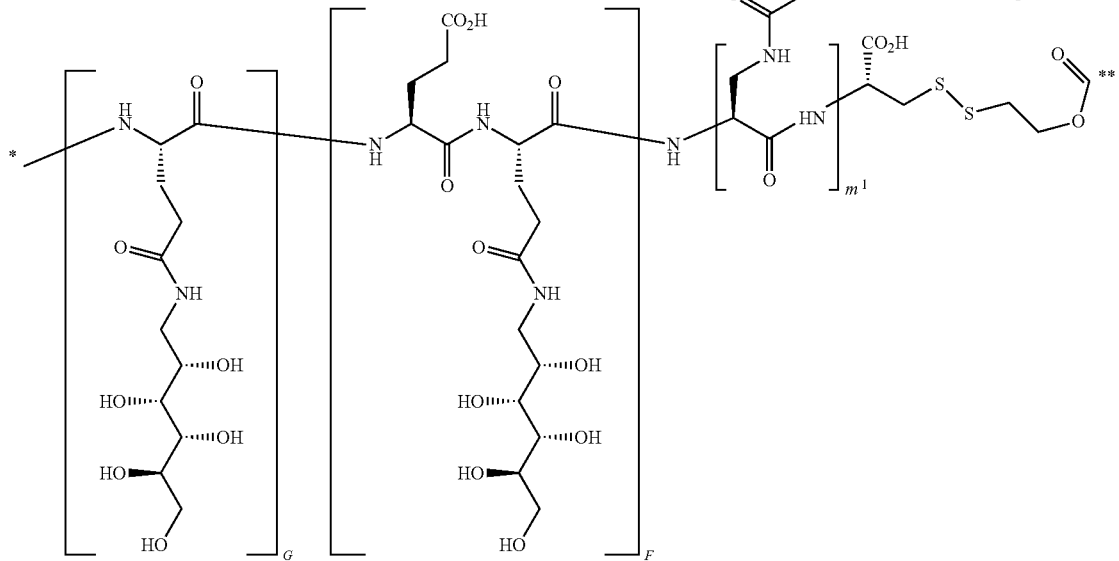

wherein * indicates the point of attachment to the folate;  indicates the point of attachment to one of A$^1$ or A$^2$; * indicates the point of attachment to the remaining A$^1$ or A$^2$; F and G are each independently 1, 2, 3 or 4; and W$^1$ is NH or O is described.

In another embodiment, the method or pharmaceutical composition of any one of the preceding embodiments wherein the folate is of the formula R$^6$ and R$^7$ are each independently selected from the group consisting of hydrogen, halo, C$_1$-C$_{12}$ alkyl, and C$_1$-C$_{12}$ alkoxy; or, R$^6$ and R$^7$ are taken together to form a carbonyl group; R$^{6a}$ and R$^{7a}$ are each independently selected from the group consisting of hydrogen, halo, C$_1$-C$_{12}$ alkyl, and C$_1$-C$_{12}$ alkoxy; or R$^{6a}$ and R$^{7a}$ are taken together to form a carbonyl group; and p, r, s and t are each independently either 0 or 1 is described.

In another embodiment, the method or pharmaceutical composition of any one of the preceding embodiments wherein the antifolate is aminopterin, or an analog, or derivative, thereof is described.

In another embodiment, the method or pharmaceutical composition of any one of the preceding embodiments wherein the antifolate is aminopterin hydrazide is described.

In another embodiment, the method or pharmaceutical composition of any one of the preceding embodiments wherein the folate is of the formula

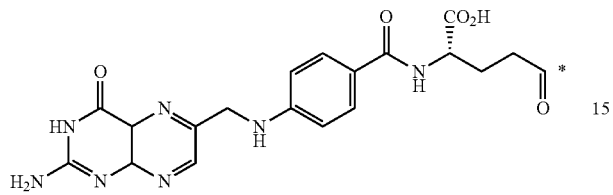

wherein * indicates the point of attachment to the linker is described.

In another embodiment, the method or pharmaceutical composition of any one of the preceding embodiments wherein $m^1$ is 1; $R^A$ and $R^B$ are hydrogen; $Y^A$ is $OCH_2CH_2OR^C$; and $R^C$ is a bond connected to L is described.

In another embodiment, the method or pharmaceutical composition of any one of the preceding embodiments wherein F is 2 and G is 1 is described.

In another embodiment, the method or pharmaceutical composition of any one of the preceding embodiments wherein the drug delivery conjugate is of the formula

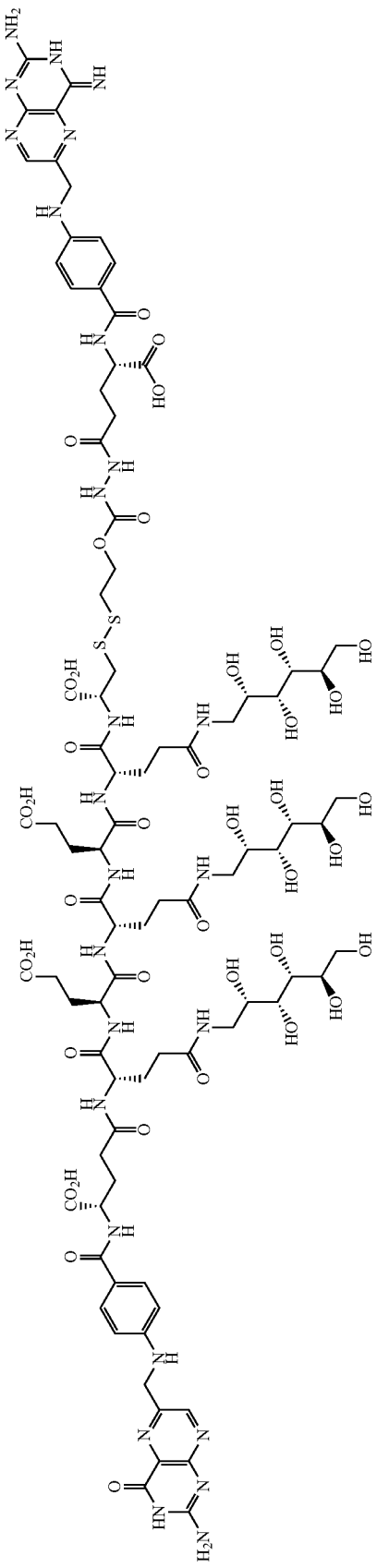

is described.

In another embodiment, the method or pharmaceutical composition of any one of the preceding embodiments wherein the drug delivery conjugate is of the formula

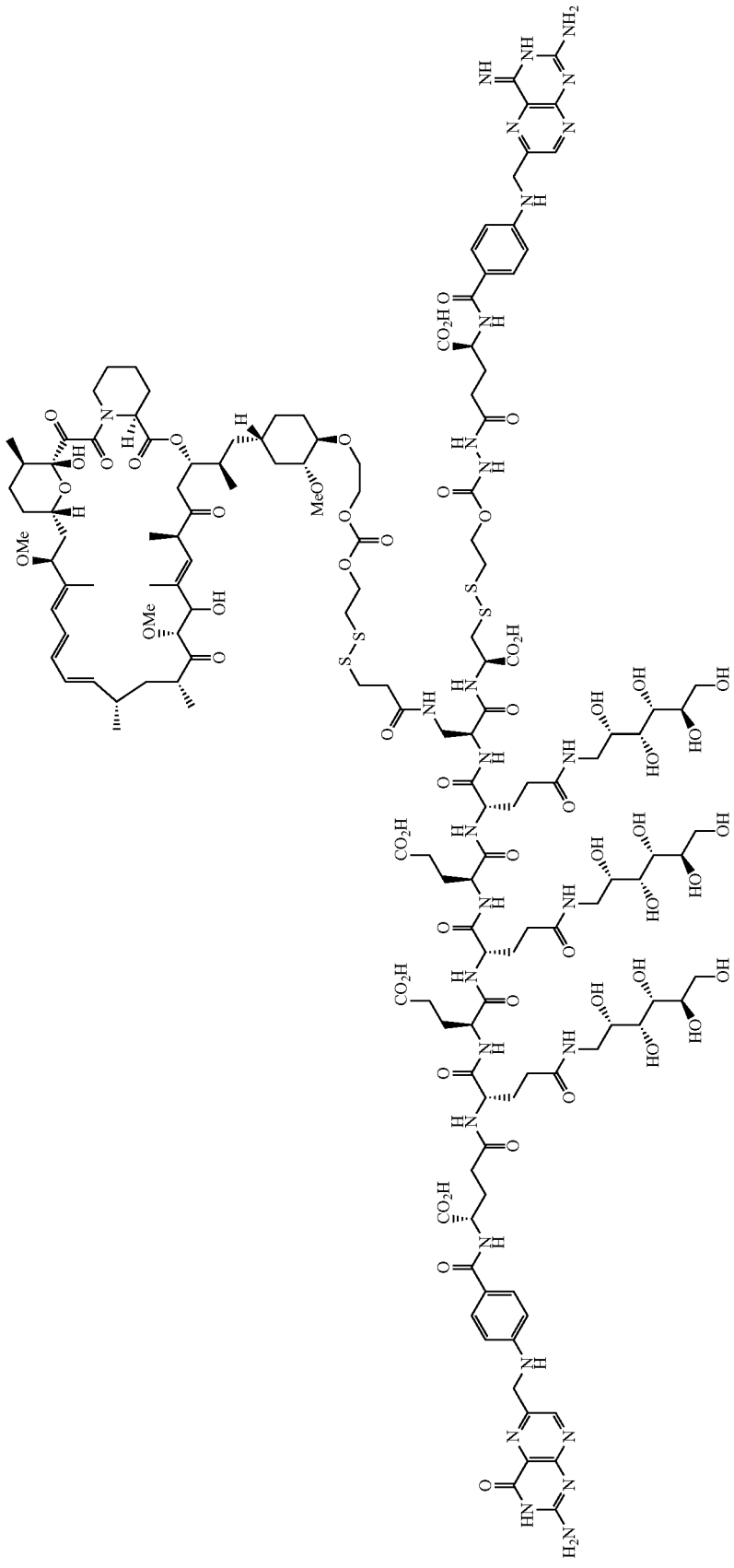

In another embodiment, the method or pharmaceutical composition of any one of the preceding embodiments wherein the drug delivery conjugate is of the formula

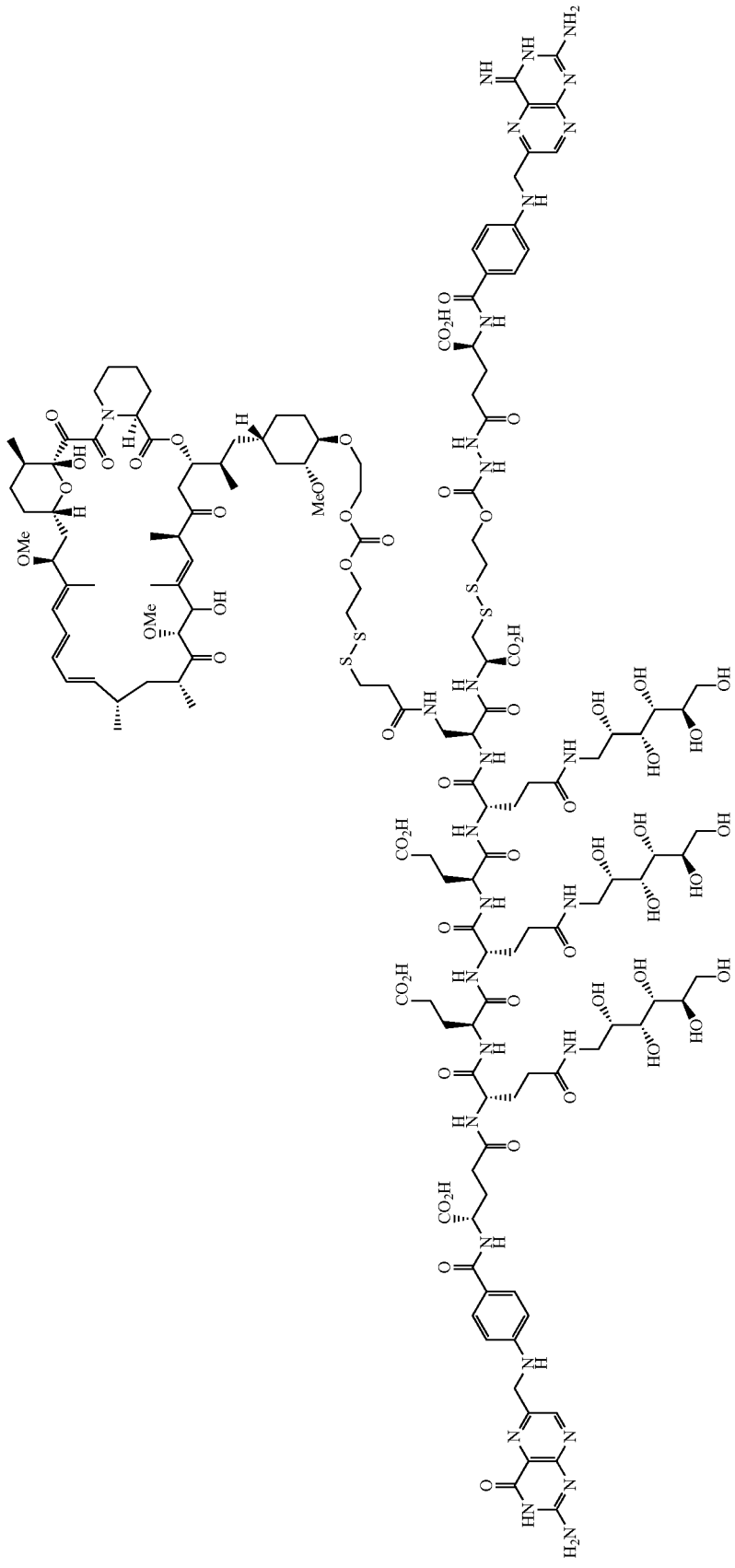

In another embodiment, the method or pharmaceutical composition of any one of the preceding embodiments wherein the composition further comprises one or more carriers, diluents, or excipients, or a combination thereof is described.

In another embodiment, the method or pharmaceutical composition of any one of the preceding embodiments wherein the purity of the drug delivery conjugate is at least 98% is described.

In another embodiment, the method or pharmaceutical composition of any one of the preceding embodiments wherein the composition is in a dosage form adapted for parenteral administration is described.

In another embodiment, the method of any one of the preceding embodiments wherein the dose of the drug delivery conjugate is in the range of 1 to 5 µg/kg is described.

In another embodiment, the method of any one of the preceding embodiments wherein the dose of the drug delivery conjugate is in the range of 1 to 3 µg/kg is described.

In another embodiment, the method or pharmaceutical composition of any one of the preceding embodiments wherein the disease is selected from the group consisting of arthritis, including rheumatoid arthritis and osteoarthritis, glomerulonephritis, proliferative retinopathy, restenosis, ulcerative colitis, Crohn's disease, fibromyalgia, psoriasis and other inflammations of the skin, inflammations of the eye, including uveitis and autoimmune uveitis, osteomyelitis, Sjögren's syndrome, multiple sclerosis, diabetes, atherosclerosis, pulmonary fibrosis, lupus erythematosus, sarcoidosis, systemic sclerosis, organ transplant rejection (GVHD), and chronic inflammations is described.

In one embodiment, a compound having the following formula

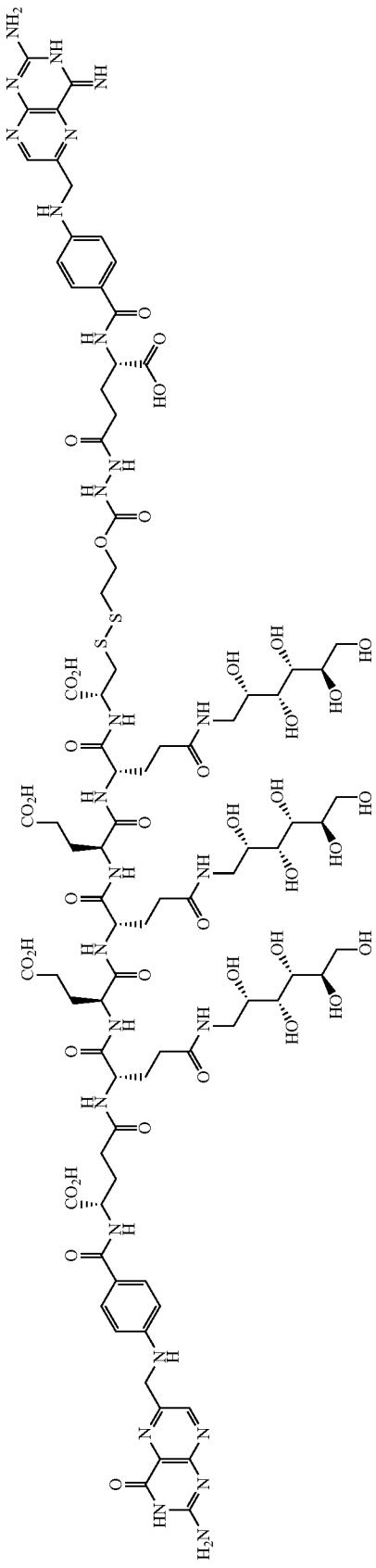

is described.

In another embodiment, a kit comprising a sterile vial, the composition or compound of any one of the preceding embodiments, and instructions for use describing use of the composition for treating a patient with an inflammatory disease is described.

In another embodiment, is described a kit comprising a sterile vial, a composition comprising the compound as a lyophilized solid of any one of the preceding embodiments, and instructions describing use of the composition for treating a patient with an inflammatory disease, wherein the vial is an amber glass vial with a rubber stopper and an aluminum tear-off seal.

In another embodiment, the kit of the preceding embodiment wherein the folate is of the formula

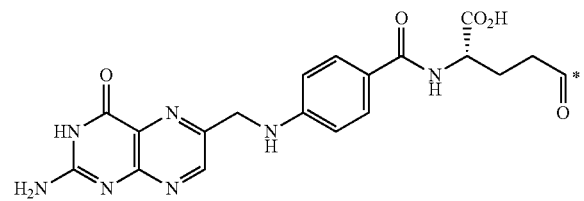

wherein * indicates the point of attachment to the linker is described.

In another embodiment, the method or pharmaceutical composition of any one of the preceding embodiments wherein the antifolate is aminopterin hydrazide is described.

In another embodiment, the kit of any one of the preceding embodiments wherein the antifolate is aminopterin hydrazide is described.

In another embodiment, the kit of any one of the preceding embodiments wherein in the conjugate $m^1$ is 1; $R^A$ and $R^B$ are hydrogen; $Y^A$ is $OCH_2CH_2OR^C$; and $R^C$ is a bond connected to L is described.

In another embodiment, the kit of any one of the preceding embodiments wherein in the conjugate F is 2 and G is 1 is described.

In another embodiment, the kit of any one of the preceding embodiments is described wherein the drug delivery conjugate is of the formula

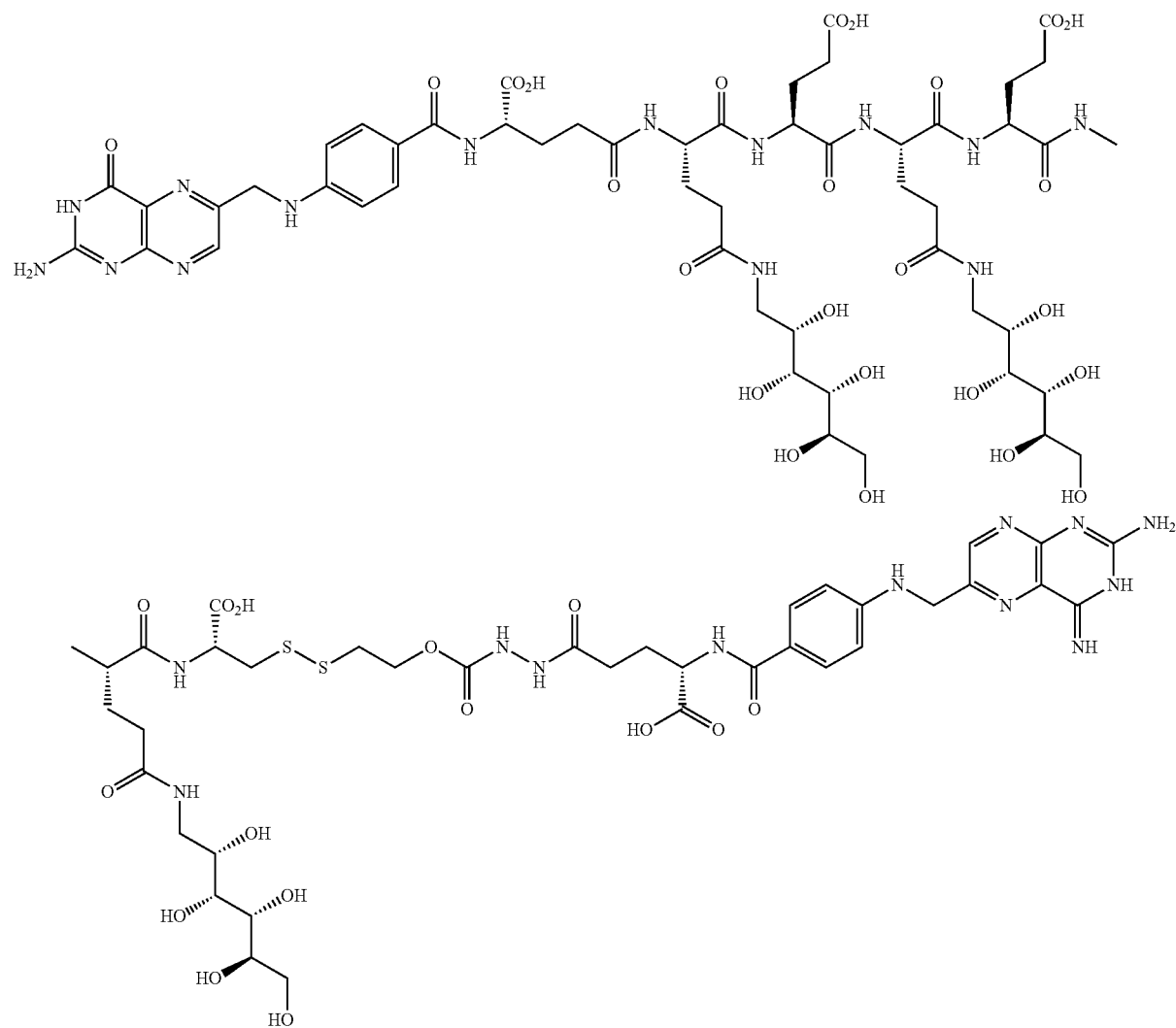

In another embodiment, the kit of any one of the preceding embodiments is described wherein the drug delivery conjugate is of the formula

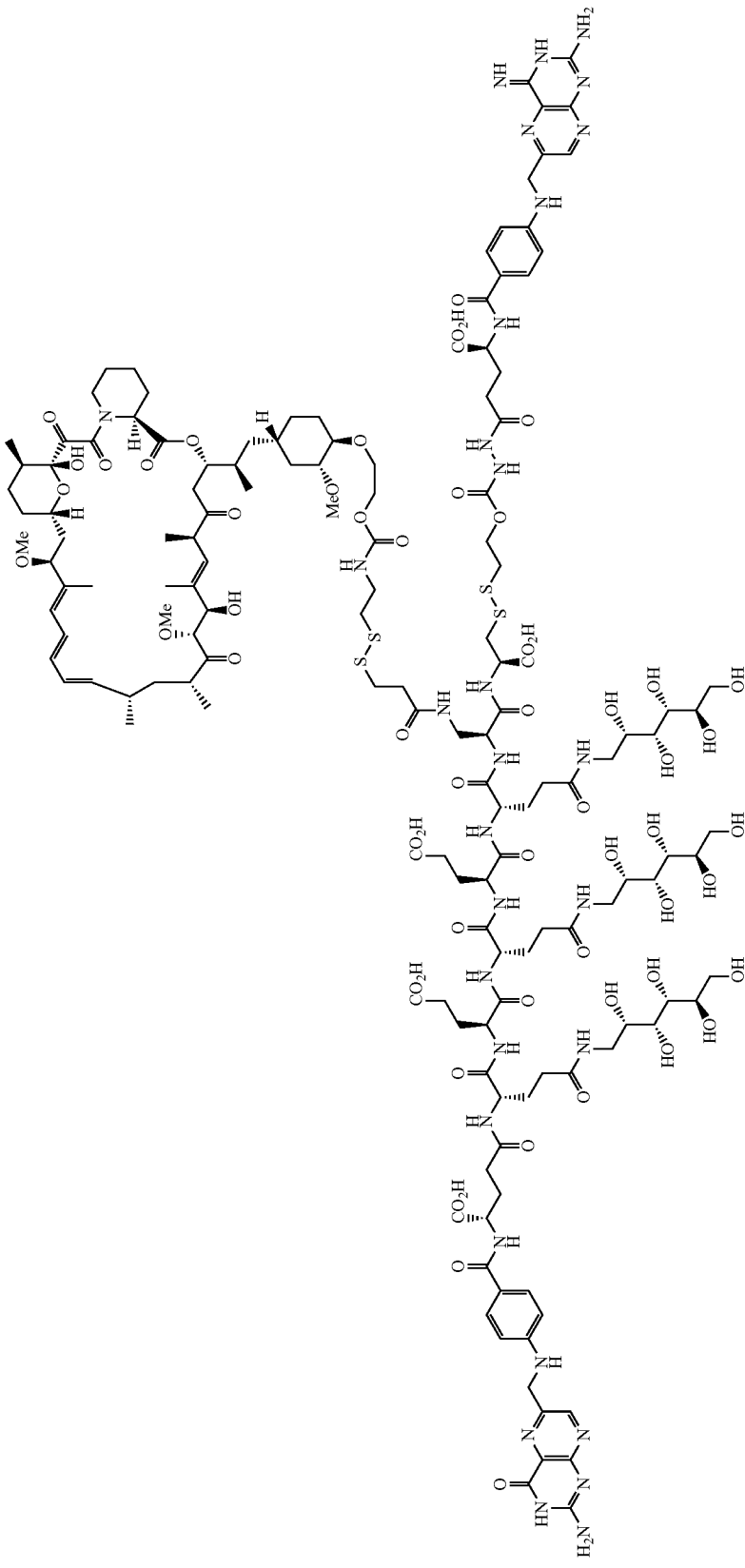

In another embodiment, the kit of any one of the preceding embodiments wherein the drug delivery conjugate is of the formula

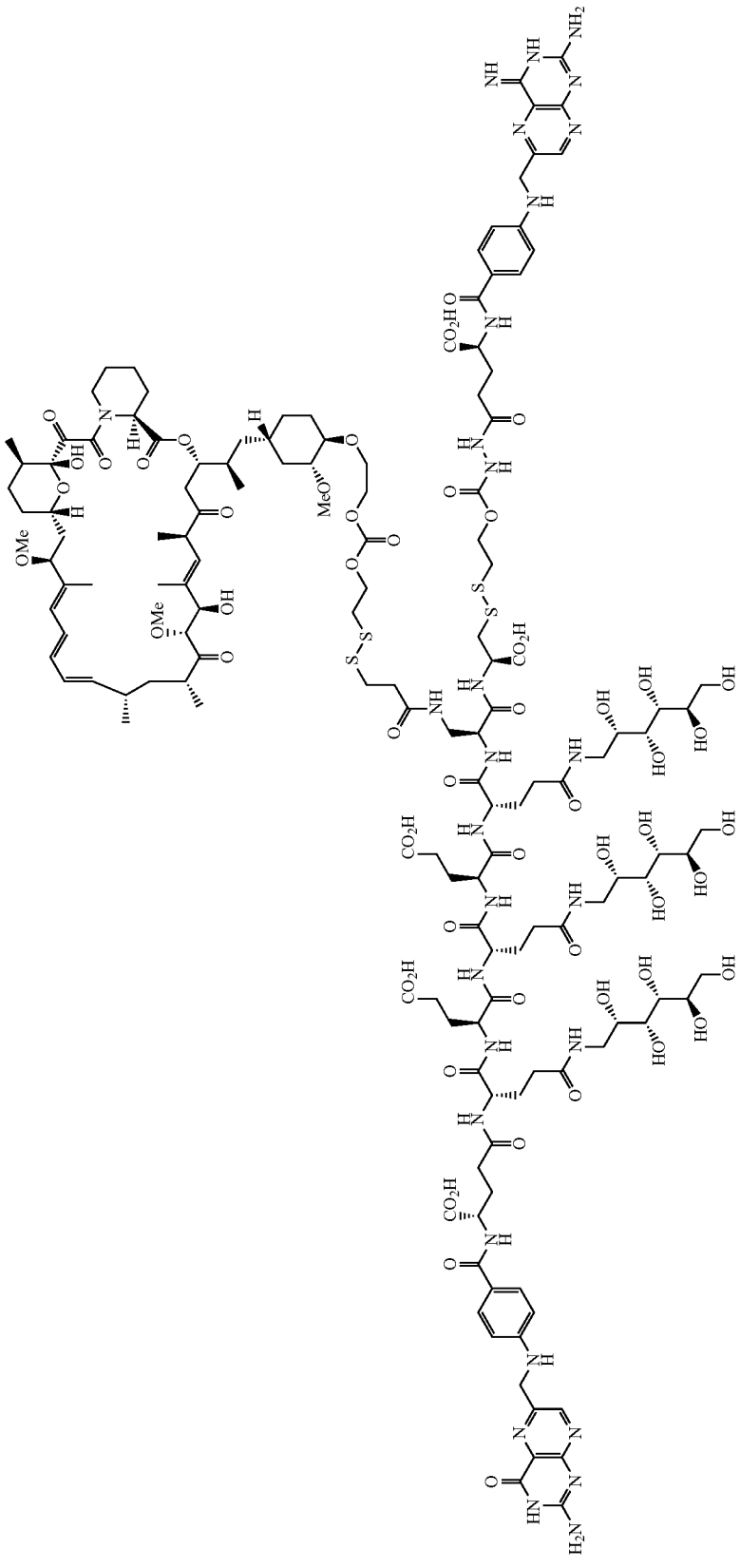

is described.

In another embodiment, the kit of any one of the preceding embodiments wherein the composition or compound is in the form of a reconstitutable lyophlizate is described.

In another embodiment, the kit of any one of the preceding embodiments wherein the dose of the drug delivery conjugate is in the range of 1 to 5 μg/kg is described.

In another embodiment, the kit of any one of the preceding embodiments wherein wherein the dose of the drug delivery conjugate is in the range of 1 to 3 μg/kg is described.

In another embodiment, the kit of any one of the preceding embodiments wherein the purity of the drug delivery conjugate is at least 98% is described.

In another embodiment, a kit is described wherein the compound of any of the preceding compound embodiments is lyophilized and is in the kit along with a composition for reconstituting the lyophilizate.

In another embodiment, one of A is a derivative or analog of rapamycin. Illustrative examples of derivatives or analogs of rapamycin are disclosed in U.S. Pat. Nos. 4,316,885, 4,650,803, 5,100,883, 5,118,677, 5,118,678, 5,120,842, 5,130,307, 5,138,051, 5,151,413, 5,169,851, 5,194,447, 5,221,670, 5,233,036, 5,258,389, 5,260,300, 5,302,584, 5,362,718, 5,378,696, 5,385,908, 5,385,909, 5,385,910, 5,389,639, 5,391,730, 5,463,048, and 5,491,231. The disclosure of each of the foregoing documents is incorporated by reference herein in its entirety. In another embodiment one of A is a derivative of everolimus.

In one illustrative embodiment of the invention a method for treating a patient with an inflammatory disease, the method comprising the step of administering to the patient a composition comprising a drug delivery conjugate of the formula

B-L-A³ or a pharmaceutically acceptable salt, isomer, mixture of isomers, crystalline form, non crystalline form, hydrate, or solvate thereof; wherein
B is a folate;
L is a linker that comprises one or more hydrophilic spacer linkers; and
A³ has the formula

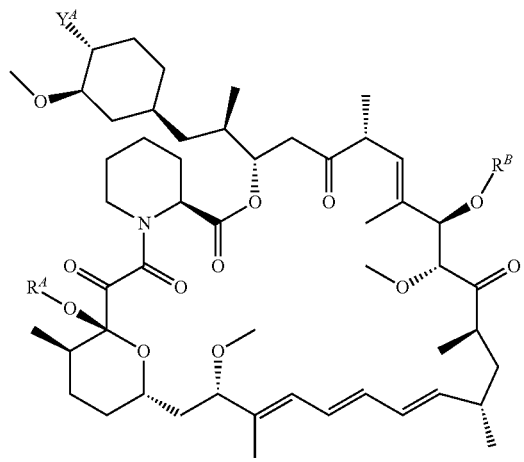

wherein
$Y^A$ is $OR^C$ or $OCH_2CH_2OR^C$;
one of $R^A$, $R^B$, or $R^C$ is a bond connected to L; and
the other two of $R^A$, $R^B$, and $R^C$ are independently selected in each case from the group consisting of hydrogen, optionally substituted heteroalkyl, prodrug foming group, and $C(O)R^D$, where $R^D$ is in each instance independently selected from the group consisting of hydrogen, and alkyl, alkenyl, heteroalkyl, cycloalkyl, cycloheteroalkyl, aryl, arylalkyl, heteroaryl, and heteroarylalkyl, each of which is optionally substituted is described.

In another embodiment, a pharmaceutical composition comprising a drug delivery conjugate of the formula

B-L-A³ or a pharmaceutically acceptable salt, isomer, mixture of isomers, crystalline form, non crystalline form, hydrate, or solvate thereof; wherein
B is a folate;
L is a linker that comprises one or more hydrophilic spacer linkers; and
A³ has the formula

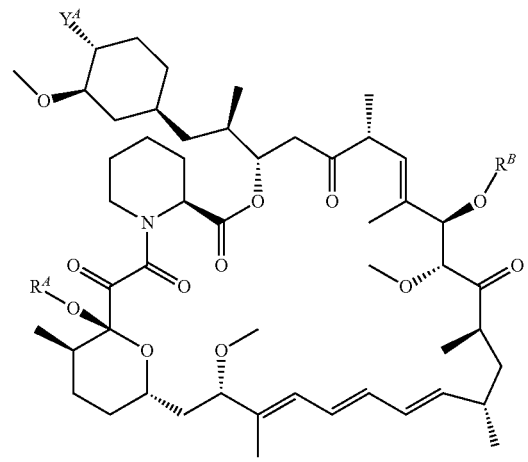

wherein
$Y^A$ is $OR^C$ or $OCH_2CH_2OR^C$;
one of $R^A$, $R^B$, or $R^C$ is a bond connected to L; and
the other two of $R^A$, $R^B$, and $R^C$ are independently selected in each case from the group consisting of hydrogen, optionally substituted heteroalkyl, prodrug forming group, and $C(O)R^D$, where $R^D$ is in each instance independently selected from the group consisting of hydrogen, and alkyl, alkenyl, heteroalkyl, cycloalkyl, cycloheteroalkyl, aryl, arylalkyl, heteroaryl, and heteroarylalkyl, each of which is optionally substituted is described.

In another embodiment, the method or pharmaceutical composition of any one of the preceding embodiments wherein
$Y^A$ is $OR^C$ or $OCH_2CH_2OR^C$;
one of $R^A$, $R^B$, or $R^C$ is a bond connected to L; and
the other two of $R^A$, $R^B$, and $R^C$ are independently selected in each case from the group consisting of hydrogen, optionally substituted heteroalkyl, and $C(O)R^D$, where $R^D$ is in each instance independently selected from the group consisting of hydrogen, and alkyl, alkenyl, heteroalkyl, cycloalkyl, cycloheteroalkyl, aryl, arylalkyl, heteroaryl, and heteroarylalkyl, each of which is optionally substituted is described.

In another embodiment, the method or pharmaceutical composition of any one of the preceding embodiments wherein L is a bivalent linker of the formula

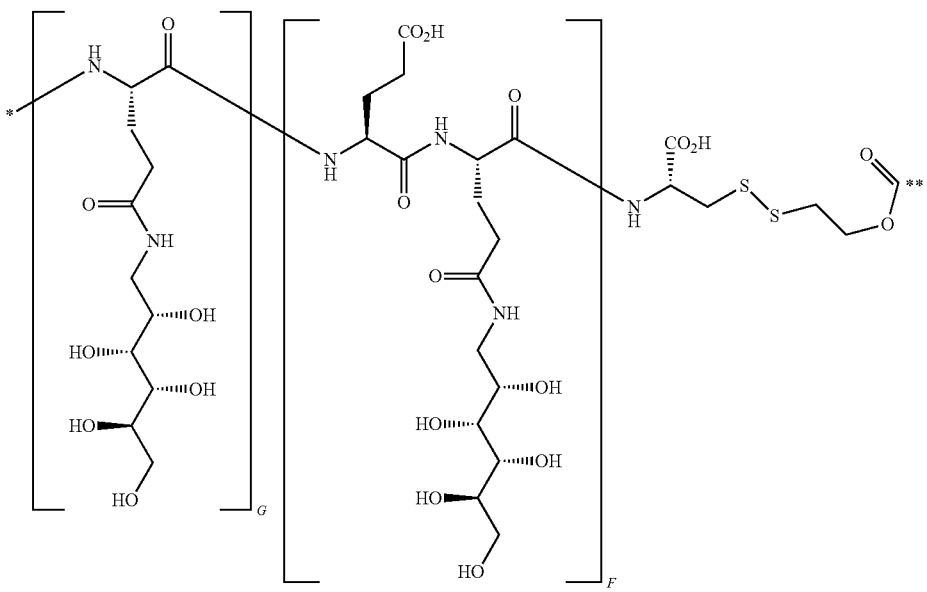

wherein * indicates the point of attachment to the folate and ** indicates the point of attachment to $A^3$; and F and G are each independently 1, 2, 3 or 4 is described.

In another embodiment, the method or pharmaceutical composition of any one of the preceding embodiments wherein the folate is of the formula

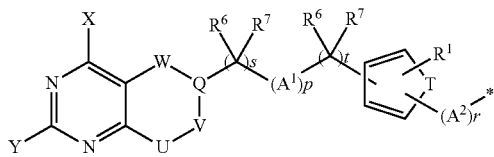

wherein * indicates the point of attachment to the linker;

X and Y are each-independently selected from the group consisting of halo, $R^2$, $OR^2$, $SR^3$, and $NR^4R^5$;

U, V, and W represent divalent moieties each independently selected from the group consisting of $-(R^{6a})C=$, $-N=$, $-(R^{6a})C(R^{7a})-$, and $-N(R^{4a})-$; Q is selected from the group consisting of C and CH; T is selected from the group consisting of S, O, N, and $-C=C-$;

$A^1$ and $A^2$ are each independently selected from the group consisting of oxygen, sulfur, $-C(Z)-$, $-C(Z)O-$, $-OC(Z)-$, $-N(R^{4b})-$, $-C(Z)N(R^{4b})-$, $-N(R^{4b})C(Z)-$, $-OC(Z)N(R^{4b})-$, $-N(R^{4b})C(Z)O-$, $-N(R^{4b})C(Z)N(R^{5b})-$, $-S(O)-$, $-S(O)_2-$, $-N(R^{4a})S(O)_2-$, $-C(R^{6b})(R^{7b})-$, $-N(C\equiv CH)-$, $-N(CH_2C\equiv CH)-$, $C_1$-$C_{12}$ alkylene, and $C_1$-$C_{12}$ alkyeneoxy, where Z is oxygen or sulfur;

$R^1$ is selected-from the group consisting of hydrogen, halo, $C_1$-$C_{12}$ alkyl, and $C_1$-$C_{12}$ alkoxy; $R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, $(C_1$-$C_{12}$ alkoxy)carbonyl, and $(C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group; $R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group; and n, p, r, s and t are each independently either 0 or 1 is described.

In another embodiment, the method or pharmaceutical composition of any one of the preceding embodiments wherein the folate is of the formula

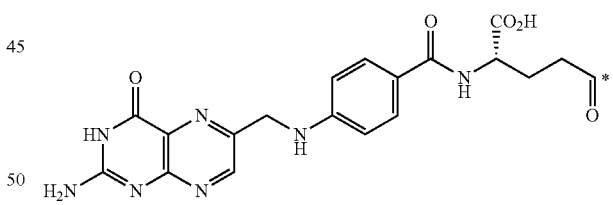

wherein * indicates the point of attachment to the linker is described.

In another embodiment, the method or pharmaceutical composition of any one of the preceding embodiments wherein $R^A$ and $R^B$ are hydrogen; $Y^A$ is $OCH_2CH_2OR^C$; and $R^C$ is a bond connected to L is described.

In another embodiment, the method or pharmaceutical composition of any one of the preceding embodiments wherein F is 2 and G is 1 is described.

In another embodiment, the method or pharmaceutical composition of any one of the preceding embodiments wherein the drug delivery conjugate is of the formula

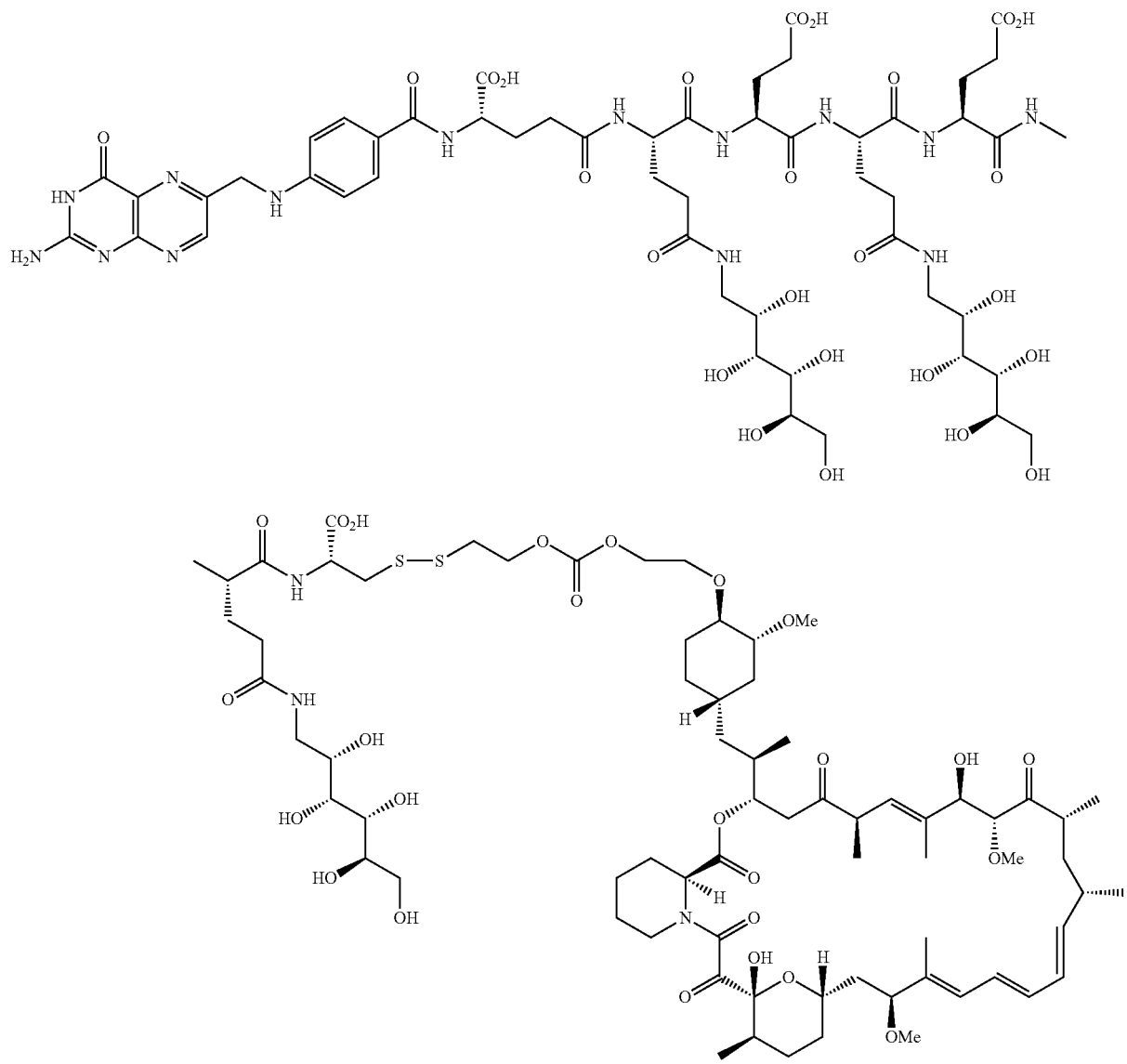

is described.

In another embodiment, the method or pharmaceutical composition of any one of the preceding embodiments wherein the composition further comprises one or more carriers, diluents, or excipients, or a combination thereof is described.

In another embodiment, the method or pharmaceutical composition of any one of the preceding embodiments wherein the purity of the drug delivery conjugate is at least 98% is described.

In another embodiment, the method or pharmaceutical composition of any one of the preceding embodiments wherein the composition is in a dosage form adapted for parenteral administration is described.

In another embodiment, the method or pharmaceutical composition of any one of the preceding embodiments wherein the dose of the drug delivery conjugate is in the range of 1 to 5 μg/kg is described.

In another embodiment, the method or pharmaceutical composition of any one of the preceding embodiments wherein the dose of the drug delivery conjugate is in the range of 1 to 3 μg/kg is described.

In another embodiment, the method or pharmaceutical composition of any one of the preceding embodiments wherein the disease is selected from the group consisting of arthritis, including rheumatoid arthritis and osteoarthritis, glomerulonephritis, proliferative retinopathy, restenosis, ulcerative colitis, Crohn's disease, fibromyalgia, psoriasis and other inflammations of the skin, osteomyelitis, Sjögren's syndrome, multiple sclerosis, diabetes, atherosclerosis, pulmonary fibrosis, lupus erythematosus, sarcoidosis, systemic sclerosis, organ transplant rejection (GVHD) and chronic inflammations is described.

In another embodiment, a kit comprising a sterile vial, the composition described in any of the preceding embodiments; and instructions for use describing use of the composition for treating a patient with an inflammatory disease is described.

In another embodiment, the kit of any one of the preceding embodiments wherein the folate is of the formula

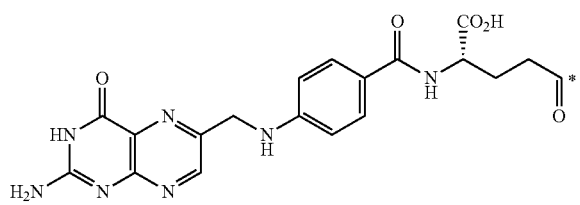

wherein * indicates the point of attachment to the linker is described.

In another embodiment, the kit of any one of the preceding embodiments wherein $R^A$ and $R^B$ are hydrogen; $Y^A$ is $OCH_2CH_2OR^C$; and $R^C$ is a bond connected to L is described.

In another embodiment, the kit of any one of the preceding embodiments wherein F is 2 and G is 1 is described.

In another embodiment, the kit of any one of the preceding embodiments wherein the drug delivery conjugate is of the formula is described.

In another embodiment, the kit of any one of the preceding embodiments wherein the composition is in the form of a reconstitutable lyophlizate is described.

In another embodiment, the kit of any one of the preceding embodiments wherein the dose of the drug delivery conjugate is in the range of 1 to 5 μg/kg is described.

In another embodiment, the kit of any one of the preceding embodiments wherein wherein the dose of the drug delivery conjugate is in the range of 1 to 3 μg/kg is described.

In another embodiment, the kit of any one of the preceding embodiments wherein the purity of the drug delivery conjugate is at least 98% is described.

The conjugates or compounds described herein may contain one or more chiral centers, or may otherwise be capable of existing as multiple stereoisomers. It is to be understood that in one embodiment, the invention described herein is not limited to any particular sterochemical requirement, and that the conjugates, compounds, and compositions, methods,

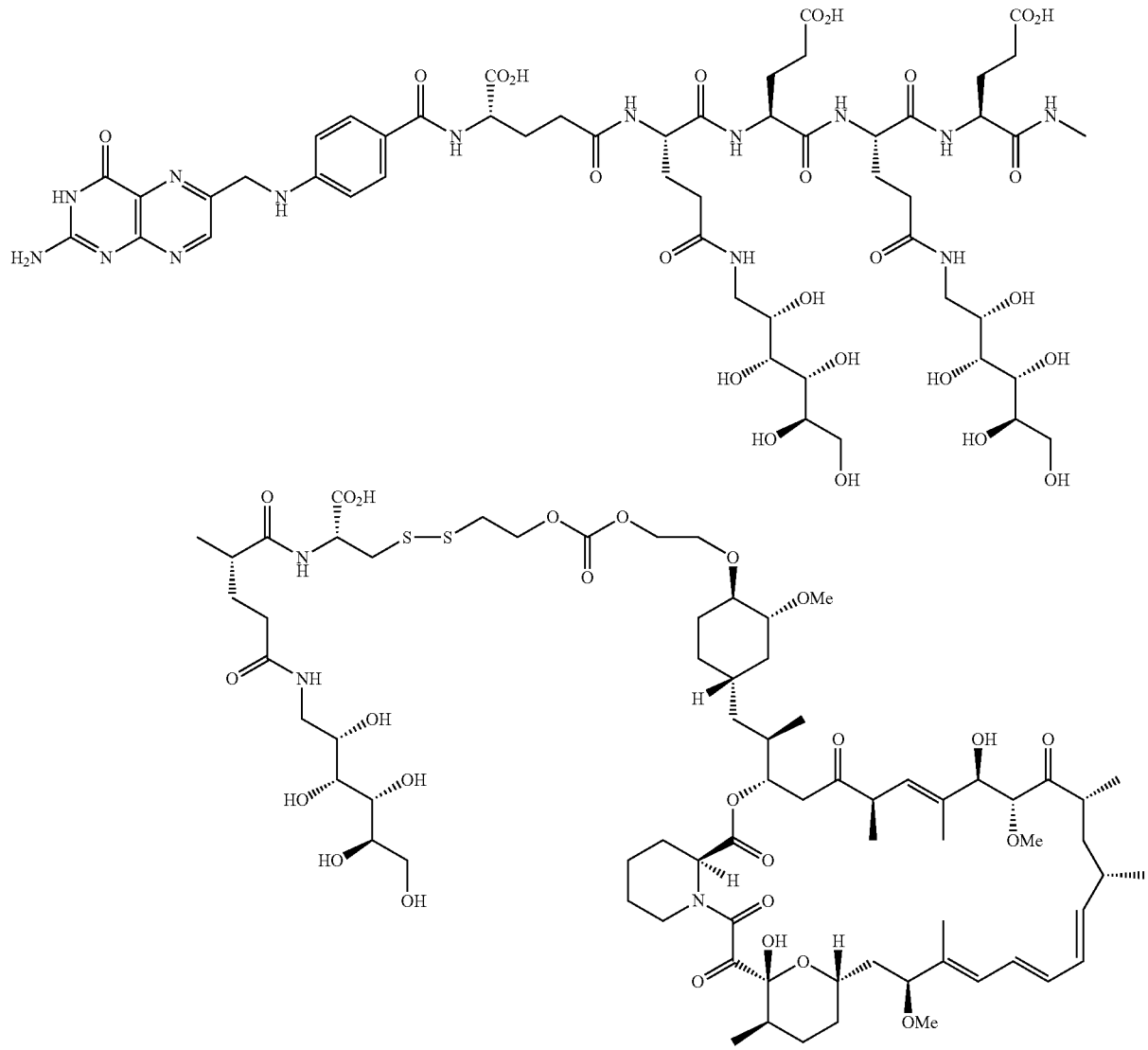

uses, and medicaments that include them may be optically pure, or may be any of a variety of steroisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds or conjugates described herein may be include geometric centers, such as cis, trans, E, and Z double bonds. It is to be understood that in another embodiment, the invention described herein is not limited to any particular geometric isomer requirement, and that the conjugates, compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. It is to be understood that alkyl is advantageously of limited length, including $C_1$-$C_{24}$, $C_1$-$C_{12}$, $C_1$-$C_8$, $C_1$-$C_6$, and $C_1$-$C_4$. It is appreciated herein that shorter alkyl groups add less lipophilicity to the conjugate and accordingly will have different pharmacokinetic behavior. As used herein, the term "cycloalkyl" includes a chain of carbon atoms, which is optionally branched, and where at least a portion of the chain is cyclic. It is to be understood that a chain forming cycloalkyl is advantageously of limited length, including $C_3$-$C_{24}$, $C_3$-$C_{12}$, $C_3$-$C_8$, $C_3$-$C_6$, and $C_3$-$C_4$. It is appreciated herein that shorter alkyl groups add less lipophilicity to the conjugate and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "heterocyclyl" including heterocycle includes a chain of atoms that includes both carbon and at least one heteroatom, and is optionally branched, where at least a portion of the chain is cyclic. Illustrative heteroatoms include nitrogen, oxygen, and sulfur. In certain variations, illustrative heteroatoms also include phosphorus, and selenium. Illustrative heteocycles include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2$N-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "optionally substituted amino" includes derivatives of amino as described herein, such as, but not limited to, acylamino, urea, and carbamate, and the like.

As used herein, the term "aryl" includes monocyclic and polycyclic aromatic carbocyclic and aromatic heterocyclic groups, each of which may be optionally substituted. As used herein, the term "heteroaryl" includes aromatic heterocyclic groups, each of which may be optionally substituted. Illustrative carbocyclic aromatic groups described herein include, but are not limited to, phenyl, naphthyl, and the like. Illustrative heterocyclic aromatic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like.

The term "optionally substituted aryl" as used herein includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like.

Illustrative substituents include, but are not limited to, a radical —$(CH_2)_mZ$, where m is an integer from 0-6 and Z is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or Z is selected from —$CO_2R^4$ and —$CONR^5R^6$, where $R^4$, $R^5$, and $R^6$ are each independently selected in each occurrence from hydrogen, $C_1$-$C_6$ alkyl, and aryl-$C_1$-$C_6$ alkyl.

The term "prodrug" as used herein generally refers to any conjugate that when administered to a biological system generates a biologically active conjugate as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the conjugate described herein by attaching groups, referred to as prodrug forming groups, that ultimately cleave in vivo to one or more functional groups present on the conjugate, such as —OH—, —SH, —CO$_2$H, —NR$_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the conjugates described herein. Further illustrative prodrugs for amino groups include, but are not limited to, (C$_3$-C$_{20}$)alkanoyl; halo-(C$_3$-C$_{20}$)alkanoyl; (C$_3$-C$_{20}$)alkenoyl; (C$_4$-C$_7$)cycloalkanoyl; (C$_3$-C$_6$)-cycloalkyl(C$_2$-C$_{16}$)alkanoyl; optionally substituted aroyl, such as unsubstituted aroyl or aroyl substituted by 1 to 3 substituents selected from the group consisting of halogen, cyano, trifluoromethanesulphonyloxy, (C$_1$-C$_3$)alkyl and (C$_1$-C$_3$)alkoxy, each of which is optionally further substituted with one or more of 1 to 3 halogen atoms; optionally substituted aryl(C$_2$-C$_{16}$)alkanoyl, such as the aryl radical being unsubstituted or substituted by 1 to 3 substituents selected from the group consisting of halogen, (C$_1$-C$_3$)alkyl and (C$_1$-C$_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, (C$_1$-C$_3$)alkyl, and (C$_1$-C$_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the conjugate described herein that is biologically active or is a precursor of the biologically active conjugate. However, it is appreciated that in some cases, the prodrug is biologically active. It is also appreciated that prodrugs may often serve to improve drug efficacy or safety through improved oral bioavailability, pharmacodynamic half-life, and the like. Prodrugs also refer to derivatives of the conjugates described herein that include groups that simply mask undesirable drug properties or improve drug delivery. For example, one or more conjugates described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

It is appreciated that such hydrophilic linkers may alter the stability, metabolism and tissue distribution of the conjugates. For example, it is understood that in certain situations, carbohydrate-protein interactions are weaker than peptide-protein interactions. Thus, it is appreciated that in various embodiments described herein, the conjugates may lead to lower binding of serum proteins. These and other physicochemical differences between the conjugates described herein and others already reported may include enhanced targeting to target cells and improved, i.e. more selective or differentially selective biodistribution profiles. The increased cyctotoxicity may be a natural consequence of the decreased serum protein binding or the better or differential biodistribution (i.e. less drug is wasted in non-specific compartments). This is especially true for the use of hydrophilic but neutral spacers. Without being bound by theory it is also suggested that the hydrophilic spacer linkers described herein may decrease toxicity that might be due at least in part to non-specific binding interactions.

In an alternate embodiment, the drug is linked to a hydrophilic spacer linker, directly or indirectly, to accomplish the goal of decreasing liver clearance. It has been found herein that the attachment of hydrophilic groups, either releasable or not, and more specifically hydrophilic neutral groups, increases renal-specific delivery.

It has been observed that liver clearance of folate-drug conjugates possessing disulfide linkers and peptidic spacers retain residual and sometimes substantial unfavorable toxicity profiles. Including the hydrophilic spacers described herein also introduced vectors for kidney-specific delivery. It is therefore appreciated that including such linkers in the drug delivery conjugates may decrease overall liver uptake and consequentially decrease overall toxicity. Without being bound by theory, it is appreciated that toxicity at MTD may be caused by non-specific liver clearance, leading to metabolism and release of free drug into bile and then the intestine. The local toxicity as well as systemic toxicity (due to re-absorption) might then occur. By including hydrophilic linkers in the conjugates described herein, it is believed that clearance through the kidney may preferentially occur, thus decreasing and/or avoiding concomitant liver metabolism based toxicity. Accordingly, measuring total bile clearance of the drug component from a series of drug-folate conjugates, may be used to predict which agent would be the least toxic.

As described above, the conjugates described herein may be used to deliver therapeutic agents A (e.g. drugs) to cells in a selective or specific manner. In one aspect of such delivery, unwanted clearance mechanisms may also be avoided. It has been discovered that the hydrophilic spacer linkers described herein when used to form conjugates of receptor binding ligands B and therapeutic agents A, can decrease the amount of clearance by the liver. It has further been discovered that these hydrophilic spacer linkers tend to favor clearance along renal pathways, such as the kidney. It has further been discovered that the conjugates described herein exhibit lower toxicity than the parent therapeutic agents A by themselves when administered in the same way. Without being bound by theory, it is suggested that the lower toxicity arises from the observed decrease in liver clearance mechanism in favor of renal clearance mechanisms.

In another embodiment, multi-drug conjugates are described herein. Several illustrative configurations of such multi-drug conjugates are contemplated herein, and include the compounds and configurations described in PCT international publication No. WO 2007/022494, the disclosure of which is incorporated herein by reference. In one aspect, the linker (L) can be a polyvalent linker. Illustratively, the polyvalent linkers may connect the folate receptor binding ligand B to the two or more therapeutic agents A (e.g. drug) in a variety of structural configurations In one illustrative embodiment, one of the therapeutic agents (e.g. drugs) is aminopterin or aminopterin hydrazide. If an additional drug is included in the conjugate, it can be a drug of formula I or a different drug.

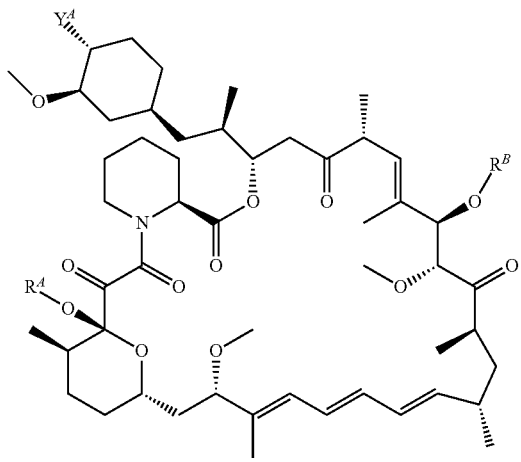

I wherein
$Y^A$ is $OR^C$ or $OCH_2CH_2OR^C$;
one of $R^A$, $R^B$, or $R^C$ is a bond connected to L; and
the other two of $R^A$, $R^B$, and $R^C$ are independently selected in each case from the group consisting of hydrogen, optionally substituted heteroalkyl, prodrug foming group, and $C(O)R^D$, where $R^D$ is in each instance independently selected from the group consisting of hydrogen, and alkyl, alkenyl, heteroalkyl, cycloalkyl, cycloheteroalkyl, aryl, arylalkyl, heteroaryl, and heteroarylalkyl, each of which is optionally substituted. If the second drug is a drug different than formula I, the second drug can be selected based on activity against one or more populations of pathogenic cells, such as inflammatory cells, with a particular mechanism of action. Illustrative mechanisms of action include alkylating agents, microtubule inhibitors, including those that stabilize and/or destabilize microtubule formation, including beta-tubulin agents, cyclin dependent kinase (CDK) inhibitors, topoisomerase inhibitors, protein synthesis inhibitors, protein kinase inhibitors, including inhibitors of Ras, Raf, PKC, PI3K, and like inhibitors, transcription inhibitor, antifolates, heat shock protein blockers, and the like.

Illustrative alkylating agents include, but are not limited to, mitomycins CBI, and the like. Illustrative cyclin dependent kinase (CDK) inhibitors include, but are not limited to, CYC202, seliciclib, R-roscovitine, AGM-1470, and the like. Illustrative topoisomerase inhibitors include, but are not limited to, doxorubicin, other anthracyclines, and the like. Illustrative protein synthesis inhibitors include, but are not limited to, bruceantin, and the like. Illustrative protein kinase inhibitors, including inhibitors of Ras, Raf, PKC, PI3K, and like inhibitors, include but are not limited to L-779,450, R115777, and the like. Illustrative transcription inhibitors include, but are not limited to, a-amanatin, actinomycin, and the like. Illustrative antifolates include, but are not limited to, methotrexate, aminopterin, and the like. Illustrative heat shock protein blockers include, but are not limited to, geldanamycin, and the like.

Illustrative microtubule inhibitors, including those that stabilize and/or destabilize microtubule formation, include β-tubulin agents, microtubule poisons, and the like. Illustrative microtubule poisons that bind to selected receptors include, but are not limited to, inhibitors binding to the vinca binding site such as arenastatin, dolastatin, halichondrin B, maytansine, phomopsin A, rhizoxin, ustiloxin, vinblastine, vincristine, and the like, stabilizers binding to the taxol binding site such as discodermalide, epothilone, taxol, paclitaxol, and the like, inhibitors binding to the colchicine binding site such as, colchicine, combretastatin, curacin A, podophyllotoxin, steganacine, and the like, and others binding to undefined sites such as cryptophycin, tubulysins, and the like.

In one embodiment, the tubulsyin is a naturally occurring tubulysin. In another embodiment, the tubulsyin is a synthetic or semi-synthetic tubulysin. Additional tubulysins that may be included in the conjugates described herein are described in PCT international application serial No. PCT/US2008/056824, the disclosure of which is incorporated herein by reference.

In one aspect of the drug delivery conjugates described herein, at least one of the drugs is an antifolate. In one illustrative example, the antifolate is aminopterin. In another illustrative example, the antifolate is aminopterin hydrazide. In other embodiments, where a second drug is included, the second drug can be a DNA alkylation agent. In another embodiment, the second drug can be a microtubule inhibitor.

In another embodiment of the drug delivery conjugates described herein, the second drug is a P-glycoprotein (PGP) inhibitor.

In another embodiment of the drug delivery conjugates described herein, the second drug is a drug having formula I.

In another embodiment of the drug delivery conjugates described herein, the second drug is a vinca alkaloid, or an analog or derivative thereof. Vinca alklaloids described herein include all members of the vinca indole-dihydroindole family of alkaloids, such as but not limited to vindesine, vinblastine, vincristine, catharanthine, vindoline, leurosine, vinorelbine, vinblastinoic acid, and the like, and analogs and derivatives thereof.

In another embodiment, methods for treating diseases caused by or evidenced by pathogenic cell populations, such as inflammatory cells, are described herein. The drug delivery conjugates can be used to treat disease states characterized by the presence of a pathogenic cell population, such as inflammatory cells, in the host wherein the members of the pathogenic cell population have an accessible binding site for the folate, or analog or derivative thereof, wherein the binding site is uniquely expressed, overexpressed, or preferentially expressed by the pathogenic cells. The selective elimination of the pathogenic cells is mediated by the binding of the drug delivery conjugate to a receptor (e.g., a folate receptor when the conjugate is folate targeted), which is uniquely expressed, overexpressed, or preferentially expressed by the pathogenic cells. A receptor (e.g., a folate receptor) uniquely expressed, overexpressed, or preferentially expressed by the pathogenic cells is not present or present at lower concentrations on non-pathogenic cells providing a means for selective elimination of the pathogenic cells.

For example, surface-expressed vitamin receptors, such as the high-affinity folate receptor, are overexpressed activated macrophages and activated monocytes. Accordingly, the drug delivery conjugates described herein can be used to treat a variety of inflammatory cell types that preferentially express folate receptors, and, thus, have surface accessible binding sites for ligands, such as folate, or folate analogs or derivatives. In one aspect, methods are described herein for targeting the conjugates to maximize targeting of the pathogenic cells for elimination.

The invention further contemplates the use of combinations of drug delivery conjugates to maximize targeting of the pathogenic cells, such as inflammatory cells, for elimination. In accordance with the invention "elimination", "eliminated", and "eliminating" a population of cells mean completely eliminating a population of cells, eliminating some cells, or reducing the symptoms of disease caused by the cells, such as inflammatory cells.

The drug delivery conjugates described herein can be used for both human clinical medicine and veterinary applications. Thus, the host animal harboring the population of pathogenic cells and treated with the drug delivery conjugates (e.g., a folate conjugate) can be human or, in the case of veterinary applications, can be a laboratory, agricultural, domestic, or wild animal. The methods described herein can be applied to host animals including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

The methods are applicable to populations of pathogenic cells that cause inflammation. For example, activated macrophages or activated monocytes capable of causing a disease state, such as inflammation, can be eliminated because they uniquely express, preferentially express, or overexpress folate receptors, or receptors that bind analogs or derivatives of folate. For example, the pathogenic cells can be inflammatory cells that are pathogenic under some circumstances such as cells of the immune system that are responsible for graft versus host disease, but not pathogenic under other circumstances.

In one embodiment, the drug delivery conjugates can be internalized into the targeted pathogenic cells upon binding of the binding ligand moiety (e.g. folate) to a receptor, transporter, or other surface-presented protein that specifically binds the ligand and which is preferentially expressed on the pathogenic cells. Such internalization can occur, for example, through receptor-mediated endocytosis. If the drug delivery conjugate contains a releasable linker, the B moiety and the drug can dissociate intracellularly and the drug can act on its intracellular target.

In an alternate embodiment, the B (e.g. folate) can bind to the pathogenic cell placing the drug in close association with the surface of the pathogenic cell. The drug can then be released by cleavage of the releasable linker. For example, the drug can be released by a protein disulfide isomerase if the releasable linker is a disulfide group. The drug can then be taken up by the pathogenic cell to which the drug delivery conjugate is bound, or the drug can be taken up by another pathogenic cell in close proximity thereto. Alternatively, the drug could be released by a protein disulfide isomerase inside the cell where the releasable linker is a disulfide group. The drug may also be released by a hydrolytic mechanism, such as acid-catalyzed hydrolysis, as described above for certain beta elimination mechanisms, or by an anchimerically assisted cleavage through an oxonium ion or lactonium ion producing mechanism. The selection of the releasable linker or linkers will dictate the mechanism by which the drug is released from the conjugate. It is appreciated that such a selection can be pre-defined by the conditions wherein the drug conjugate will be used. Alternatively, the drug delivery conjugates can be internalized into the targeted cells upon binding, and the receptor binding ligand (B) and the drug can remain associated intracellularly with the drug exhibiting its effects without dissociation from the vitamin moiety.

In still another embodiment where the receptor binding ligand (B) is a folate, the drug delivery conjugate can act through a mechanism independent of cellular folate receptors. For example, the drug delivery conjugates can bind to soluble folate receptors present in the serum or to serum proteins, such as albumin, resulting in prolonged circulation of the conjugates relative to the unconjugated drug, and in increased activity of the conjugates towards the pathogenic cell population, such as inflammatory cells, relative to the unconjugated drug.

In another embodiment, where the linker (L) does not comprise a releasable linker, and B is folate, the folate moiety of the drug delivery conjugate can bind to the pathogenic cell placing the drug on the surface of the pathogenic cell to target the pathogenic cell for attack by other molecules capable of binding to the drug. Alternatively, in this embodiment, the drug delivery conjugates can be internalized into the targeted cells upon binding, and the vitamin moiety and the drug can remain associated intracellularly with the drug exhibiting its effects without dissociation from the folate.

The drug delivery conjugates described herein can comprise a receptor binding ligand (B) (e.g. a folate), a linker (L), a drug, and, optionally, heteroatom linkers to link the receptor binding ligand (B) and the drug to the linker (L). The linker (L) can comprise a spacer linker, a releasable (i.e., cleavable) linker, and an heteroatom linker, or combinations thereof.

In one embodiment, the drug is aminopterin. In another embodiment, a second drug may be present. Suitable second drugs can include, but are not limited to: peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; toxins; analgesics; bronchodilators; beta-blockers; antihypertensive agents; cardiovascular agents including antiarrhythmics, cardiac glycosides, antianginals and vasodilators; central nervous system agents including stimulants, psychotropics, antimanics, and depressants; antihistamines; tranquilizers; anti-depressants; II-2 antagonists; anticonvulsants; antinauseants; prostaglandins and prostaglandin analogs; muscle relaxants; anti-inflammatory substances; stimulants; decongestants; antiemetics; diuretics; antispasmodics; antiasthmatics; cough suppressants; mucolytics; mineral and nutritional additives;

adrenocorticoids and corticosteroids; alkylating agents; antiandrogens; antiestrogens; androgens; aclamycin and aclamycin derivatives; estrogens; antimetabolites such as cytosine arabinoside; purine analogs; pyrimidine analogs; and methotrexate; busulfan; carboplatin; chlorambucil; cisplatin and other platinum compounds; tamoxiphen; taxol; paclitaxel; paclitaxel derivatives; Taxotere®; cyclophosphamide; daunomycin; daunorubicin; doxorubicin; rhizoxin; T2 toxin; plant alkaloids; prednisone; hydroxyurea; teniposide; mitomycins; discodermolides; microtubule inhibitors; epothilones; tubulysin; cyclopropyl benz[e]indolone; seco-cyclopropyl benz[e]indolone; O-Ac-seco-cyclopropyl benz[e]indolone; bleomycin and any other antibiotic; nitrogen mustards; nitrosureas; vincristine; vinblastine; analogs and derivative thereof such as deacetylvinblastine monohydrazide; and other vinca alkaloids; including those described in PCT international publication No. WO 2007/022493; the disclosure of which is incorporated herein by reference; colchicine; colchicine derivatives; allocolchicine; thiocolchicine; trityl cysteine; Halicondrin B; dolastatins such as dolastatin 10; amanitins such as a-amanitin; camptothecin; irinotecan; and other camptothecin derivatives thereof; maytansines; geldanamycin and geldanamycin derivatives; estramustine; nocodazole; MAP4; colcemid; inflammatory and proinflammatory agents; peptide and peptidomimetic signal transduction inhibitors; and any other art-recognized drug or toxin.

In another embodiment, the second drug can be selected from a vinca alkaloid, such as DAVLBH, a cryptophycin, bortezomib, thiobortezomib, a tubulysin, aminopterin, rapamycin, paclitaxel, docetaxel, doxorubicin, daunorubicin, everolimus, α-amanatin, verucarin, didemnin B, geldanamycin, purvalanol A, ispinesib, budesonide, dasatinib, an epothilone, a maytansine, and a tyrosine kinase inhibitor, including analogs and derivatives of the foregoing. In one variation, the therapeutic agents (A) (e.g. drugs) are the same and are antifolate compounds. In one variation, the therapeutic agents (A) (e.g. drugs) are the same and are aminopterin hydrazide. In another variation, the therapeutic agents (A) (e.g. drugs) are different, but at least one of the therapeutic agents (A) is an antifolate.

In one embodiment, the drugs for use in the methods described herein remain stable in serum for at least 4 hours. In another embodiment the drugs have an $IC_{50}$ in the nanomolar range, and, in another embodiment, the drugs are water soluble. If the drug is not water soluble, the linker (L) can be derivatized to enhance water solubility. The term "drug" also means any of the drug analogs or derivatives described hereinabove. It should be appreciated that in accordance with this invention, a drug analog or derivative can mean a drug that incorporates a heteroatom through which the drug analog or derivative is covalently bound to the linker (L).

The drug delivery conjugates can comprise a receptor binding ligand (B) (e.g. a folate), a linker (L), a drug, and, optionally, heteroatom linkers to link the receptor binding ligand (B) and the drug to the linker (L). In one illustrative embodiment, it should be appreciated that a folate analog or derivative can mean a folate that incorporates a heteroatom through which the folate analog or derivative is covalently bound to the linker (L). Thus, in this illustrative embodiment, the folate can be covalently bound to the linker (L) through a heteroatom linker, or a vitamin analog or derivative (i.e., incorporating an heteroatom) can be directly bound to the linker (L). In similar illustrative embodiments, a drug analog or derivative is a drug, and a drug analog or derivative can mean a drug that incorporates an heteroatom through which the drug analog or derivative is covalently bound to the linker (L). Thus, in these illustrative aspects, the drug can be covalently bound to the linker (L) through an heteroatom linker, or a drug analog or derivative (i.e., incorporating an heteroatom) can be directly bound to the linker (L). The linker (L) can comprise a spacer linker, a releasable (i.e., cleavable) linker, and a heteroatom linker to link the spacer linker to the releasable linker in conjugates containing both of these types of linkers. The linker can be a bivalent linker.

Generally, any manner of forming a conjugate between the linker (L) and the folate or analog or derivative thereof, between the linker (L) and the drug, or analog or derivative thereof, including any intervening heteroatom linkers, can be utilized. Also, any art-recognized method of forming a conjugate between the spacer linker, the releasable linker, and the heteroatom linker to form the bivalent linker can be used. The conjugate can be formed by direct conjugation of any of these molecules, for example, through complexation, or through hydrogen, ionic, or covalent bonds. Covalent bonding can occur, for example, through the formation of amide, ester, disulfide, or imino bonds between acid, aldehyde, hydroxy, amino, sulfhydryl, or hydrazo groups.

In another embodiment, the (L) linker includes a chain of atoms selected from C, N, O, S, Si, and P that covalently connects the receptor binding ligand (B), the hydrophilic linker, and/or the therapeutic agent (A). The linker (L) may have a wide variety of lengths, such as in the range from about 2 to about 100 atoms. The atoms used in forming the linker (L) may be combined in all chemically relevant ways, such as chains of carbon atoms forming alkylene, alkenylene, and alkynylene groups, and the like; chains of carbon and oxygen atoms forming ethers, polyoxyalkylene groups, or when combined with carbonyl groups forming esters and carbonates, and the like; chains of carbon and nitrogen atoms forming amines, imines, polyamines, hydrazines, hydrazones, or when combined with carbonyl groups forming amides, ureas, semicarbazides, carbazides, and the like; chains of carbon, nitrogen, and oxygen atoms forming alkoxyamines, alkoxylamines, or when combined with carbonyl groups forming urethanes, amino acids, acyloxylamines, hydroxamic acids, and the like; and many others. In addition, it is to be understood that the atoms forming the chain in each of the foregoing illustrative embodiments may be either saturated or unsaturated, such that for example, alkanes, alkenes, alkynes, imines, and the like may be radicals that are included in the linker (L). In addition, it is to be understood that the atoms forming the linker (L) may also be cyclized upon each other to form divalent cyclic structures that form the linker, including cyclo alkanes, cyclic ethers, cyclic amines, arylenes, heteroarylenes, and the like in the linker (L). The linker (L) may be bivalent.

In another embodiment, pharmaceutical compositions comprising an amount of a drug delivery conjugate effective to eliminate a population of pathogenic cells, such as inflammatory cells, in a host animal when administered in one or more doses are described. The drug delivery conjugate is preferably administered to the host animal parenterally, e.g., intradermally, subcutaneously, intramuscularly, intraperitoneally, intravenously, or intrathecally. Alternatively, the drug delivery conjugate can be administered to the host animal by other medically useful processes, such as orally, and any effective dose and suitable therapeutic dosage form, including prolonged release dosage forms, can be used.

Examples of parenteral dosage forms include aqueous solutions of the conjugates, in an isotonic saline, 5% glucose or other well-known pharmaceutically acceptable liquid carriers such as liquid alcohols, glycols, esters, and amides. The parenteral dosage form can be in the form of a reconstitutable lyophilizate comprising the dose of the drug delivery conjugate. In one aspect of the present embodiment, any of a number of prolonged release dosage forms known in the art can be administered such as, for example, the biodegradable carbohydrate matrices described in U.S. Pat. Nos. 4,713,249; 5,266,333; and 5,417,982, the disclosures of which are incorporated herein by reference, or, alternatively, a slow pump (e.g., an osmotic pump) can be used.

In one illustrative aspect, at least one additional composition comprising a therapeutic factor can be administered to the host in combination or as an adjuvant to the above-detailed methodology, to enhance the drug delivery conjugate-mediated elimination of the population of pathogenic cells, or more than one additional therapeutic factor can be administered. The therapeutic factor can be selected from a chemotherapeutic agent, or another therapeutic factor capable of complementing the efficacy of the administered drug delivery conjugate.

In one illustrative aspect, therapeutically effective combinations of these factors can be used. In one embodiment, for example, therapeutically effective amounts of the therapeutic factor, for example, in amounts ranging from about 0.1 MIU/m$^2$/dose/day to about 15 MIU/m$^2$/dose/day in a multiple dose daily regimen, or for example, in amounts ranging from about 0.1 MIU/m$^2$/dose/day to about 7.5 MIU/m$^2$/dose/day in a multiple dose daily regimen, can be used along with the drug delivery conjugates to eliminate, reduce, or neutralize pathogenic cells in a host animal harboring the pathogenic cells (MIU=million international units; m$^2$=approximate body surface area of an average human).

Additionally, more than one type of drug delivery conjugate can be used. Illustratively, for example, the patient can be treated with conjugates with different vitamins (e.g. folates), but the same drug in a co-dosing protocol. In other embodiments, the patient can be treated with conjugates comprising the same receptor binding ligand (B) (e.g. a folate) linked to different drugs, or various receptor binding ligands (B) linked to various drugs. In another illustrative embodiment, drug delivery conjugates with the same or different vitamins (e.g. folates), and the same or different drugs comprising multiple vitamins and multiple drugs as part of the same drug delivery conjugate could be used.

The unitary daily dosage of the drug delivery conjugate can vary significantly depending on the host condition, the specific inflammatory disease state being treated, the molecular weight of the conjugate, its route of administration and tissue distribution, and the possibility of co-usage of other therapeutic treatments such as radiation therapy. The effective amount to be administered to a patient is based on body surface area, patient weight, and physician assessment of patient condition. In illustrative embodiments, effective doses can range, for example, from about 1 ng/kg to about 10 mg/kg, from about 100 ng to about 1 mg, from about 1 µg/kg to about 500 µg/kg, from about 1 µg/kg to about 100 µg/kg, from about 1 µg/kg to about 50 µg/kg, and from about 1 µg/kg to about 10 µg/kg. The reference to kg is kg of patient body weight.

In another illustrative aspect, any effective regimen for administering the drug delivery conjugates can be used. For example, the drug delivery conjugates can be administered as single doses, or can be divided and administered as a multiple-dose daily regimen. In other embodiments, a staggered regimen, for example, one to three days per week can be used as an alternative to daily treatment, and such intermittent or staggered daily regimen is considered to be equivalent to every day treatment and within the scope of the methods described herein. In one embodiment, the patient is treated with multiple injections of the drug delivery conjugate to eliminate the population of pathogenic cells, such as inflammatory cells. In another embodiment, the patient is injected multiple times (preferably about 2 up to about 50 times) with the drug delivery conjugate, for example, at 12-72 hour intervals or at 48-72 hour intervals. In other embodiments, additional injections of the drug delivery conjugate can be administered to the patient at an interval of days or months after the initial injections(s) and the additional injections prevent recurrence of the disease state caused by the pathogenic cells, such as inflammatory cells.

In one embodiment, folates, or analogs or derivatives thereof that can be used in the drug delivery conjugates include those that bind to folate receptors expressed specifically on activated macrophages or activated monocytes. The folate-linked conjugates, for example, can be used to kill or suppress the activity of activated macrophages or activated monocytes that cause disease states in the patient. Such conjugates, when administered to a patient suffering from inflammation, work to concentrate and associate the conjugated drug in the population of inflammatory cells to kill the inflammatory cells or suppress their function. Elimination, reduction, or deactivation of the inflammatory cell population works to stop or reduce the pathogenesis characteristic of the disease state being treated. Exemplary of inflammatory diseases include arthritis, including rheumatoid arthritis and osteoarthritis, glomerulonephritis, proliferative retinopathy, restenosis, ulcerative colitis, Crohn's disease, fibromyalgia, psoriasis and other inflammations of the skin, inflammations of the eye, including uveitis and autoimmune uveitis, osteomyelitis, Sjögren's syndrome, multiple sclerosis, diabetes, atherosclerosis, pulmonary fibrosis, lupus erythematosus, sarcoidosis, systemic sclerosis, organ transplant rejection (GVHD) and chronic inflammations is described Administration of the drug delivery conjugate is typically continued until symptoms of the disease state are reduced or eliminated.

As used herein the term uveitis generally refers to an intraocular inflammatory disease including iritis, cyclitis, panuveits, posterior uveitis and anterior uveitis. Iritis is inflammation of the iris. Cyclitis is inflammation of the ciliary body. Panuveitis refers to inflammation of the entire uveal (vascular) layer of the eye. Intermediate uveitis, also called peripheral uveitis, is centered in the area immediately behind the iris and lens in the region of the ciliary body and pars plana, and is also termed "cyclitis" and "pars planitis."

Autoimmune uveitis may occur as a component of an autoimmune disorder (such as rheumatoid arthritis, Bechet's disease, ankylosing spondylitis, sarcoidosis, and the like), as an isolated immune mediated ocular disorder (such as pars planitis or iridocyclitis, and the like), as a disease unassociated with known etiologies, and following certain systemic diseases which cause antibody-antigen complexes to be deposited in the uveal tissues.

Illustratively, the drug delivery conjugates administered to kill inflammatory cells or suppress their function can be administered parenterally to the animal or patient suffering from the disease state, for example, intradermally, subcutaneously, intramuscularly, intraperitoneally, or intravenously in combination with a pharmaceutically acceptable carrier. In another embodiment, the drug delivery conjugates can be administered to the animal or patient by other medically useful procedures and effective doses can be administered in standard or prolonged release dosage forms. In another aspect, the therapeutic method can be used alone or in combination with other therapeutic methods recognized for treatment of inflammation.

In other embodiments of the methods described herein, pharmaceutically acceptable salts of the conjugates described herein can be used. Pharmaceutically acceptable salts of the conjugates described herein include the acid addition and base salts thereof.

Suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts of the conjugates described herein are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemi-salts of acids and bases may also be formed, for example, hemi-sulphate and hemi-calcium salts.

In various embodiments of the methods described herein, the conjugates described herein may be administered alone or in combination with one or more other conjugates described herein or in combination with one or more other drugs (or as any combination thereof). In one embodiment, the conjugates described herein may be administered as a formulation in association with one or more pharmaceutically acceptable carriers. The carriers can be excipients. The choice of carrier will to a large extent depend on factors such as the particular mode of administration, the effect of the carrier on solubility and stability, and the nature of the dosage form. Pharmaceutical compositions suitable for the delivery of conjugates described herein and methods for their preparation will be readily apparent to those skilled in the art. Such compositions and methods for their preparation may be found, for example, in Remington: The Science & Practice of Pharmacy, 21th Edition (Lippincott Williams & Wilkins, 2005), incorporated herein by reference.

In one illustrative aspect, a pharmaceutically acceptable carrier includes any and all solvents, dispersion media, coatings, antibacterial and antifungal agents, isotonic and absorption delaying agents, and the like, and combinations thereof, that are physiologically compatible. In some embodiments, the carrier is suitable for parenteral administration. Pharmaceutically acceptable carriers include sterile aqueous solutions or dispersions and sterile powders for the extemporaneous preparation of sterile injectable solutions or dispersions.

In various embodiments, liquid formulations may include suspensions and solutions. Such formulations may comprise a carrier, for example, water, ethanol, polyethylene glycol, propylene glycol, methylcellulose or a suitable oil, and one or more emulsifying agents and/or suspending agents. Liquid formulations may also be prepared by the reconstitution of a solid, for example, from a sachet.

In one embodiment, an aqueous suspension may contain the conjugates described herein in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ascorbic acid, ethyl, n-propyl, or p-hydroxybenzoate; or one or more coloring agents.

In one illustrative embodiment, dispersible powders and granules suitable for preparation of an aqueous suspension by the addition of water provide the conjugate in admixture with a dispersing or wetting agent, suspending agent and one or more preservatives. Additional excipients, for example, coloring agents, may also be present.

Suitable emulsifying agents may be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate.

In other embodiments, isotonic agents, for example, sugars, polyalcohols such as mannitol, sorbitol, or sodium chloride can be included in the composition. Prolonged absorption of the injectable compositions can be brought about by including in the composition an agent which delays absorption, for example, monostearate salts and gelatin.

In one aspect, a conjugate as described herein may be administered directly into the blood stream, into muscle, or into an internal organ. Suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. Suitable means for parenteral administration include needle (including microneedle) injectors, needle-free injectors and infusion techniques.

In one illustrative aspect, parenteral formulations are typically aqueous solutions which may contain carriers or excipients such as salts, carbohydrates and buffering agents (preferably at a pH of from 3 to 9), but, for some applications, they may be more suitably formulated as a sterile non-aqueous solution or as a dried form to be used in conjunction with a suitable vehicle such as sterile, pyrogen-free water. In other embodiments, any of the liquid formulations described herein may be adapted for parenteral administration of the conjugates described herein. The preparation of parenteral formulations under sterile conditions, for example, by lyophilization under sterile conditions, may readily be accomplished using standard pharmaceutical techniques well known to those skilled in the art. In one embodiment, the solubility of a conjugate used in the preparation of a parenteral formulation may be increased by the use of appropriate formulation techniques, such as the incorporation of solubility-enhancing agents.

In various embodiments, formulations for parenteral administration may be formulated to be for immediate and/or modified release. In one illustrative aspect, conjugates of the invention may be administered in a time release formulation, for example in a composition which includes a slow release polymer. The conjugates can be prepared with carriers that will protect the conjugates against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PGLA). Methods for the preparation of such formulations are generally known to those skilled in the art. In another embodiment, the conjugates described herein or compositions comprising the conjugates may be continuously administered, where appropriate.

In one embodiment, sterile injectable solutions can be prepared by incorporating the conjugate in the required amount in an appropriate solvent with one or a combination of ingredients described above, as required, followed by filtered sterilization. Typically, dispersions are prepared by incorporating the conjugate into a sterile vehicle which contains a dispersion medium and any additional ingredients from those described above. In the case of sterile powders for the preparation of sterile injectable solutions, the preferred methods of preparation are vacuum drying and freeze-drying which yields a powder of the conjugate plus any additional desired ingredient from a previously sterile-filtered solution thereof.

The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. In one embodiment, the proper fluidity can be maintained, for example, by the use of a coating such as lecithin, by the maintenance of the required particle size in the case of dispersion and by the use of surfactants.

In one embodiment, compositions described herein comprise a drug delivery conjugate having a purity of at least 90%. In another embodiment, the drug delivery conjugate has a purity of at least 95%. In another embodiment, the drug delivery conjugate has a purity of at least 96%. In another embodiment, the drug delivery conjugate has a purity of at least 97%. In another embodiment, the drug delivery conjugate has a purity of at least 98%. In another embodiment, the drug delivery conjugate has a purity of at least 99%.

The drug delivery conjugates described herein can be prepared by art-recognized synthetic methods. The synthetic methods are chosen depending upon the selection of the optionally addition heteroatoms or the heteroatoms that are already present on the spacer linkers, releasable linkers, the drug, and/or or the receptor binding ligand (B). In general, the relevant bond forming reactions are described in Richard C. Larock, "Comprehensive Organic Transformations, a guide to functional group preparations," VCH Publishers, Inc. New York (1989), and in Theodora E. Greene & Peter G. M. Wuts, "Protective Groups ion Organic Synthesis," 2d edition, John Wiley & Sons, Inc. New York (1991), the disclosures of which are incorporated herein by reference. Additional details for preparing functional groups, including amides and esters, ketals and acetals, succinimides, silyloxys, hydrazones, acyl hydrazines, semicarbazones, disulfides, carbonates, sulfonates, and the like contained in the linker, including releasable linkers are described in U.S. patent application publication No. US 2005/0002942 A1, incorporated herein by reference in its entirety.

General formation of folate-peptides. The folate-containing peptidyl fragment Pte-Glu-$(AA)_n$-NH$(CHR_2)CO_2H$ (3) can be prepared by a polymer-supported sequential approach using standard methods, such as the Fmoc-strategy on an acid-sensitive Fmoc-AA-Wang resin (1), as shown in Scheme 1.

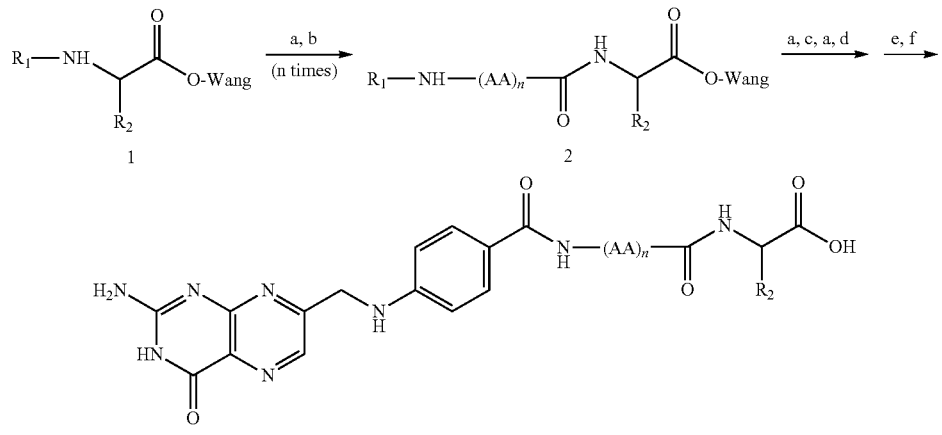

(a) 20% piperidine/DMF; (b) Fmoc—AA—OH, PyBop, DIPEA, DMF; (c) Fmoc-Glu(O-t-Bu)-OH, PyBop, DIPEA, DMF; (d) 1. $N^{10}$(TFA)-Pte-OH; PyBop, DIPEA, DMSO; (e) TFAA,$(CH_2SH)_2$, i-$Pr_3SiH$; (f) $NH_4OH$, pH 10.3.

In this illustrative embodiment of the processes described herein, $R_1$ is Fmoc, $R_2$ is the desired appropriately-protected amino acid side chain, and DIPEA is diisopropylethylamine. Standard coupling procedures, such as PyBOP and others described herein or known in the art are used, where the coupling agent is illustratively applied as the activating reagent to ensure efficient coupling. Fmoc protecting groups are removed after each coupling step under standard conditions, such as upon treatment with piperidine, tetrabutylammonium fluoride (TBAF), and the like. Appropriately protected amino acid building blocks, such as Fmoc-Glu-OtBu, $N^{10}$-TFA-Pte-OH, and the like, are used, as described in Scheme 1, and represented in step (b) by Fmoc-AA-OH.

Thus, AA refers to any amino acid starting material that is appropriately protected. It is to be understood that the term amino acid as used herein is intended to refer to any reagent having both an amine and a carboxylic acid functional group separated by one or more carbons, and includes the naturally occurring alpha and beta amino acids, as well as amino acid derivatives and analogs of these amino acids. In particular, amino acids having side chains that are protected, such as protected serine, threonine, cysteine, aspartate, and the like may also be used in the folate-peptide synthesis described herein. Further, gamma, delta, or longer homologous amino acids may also be included as starting materials in the folate-peptide synthesis described herein. Further, amino acid analogs having homologous side chains, or alternate branching structures, such as norleucine, isovaline, β-methyl threonine, β-methyl cysteine, β,β-dimethyl cysteine, and the like, may also be included as starting materials in the folate-peptide synthesis described herein.

The coupling sequence (steps (a) & (b)) involving Fmoc-AA-OH is performed "n" times to prepare solid-support peptide 2, where n is an integer and may equal 0 to about 100. Following the last coupling step, the remaining Fmoc group is removed (step (a)), and the peptide is sequentially coupled to a glutamate derivative (step (c)), deprotected, and coupled to TFA-protected pteroic acid (step (d)). Subsequently, the peptide is cleaved from the polymeric support upon treatment with trifluoroacetic acid, ethanedithiol, and triisopropylsilane (step (e)). These reaction conditions result in the simultaneous removal of the t-Bu, t-Boc, and Trt protecting groups that may form part of the appropriately-protected amino acid side chain. The TFA protecting group is removed upon treatment with base (step (f)) to provide the folate-containing peptidyl fragment 3.

In each of the foregoing synthetic processes, the intermediates may be coupled with any additional hydrophilic spacer linkers, other spacer linkers, releasable linkers, or the therapeutic agent A. In variations of each of the foregoing processes, additional hydrophilic spacer linkers, other spacer linkers, or releasable linkers may be inserted between the receptor binding ligand B and the indicated hydrophilic spacer linkers. In addition, it is to be understood that the left-to-right arrangement of the bivalent hydrophilic spacer linkers is not limiting, and accordingly, the therapeutic agent A, the receptor binding ligand B, additional hydrophilic spacer linkers, other spacer linkers, and/or releasable linkers may be attached to either end of the hydrophilic spacer linkers described herein.

METHOD EXAMPLES

Example

Adjuvant-Induced Arthritis (AIA) Model

Female Lewis rats were fed a folate-deficient diet (Harlan Teklad, Indianapolis, Ind.) for 9-10 days prior to arthritis induction. The adjuvant-induced arthritis (AIA) was induced by intradermal inoculation (at the base of tail) of 0.5 mg of heat-killed *Mycobacteria butyricum* (BD Diagnostic Systems, Sparks, Md.) in 100 μL light mineral oil (Sigma). Ten days after arthritis induction, paw edema in rats was assessed using a modified arthritis scoring system: 0=no arthritis; 1=swelling in one type of joint; 2=swelling in two types of joint; 3=swelling in three types of joint; 4=swelling of the entire paw. A total score for each rat is calculated by summarizing the scores for each of the four paws, giving a maximum score of 16 for each rat. On Day 10 post arthritis induction, rats with a total arthritis score of ≥2 were removed from the study and the remaining rats were distributed evenly across the control and treatment groups (n=5 for all groups except that n=2-3 for healthy controls). All treatments started on Day 10 unless mentioned otherwise.

Example

EC0746 Demonstrated FR-Mediated Inhibition of DHFR, Viability, and LPS-Stimulated TNF-α Production in RAW264.7 Cells RAW264.7 cells were treated with vehicle (medium), EC0746 (100 nM) without or with 100-fold excess free folate, aminopterin (AMT, 100 nM), methotrexate (MTX, 100 nM), or excess free folate alone (10 μM). After 1 h incubation, the drug-containing media were replaced with fresh medium and the cells were allowed to incubate further for 24 h. At the end of incubation, the cells were lysed and the DHFR activity in cell lysates was measured using a commercial DHFR assay kit (Sigma-Aldrich, Saint Louis, Mo.). See FIG. 1.

Figure 2A:
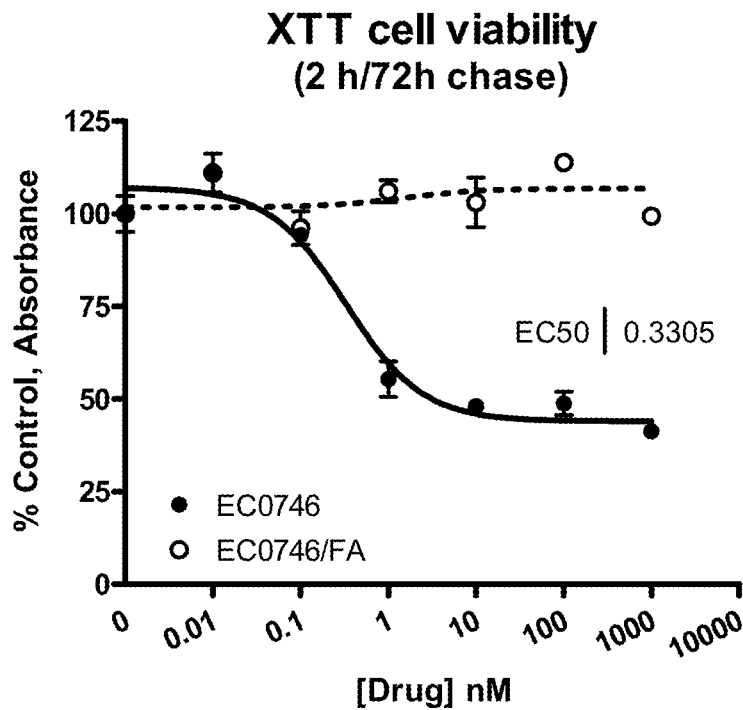
FIG. 2A—Viability of RAW264.7 cells, measured using the XTT assay, treated with EC0746 ($EC_{50}$ 0.33 nM, 2 hour treatment followed by 72 hours in treatment-free medium) and treated with EC0746 and excess folic acid (EC0746/FA, 2 hour treatment followed by 72 hours in treatment-free medium).
Figure 2B:
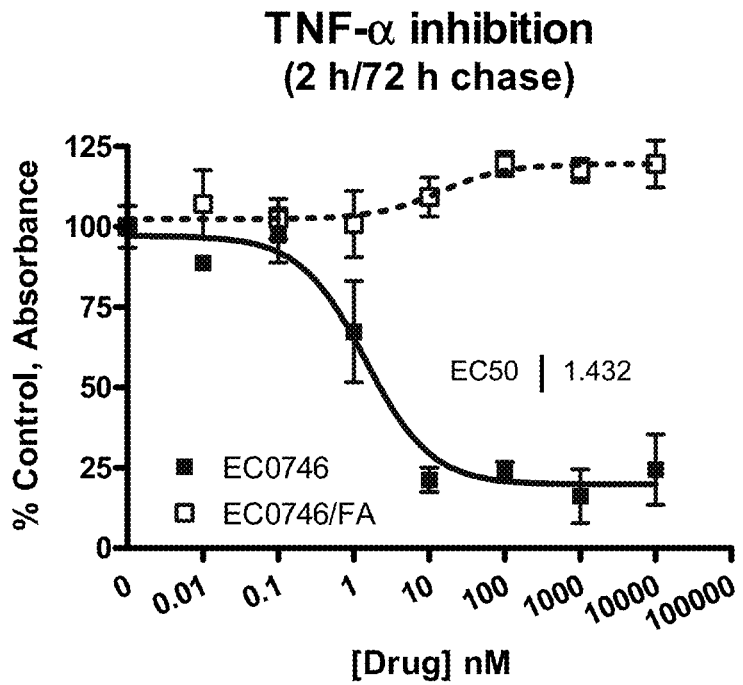
FIG. 2B—Inhibition of LPS-stimulated TNF-a production in RAW264.7 cells treated with EC0746 ($EC_{50}$ 1.43 nM, 2 hour treatment followed by 72 hours in treatment-free medium) and treated with EC0746 and excess folic acid (EC0746/FA, 2 hour treatment followed by 72 hours in treatment-free medium).

For XTT cell viability and TNF-a inhibition assays. RAW264.7 cells in 96-well plates were treated with vehicle (culture medium) or 10-fold serial dilutions of EC0746 without or with 100-fold excess free folate. After 2 h incubation, the drug-containing media were replaced and the cells were allowed to incubate further for 70 h. Four hours prior to the end of incubation, LPS was added to the treated cells at a final concentration of 100 ng/mL. 100 μL of the culture supernatants were collected for TNF-α analysis using a commercial ELISA kit. See FIG. 2B. The cell viability was assessed by adding XTT (2,3-bis(2-methoxy-4-nitro-5-sulfo-phenyl)-2H-tetrazolium-5-carboxanilide) to the remaining medium for an additional 4 h following the manufacturer's instructions (Roche Applied Science, Indianapolis, Ind.) See FIG. 2A. Both results were expressed as % absorbance (minus background) relative to untreated control in triplicates. The results demonstrated that EC0746 inhibited the viability of RAW264.7 cells and the ability of these cells to produce TNF-α in response to LPS.

Example

EC0746 Inhibited Lps-Stimulated Cytokine Production from Thioglycollate-Elicited Macrophages in A Fr-Dependent Manner To obtain thioglycollate-elicited macrophages, female Lewis rats were dosed once intraperitoneally with an aged thioglycollate medium (20 ml/kg) and euthanized 3 days later. The peritoneal cavity of the animals was lavaged with 60-70 ml of ice-cold PBS buffer to collect peritoneal extrudate. Thioglycollate-elicited macrophages in the peritoneal fluids were obtained after a red cell lysing step and a 2-hour adherence in cell culture medium containing 1% heat-inactivated fetal bovine serum.

Rat thioglycollate-elicited macrophages were treated with medium only, methotrexate (100 nM), aminopterin (100 nM), EC0746 (100 nM) without or with 100-fold excess free folate (10 μM), or excess free folate alone (10 μM). The drug-containing media were removed after 2 h incubation and the cells were allowed to incubate further for an additional 70 h in fresh medium. Twenty-four hours prior to the end of incubation, LPS (5 μg/mL) and IFN-γ (100 ng/mL) were added to the above cells to stimulate cytokine production. Cytokines (TNF-α, IL-1α, IL-6, IL-10, MIP-1α, etc.)

released into the cell culture medium were measured using a rat cytokine array assay kit (R&D Systems, Minneapolis, Minn.). See FIG. 3.

Example

Figure 4A:
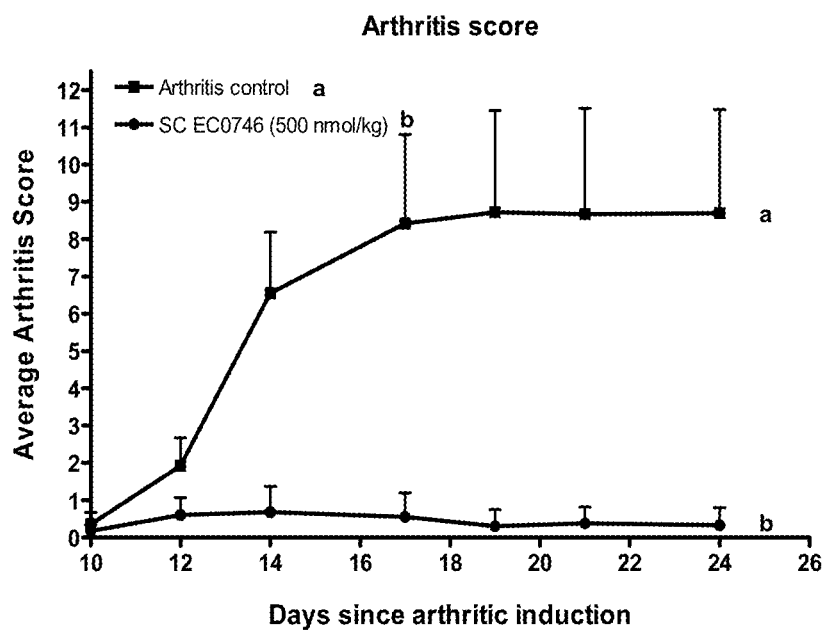
FIG. 4A—Arthritis scores for a) untreated animals with adjuvant induced arthritis and b) animals treated with EC0746 (500 nmol/kg).
Figure 4B:
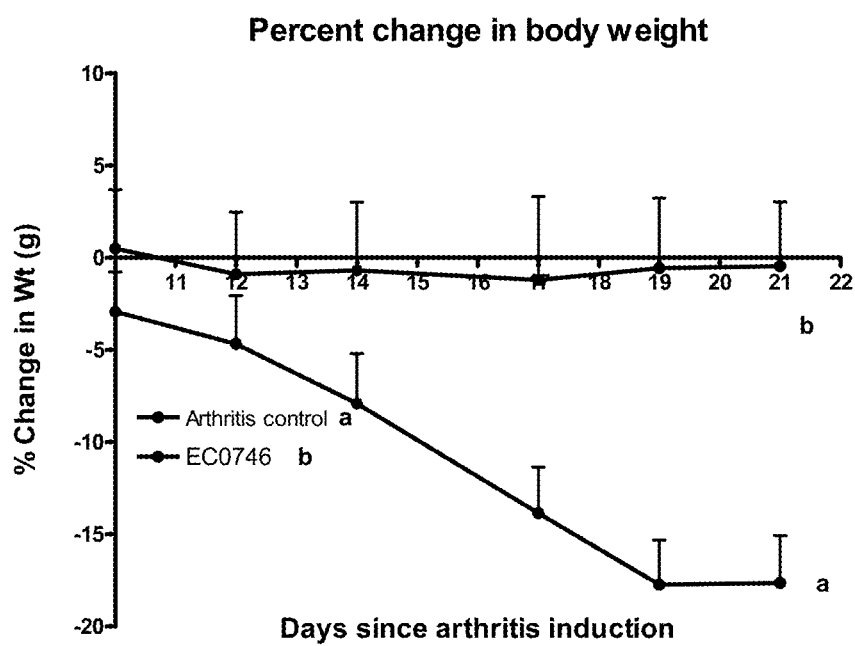
FIG. 4B—Percentage change in body weight measured for a) untreated animals with adjuvant induced arthritis and b) animals treated using EC0746 (500 nmol/kg).
Figure 5A:
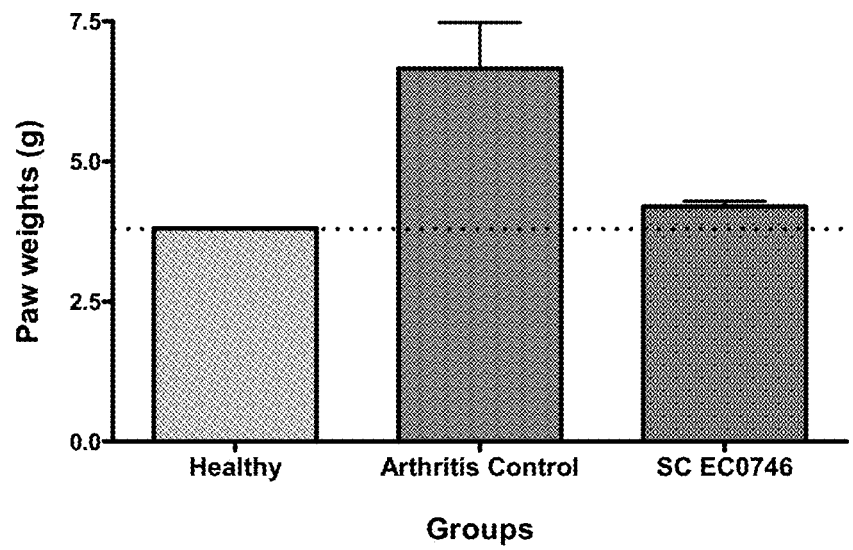
FIG. 5A—Paw weights measured after the end of the treatment period for healthy animals, untreated animals with adjuvant induced arthritis and b) animals treated with EC0746 (500 nmol/kg).
Figure 5B:
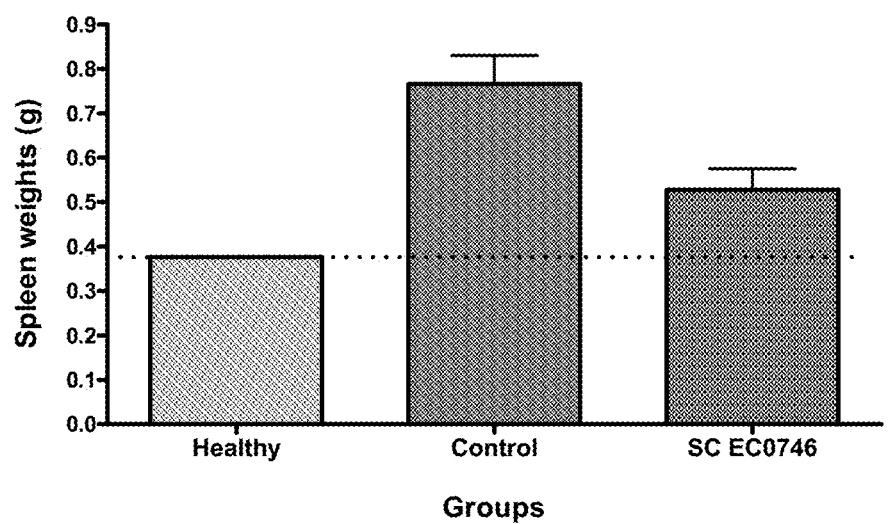
FIG. 5B—Spleen weights measured after the end of the treatment period for healthy animals, untreated animals with adjuvant induced arthritis and b) animals treated with EC0746 (500 nmol/kg).

EC0746 Treatment Reduced Local (Paw) and Systemic (Spleen) Inflammation in Rats with Adjuvant Arthritis Rats with adjuvant arthritis were treated subcutaneously with EC0746 (500 nmol/kg) on days 10, 13, 17, and 20 post arthritis induction. The animals in the healthy and arthritis control groups were left untreated. The arthritis scores and animal body weights were recorded three times a week (see FIGS. 4A, B). At the completion of study (days 24-25), the rats were euthanized by $CO_2$ asphyxiation and processed for paw and spleen weights. The results showed that EC0746-treatment rats had significantly less arthritis score, paw weight (i.e. paw swelling), and spleen weights (see FIGS. 5A, B). The overall reduction of local and systemic inflammation in the EC0746-treated rats rendered these animals better body weight compared to animals in the untreated arthritis control group.

Example

EC0746 Treatment Prevented Bone Damage in Rats with Adjuvant Arthritis

Figure 6A:
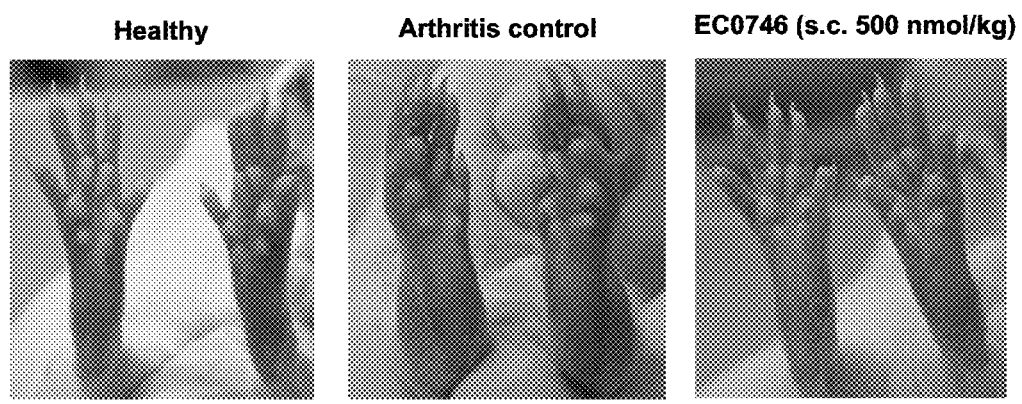
FIG. 6A—Photographs of the hind paws of a healthy control animal, an untreated animal with adjuvant induced arthritis, and an animal treated with EC0746 (500 nmol/kg)
Figure 6B:
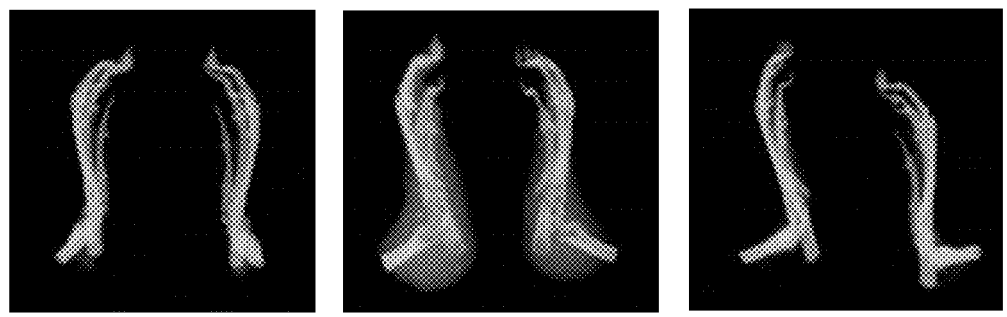

Rats with adjuvant arthritis were treated subcutaneously with EC0746 (500 nmol/kg) on days 10, 13, 17, and 20 post arthritis induction. The animals in the healthy and arthritis control groups were left untreated. At the completion of study, rat hind paws were photographed and the animals were euthanized by $CO_2$ asphyxiation. X-ray radiographic images of hind paws were taken immediately using a Kodak Imaging Station In Vivo FX (Carestream Molecular Imaging, New Haven, Conn.). The representative X-ray images of hind paws were shown for a healthy rat and EC0746-treated or untreated arthritic rats. Compared to severe bone erosion seen with the untreated arthritis control animal, EC0746 treatment starting at the on-set of arthritis development (day 10) effectively halted paw swelling/inflammation and prevented bone erosion. See FIGS. 6A, B.

Example

EC0746 was as Effective as Mtx at Equal Molar Subcutaneous Doses

Figure 7A:
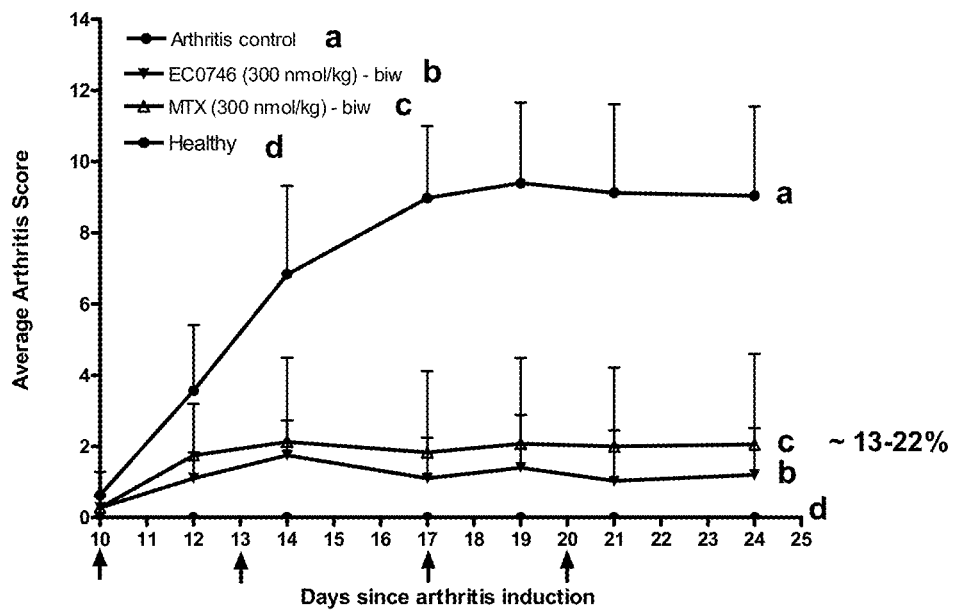
FIG. 7A—Average arthritis scores measured during the treatment period for a) untreated animals with adjuvant induced arthritis, b) animals treated bi-weekly with EC0746, 300 nmole/kg; c) with methotrexate, 300 nmole/kg; and d) healthy untreated animals. Treatments administered on the days indicated with the arrows.
Figure 7B:
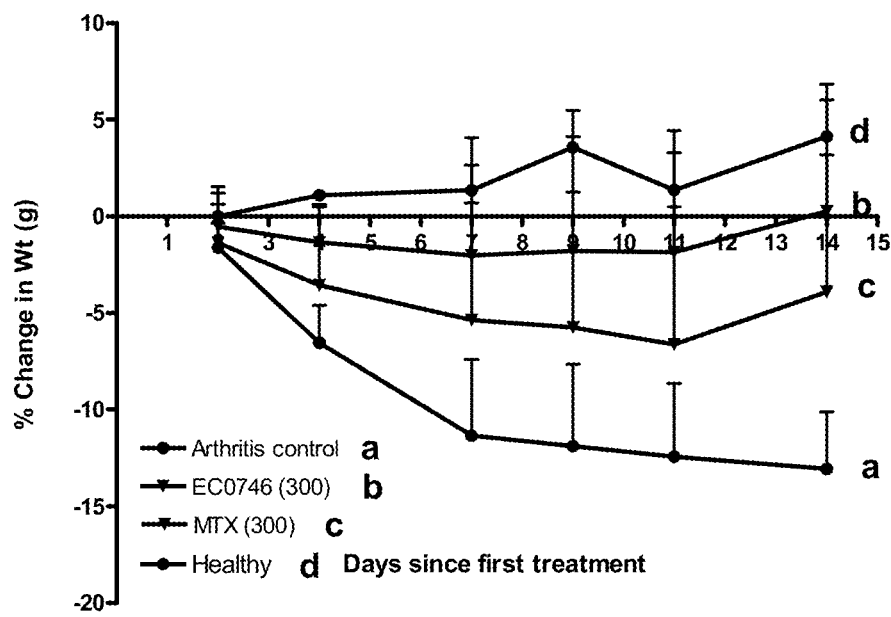
FIG. 7B—Percentage weight change measured during the treatment period for a) untreated animals with adjuvant induced arthritis, b) animals treated bi-weekly with EC0746, 300 nmole/kg; c) animals treated bi-weekly with methotrexate, 300 nmole/kg; and d) healthy untreated animals.
Figure 8A:
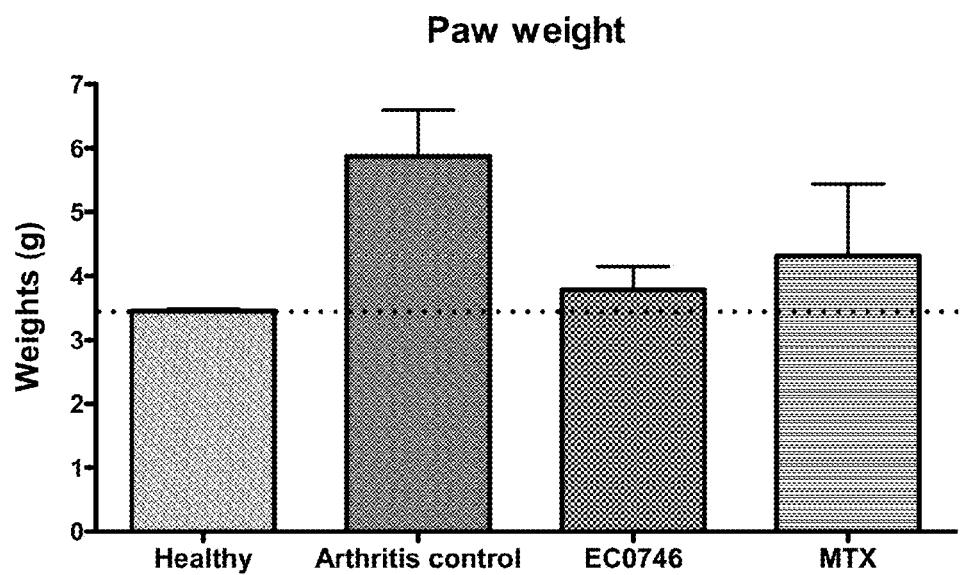
FIG. 8A—Paw weights measured at the end of the treatment period for healthy untreated animals, untreated arthritic animals, animals treated bi-weekly with EC0746 (300 nmole/kg), and animals treated bi-weekly with methotrexate (300 nmole/kg).
Figure 8B:
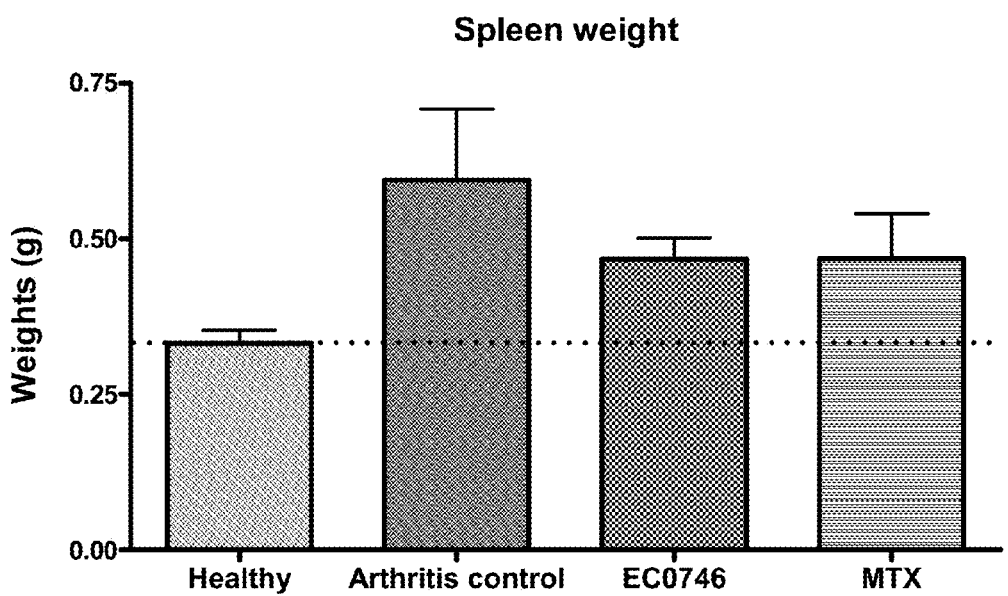
FIG. 8B—Spleen weights measured at the end of the treatment period for healthy untreated animals, untreated arthritic animals, animals treated bi-weekly with EC0746 (300 nmole/kg), and animals treated bi-weekly with methotrexate (300 nmole/kg).
Figure 9:
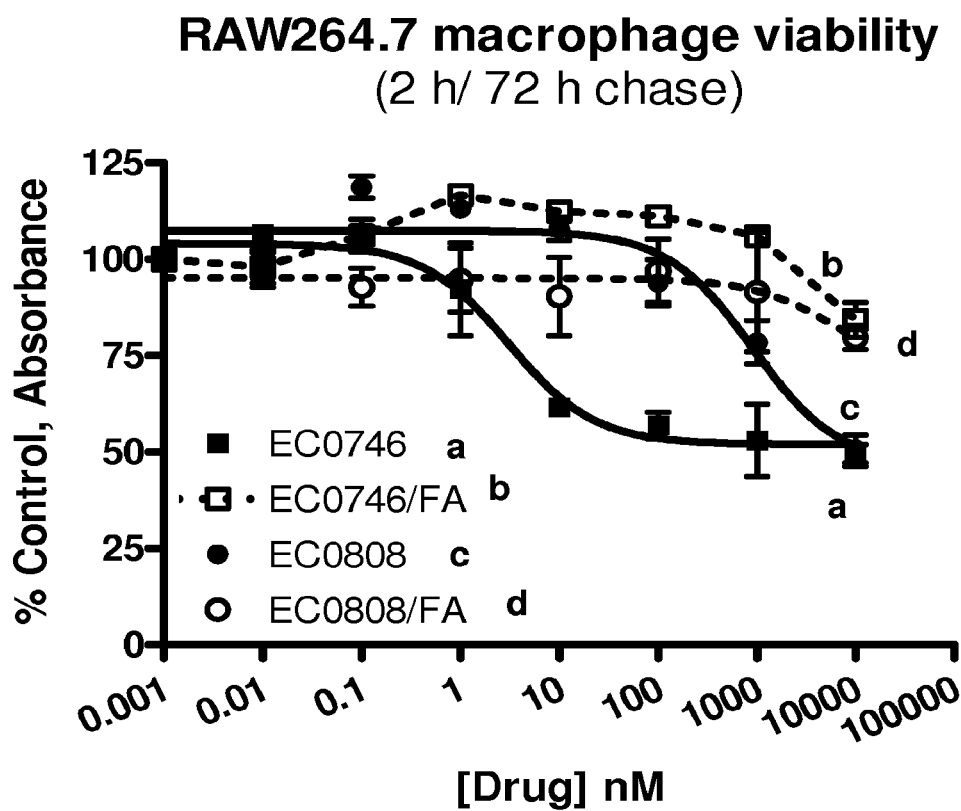
FIG. 9. Viability of RAW264.7 macrophage cells treated in media containing the test compound or compounds for 2 hours at the concentration shown in the graph, followed by 72 hours in fresh medium without the test compound(s); a) EC0746; b) EC0746+excess folic acid; c) EC0808 (a D-aminopterin diastereoisomer of EC0746); and EC0808+excess folic acid.
Figure 10:
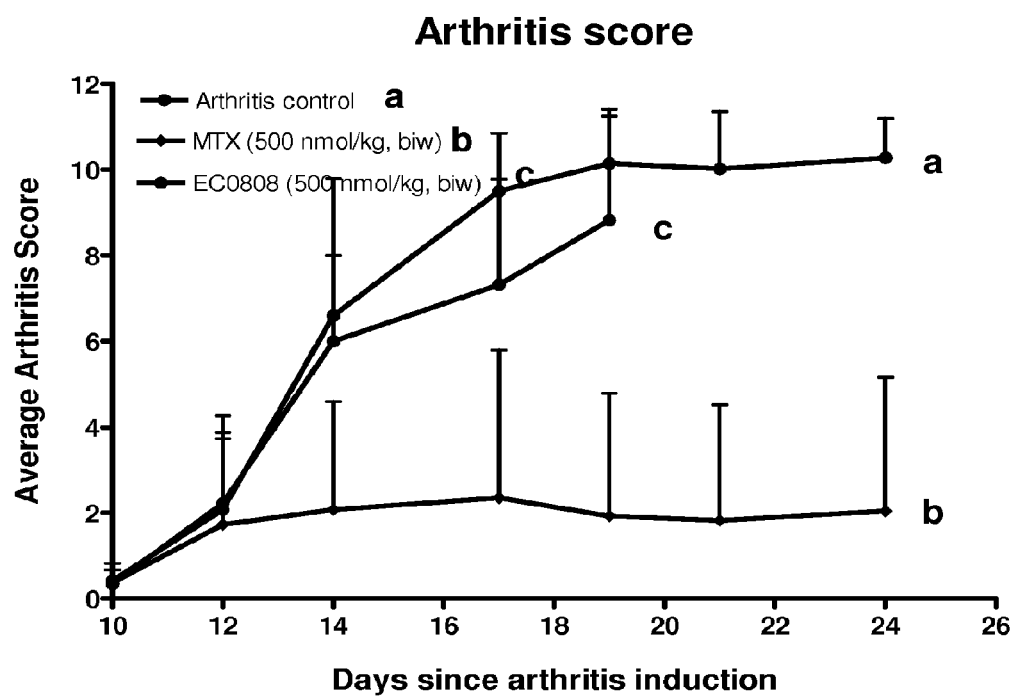
FIG. 10. Arthritis score measured for a) untreated arthritic animals; b) animals treated bi-weekly with methotrexate (500 nmole/kg), and c) animals treated bi-weekly with EC0808 (500 nmole/kg).
Figure 11A:
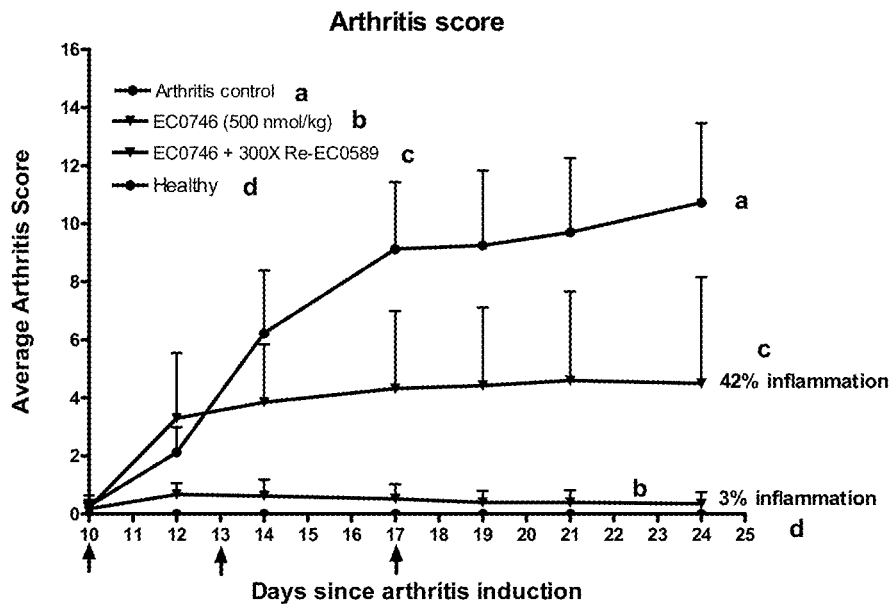
FIG. 11A—Arthritis score measured for a) untreated arthritic animals; b) animals treated bi-weekly with EC0746 (500 nmole/kg), c) animals treated bi-weekly with EC0746 (500 nmole/kg)+300-fold excess of Re-EC0589), and d) healthy untreated animals.
Figure 11B:
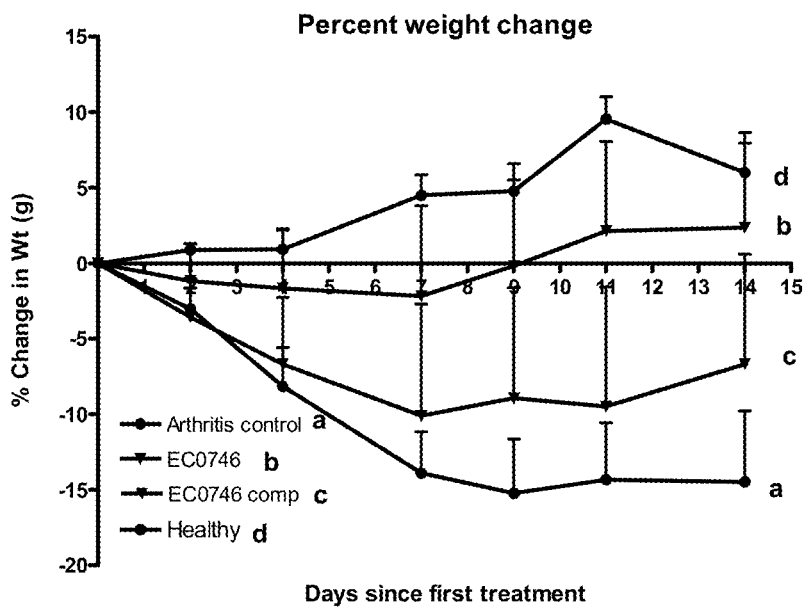
FIG. 11B—The percentage body weight change measured for the same animals used to obtain the arthritis scores in FIG. 11A. Percentage weight change measured for a) untreated arthritic animals; b) animals treated bi-weekly with EC0746 (500 nmole/kg), c) animals treated bi-weekly with EC0746 (500 nmole/kg)+300-fold excess of Re-EC0589), and d) healthy untreated animals.
Figure 11C:
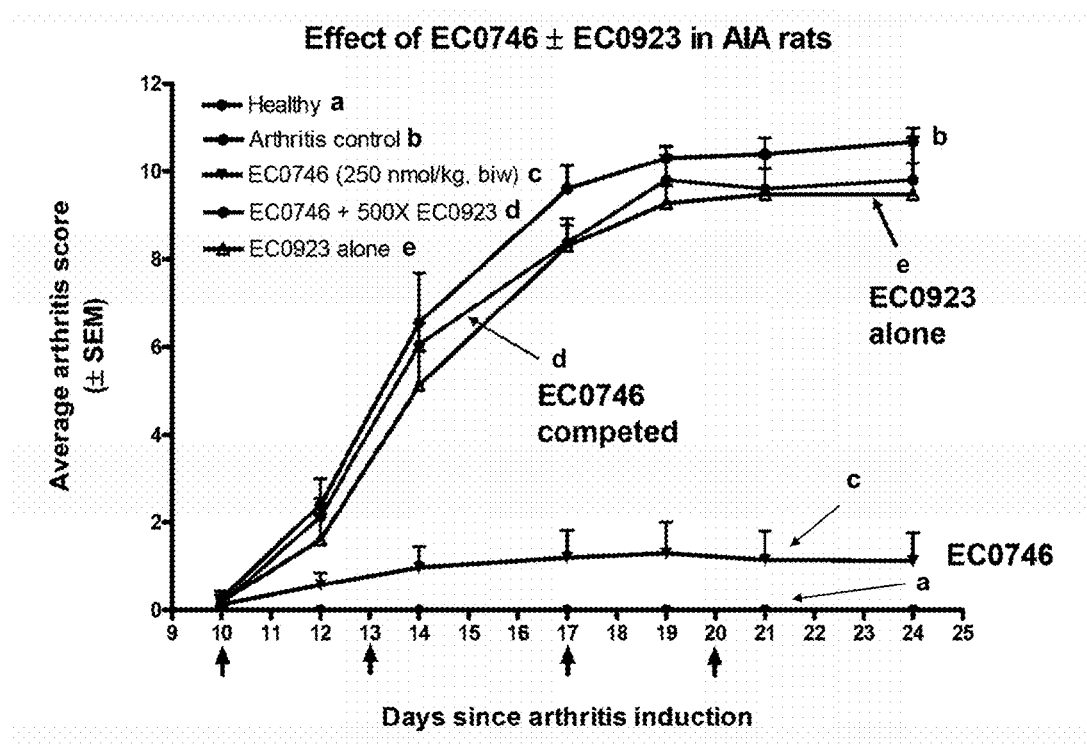
FIG. 11C—Arthritis score measured for a) healthy animals, b) untreated arthritic animals; c) animals treated bi-weekly with EC0746 (250 nmole/kg), d) animals treated bi-weekly with EC0746 (250 nmole/kg)+500-fold excess of EC0923), and e) animals treated biweekly with EC0923 alone.
Figure 12A:
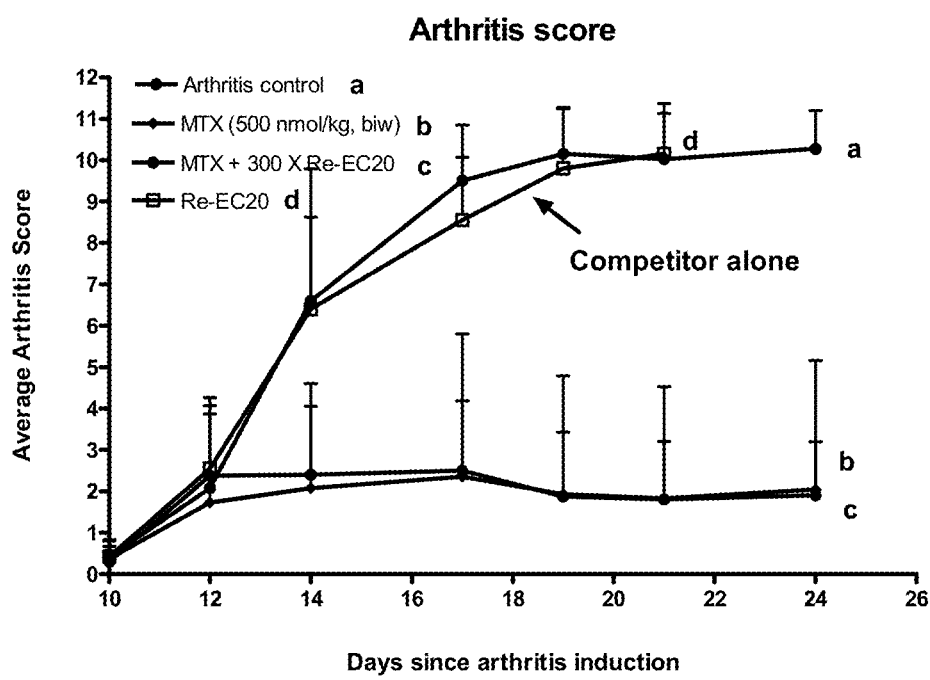
FIG. 12A—Arthritis score measured for a) untreated arthritic animals; b) animals treated bi-weekly with methotrexate (500 nmole/kg), c) animals treated bi-weekly with methotrexate (500 nmole/kg)+300-fold excess of Re-EC20), and d) arthritic animals treated with Re-EC20.
Figure 12B:
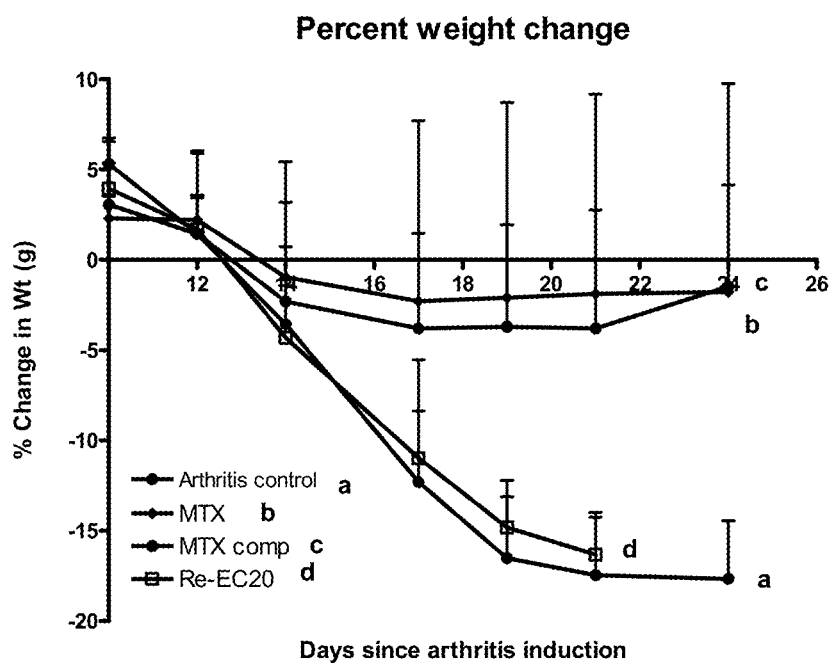
FIG. 12B—The percentage body weight change measured for the same animals used to obtain the arthritis scores in FIG. 12A. The percentage weight change measured for a) Untreated arthritic animals; b) animals treated bi-weekly with methotrexate (500 nmole/kg), c) animals treated bi-weekly with methotrexate (500 nmole/kg)+300-fold excess of Re-EC20), and d) arthritic animals treated with Re-EC20.

Rats with adjuvant arthritis were treated subcutaneously with EC0746 (300 nmol/kg) or methotrexate (MTX, 300 nmol/kg) on days 10, 13, 17, and 20 post arthritis induction. The animals in the healthy and arthritis control groups were left untreated. The arthritis score and animal body weight were recorded three times a week (see FIGS. 7A, B). At the completion of study, the rats were euthanized by $CO_2$ asphyxiation and processed for paw and spleen weights. The results showed that biweekly subcutaneously dosed EC0746 and methotrexate were similarly active in reducing local (paw) and systemic (spleen) inflammation in these arthritic animals. See FIGS. 8A, B.

Example

Anti-Arthritis Activity of EC0746 (But Not MTX) Could Be Partially Blocked By a Co-Injected Folate Competitor Rats with adjuvant arthritis were treated subcutaneously with EC0746 (500 nmol/kg) or MTX (500 nmol/kg) in the absence or presence of 300-fold excess of Re-EC0589 (150 μmol/kg, Rhenium complex of EC0589) or Re-EC20 (150 μmol/kg, Rhenium complex of EC20), respectively, on days 10, 13, 17, and 20 post arthritis induction. The arthritis score and animal body weight were recorded three times a week. Both EC0589 and Re-EC20 served as a FR-binding competitor. The animals in the arthritis control group were left untreated. The results showed that the anti-arthritis activity of EC0746 but not MTX could be partially blocked by excess amount of a FR-binding competitor.

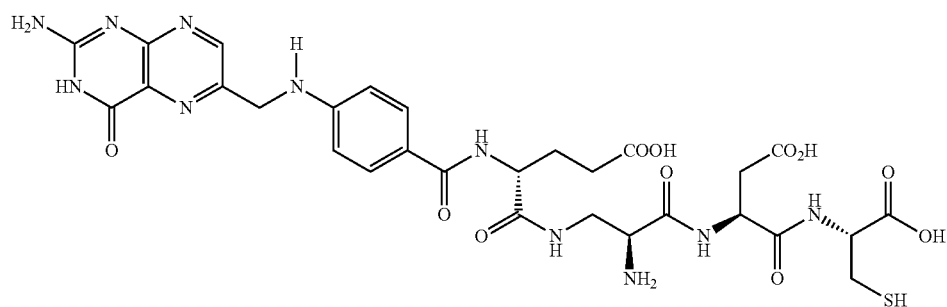

EC0589

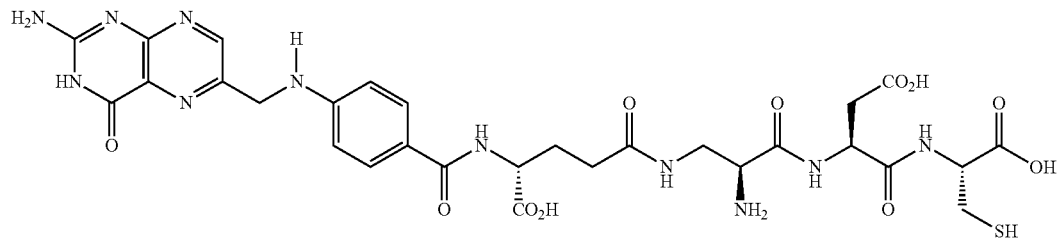

EC20

Example

Collagen-Induced Arthritis (CIA) Model

Figure 13A:
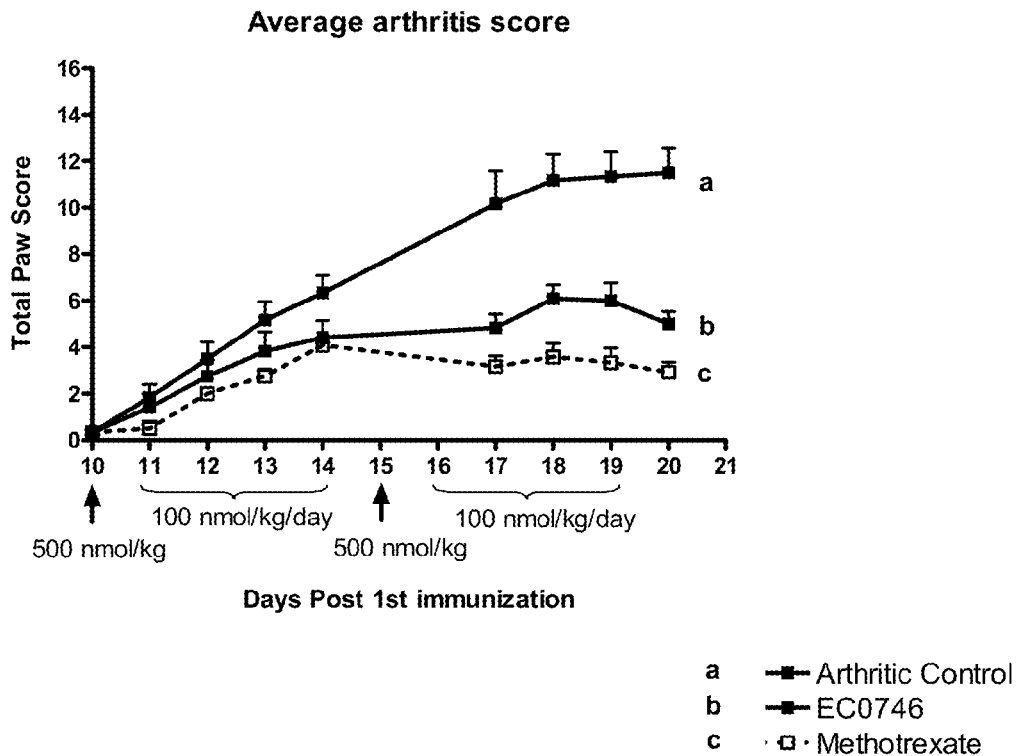
FIG. 13A—The average arthritis score measured using a two-dosage level treatment schedule, a 500 nmole/kg dose was administered on days 10 and 15 post-arthritis induction and a 100 nmole/kg dose was administered on day 11-14 and 16-19. a) untreated arthritic animals (collagen-induced arthritis, rats induced treatment with 500 µg Type II collagen/Freund's complete adjuvant at day 0 followed by 500 µg Type II collagen/Freund's incomplete adjuvant at day 7, b) animals treated with EC0746, and c) animals treated with methotrexate.
Figure 13B:
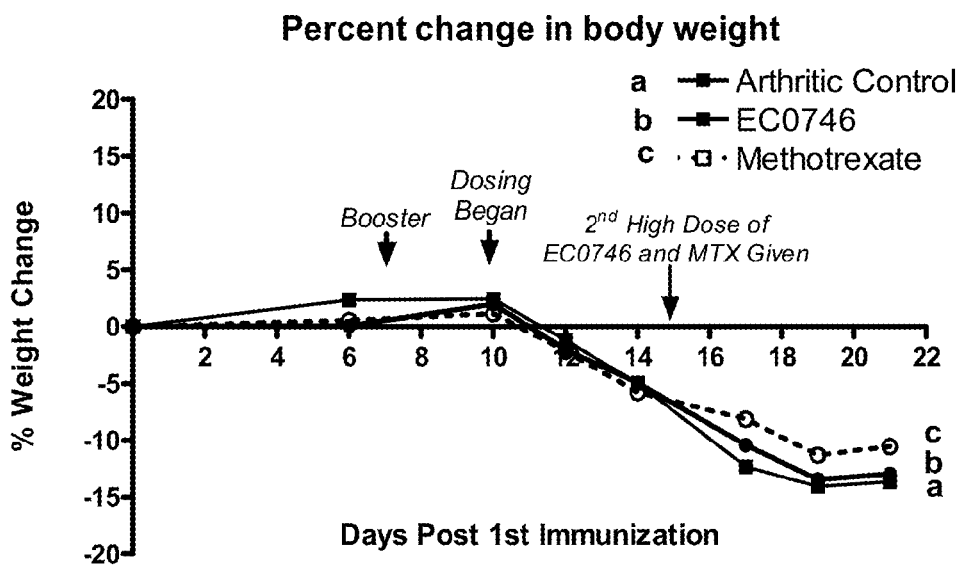
FIG. 13B—The percentage weight change measured for the animals used to obtain the arthritis scores shown in FIG. 13A. a) Untreated arthritic animals, b) animals treated with EC0746, and c) animals treated with methotrexate.

The collagen-induced arthritis (CIA) was induced in female Lewis rats on folate-deficient diet (Harlan Teklad, Indianapolis, Ind.). On Day 0, rats were immunized with 500 μg of bovine collagen Type II (Chondrex, Redmond, Wash.) formulated with Freund's complete adjuvant. A booster immunization was given on Day 7 with 250 μg of the bovine collagen formulated with Freund's incomplete adjuvant. Arthritis disease was assessed by a qualitative clinical score system described by the manufacturer (Chondrex, Redmond, Wash.): 0=normal, 1=Mild, but definite redness and swelling of the ankle or wrist, or apparent redness and swelling limited to individual digits, regardless of the number of affected digits, 2=Moderate redness and swelling of ankle of wrist, 3=Severe redness and swelling of the entire paw including digits, and 4=Maximally inflamed limb with involvement of multiple joints. On Day 10 post first immunization, rats were distributed evenly (according to the arthritis score) across the control and treatment groups. The CIA rats were given ten consecutive subcutaneous doses of EC0746 and methotrexate on days 10-19. For both drugs, an induction dose (500 nmol/kg) was given on days 10 and 15 and a maintenance dose (100 nmol/kg) was given on days 11-14 and 16-19. The animals in the arthritis control group were left untreated. The arthritis score and animal body weight were recorded five times a week. The result showed that EC0746 was also effective in rats with collagen-induced arthritis. See FIGS. 13A, B.

Example

EC0746 Plasma Pharmacokinetics After a Single S.C. Dose

Figures 14A, 14B:
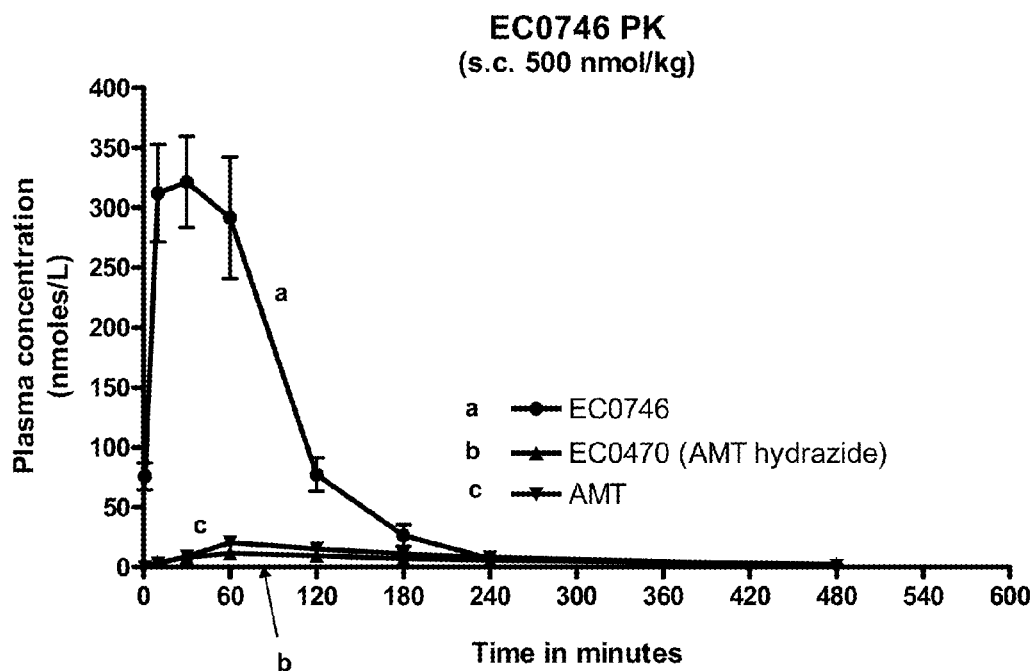
FIG. 14A—Plasma concentrations measured after a single subcutaneous dose of EC0746 (500 nmole/kg). a) EC0746, b) EC0470 (aminopterin gamma-hydrazide), and c) aminopterin.
FIG. 14B—The $C_{max}$ for EC0746 of 321 nmole/L is reached at 30 minutes post injection. The $C_{max}$ for free drug (aminopterin+aminopterin hydrazide) of 34 nmole/L is reached at 60 minutes. $C_{max}$ for free drug is 9.6% of the total dose. The Area Under Curve value for EC0746 is 32.5 nmole-min/mL, the Area Under Curve valuefor free drug is 7.3 nmole-min/mL (18% of the total).
Figure 15:
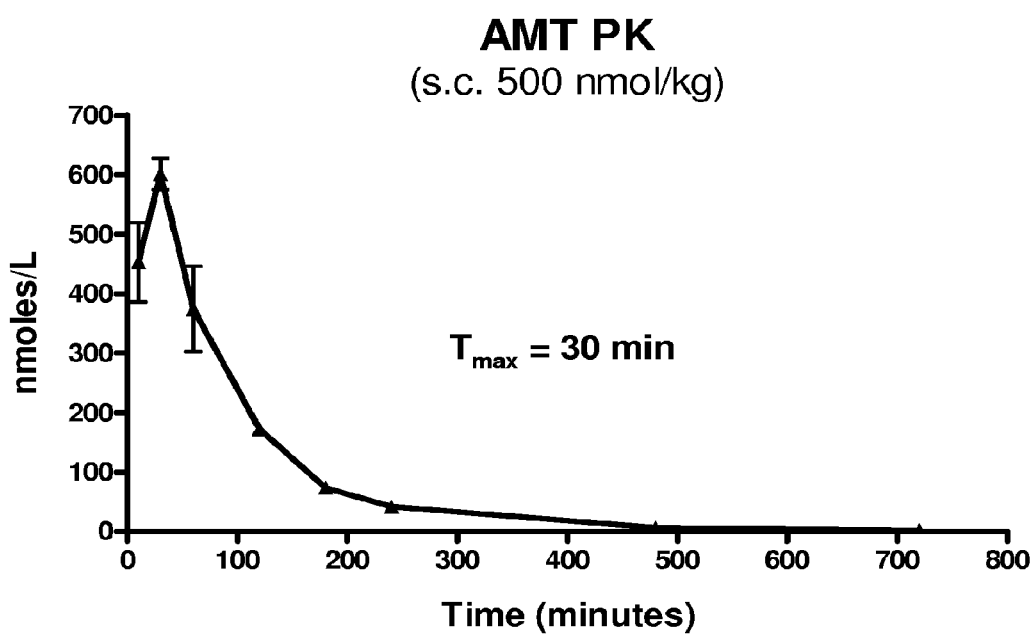
FIG. 15. Plasma concentrations measured after a single subcutaneous dose of aminopterin (500 nmole/kg). The maximum plasma concentration was measured at 30 minutes post administration.

Female Lewis rats with rounded tip jugular vein catheters (Harlan) were fed regular rodent diet and used in this study. The animals were given a single subcutaneous dose of EC0746 at 500 nmol/kg. Whole blood samples (300 μl) were collected from the animals at the following time points: 1 min, 10 min, 30 min, 1 h, 2 h, 3 h, 4 h, and 8 h after injection. The blood samples were placed into anti-coagulant tubes containing 1.7 mg/mL of K3-EDTA and 0.35 mg/mL of N-Maleoyl-beta-alanine (0.35 mg/mL). Plasma samples were obtained by centrifugation for 3 min at ~2,000 g and stored at −80° C. The amount of EC0746 and its released base drugs (EC0470 & aminopterin) were determined by HPLC using the EC0746 injection solution as the standard (see FIG. 14). The result showed that approximately 18% of free drug exposure/release (EC0470 & aminopterin) was detected in the plasma after a single subcutaneous dose of EC0746. However, the Tmax of EC0746 was observed at ~30 min while EC0470 and aminopterin showed a delayed Tmax at ~1 h. See FIG. 14. A similar method was used to determine the plasma pharmacokinetics of aminopterin (see FIG. 15).

Example

Maximum Tolerated Dose (MTD) of Aminopterin and EC0746

Figure 16A:
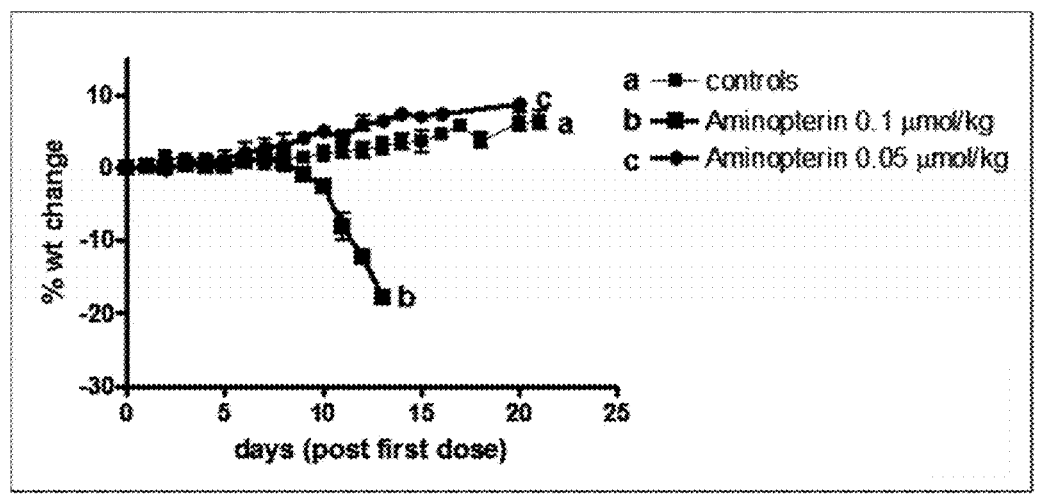
FIG. 16A—Percentage body weight change measured for animals after subcutaneous administration of the indicated dose of aminopterin biweekly for 2 weeks a) control, 0 nmole/kg, b) 100 nmole/kg, and c) 50 nmole/kg.
Figure 16B:
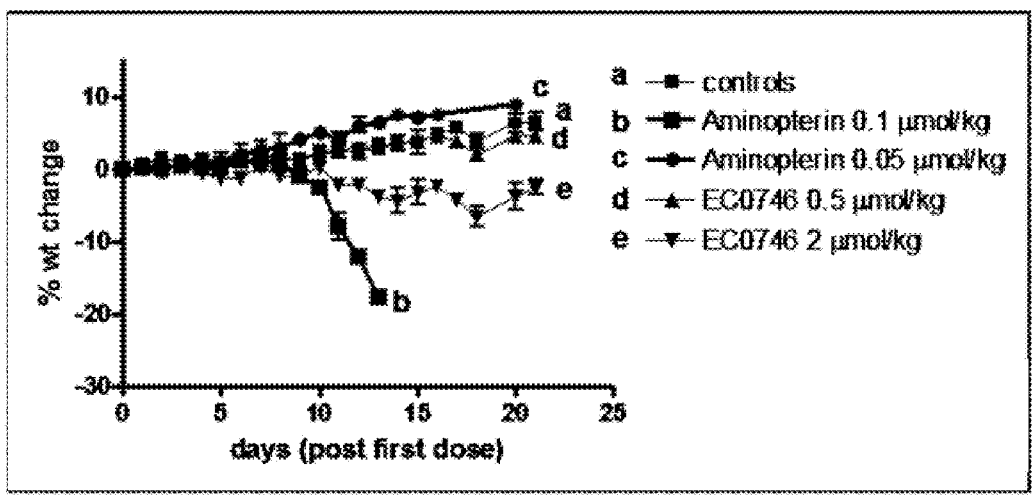
FIG. 16B—Percentage body weight change measured for animals after subcutaneous administration of the indicated dose of treatment compound biweekly for 2 weeks a) control, no treatment, b) 100 nmole/kg aminopterin, and c) 50 nmole/kg aminopterin, d) 500 nmole/kg EC0746, or e) 2000 nmole/kg EC0746.

Healthy rats were administered a subcutaneous injection of the indicated dose of aminopterin or EC0746 biweekly for 2 weeks; control animals, no treatment, 100 nmole/kg aminopterin, 50 nmole/kg aminopterin, 500 nmole/kg EC0746, or 2000 nmole/kg EC0746. The animals were weighed daily. See FIGS. 16A, B. A dose of 0.1 μmol/kg of aminopterin in folate deficient rats is above the MTD; therefore, the projected MTD of EC0746 would be <0.5 μmol/kg based solely on ~20% free drug release shown in the previous Example. However, the MTD of EC0746 is actually 2.0 μmol/kg, which is equivalent to 0.4 μmol/kg, or ~8× higher than the MTD for free aminopterin. On a molar basis for total aminopterin, the MTD is 40×higher. The therapeutic index (MTD for healthy animals/$ED_{50}$ for treatment of adjuvant-induced arthristis in female Lewis rats) for EC746 is about 9.5 (2000/210).

Example

Mechanism of Action: EC0932 as a Folate-Targeted Antifolate

Figure 17A:
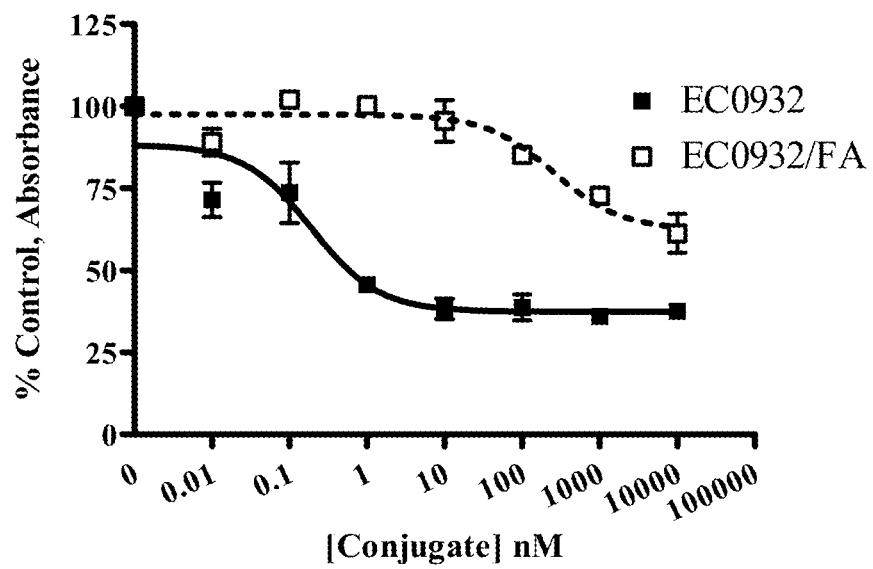
FIG. 17A—Viability of RAW264.7 cells, measured using the XTT assay, treated with EC0932 (2 hour treatment followed by 72 hours in treatment-free medium) and treated with EC0932 and excess folic acid (EC0932/FA, 2 hour treatment followed by 72 hours in treatment-free medium).
Figure 17B:
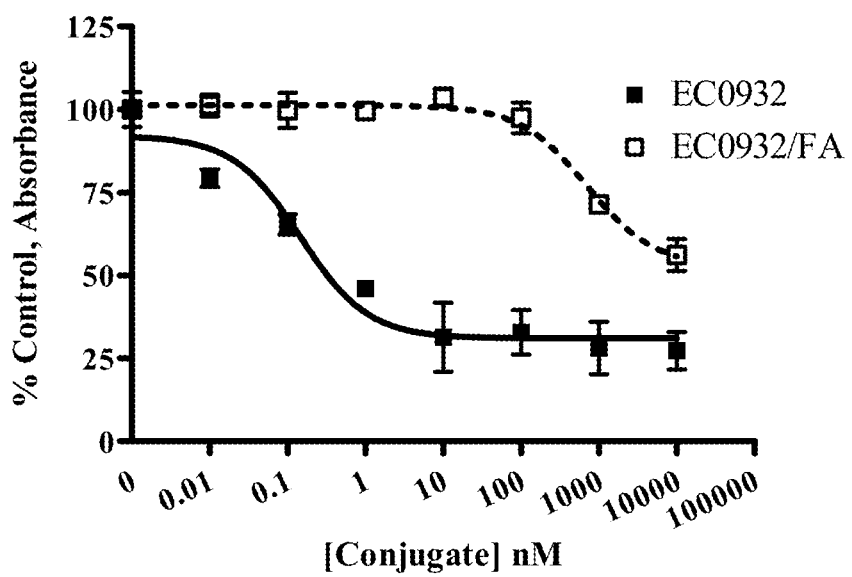
FIG. 17B—Inhibition of LPS-stimulated TNF-a production in RAW264.7 cells treated with EC0932 (2 hour treatment followed by 72 hours in treatment-free medium) and treated with EC0932 and excess folic acid (EC0932/FA, 2 hour treatment followed by 72 hours in treatment-free medium).

RAW264.7 cells in 96-well plates were treated with vehicle (culture medium) or 10-fold serial dilutions of EC0932 without or with 100-fold excess free folate. The drug-containing medium was replaced after 2 h treatment and the cells were allowed to incubate further in standard medium for 70 h. Four hours prior to the end of incubation, LPS was added to the treated cells at a final concentration of 100 ng/mL. 100 μL of the culture supernatants were collected for TNF-α analysis using a commercial ELISA kit (see FIG. 17B). The cell viability was assessed by adding XTT (2,3-bis(2-methoxy-4-nitro-5-sulfo-phenyl)-2H-tetrazolium-5-carboxanilide) to the remaining medium for an additional 4 h following the manufacturer's instructions (Roche Applied Science, Indianapolis, Ind.). See FIG. 17A. Both results were expressed as % absorbance (minus background) relative to untreated control in triplicates. The results demonstrated that EC0932 inhibited the viability of RAW264.7 cells and their ability to produce TNF-α in response to LPS.

Example

Mechanism of Action: EC0932 as a Folate-targeted mTOR Inhibitor

Figure 18A:
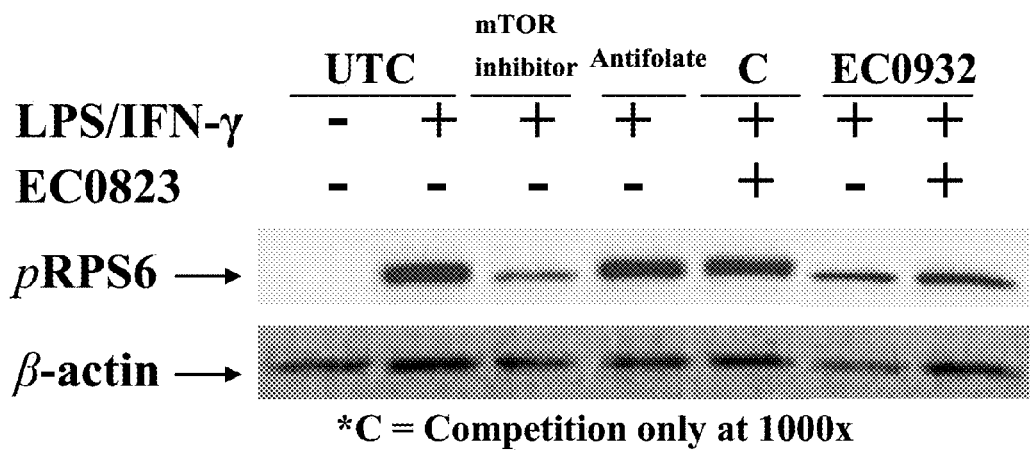
FIG. 18A—A Western blot showing inhibition of mTOR signaling in LPS/IFN-γ stimulated RAW264.7 cells. Comparison between unstimulated cells, untreated stimulated cells, stimulated cells treated with an mTOR inhibitor (everolimus), stimulated cells treated with an antifolate (aminopterin), stimulated cells treated with EC0932, stimulated cells treated with EC0932 plus excess competitor (EC0823), and stimulated cells treated excess competitor (EC0823) alone. Treatments with 100 nM compound in cell medium for 2 hours followed by fresh untreated medium.
Figure 18B:
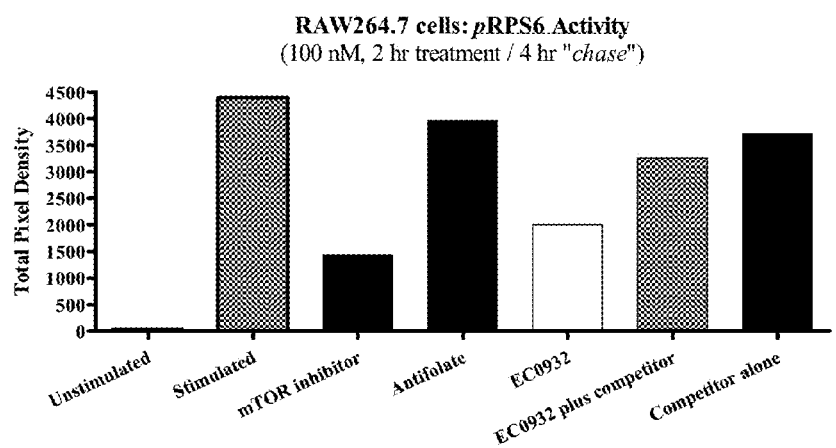
FIG. 18B—measurement treatment response on pRPS6.

RAW264.7 cells were treated with medium only (UTC), 100 nM everolimus (mTOR inhibitor), 100 nM aminopterin (antifolate), 100 μM EC0823 (C, a FR-binding competitor), or 100 nM EC0932 without or with 100 μM of EC0823. The drug-containing media were removed after 2 h and the cells were allowed to incubate for 4 h in fresh medium. Afterwards, the cell lysates were collected and subjected to Western blot analysis for phosphorylation of S6 ribosomal protein (p-RPS6), a downstream target in the mTOR signaling pathway. The data showed that EC0932 treatment resulted in down-regulation of p-RPS6 and its inhibitory effect could be partially blocked by excess EC0823, a FR-binding competitor. See FIG. 18.

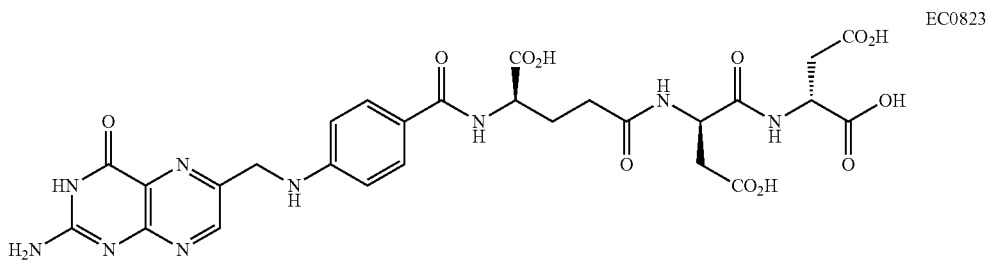 [SMILES: Nc1nc2ncc(CNc3ccc(C(=O)N[C@H](CCC(=O)N[C@H](CC(=O)O)C(=O)N[C@H](CC(=O)O)C(=O)O)C(=O)O)cc3)nc2c(=O)[nH]1]

EC0823

Example

EC0932 Demonstrates FR-specific Activity Against Adjuvant Arthritis

Figure 19A:
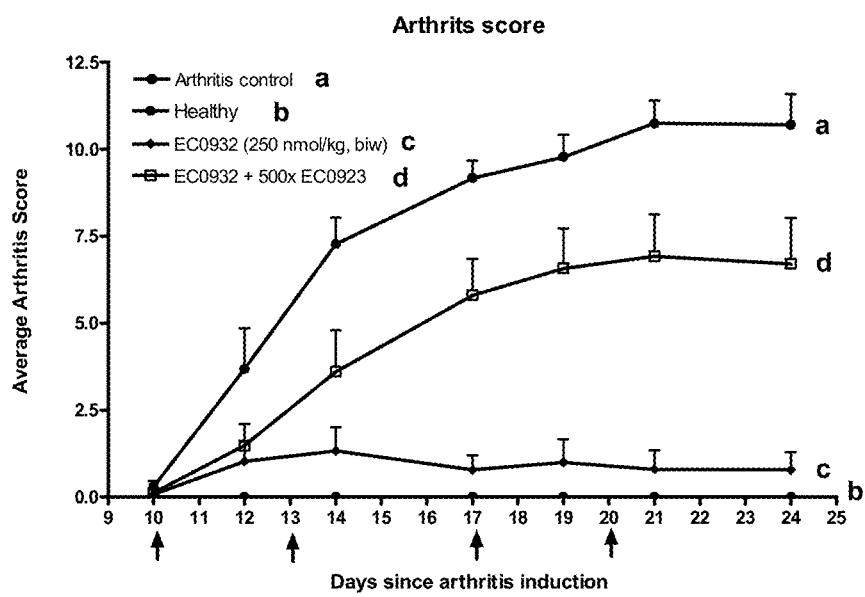
FIG. 19A—Arthritis score measured for a) untreated animals with induced arthritis, b) healthy untreated animals, c) animals treated with EC0932 (250 nmole/kg, biweekly on indicated days), and d) animals treated with EC0932 and a 500-fold excess of EC0923 (250 nmole/kg, biweekly, on indicated days).
Figure 19B:
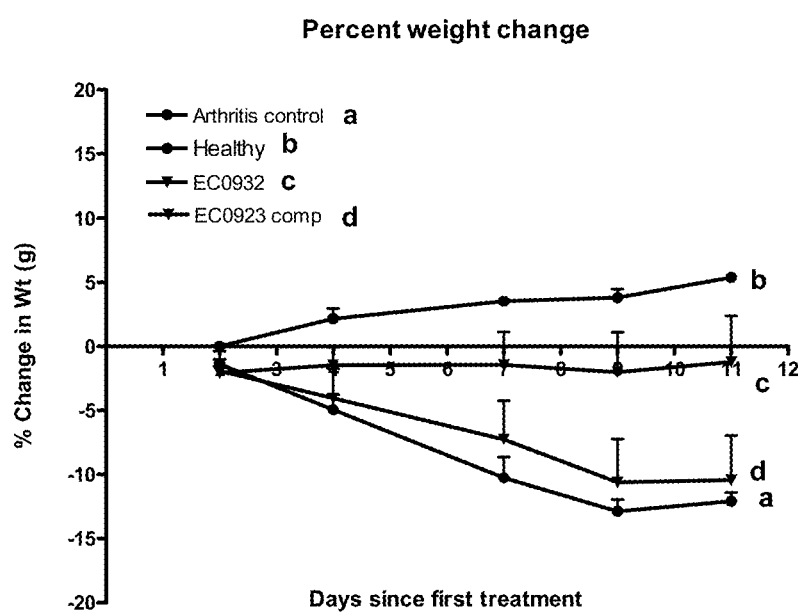
FIG. 19B—Percentage change in body weight measured for the animals used to obtain the arthritis scores shown in FIG. 19A; a) untreated animals with induced arthritis, b) healthy untreated animals, c) animals treated with EC0932 (250 nmole/kg, biweekly on indicated days), and d) animals treated with EC0932 and a 500-fold excess of EC0923 (250 nmole/kg, biweekly, on indicated days).
Figure 20A:
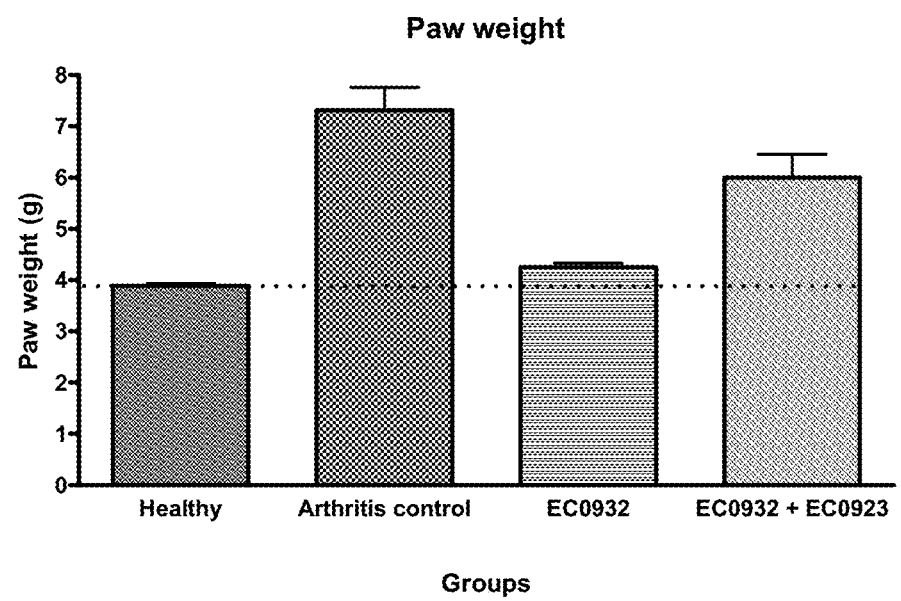
FIG. 20A—Paw weights measured after the completion of the treatment and observation period used to obtain the data in FIG. 19 for a) untreated animals with induced arthritis, b) healthy untreated animals, c) animals treated with EC0932 (250 nmole/kg, biweekly on indicated days), and d) animals treated with EC0932 and a 500-fold excess of EC0923 (250 nmole/kg, biweekly, on indicated days).
Figure 20B:
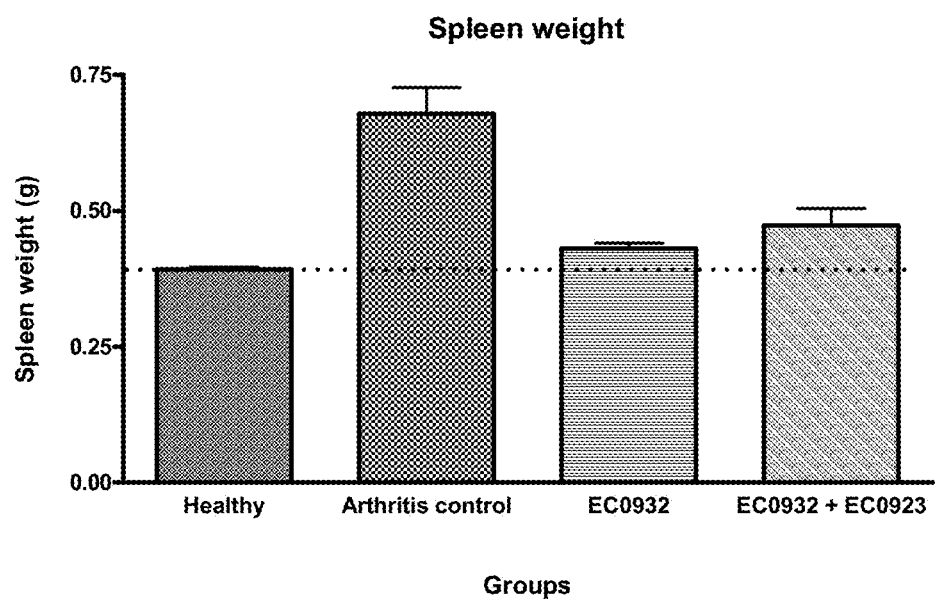
FIG. 20B—Spleen weights measured after the completion of the treatment and observation period used to obtain the data in FIG. 20A for a) untreated animals with induced arthritis, b) healthy untreated animals, c) animals treated with EC0932 (250 nmole/kg, biweekly on indicated days), and d) animals treated with EC0932 and a 500-fold excess of EC0923 (250 nmole/kg, biweekly, on indicated days).
Figure 21A:
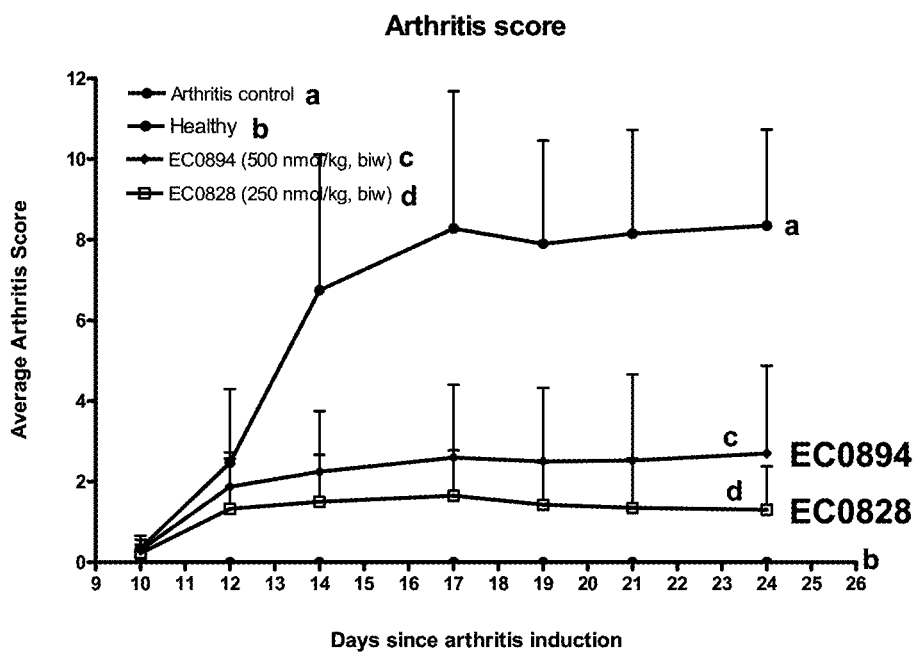
FIG. 21A—Arthritis score measured for a) untreated animals with induced arthritis, b) healthy untreated animals, c) animals treated with EC0894 (500 nmole/kg, biweekly), and d) animals treated with EC0828 (250 nmole/kg, biweekly).
Figure 21B:
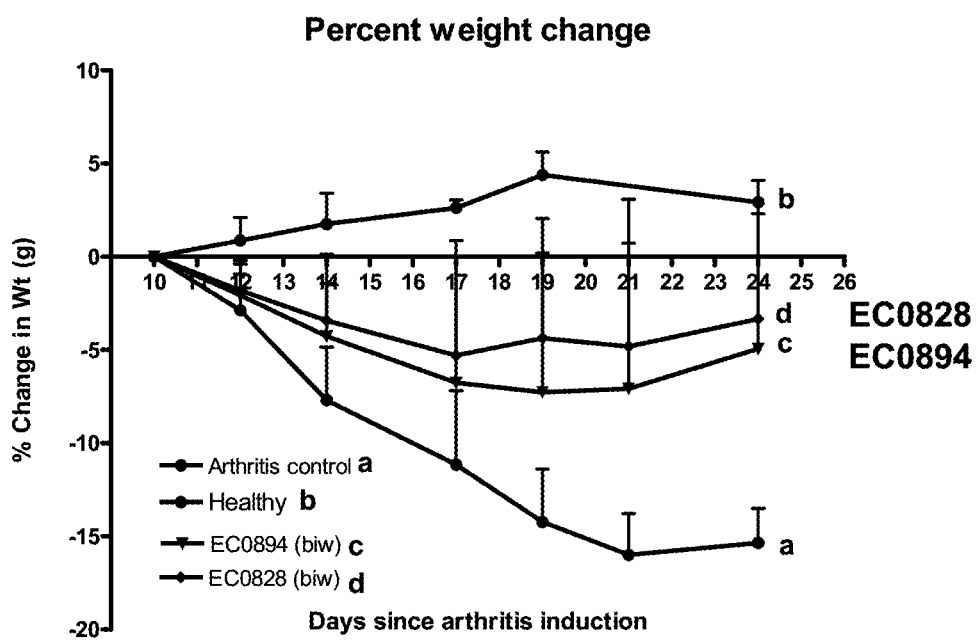
FIG. 21B—Percentage change in body weight measured for the animals used to obtain the arthritis scores shown in FIG. 21A; a) untreated animals with induced arthritis, b) healthy untreated animals, c) animals treated with EC0894 (500 nmole/kg, biweekly), and d) animals treated with EC0828 (250 nmole/kg, biweekly).
Figure 22A:
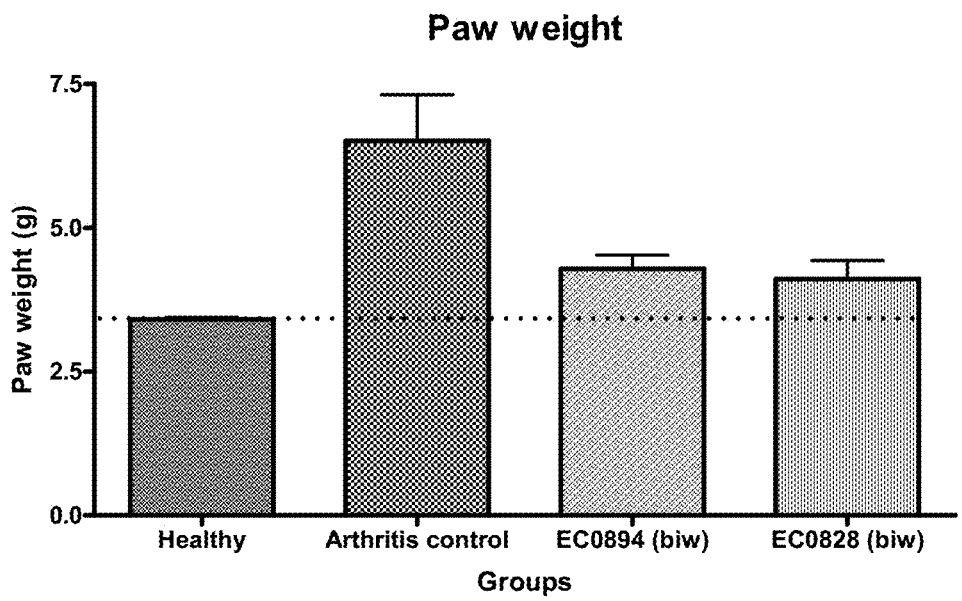
FIG. 22A—Paw weight measured after completion of the treatment and observation period used to obtain the data in FIG. 21 for a) untreated animals with induced arthritis, b) healthy untreated animals, c) animals treated with EC0894 (500 nmole/kg, biweekly), and d) animals treated with EC0828 (250 nmole/kg, biweekly).
Figure 22B:
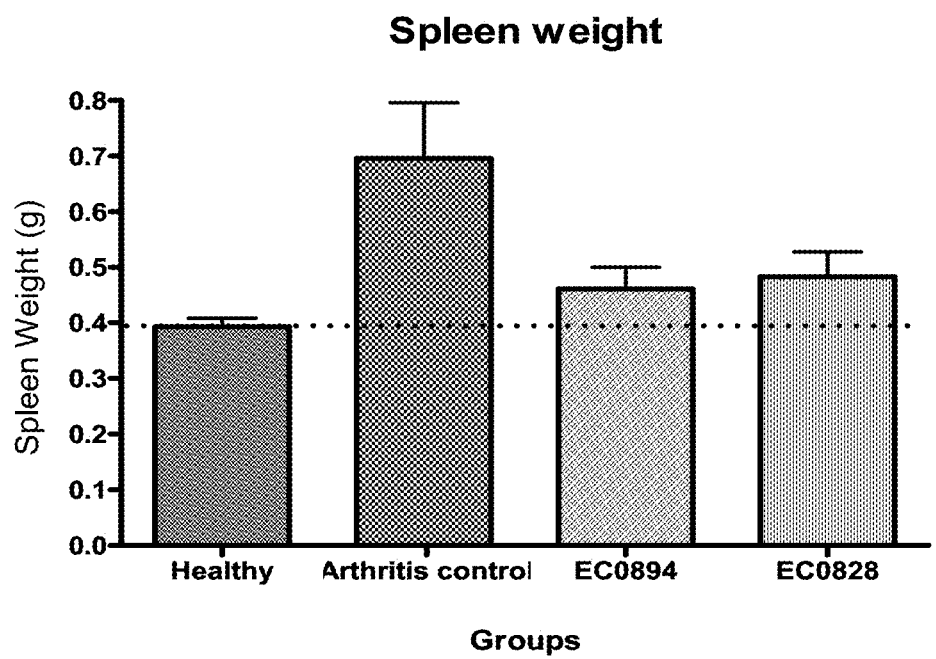
FIG. 22B—Spleen weight measured after completion of the treatment and observation period used to obtain the data in FIG. 21 for a) untreated animals with induced arthritis, b) healthy untreated animals, c) animals treated with EC0894 (500 nmole/kg, biweekly), and d) animals treated with EC0828 (250 nmole/kg, biweekly).
Figure 23A:
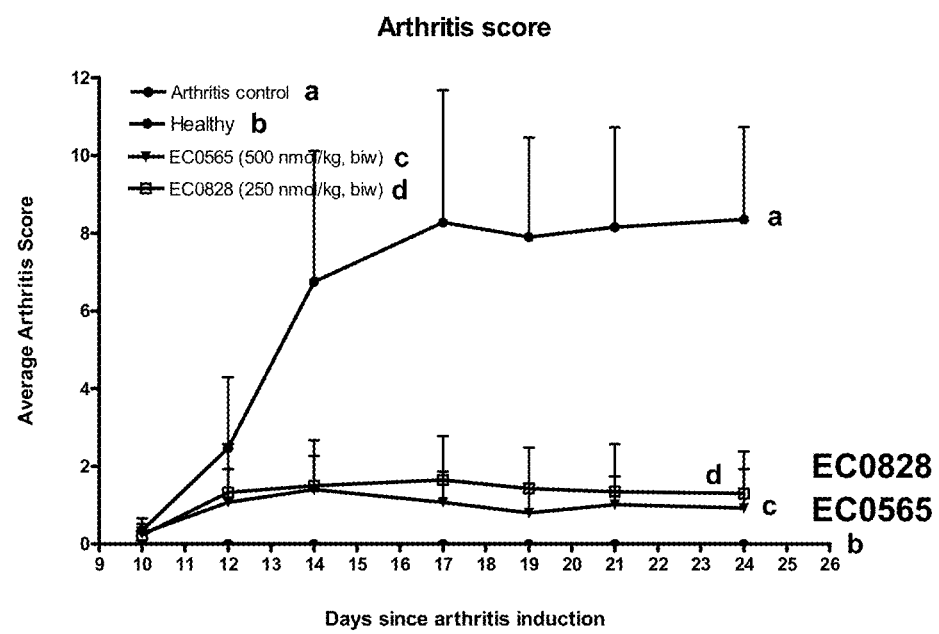
FIG. 23A—Arthritis score measured for a) untreated animals with induced arthritis, b) healthy untreated animals, c) animals treated with EC0565 (500 nmole/kg, biweekly), and d) animals treated with EC0828 (250 nmole/kg, biweekly).
Figure 23B:
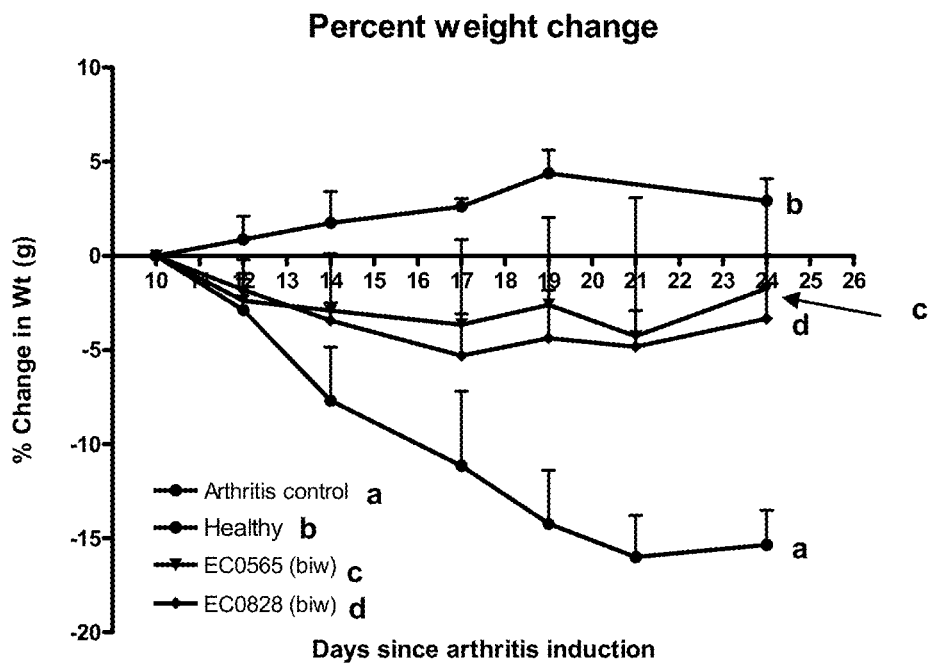
FIG. 23B—Percentage change in body weight measured for the animals used to obtain the arthritis scores shown in FIG. 23A; a) untreated animals with induced arthritis, b) healthy untreated animals, c) animals treated with EC0894 (500 nmole/kg, biweekly), and d) animals treated with EC0828 (250 nmole/kg, biweekly).
Figure 24A:
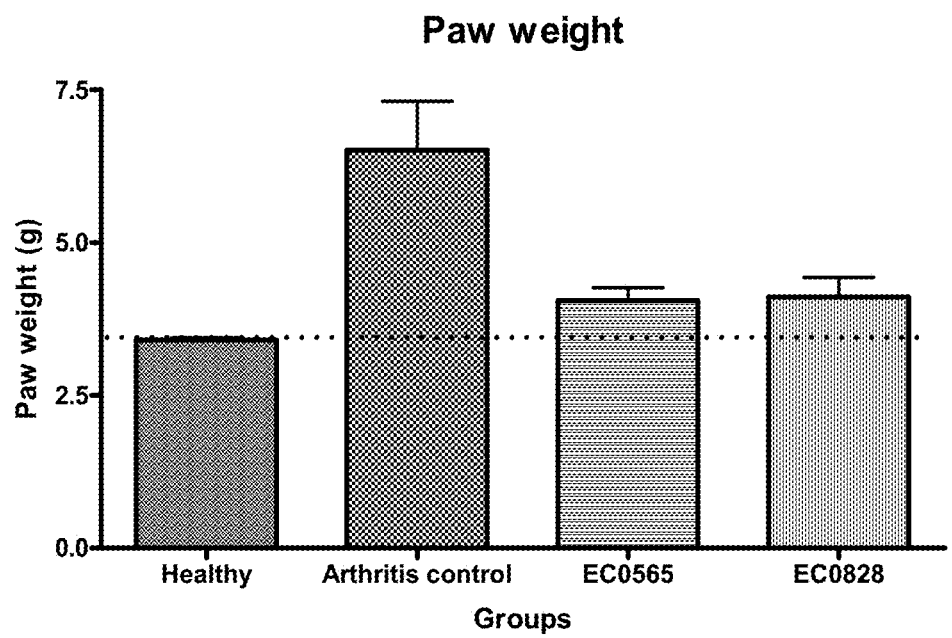
FIG. 24A—Paw weight measured after completion of the treatment and observation period used to obtain the data in FIG. 23 for a) untreated animals with induced arthritis, b) healthy untreated animals, c) animals treated with EC0565 (500 nmole/kg, biweekly), and d) animals treated with EC0828 (250 nmole/kg, biweekly).
Figure 24B:
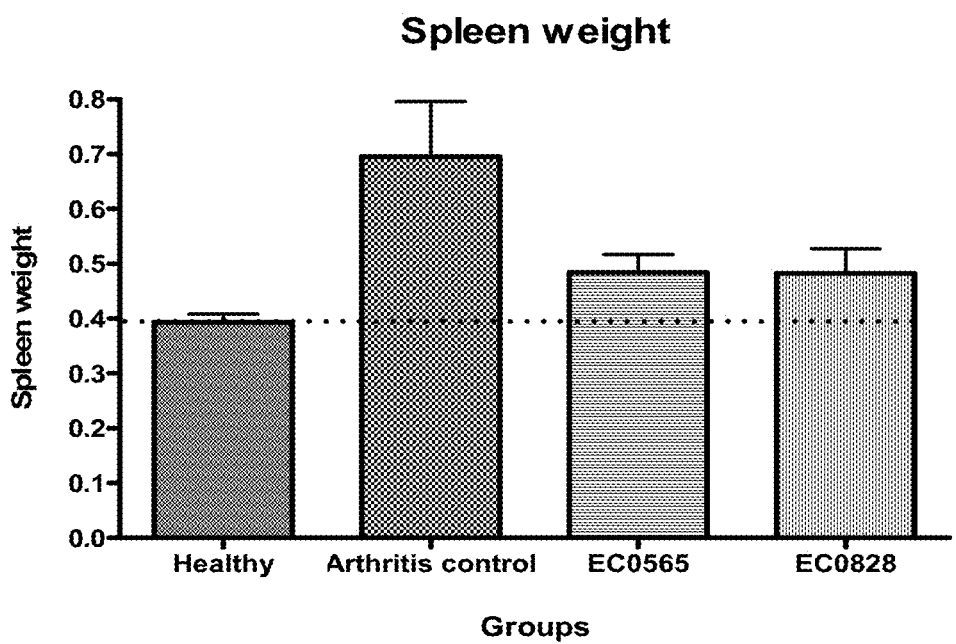
FIG. 24B—Spleen weight measured after completion of the treatment and observation period used to obtain the data in FIG. 23 for a) untreated animals with induced arthritis, b) healthy untreated animals, c) animals treated with EC0894 (500 nmole/kg, biweekly), and d) animals treated with EC0828 (250 nmole/kg, biweekly).

Rats with adjuvant arthritis were treated subcutaneously with EC0932 (250 nmol/kg) in the absence or presence of 500-fold excess of EC0923 (125 μmol/kg) on days 10, 13, 17, and 20 post arthritis induction. The animals in the healthy and arthritis control groups were left untreated. The arthritis scores and animal body weights were recorded three times a week (see FIGS. 19A, B). At the completion of study (day 24), the rats were euthanized by $CO_2$ asphyxiation and processed for paw and spleen weights (see FIGS. 20A, B). The results showed that the anti-arthritis activity of EC0932 was blocked by EC0923, a folate competitor with similar affinity as free folic acid.

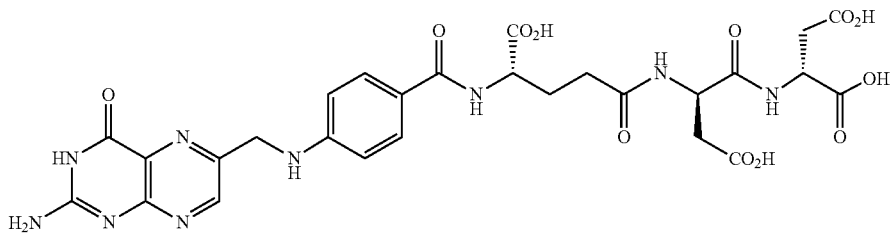

EC0923

Example

EC0828 Demonstrates FR-Specific Activity Against Adjuvant Arthritis

Using similar methods to those herein described, the effect of EC0828 on arthritis was measured. See FIGS. 21-24.

Example

Relative Folate Receptor Affinity

Using displacement of $^3$H-folic acid from folate-receptor-α positive KB cells the relative folate affinity (FA) for several compounds was measured. Folic acid (1.0), aminopterin (0.008), methotrexate (0.018), EC0746 (0.5), and EC0932 (0.26). See FIGS. 25A-D.

Using displacement of $^3$H-folic acid from folate-receptor-beta positive CHO-FR-β cells, the relative folate affinity (FA) for several compounds was measured. Folic acid (1.0), aminopterin (0.004), methotrexate (0.005), and EC0746 (0.27). See FIG. 25F.

Example

EC0746 is a High-Affinity FR-Specific DHFR Inhibitor

Figure 25A:
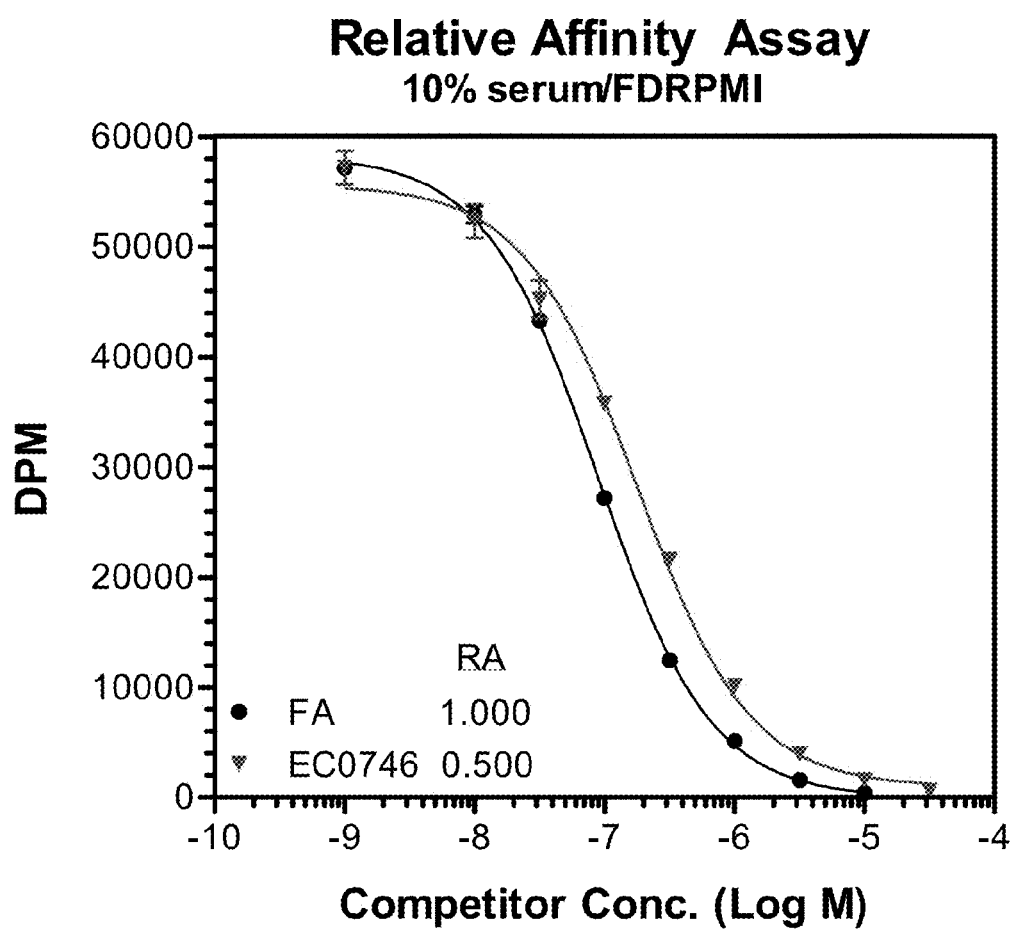
FIGS. 25A-D—Relative affinities of EC0746 (FIG. 25A), aminopterin (AMT) (FIG. 25B), methotrexate (MTX) (FIG. 25C), and EC0932 (FIG. 25D), compared to folic acid (FA), set as 1, to folate receptors (FR-α) of KB cells.
Figure 25B:
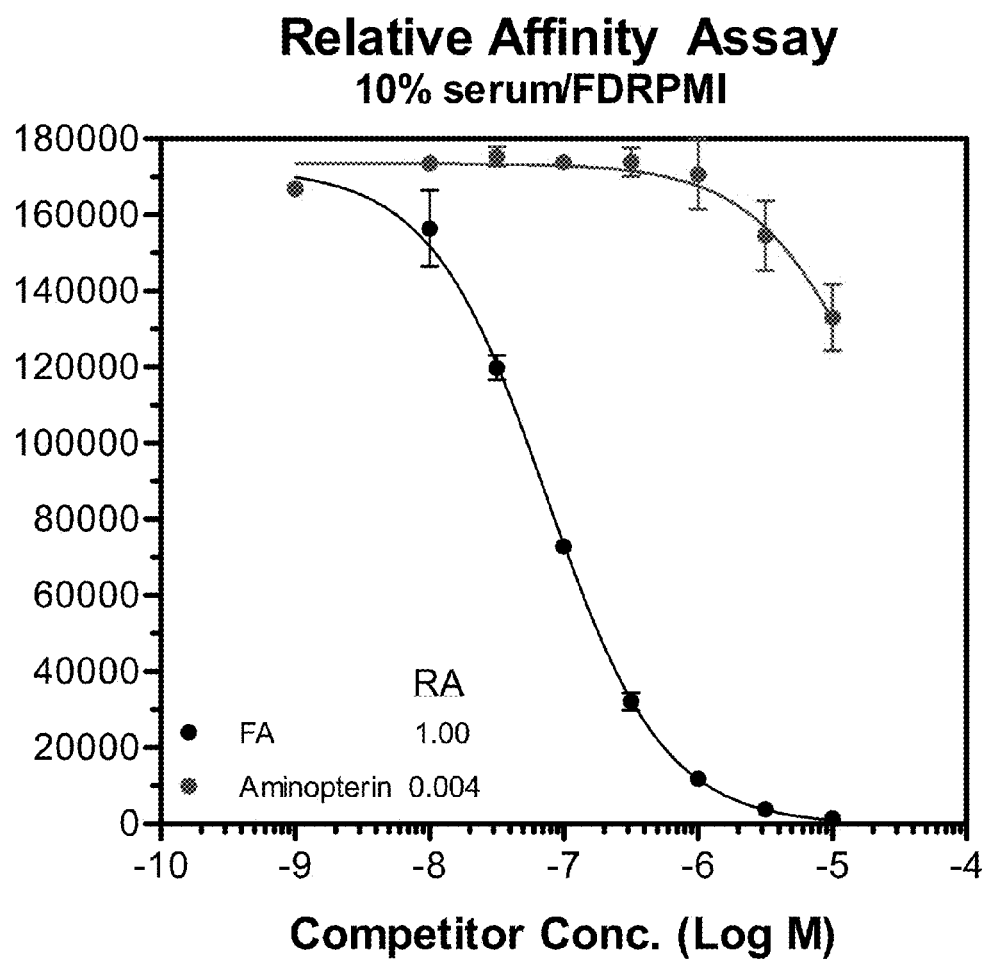
Figure 25C:
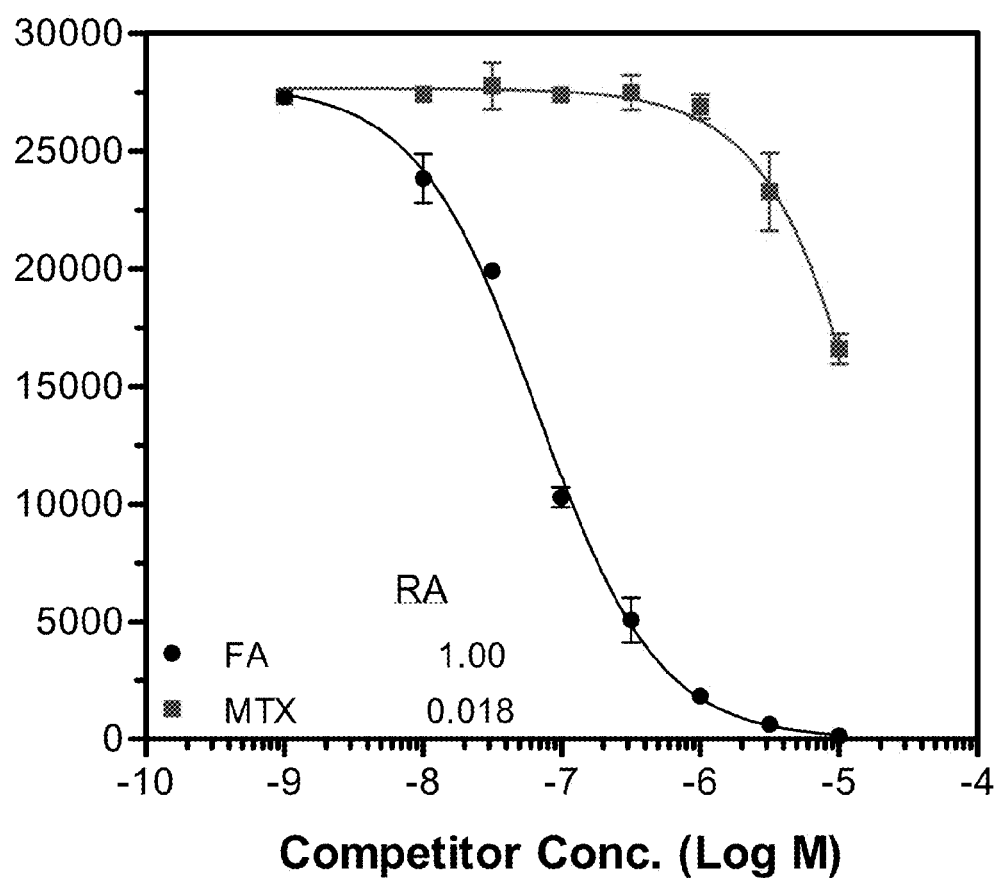
Figure 25D:
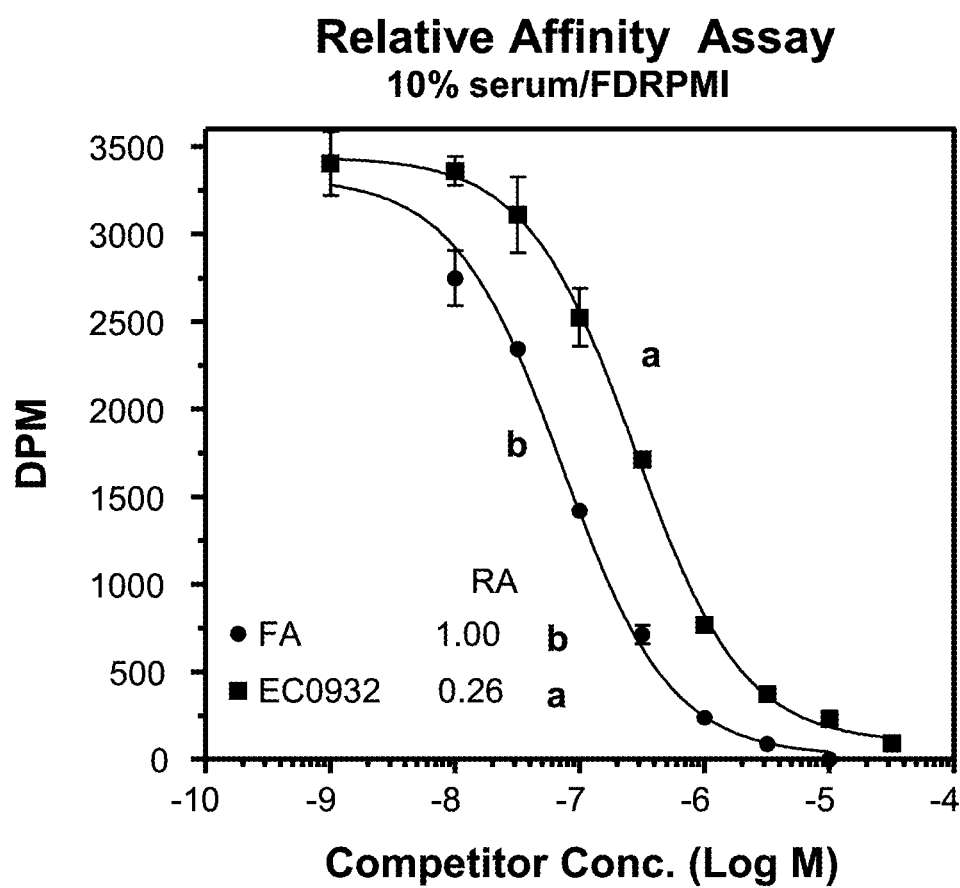
Figure 25E:
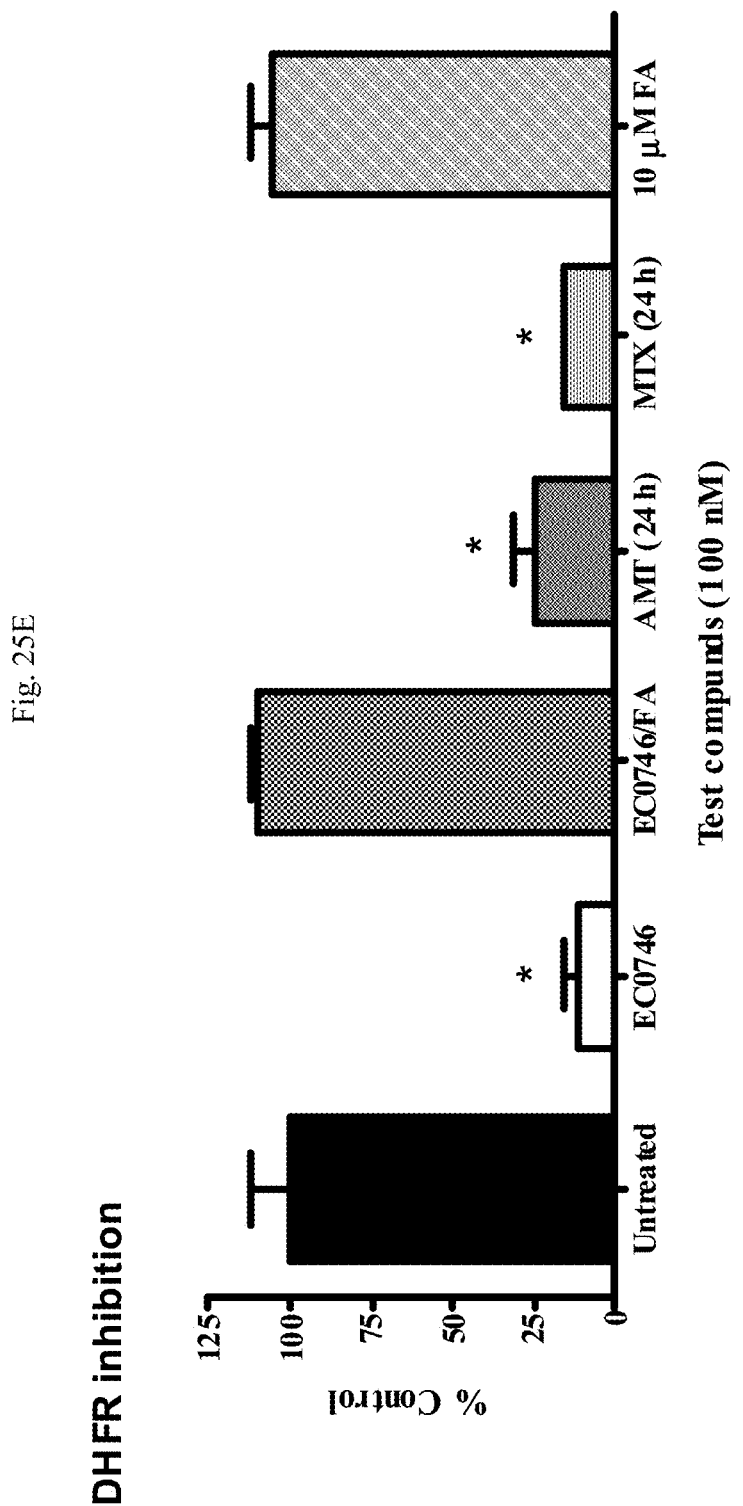
FIG. 25E—In vitro inhibition of DHFR in FR-positive RAW264.7 cells: Untreated control; EC0746 (2 h pulse of 100 nm, followed by 22 h "chase" in drug free medium); EC0746 with excess FA (2 h pulse of 100 nm EC0746 with 100-fold excess folic acid (folate competition), followed by 22 h "chase"); AMT (2 h pulse of 100 nm, followed by 22 h "chase" in drug free medium); MTX (2 h pulse of 100 nm, followed by 22 h "chase" in drug free medium); FA alone (2 h pulse of 10 μm, followed by 22 h "chase" in drug free medium).
Figure 25F:
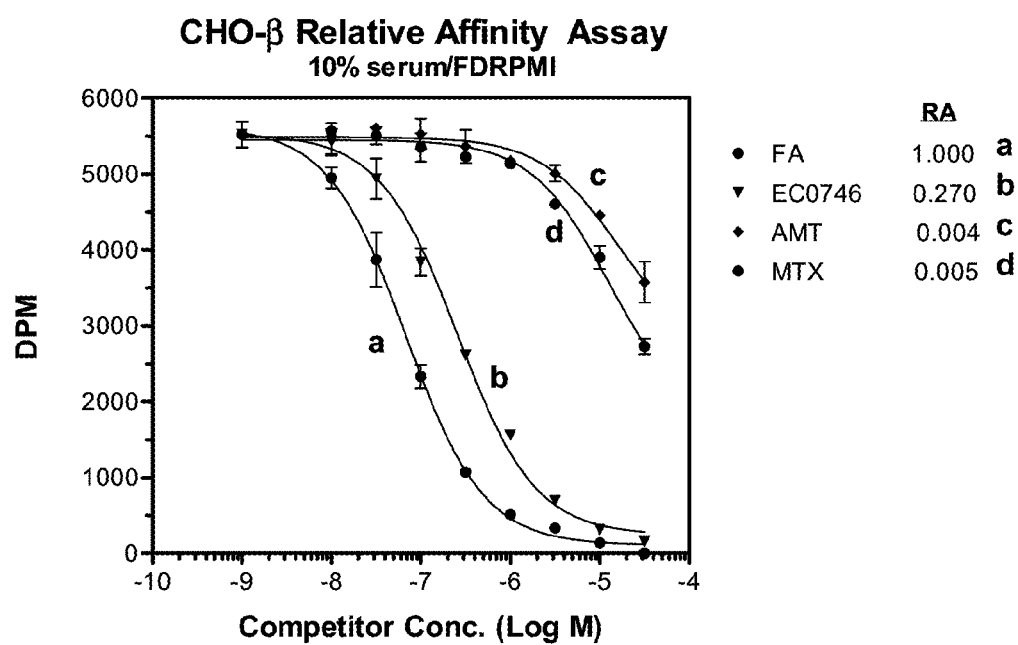
FIG. 25F—Relative affinities of EC0746, aminopterin (AMT), and methotrexate (MTX) compared to folic acid (FA), set as 1, to folate receptors (FR-β) of CHO cells. a. folic acid (relative affinity set to 1.0), b. EC0746 (relative affinity 0.270), c. aminopterin (relative affinity 0.004), and d. methotrexate (relative affinity 0.005).

The FR-binding affinity of EC0746 was directly compared to that of aminopterin (AMT) and methotrexate (MTX) in a competitive binding assay using KB cells as the source of FR. $^3$H-folic acid was used as the competitive ligand and the relative affinity of folate itself was set to 1. As shown in FIGS. 25A-D, EC0746 displayed a much higher affinity to KB cells (FR-α positive) than AMT and MTX with relative affinity values of 0.50, 0.004, and 0.018 respectively. To demonstrate FR-specific activities in-vitro, we first tested the ability of EC0746 to inhibit DHFR, an intracellular target involved in cellular division. FR-positive RAW264.7 cells were given a 2-h pulse of 100 nM EC0746 without or with 100-fold excess folic acid (folate competition) followed by a 22-h "chase" in a drug-free medium. As shown in FIG. 25E, EC0746 inhibited DHFR activity in RAW264.7 cells to a similar degree as AMT and MTX, but excess folic acid completely abolished its inhibitory effect. Since excess folic acid alone (10 μM) did not have any impact, our data suggested that EC0746 may be similar to AMT and MTX with regard to DHFR inhibition but its activity is FR-specific.

Example

EC0746 Demonstrates an Anti-proliferative Effect on RAW264.7 cells

Figure 26A:
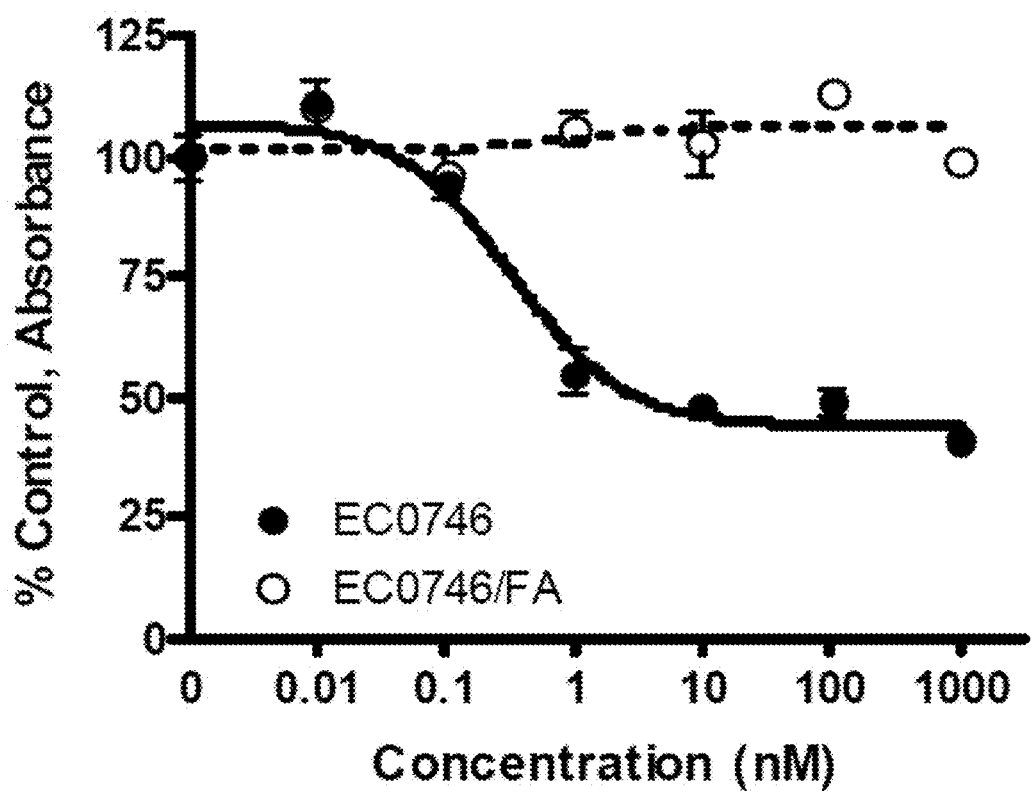
FIG. 26A—Viability of RAW264.7 cells, measured using the XTT assay, LPS (100 ng/mL) added at 4 h before end of incubation to stimulate cytokine production, treated with EC0746 ($EC_{50}$ about 0.3 nM, 2 hour treatment followed by 70 h "chase" in drug-free medium) and treated with EC0746 and excess folic acid (EC0746/FA, 2 hour treatment followed by 70 h "chase" in drug-free medium).
Figure 26B:
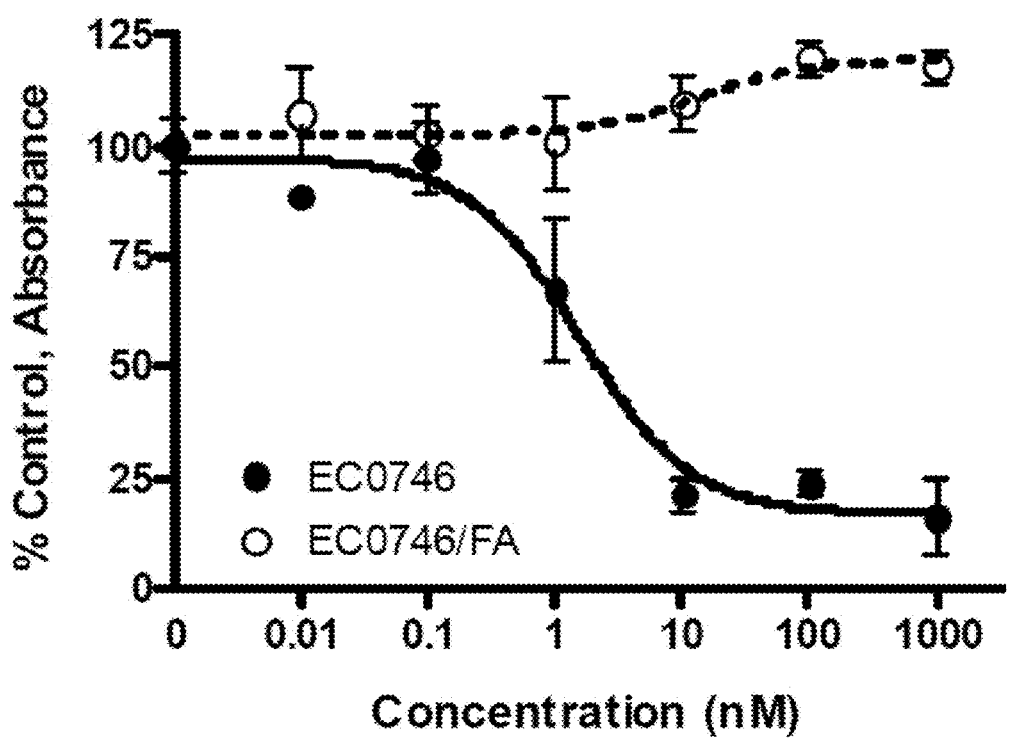
FIG. 26B—TNF-α production from cells treated as in part a, upon LPS exposure ($ED_{50}$ about 1.6 nM). Flow cytometric analysis (FACS) with propidium iodide (PI) staining of the cell cycle of the cells of part a for Untreated (FIG. 26C), EC0746-treated (FIG. 26D) and EC0746/FA-treated cells (FIG. 26E).
Figure 26C:
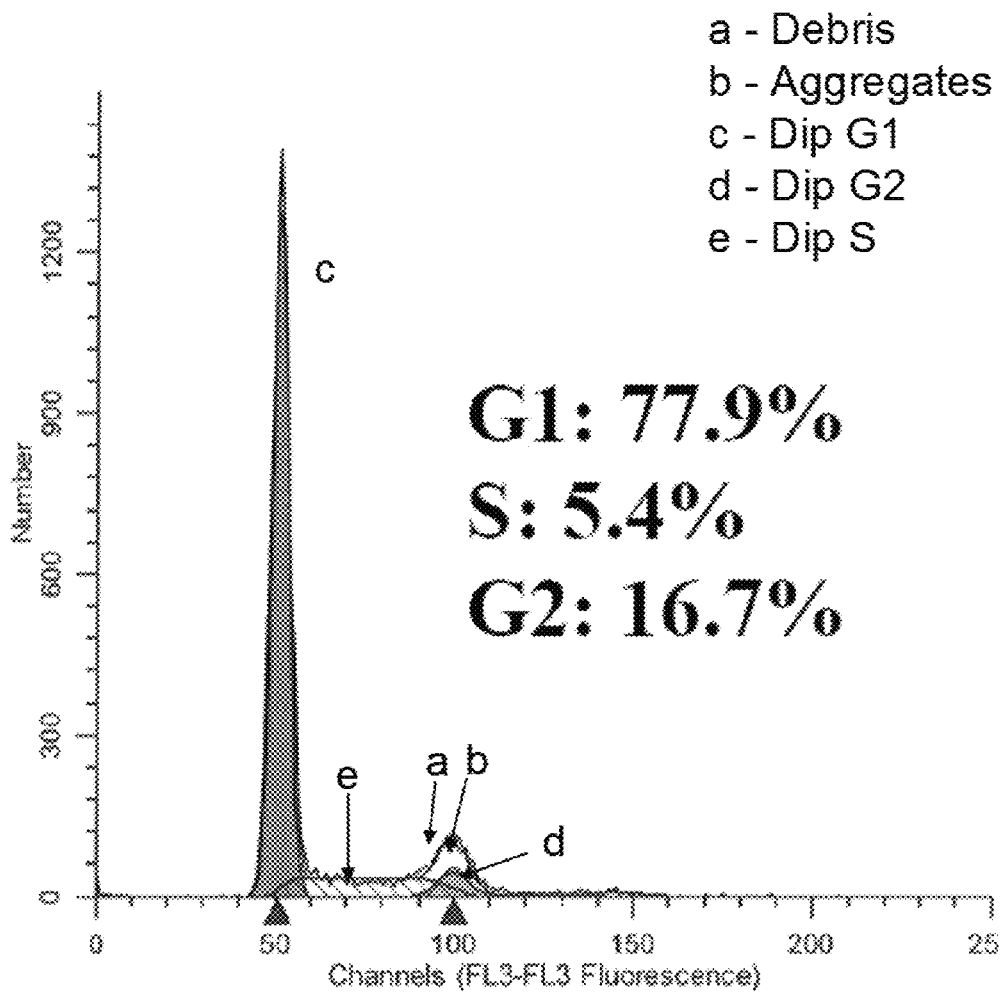
FIG. 26. Anti-proliferative Effect on RAW264.7 cells.
FIG. 26F—Cell cycle distribution for Untreated, EC0746 treated and EC0746/FA treated cells.
FIG. 26G—Western blot analysis of cell-cycle distribution (d) and PCNA expression (e) on whole cell lysates using a PCNA-specific monoclonal antibody for Untreated (UTC), EC0746-treated (EC0746−FA) and EC0746/FA (EC0746+FA)-treated cells.
FIGS. 26H, I—Anti-proliferative Effect on RAW264.7 cells.
FIG. 26I—TNF-α production from cells treated as in part a upon LPS exposure. Comparison of EC0746, EC0746 with excess folic acid (EC0746/FA), aminopterin (AMT), and methotrexate (MTX).
Figure 26D:
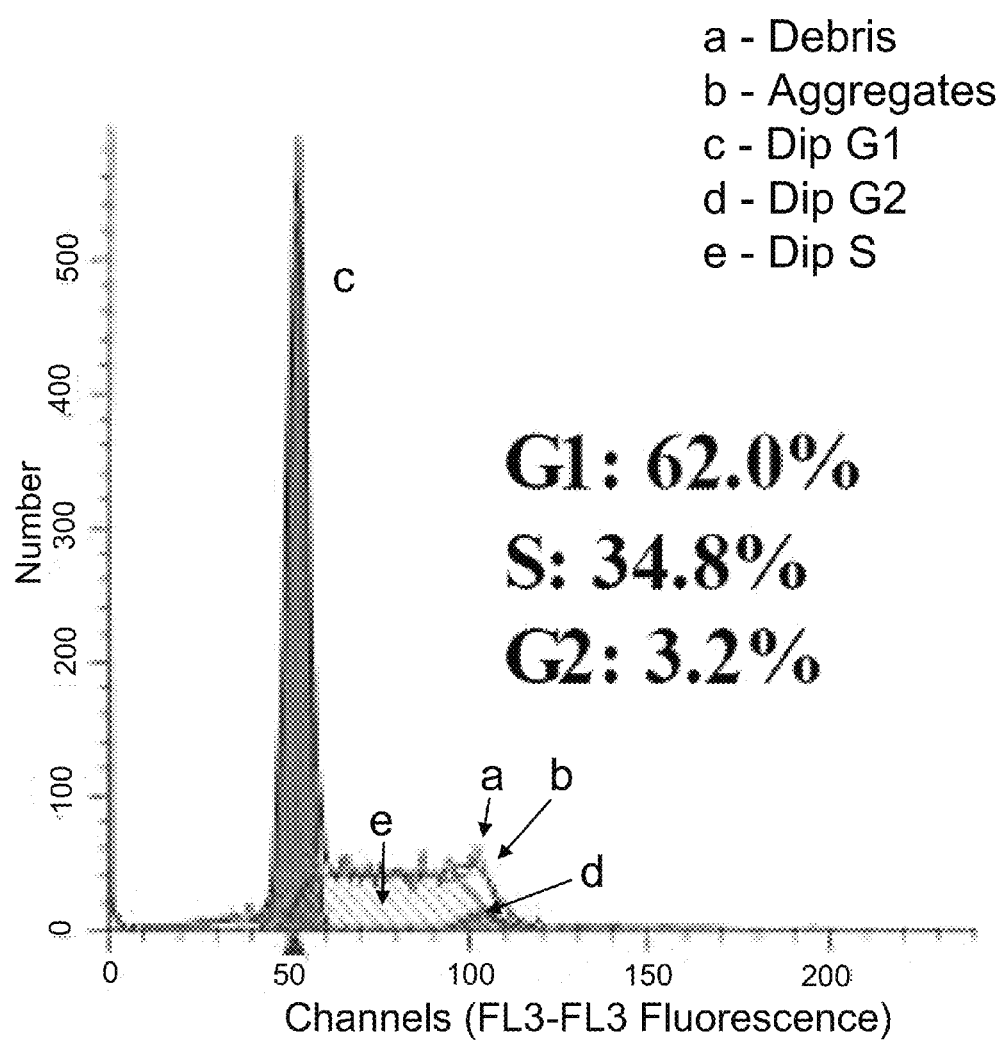
Figure 26E:
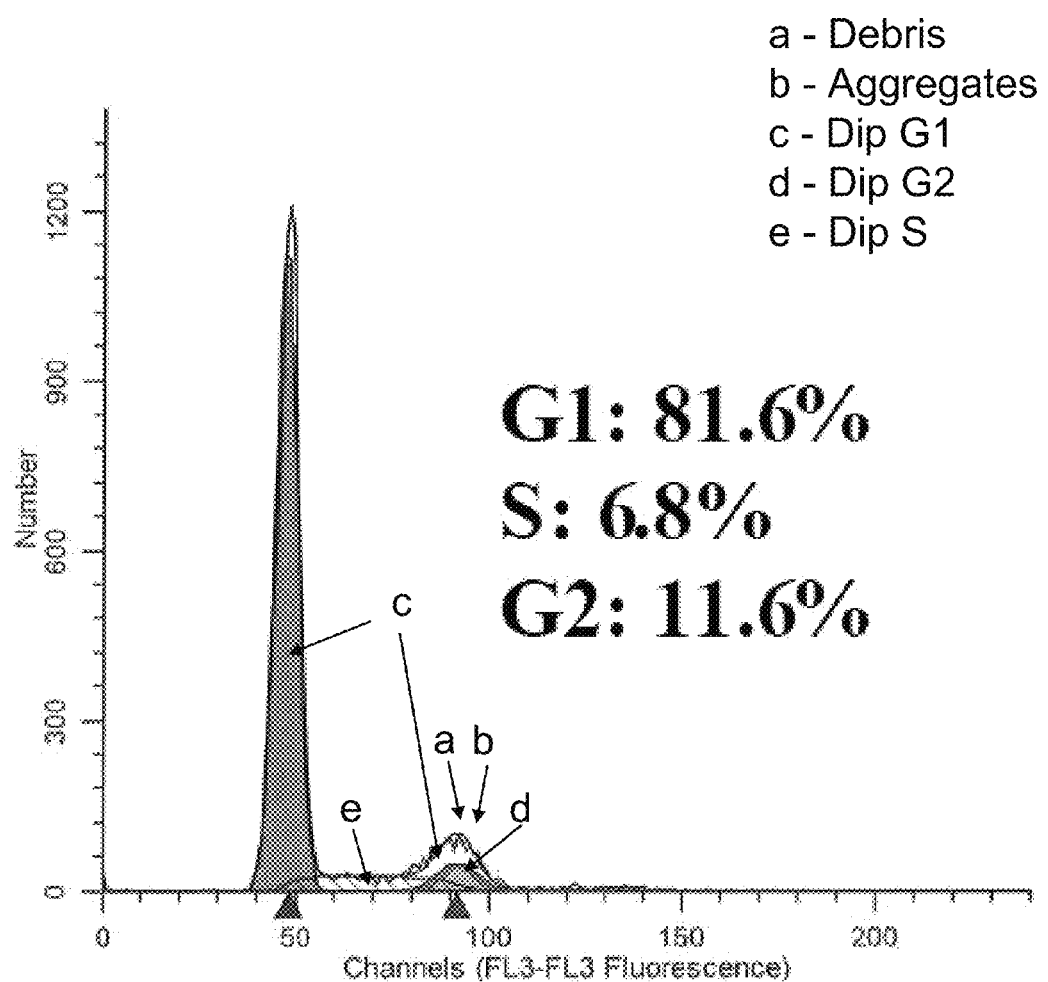
Figure 26F:
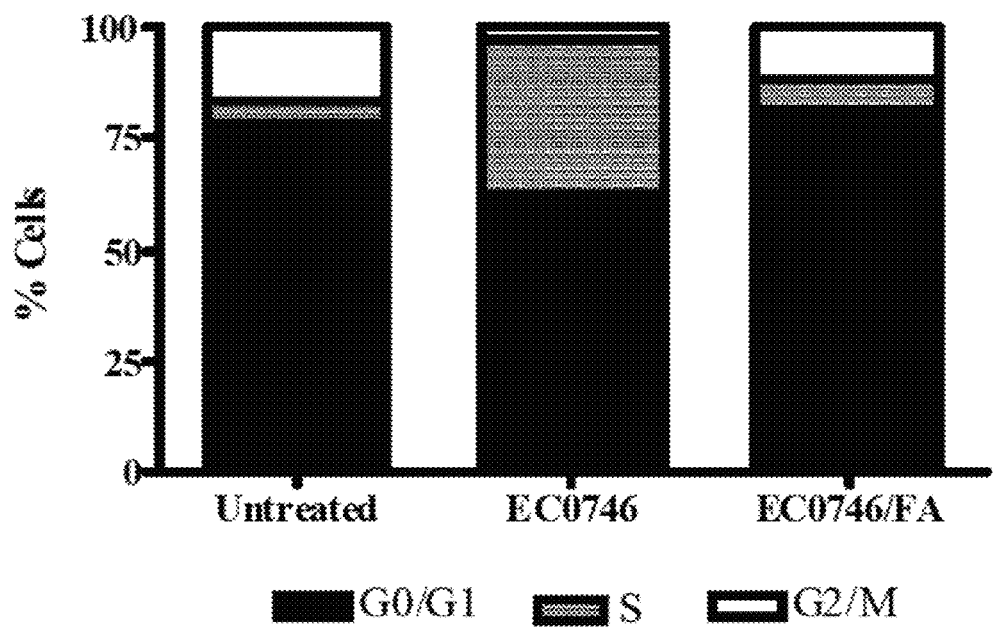
Figure 26G:
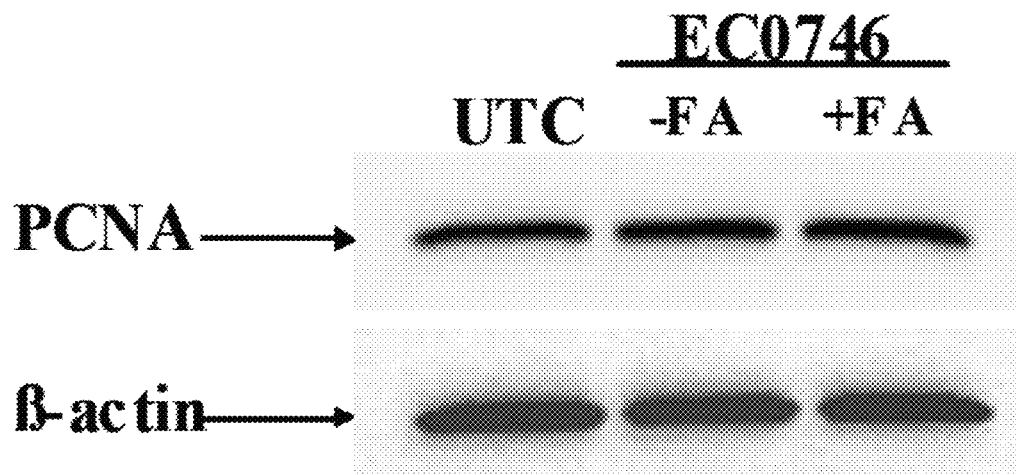
Figure 26H:
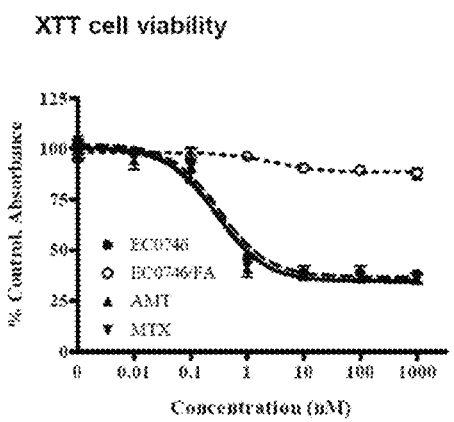
Figure 26I:
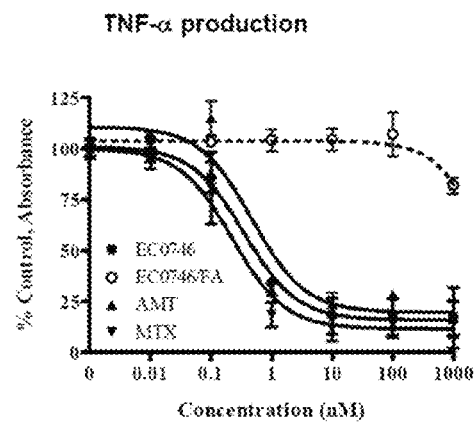

To study the anti-proliferative effect of EC0746, RAW264.7 cells (~40% confluency) were given a 2 h treatment of serial dilutions of EC0746 without or with excess folic acid and followed by a 70-h "chase" in drug-free medium. At 4 h before the end of incubation, LPS (100 ng/ml) was added to the culture medium to stimulate cytokine production. As determined by the XTT assay (FIG. 26A), EC0746 showed a dose-dependent inhibition of cell proliferation ($ED_{50}\approx 0.3$ nM); however, the maximum effect was ~50% when compared to the untreated cells. The EC0746-treated RAW264.7 cells produced less TNF-α upon LPS exposure ($ED_{50}\approx 1.6$ nM) (FIG. 26B). The anti-proliferative and anti-TNF activities of EC0746 were 100% competable with excess folic acid. Interestingly, RAW264.7 cells that had "survived" the EC0746 treatment at ≥1 nM concentrations showed no sign of additional growth when redispersed in fresh medium for 72 h. Because DHFR is an S-phase enzyme that increases during the S-phase of mitosis, RAW264.7 cells pre-treated with EC0746 were stained with propidium iodide and analyzed for the status of cell cycle and the expression of proliferating cell nuclear antigen (PCNA). For flow cytometric analysis (FACS) of the cell cycle, the cells were recovered, fixed in 70% ethanol/PBS solution, and resuspended in FACS buffer (PBS supplemented with 1% BSA). After a brief treatment with RNase A (Roche Molecular Biochemicals), the cells were stained with 50 μg/ml of propidium iodide (Invitrogen, Carlsbad, Calif.) before FACS analysis. Western blot analysis was carried out on whole cell lysates using a monoclonal antibody specific for PCNA (PC10, Cell Signaling, Danvers, Mass.). After incubation with a peroxidase-conjugated secondary antibody, the signals were visualized using SuperSignal West Pico Chemiluminescent Substrate system (ThermoScientific, Waltham, Mass.) following the manufacturer's instructions. The images were acquired using a G:BOX Chemi HR 16 gel imaging system (Syngene, Frederick, Md.). As shown in FIGS. 26C-F, EC0746 treated RAW264.7 cells showed an increase in number of cells in the S-phase, but the effect was again competable by excess folic acid. Western blot analysis indicated no change in PCNA expression in EC0746-treated and untreated cells (FIG. 26G). Taken together, these data demonstrated that EC0746 completely halted the proliferation of RAW264.7 cells in a FR-dependent manner, but did not appear to kill them; instead, the cells were arrested at the S-phase of the cell cycle.

Example

EC0746 Modulates Cytokine Responses in Rat Thioglycollate-elicited Macrophages

Figure 27C:
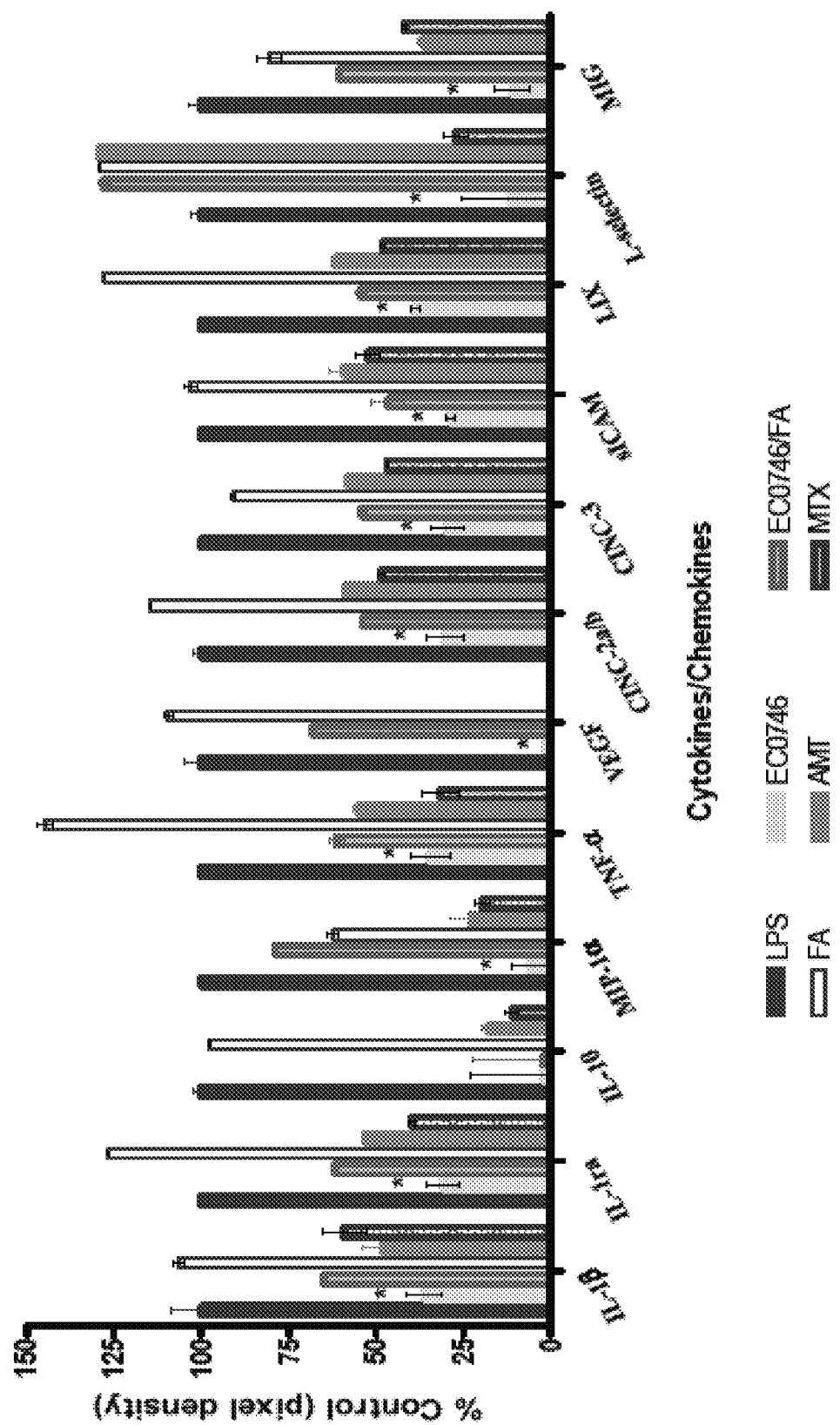
FIG. 27. EC0746 Modulation of Cytokine Responses in Thioglycollate-elicited Macrophages (TG-macs).
FIGS. 27A, B—Rat cytokine antibody array and plotted results for cytokines/chemokines (FIG. 27C) for rat TG-macs untreated (LPS) or with indicated treatment of 100 nM of treatment for 2 h plus a 70 h chase, and with addition at 24 h prior to end of incubation of LPS (5 µg/mL) and IFN-γ (100 ng/mL) for EC0746, EC0746 plus 100-fold excess FA (EC0746/FA), folic acid alone (FA), aminopterin (AMT), and methotrexatre (MTX), respectively, as to IL-1β, IL-1ra, IL-10, MIP-Iα, TNF-α, VEGF, CINC-2a/b, CINC-3, sICAM, LIX, L-selectin, and MIG.

Because rat TG-macs are responsive to inflammation stimuli in-vitro, we examined the ability of EC0746 to block cytokine response after exposure to LPS and IFN-γ, two signals required for full activation of macrophages. Thus, rat TG-macs were treated with 100 nM of EC0746 following our standard condition of 2 h pulse plus a 70-h chase and without or with folate competition. At 24 h prior to the end of incubation, LPS (5 μg/mL) and IFN-γ (100 ng/mL) were added to the culture medium to stimulate the release of cytokines, chemokines, and other inflammatory mediators. As detected with a rat cytokine antibody array (FIG. 27), EC0746 inhibited a range of cytokines/chemokines, 11 of which showed a significant FR-specific inhibition ($P<0.05$, EC0746 versus EC0746 plus folic acid), including IL-1β, IL-1γa, MIP-1α, TNF-α, VEGF, CINCs, sICAM, LIX, L-selectin, and MIG. These data also indicated that (i) the levels of FRs on rat TG-macs were sufficient for EC0746 to take a remedial effect on cytokine responses associated with macrophage activation and (ii) the observed anti-inflammatory action of EC0746 can be independent of macrophage proliferation.

Example

Figure 28A:
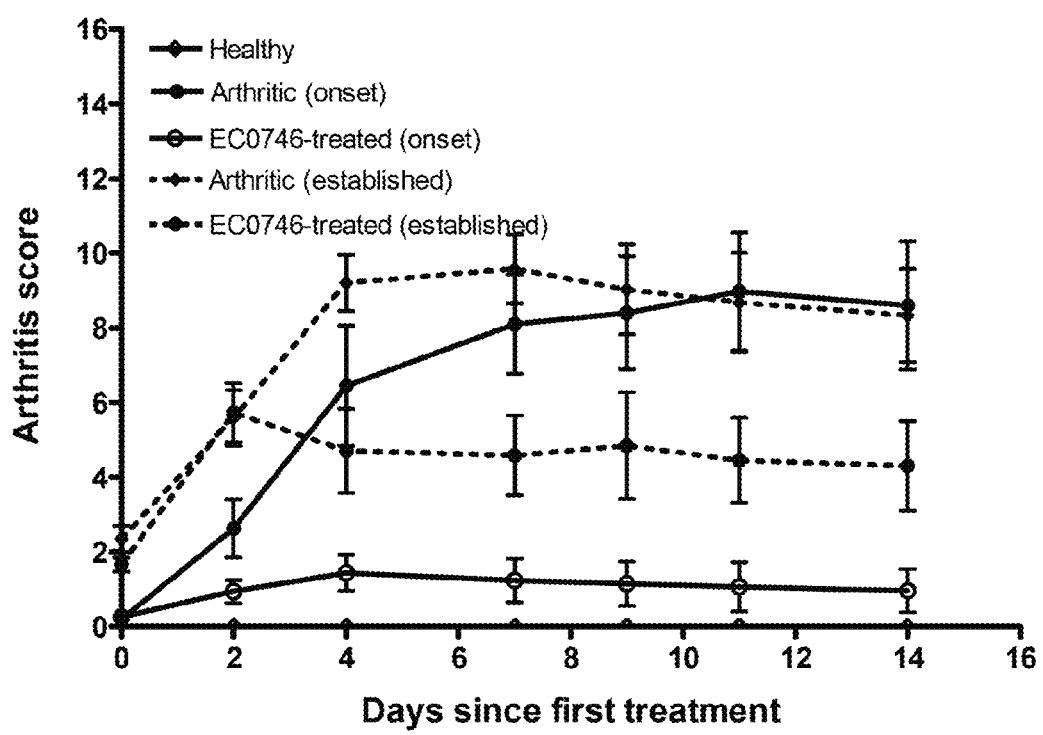
FIG. 28A—Arthritis score with time in days since first treatment.
Figure 28B:
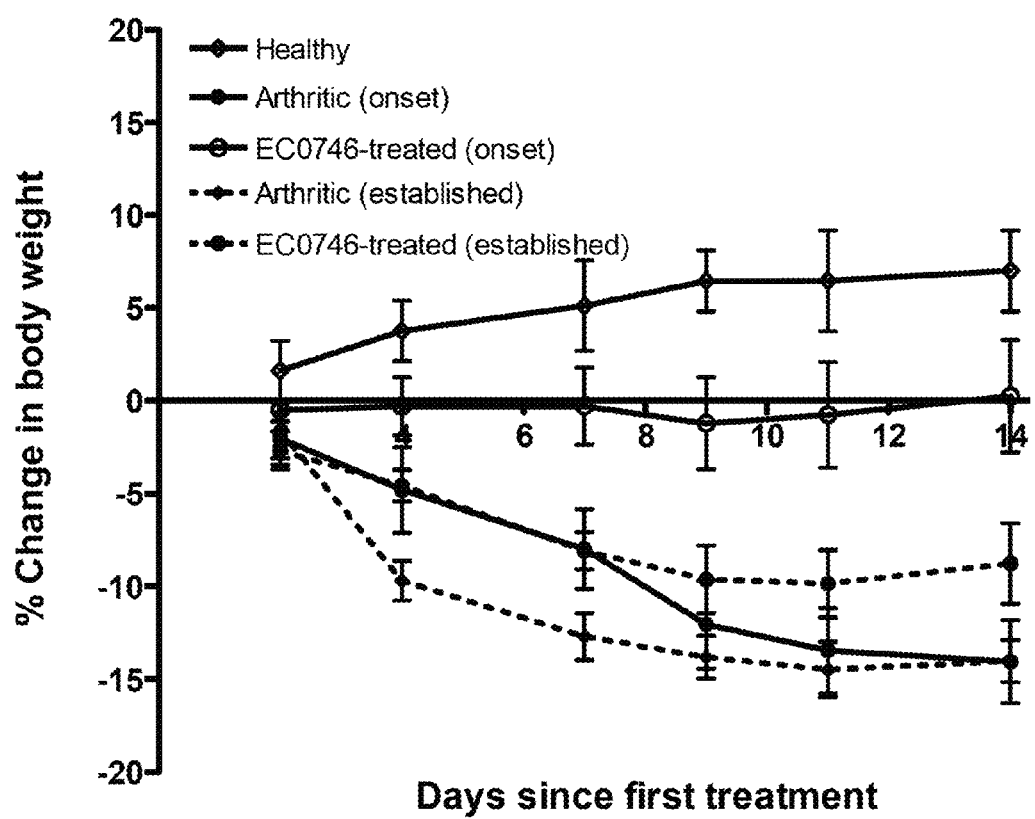
FIG. 28B—% Change in body weight with time in days since first treatment.
Figure 28C:
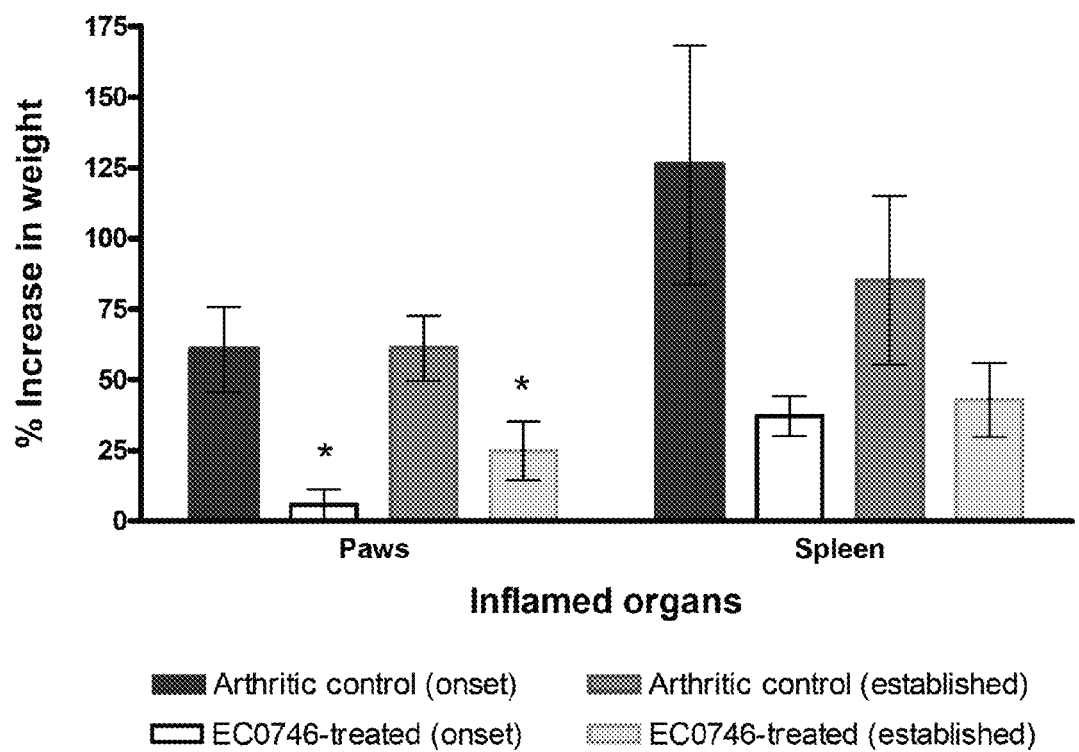
FIG. 28C—% Increase in weight of Paws and Spleen for Healthy, Arthritic (onset), EC0746-treated (onset), Arthritic (established) and EC0746-treated (established) AIA rats.

EC0746 Ameliorates Local and Systemic Inflammation in Rats with Adjuvant Arthritis The rat adjuvant induced arthritis (AIA) model resembles the characteristics of RA in humans and has been widely used to study the impact of novel anti-inflammatory agents. In this study, AIA rats with early-onset or established disease (mean arthritis scores of 0 and 2, respectively) were given a biweekly regimen of EC0746 (s.c., 500 nmol/kg/dose) for 2-week starting on day 10-13 after arthritis induction. Multiple study endpoints were taken to assess the efficacy including (i) arthritis score and body weight obtained during the course of therapy and (ii) paw and spleen weights collected 4 days after the last dose. As measured by the semiquantitative visual scoring system, EC0746 was found to be very effective in rats with low arthritis at the first day of treatment (FIG. 28A). In rats with more established AIA, the same treatment improved, although to a lesser degree, the overall severity of the joint disease. While the untreated arthritic controls lost approximately 14-16% of their original weight, the animals treated with EC0746 from the early-onset maintained a good body weight (FIG. 28B). On the other hand, EC0746 did not stop the animals with more established arthritis at the time of treatment from losing weight, but to a lesser extent in relation to the untreated arthritic controls. When the percent increase in paw/spleen weights was evaluated (FIG. 28C), EC0746 treatment resulted in approximately 10-(paw) and 3-fold (spleen) improvements in rats with low arthritis, and the corresponding improvements in rats with more established arthritis were at ~2.5- and 2-fold, respectively (see P values in the figure legend).

To further investigate dose-response relationship and schedule-dependency, EC0746 was administered to rats with developing AIA (day 10) at 25-500 nmol/kg/dose (biweekly) or 1000 nmol/kg/dose (once weekly). As summarized in Table 1, below, biweekly EC0746 dosed for 2 weeks displayed a linear dose response in inhibiting paw edema from 25 to 250 nmol/kg/dose with an R-squared value of 0.997, and no statistical differences between 250 and 500 nmol/kg/dose were seen. When dosed once weekly for 2 weeks, EC0746 at 1000 nmol/kg/dose remained to be highly effective, but this schedule did not control the fast progressing AIA to the same degree as the biweekly regimen at 250-500 nmol/kg/dose. Overall, EC0746 was found very effective against AIA and capable of controlling local (joints) and systemic (spleen) inflammation and halting the progression of arthritis.

TABLE 1

| Treatment | Dose (nmol/kg) | Frequency | % Inhibition in paw edema[1] | Splenomagly[2] | % Weight loss[3] |
|---|---|---|---|---|---|
| Control | — | — | 0 | 117 ± 22 | −16 ± 1 |
| EC0746 (sc) | 25* | biw | 0 ± 25* | 73 ± 8 | −17 ± 1 |
|  | 100* | biw | 35 ± 11* | 52 ± 13 | −14 ± 1 |
|  | 250* | biw | 91 ± 4* | 25 ± 6 | −0.5 ± 3 |
|  | 500 | biw | 91 ± 9 | 37 ± 7 | 0.4 ± 4 |
|  | 1000 | qw | 72 ± 12 | 39 ± 5 | −7 ± 3 |

TABLE 1-continued

| Treatment | Dose (nmol/kg) | Frequency | % Inhibition in paw edema[1] | Splenomagly[2] | % Weight loss[3] |
|---|---|---|---|---|---|
| MTX (oral) | 250 | biw | 70 ± 5 | 42 ± 17 | −14 ± 2 |
|  | 1650 | qw | 47 ± 10† | — | −10 ± 2 |
| MTX (sc) | 250 | biw | 78 ± 10 | 24 ± 3 | −2 ± 4 |
|  | 500 | biw | 88 ± 7 | 20 ± 4 | −2 ± 7 |
| Enbrel (sc) | 10 mg/kg | q3d | 46 ± 9 | 42 ± 7 | −15 ± 2 |

[1]% Inhibition in paw edema is calculated based on paw weight on Day 24: 100 × (Arthritic control − Treated)/(Arthritic control − Healthy).
[2]Splenomagly is defined as % increase in spleen weight relative to the spleen weights of healthy rats.
[3]On Day 24 relative to body weight on the first day of treatment.
*Linear regression analysis showed an R-squared value of 0.997.
†Calculated based on arthritis scores on Day 24 (paw weights were not obtained).

Example

EC0746 Anti-arthritic Activity was FR-Mediated and Different from MTX

RA patients receiving MTX are frequently given folate supplementation to reduce its side effects. We found simply mixing AMT with free folic acid (1:1) to match the dose of EC0746 (500 nmol/kg/dose, biweekly) was 100% lethal to AIA rats. Thus, the anti-arthritic effect of EC0746 in AIA rats was not due to the apparent "folate supplementation of AMT". Given the difference in FR-binding affinity, we suspected that EC0746 and its active comparator MTX would have a different mechanism of action in the AIA model where FR-positive macrophages are abundant. To verify this theory, we undertook in-vivo folate competition studies using EC0923, a water-soluble folate-containing competitor (relative affinity value of 0.84 on KB cells), as a FR-blocking agent in the AIA rats. All test compounds (EC0746, 250 nmol/kg/dose; MTX, 250 nmol/kg/dose; EC0923, 125 μmol/kg/dose) were administered biweekly for 2 weeks. EC0923 was pre- and co-administered at a total of 500-fold excess of EC0746 and MTX.

Figure 30A:
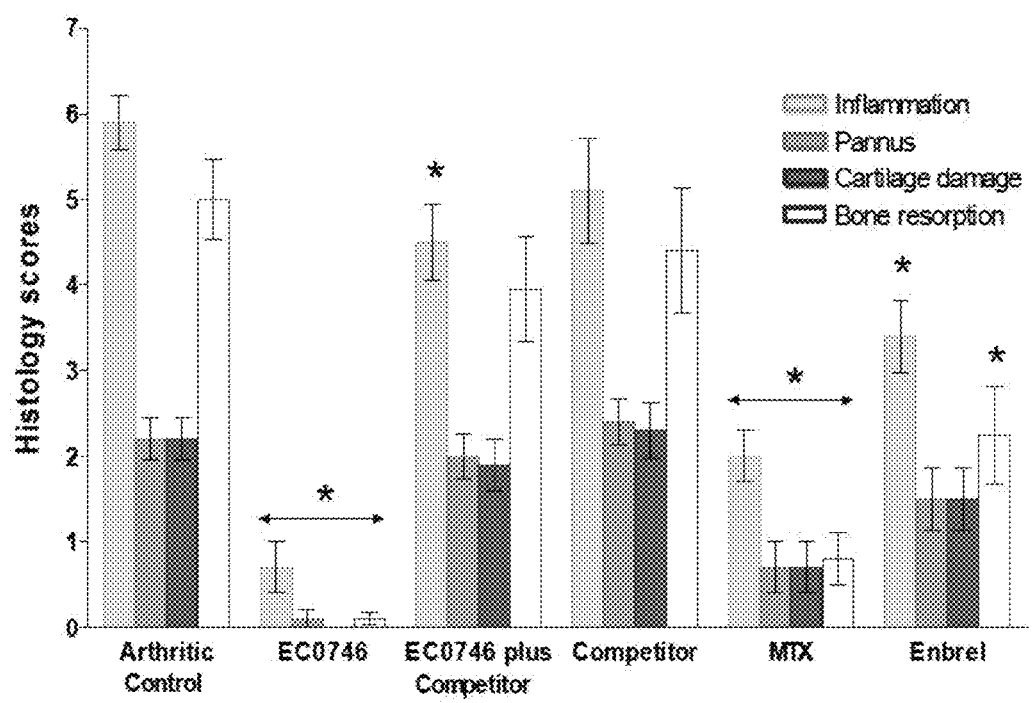
FIG. 30A—Histology scores for Inflammation, Pannus, Cartlige damage and Bone Resorption.
Figure 30B:
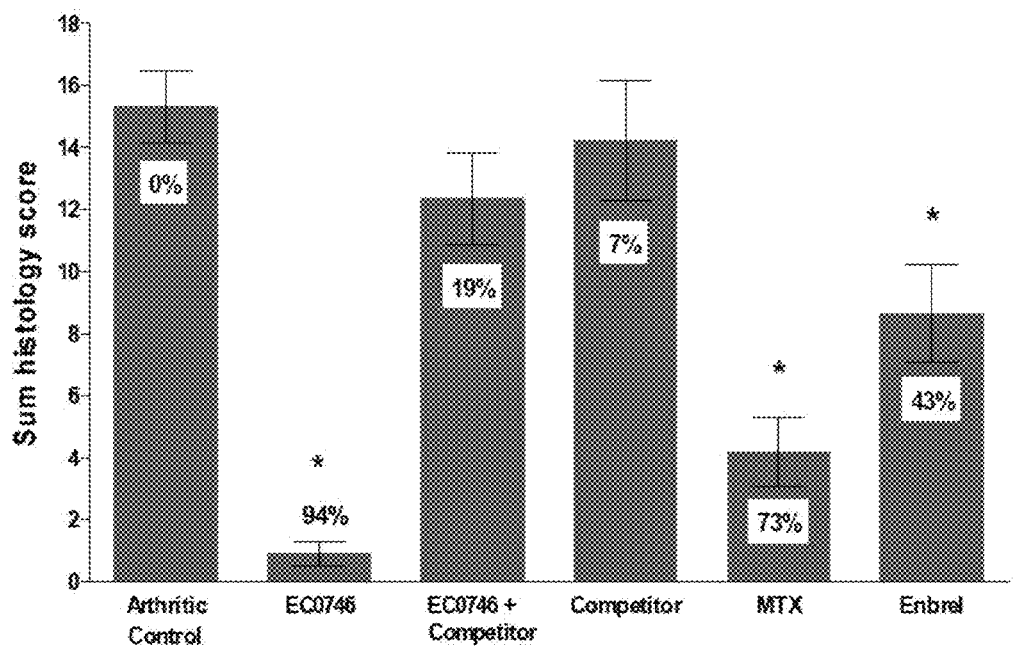
FIG. 30B—Sum histology scores.
Figure 30C:
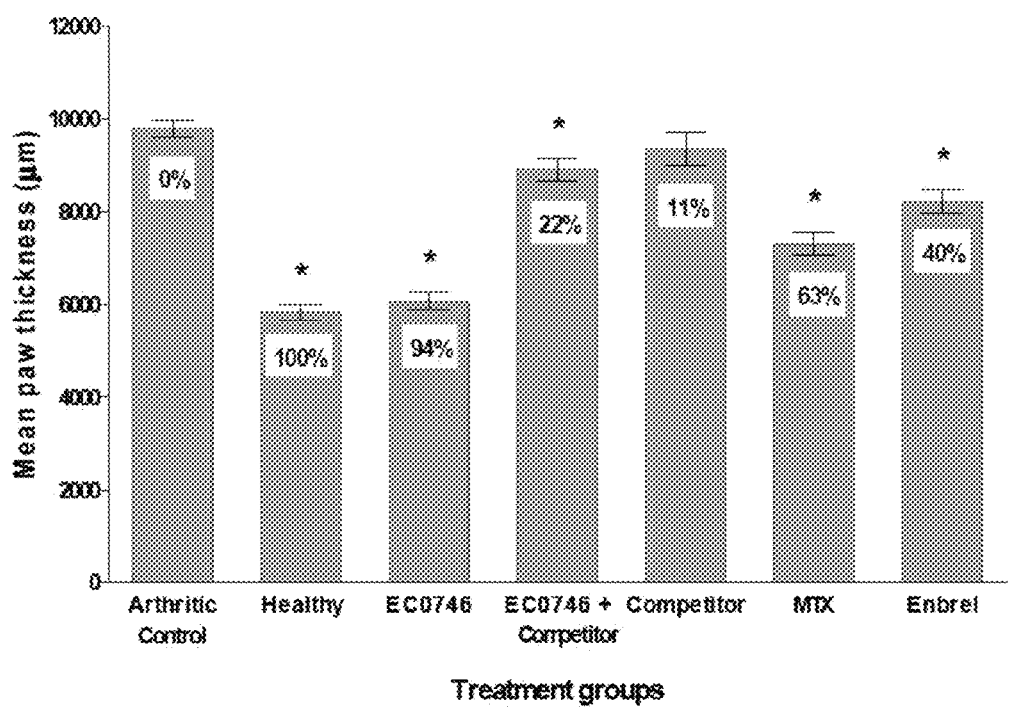
FIG. 30C—Mean paw thickness (µm) and FIG. 30D—images from paws for Healthy (where indicated), Arthritic Control (untreated), and animals treated with EC0746, EC0746+Competitor, Competitor alone, methotrexate (MTX), or Enbrel in AIA rats, with EC0923 as the folate-containing competitor.
Figure 30D:
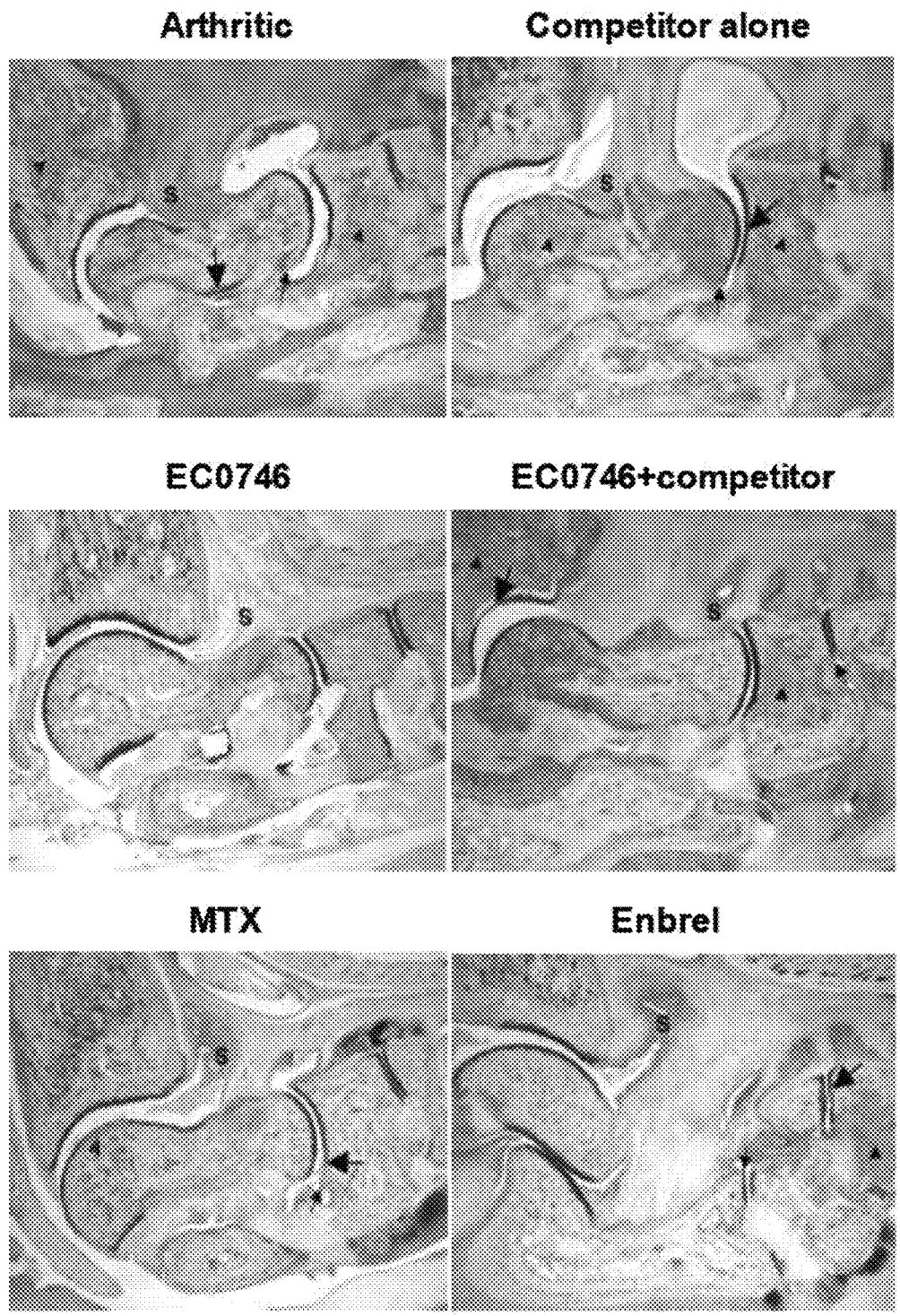
FIG. 30. Histology of Rats with Adjuvant Induced Arthritis (AIA).
Figure 31A:
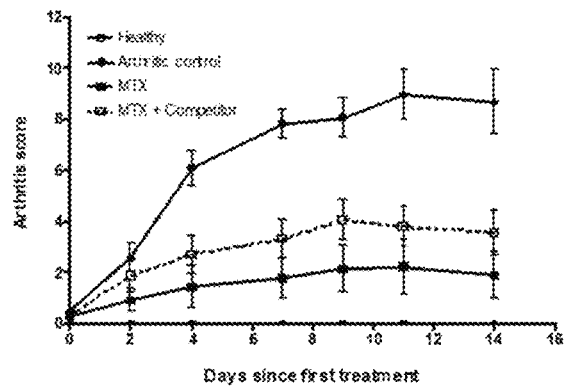
FIG. 31A—Arthritis score with time in days since first treatment.
Figure 31B:
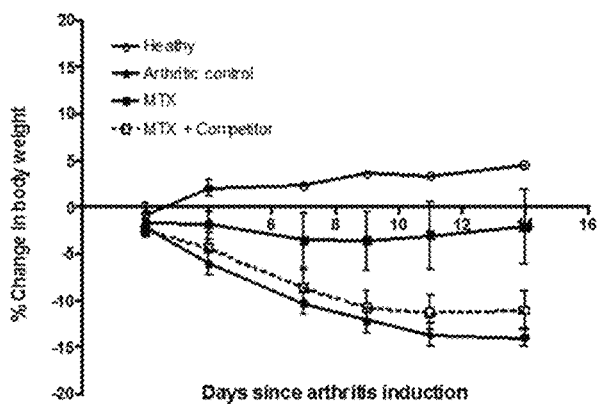
FIG. 31B—% Change in body weight with time in days since arthritis induction.
Figure 31C:
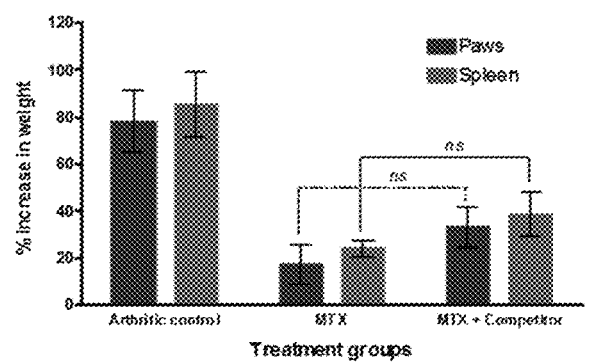
FIG. 31C—% Increase in weight of Paws and Spleen for Healthy (where indicated), Arthritic Control (untreated), and animals treated with methotrexate (MTX) or MTX+Competitor in AIA rats, with EC0923 as the folate-containing competitor.

As shown in FIG. 29, EC0746 alone was very effective, but its activity could be nearly completely blocked by the presence of excess EC0923. This included all parameters assessed: arthritis score (FIG. 29A), change in body weight (FIG. 29B), and percent increases in paw and spleen weights (FIGS. 29C, D) (see P values in the figure legend). EC0923 treatment alone did not have any impact on the development or severity of the disease compared to the untreated arthritic controls (FIG. 29). Radiographic analysis (hind paws) confirmed severe periarticular soft tissue swelling, joint space narrowing, bone erosion, periostal new bone formation, and osteolysis in arthritic control animals and the animals treated with EC0923 (FIGS. 29E, F). There were minimum radiographic changes seen in EC0746-treated animals, but the animals treated with EC0746 plus EC0923 showed a significant joint damage (P<0.05). Histologically, animals treated with EC0923 alone were also similar to untreated arthritic controls in all parameters assessed (i.e. ankle inflammation, bone resorption, pannus formation, and cartilage damage) (FIG. 30A). As shown in FIG. 30B, the mean sum of histology scores (out of a maximum score of 20) was ~15.3 and 14.2 for the arthritic control and EC0923-treated animals, respectively. The corresponding dorsal to ventral paw thickness was ~9 8 mm and ~9.4 mm, compared ~5.8 mm for the healthy animals (FIG. 30C). In contrast, 3 of 5 animals treated with EC0746 had no lesions (FIG. 30D), resulting in 88-100% decreases in individually scored parameters (FIG. 30A) and an overall 94% decrease in summed scores when compared to untreated arthritic controls (FIG. 30B). The dorsal to ventral thickness of EC0746-treated paws was also significantly decreased by 94% (FIG. 30C). The animals treated with EC0746 plus the 500-fold excess EC0923 did have significantly decreased inflammation scores (24%), but all other scored parameters were non-significantly decreased (9-21%, FIGS. 30A, B). The dorsal to ventral paw thickness in EC0746/EC0923-treated paws was also significantly decreased by 22% from that of the arthritic control animals (FIG. 30C), suggesting a small non FR-targeted effect. On an equimolar basis, s.c. MTX treatment (250 nmol/kg/dose, 4 dose×2 weeks) also significantly improved the development and severity of arthritis (Table 1, above, FIG. 31). However, the anti-arthritic activity of MTX was not significantly blocked by excess EC0923 in arthritis score (FIG. 31A) and percent increases in paw and spleen weights (FIG. 31B). The animals treated with MTX plus the folate competitor did actually lose more body weight compared to the animals treated with MTX (FIG. 31C). Taken together, our data suggested that EC0746 and MTX are different from each other in terms of treating active inflammation via FR-targeted and non-targeted mechanisms of action, respectively.

Example

EC0746 is More Efficacious than Oral methotrexate and Subcutaneous Etanercept Since methotrexate (MTX) and etanercept are part of the current standard of care for RA, we compared EC0746 against both drugs in rats with adjuvant arthritis using clinically relevant dosing routes. The animals were treated with subcutaneous EC0746 (250 nmo/kg) and oral MTX (250 nmol/kg) on days 10, 13, 17, and 20 post arthritis induction. Etanercept was given subcutaneously at 10 mg/kg once every 3 days starting on day 10. At the completion of any study (day 24), rats were euthanized by $CO_2$ asphyxiation and processed for paw weight (cut at the hairline) and spleen weight. The differences in total paw weight between arthritic rats after treatment and that of healthy rats from the same experiment were used to verify the extent of paw edema. The removed hind paws were immersion-fixed in 10% buffered formalin and subjected to radiographic and/or histopathological analyses. In some cases, X-ray radiographic images of the arthritic hind paws were taken using a Kodak Imaging Station In Vivo FX system (Carestream Molecular Imaging, New Haven, Conn.).

Figure 29A:
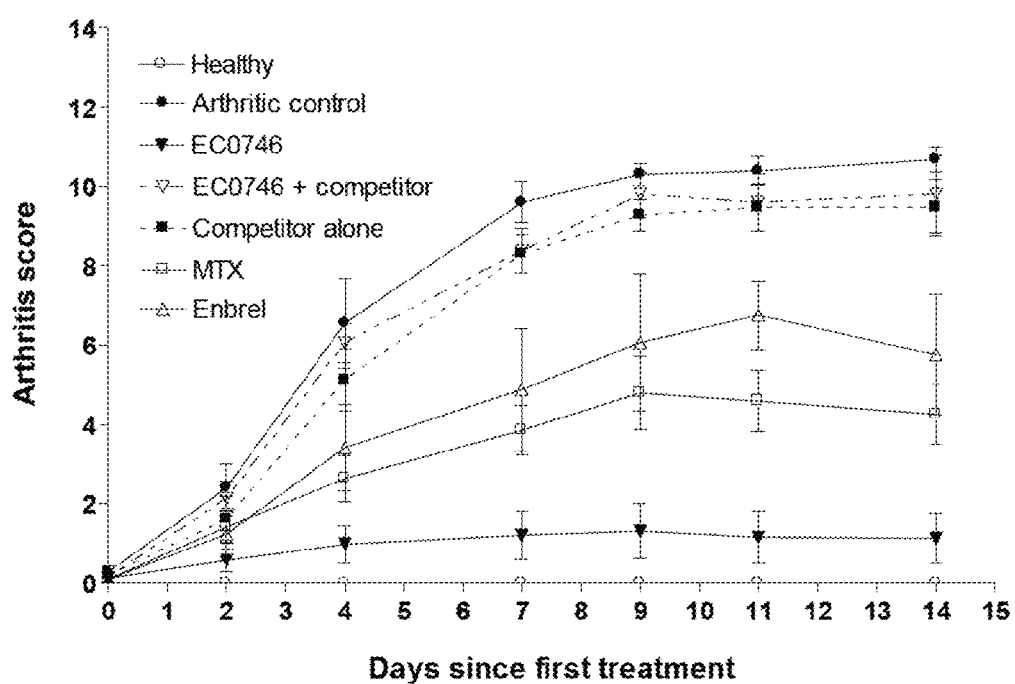
FIG. 29A—Arthritis score with time in days since first treatment.
Figure 29B:
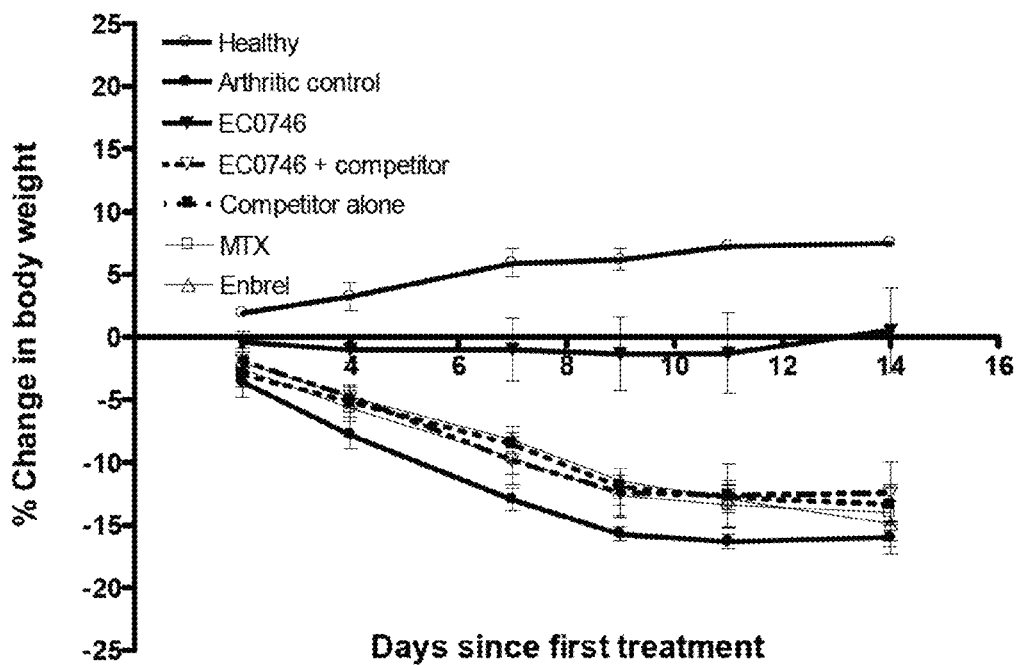
FIG. 29B—% Change in body weight with time in days since first treatment.
Figure 29C:
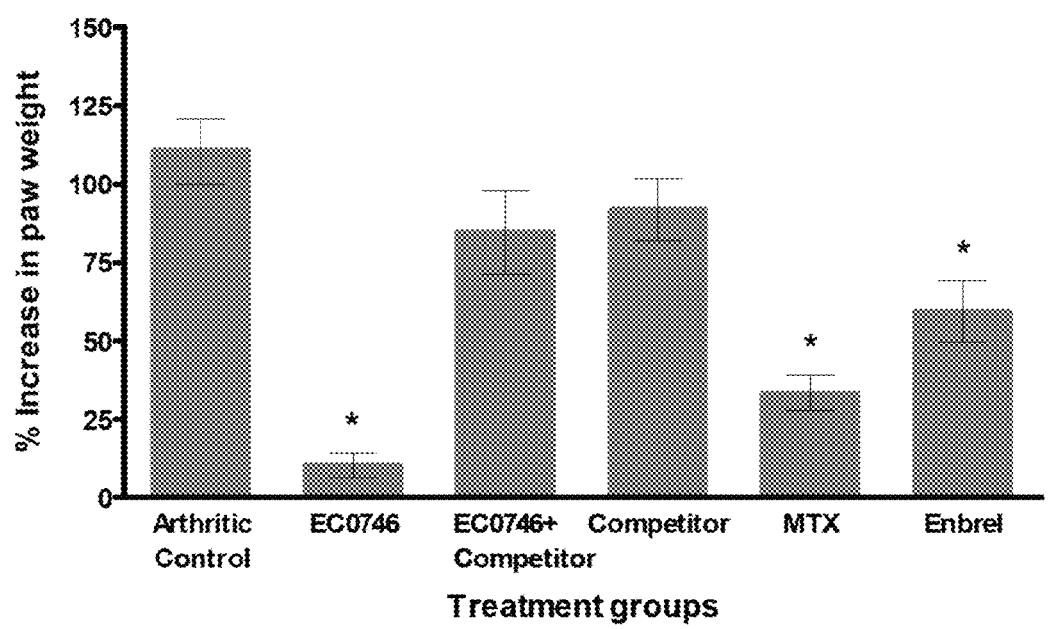
FIG. 29C—% Increase in weight of Paws.
Figure 29D:
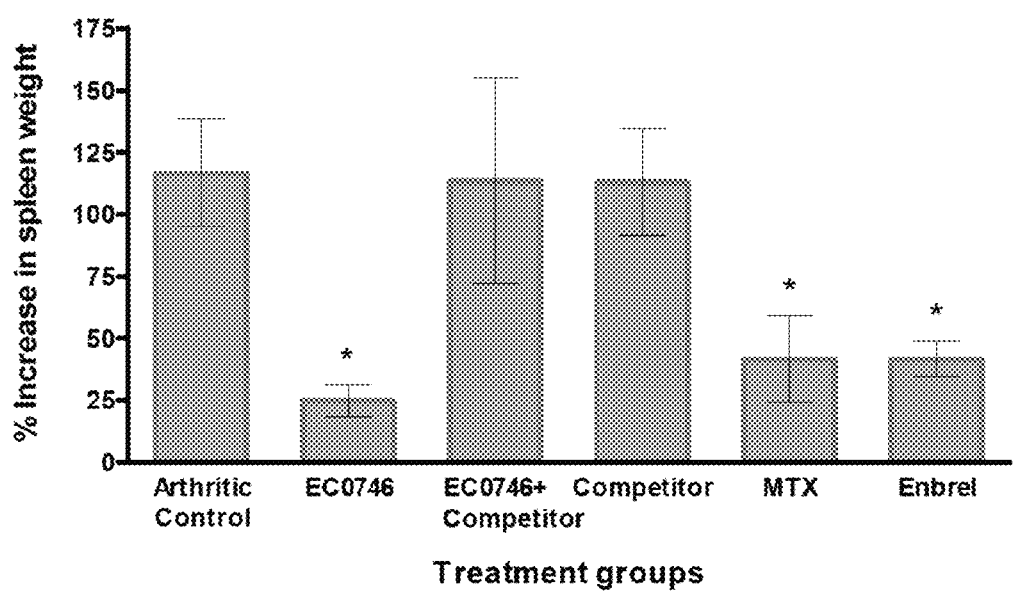
FIG. 29D—% Increase in weight of Spleen.
Figure 29E:
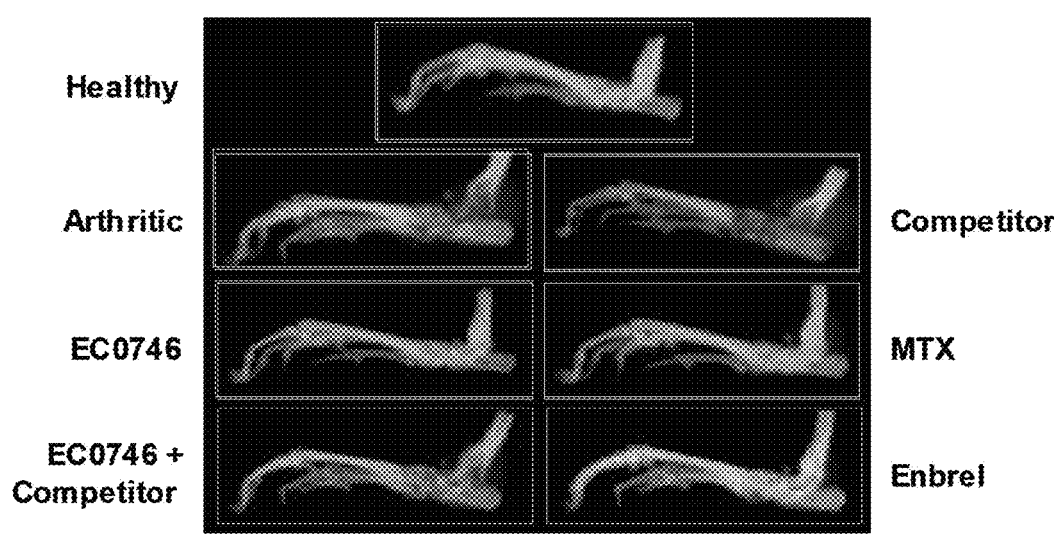
FIG. 29E—radiograph of hind paw.
Figure 29F:
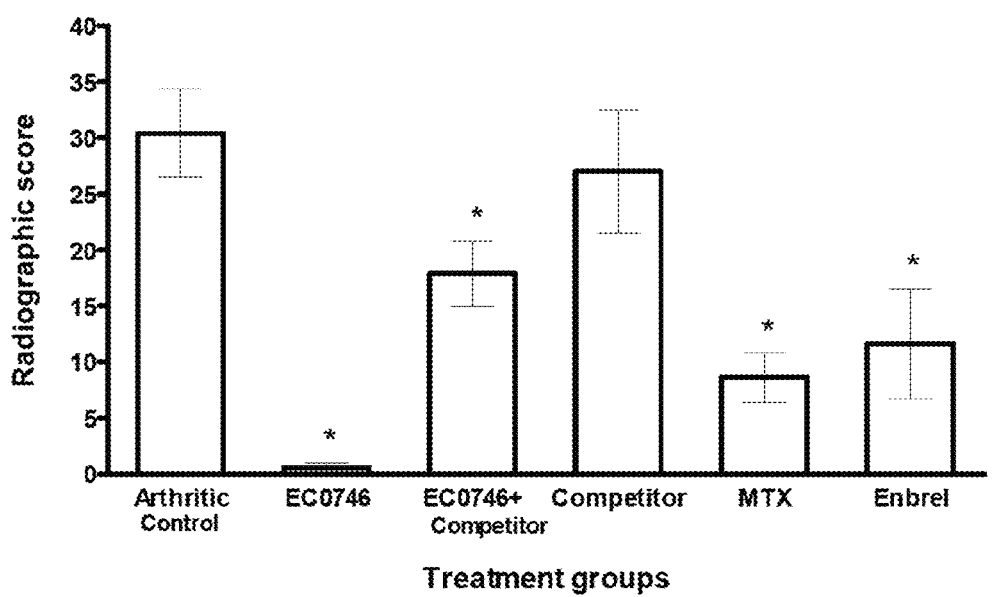
FIG. 29F—Radiographic score for Healthy (where indicated), Arthritic Control (untreated), and animals treated with EC0746, EC0746+Competitor, Competitor alone, methotrexate (MTX), or Enbrel (etanercept) in AIA rats, with EC0923 as the folate-containing competitor.

As shown in FIG. 29 and Table 1, above, subcutaneously administered EC0746 (250 nmol/kg/dose, 4 doses×2 weeks) was found more efficacious than oral MTX on an equimolar basis in most clinical and radiographic parameters assessed: arthritis score (FIG. 29A), change in body weight (FIG. 29B), percent inhibition in paw edema (Table 1, above, calculated from FIG. 29C) and radiographic score (FIGS. 29E, F). Although EC0746 and MTX-treated arthritic animals had significantly decreased spleen weight compared to arthritic controls, they were not statistically different from each other (FIG. 29D, Table 1, above). In the same study, EC0746 was found more effective than etanercept in all parameters assessed except for the spleen. Histological grading of arthritis compared to the untreated controls showed oral MTX-treated animals had significant reductions (66-84%) in all scored parameters (i.e. ankle inflammation, bone resorption, pannus formation, and cartilage damage (FIG. 30A). There was a 73% significant decrease in the summed histological score (FIG. 30B). While etanercept was not as effective as oral MTX, animals treated with etanercept also had significant reductions in inflammation (42%) and bone resorption (55%), which contributed to a significant 43% decrease in the summed score (FIGS. 30A, B). The dorsal to ventral paw thicknesses in both MTX and etanercept-treated rats were significantly decreased by 63% and 40%, respectively (FIG. 30C). Overall, EC0746 consistently outperformed both oral MTX and s.c. etanercept in all histological parameters assessed, with further decreases in the summed scores and dorsal to ventral paw thicknesses.

Example

EC0746 is Less Toxic than Aminopterin and Methotrexate in Folate-deficient Rats

Since the toxicity of antifolates can be easily masked by rodent diets enriched with folate, healthy rats on a folate-deficient diet (Harlan) were used to determine the maximum-tolerated-dose levels (MTD) of EC0746, AMT and MTX. The animals were given biweekly injections of EC0746, AMT, and MTX for two weeks. The MTD dose was defined as the dose that had caused at least 13-14% weight loss combined with clinical signs of stress and at least one animal in the >MTD dose group needed to be euthanized. Standard hematologic and blood chemistry parameters were examined as needed along with histopathology. The MTDs of EC0746, MTX and AMT were determined to be 2000, 1000, and 50 nmol/kg, respectively. At above the MTD dose level, the main toxicities of EC0746 were similar to those of AMT and MTX, including manifested gastrointestinal distress (diarrhea), swollen muzzle, immunosuppression (bone marrow, thymus), low white-blood-cell count, low platelet count, and infections. While immunosuppression is the dose-limiting toxicity of all three of these compounds, EC0746 at its MTD dose in rats showed less gastrointestinal-associated toxicities than AMT and MTX. Overall, EC0746 was approximately 40-fold less toxic than AMT and 2-fold less toxic than MTX on an equimolar basis in these folate-deficient animals; however, its toxicity profile at above MTD levels was not dissimilar from that of AMT and MTX.

Example

EC0746 Pharmacokinetics in Rats

Figure 32A:
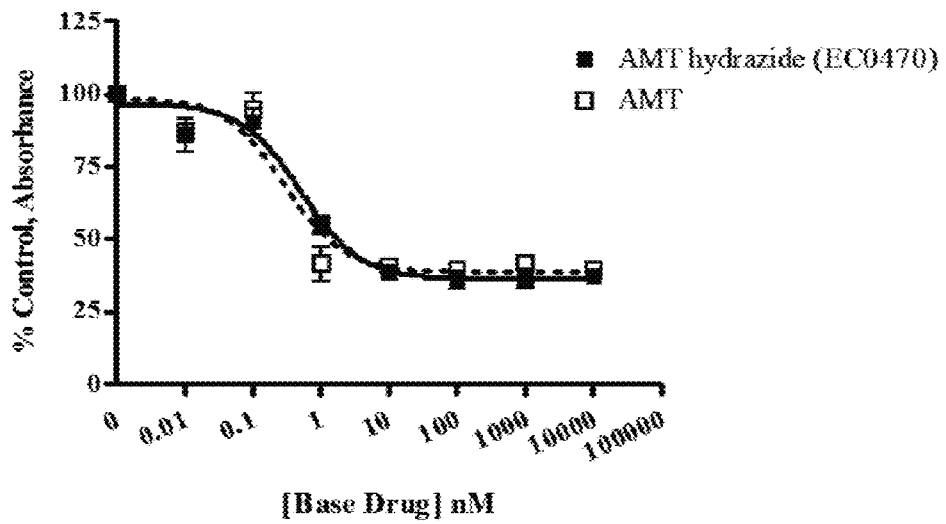
FIG. 32A—Cell proliferation in the XTT assay, and FIG. 32B—LPS-stimulated TNF-α production.
Figure 32B:
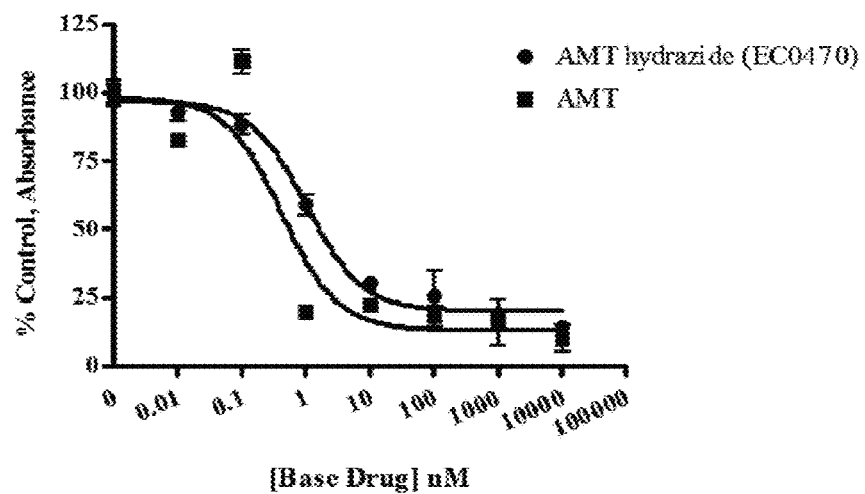
Figure 33A:
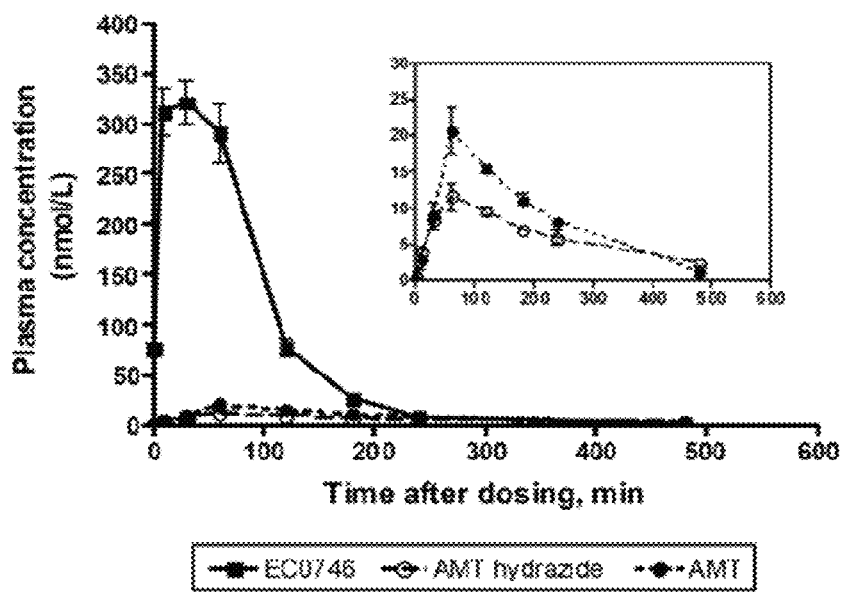
FIG. 33A—Plasma concentrations (nmol/L) of EC0746, AMT and AMT hydrazide following single subcutaneous EC0746 (500 nmol/kg) administration.
Figure 33B:
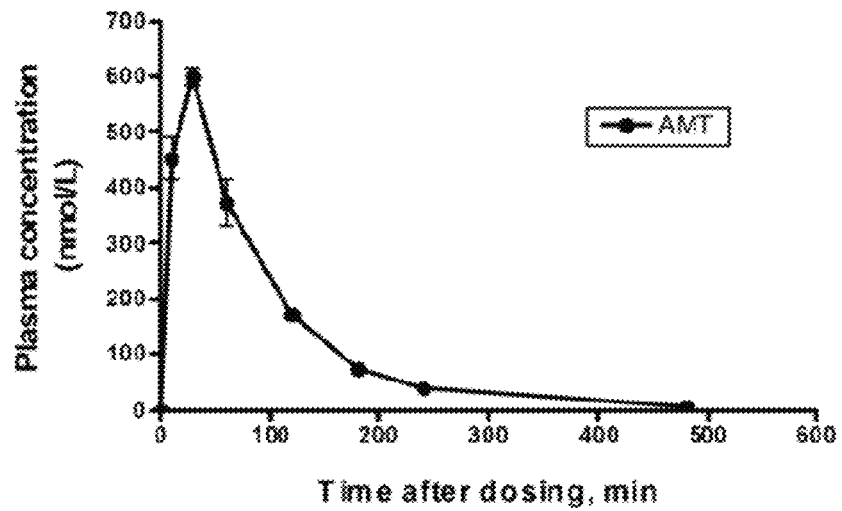
FIG. 33B—Plasma concentrations (nmol/L) of AMT following single subcutaneous AMT (500 nmol/kg) administration.

EC0746 is bioavailable after subcutaneous administration in rats and has a serum protein binding of ~46%. Both AMT and AMT hydrazide are anticipated metabolites because EC0746 contains a hydrazide/disulfide-based releasable linker. Notably, AMT hydrazide and AMT are equally potent on RAW264.7 cells by inhibiting cell proliferation (FIG. 32A) and LPS-stimulated TNF-α production (FIG. 32B). Thus, the plasma concentrations of EC0746 and two primary metabolites, AMT and AMT hydrazide, were determined by LC/MS/MS after a single subcutaneous EC0746 administration. As shown in FIG. 33A, subcutaneously administered EC0746 (500 nmol/kg) reached the blood stream within minutes, peaked around 10-30 min, and maintained a plateau until 60 minutes. EC0746 was cleared rapidly from the blood with an elimination half-life of ~35 min Interestingly, the peak appearances of AMT and AMT hydrazide in the plasma were nearly superimposable in the EC0746-dosed rats with a 30-min delay from the EC0746 Cmax. For comparison, the pharmacokinetics of subcutaneously dosed AMT (500 nmol/kg) was also examined (FIG. 33B). The AMT Cmax was more similar to that of EC0746 than to those of EC0746-derived AMT/AMT hydrazide seen in FIG. 33A. However, the elimination half-life of subcutaneously administered free AMT was ~140 min, more similar to that of AMT (~117 min) and AMT hydrazide (~187 min) released from EC0746. Based on area-under-the-curve, ~18% of active drug exposure/release (AMT plus AMT hydrazide) was detected in the plasma over 8 h collection period in the EC0746 dosed animals (FIG. 33C).

Example

Animal Experimental Autoimmune Uveitis Model

Figure 34:
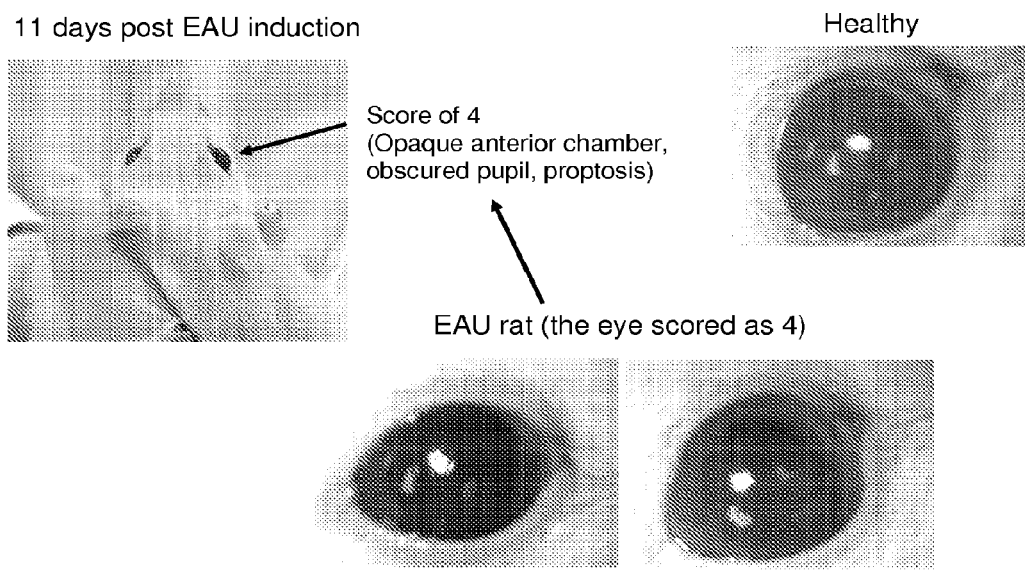
FIG. 34. An animal model for autoimmune disease uveitis. Rats were immunized with a bovine S antigen peptide emulsified with Freund's incomplete adjuvant containing *M. Tuberculosi* and boosted with pertussis toxin.

Experimental autoimmune uveitis (EAU) was induced in female Lewis rats maintained on a folate-deficient diet (Harlan Teklad, Indianapolis, Ind.). On Day 0, the animals were immunized subcutaneously with 25 μg of bovine S-Ag PDSAg peptide formulated with Freund's incomplete adjuvant containing 0.5 mg of *M. Tuberculosis* H37Ra. Purified pertussis toxin (PT) was given at a dosage of 1 μg per animal on the same day via intraperitoneal injection. The severity of uveitis in each eye was assessed by a qualitative visual score system: 0=No disease, eye is translucent and reflects light (red reflex); 0.5 (trace)=Dilated blood vessels in the iris, 1=Engorged blood vessels in iris, abnormal pupil contraction; 2=Hazy anterior chamber, decreased red reflex; 3=Moderately opaque anterior chamber, but pupil still visible, dull red reflex; and 4=Opaque anterior chamber and obscured pupil, red reflex absent, proptosis. This assessment yields a maximum uveitis score of 8 per animal. FIG. 34 shows images the eyes of an animal (upper right) with severe uveitis on its right eye (bottom) and a healthy eye (upper right).

Example

EC0746 Treatment Effectively Reduced EAU Inflammation

Figure 35:
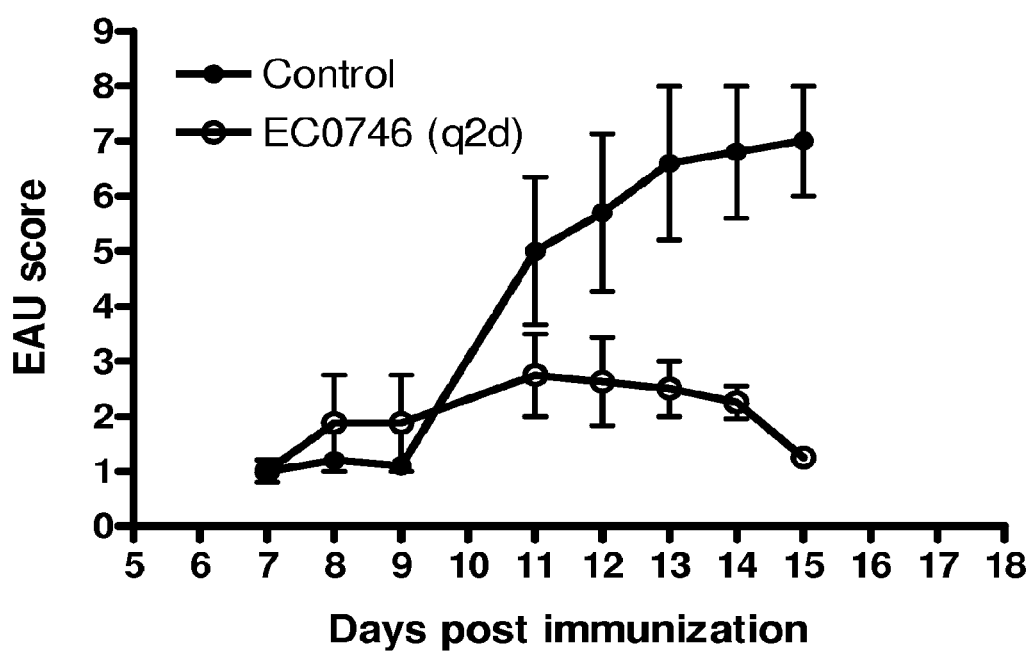
FIG. 35. Uveitis total scores (both eyes) for animals treated with 500 nmol/kg EC0746 every other day starting on day 7 after EAU induction (open circles) or from untreated animals (closed circles).
Figure 36:
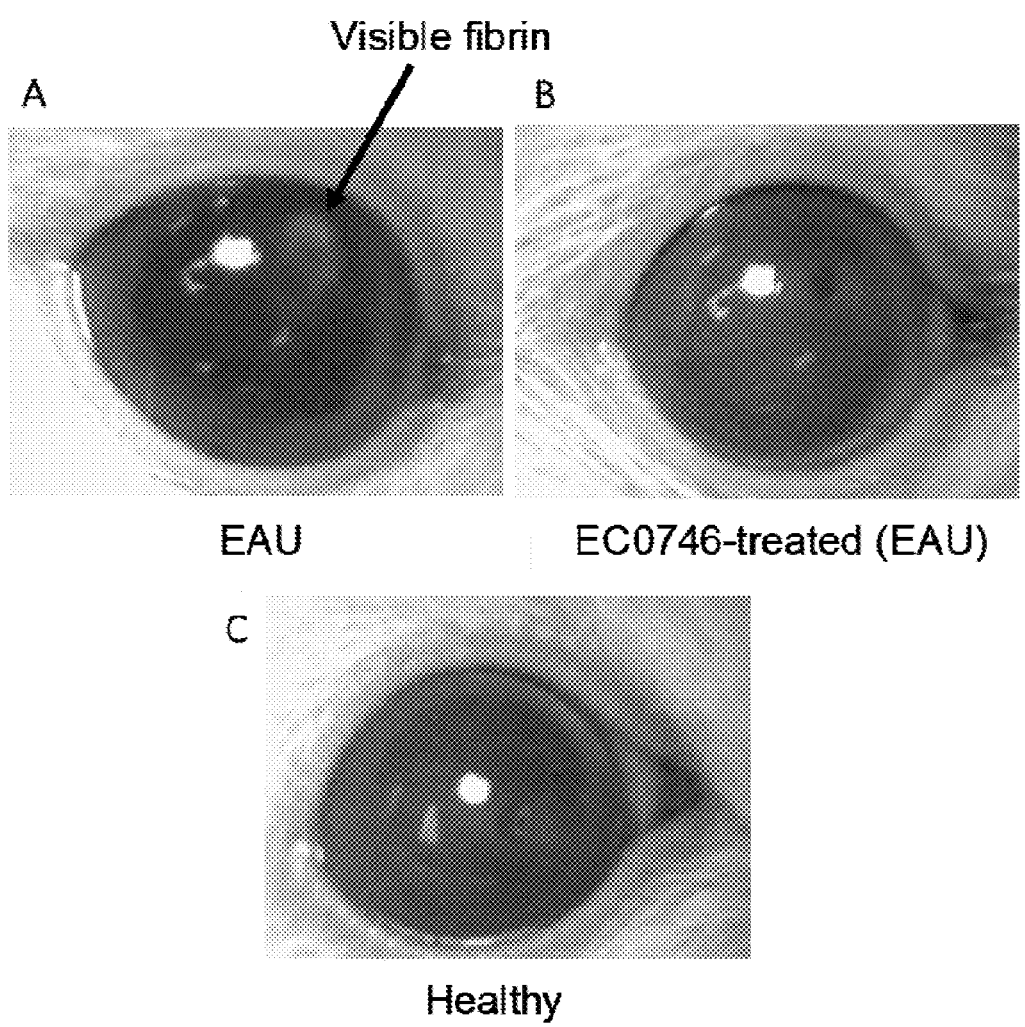
FIG. 36. Representative photographs of rat eyes were taken on day 15.
Figure 37:
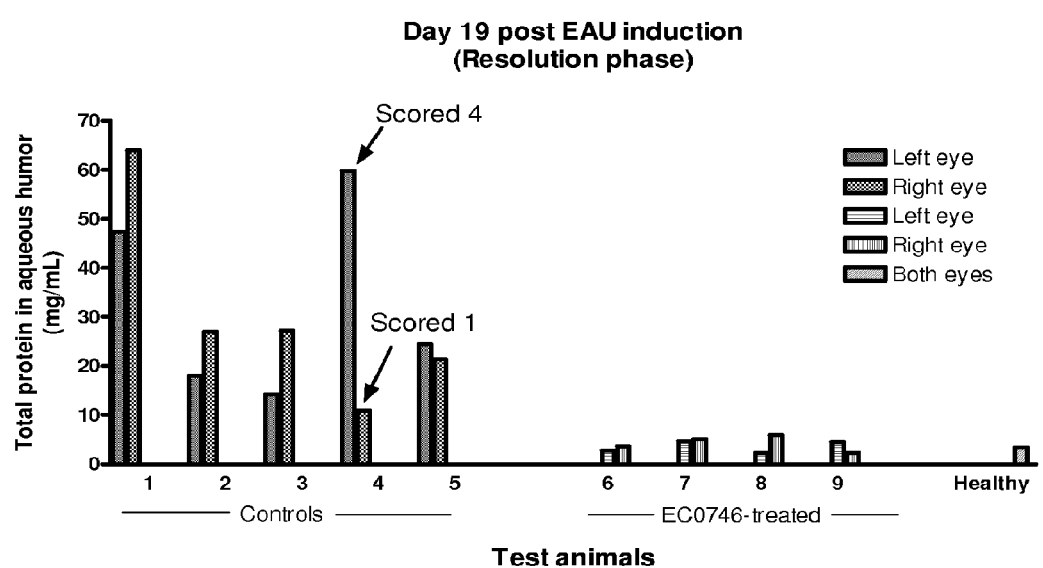
FIG. 37. The effect of EC0746 treatment on protein levels in the aqueous humor. The protein levels (mg/mL) at day 19 in the aqueous humor in the anterior portion of the eye are shown for the left and right eye of each tested animal. Animals 1-5 were untreated after induction of the EAU. Animals 6-9 were treated with EC0746 every other day starting on day 7 after EAU induction. On the far right of the chart, the total of the protein levels in the aqueous humor samples pooled from both eyes of an untreated, healty animal.

Animals treated according to the preceding method to induce EAU were randomized and distributed into two groups: (1) the untreated experimental autoimmune uveitis control group and (2) the EC0746 treated experimental autoimmune uveitis group. The animals in the experimental autoimmune uveitis control group were untreated. The animals in the EC0746 treatment group were given subcutaneous doses of EC0746 at a dosage of 500 nmol/kg every other day starting on day 7 after EAU induction. The uveitis score and animal body weight were recorded for each animal on days 7-9 and 11-15, see FIG. 35 (the uveitis score, calculated as described in the preceding example, is shown). On day 19, the animals were euthanized and the aqueous humor samples were collected from the anterior chamber for total protein analysis (see FIG. 37). Increased protein levels in aqueous humor are symptomatic of ocular inflammation.

Example

Adjuvant-Induced Arthritis (AIA) Model

Female Lewis rats were fed a folate-deficient diet (Harlan Teklad, Indianapolis, Ind.) for 9-10 days prior to arthritis induction. The adjuvant-induced arthritis (AIA) was induced by intradermal inoculation (at the base of tail) of 0.5 mg of heat-killed *Mycobacteria butyricum* (BD Diagnostic Systems, Sparks, Md.) in 100 μL light mineral oil (Sigma). Ten days after arthritis induction, paw edema in rats was assessed using a modified arthritis scoring system: 0=no arthritis; 1=swelling in one type of joint; 2=swelling in two types of joint; 3=swelling in three types of joint; 4=swelling of the entire paw. A total score for each rat is calculated by summarizing the scores for each of the four paws, giving a maximum score of 16 for each rat. On Day 10 post arthritis induction, rats with a total arthritis score of ≥2 were removed from the study and the remaining rats were distributed evenly across the control and treatment groups (n=5 for all groups except that n=2-3 for healthy controls). All treatments started on Day 10 unless mentioned otherwise.

Example

EC0565 Mediated FR-Specific Inhibition of Mtor Signaling in Macrophages

To examine the targeting effect of EC0565 on FR-positive macrophages, RAW264.7, thioglycolate-elicited macrophages (TG-macs), and arthritic macrophages from AIA rats (AIA-macs) were treated with medium only (UTC), everolimus (10 and 100 nM), EC0565 (1, 10, 30, and 100 nM), or EC0565 (1, 10, 30, and 100 nM) plus 100 μM excess of a folate competitor (EC17 or free folate). The drug-containing media were removed after 1 h and the cells were allowed to incubate from 6 h in fresh medium. Afterwards, the cell lysates were collected and subjected to Western blot analysis for phosphorylation of S6 ribosomal protein (p-RPS6), a downstream target in the mTOR signaling pathway.

Figure 38A:
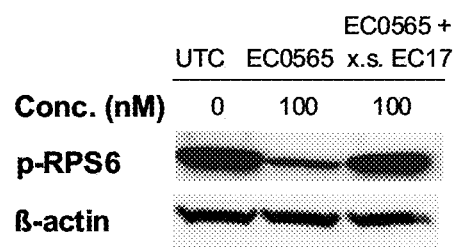
FIG. 38A shows that EC0565 induces inhibition of RPS6 in RAW264.7 cells (1 h pulse/6 h chase), where UTC=Control (untreated cells); EC0565=(100 nM) and EC0565+x.s. EC17=treatment plus an excess amount of a non-cytotoxic folate conjugate.
Figure 38B:
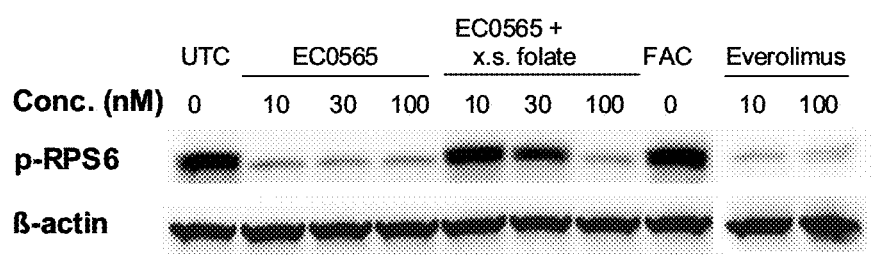
FIG. 38B shows that EC0565 induces inhibition of RPS6 in TG-elicited macrophages (1 h pulse/6 h chase), in a dose dependent manner, where UTC=Control (untreated cells); EC0565=treatment (10 nmol, 30 nmol, 100 nmol); EC0565+x.s. folate=treatment (10 nmol, 30 nmol, 100 nmol) plus an excess of a folic acid conjugate (100 µmole); FAC=treatment with folic acid and 0 nmol of EC0565; and Everolimus=treatment with unconjugated everolimus (10 nmol, 100 nmol)
Figure 38C:
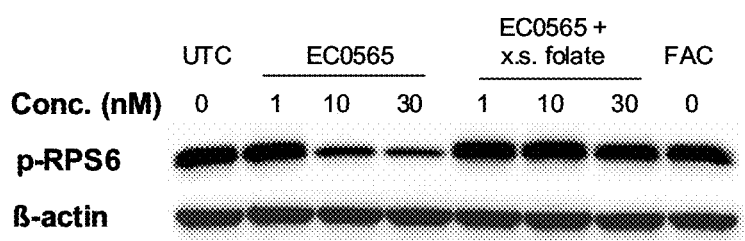
FIG. 38C shows that EC0565 induces inhibition of RPS6 in arthritic macrophages (1 h pulse/6 h chase), in a dose dependent manner, where UTC=Control (untreated cells); EC0565=treatment (1 nmol, 10 nmol and 30 nmol); EC0565+excess folate=treatment (1 nmol, 10 nmol and 30 nmol) plus an excess of a folic acid (100 μmole); and FAC=treatment with folic acid and 0 nmol of EC0565.

EC0565 treatment resulted in down-regulation of p-RPS6 at nanomolar concentrations in all macrophages tested (see FIGS. 38A-C). EC0565 appeared to be less potent than everolimus (see FIG. 38B), but its inhibitory effect was dose dependent (see FIG. 38C) and mediated by the FR (see FIGS. 38A-C). The presence of excess EC17 (see FIG. 38A, a folate-containing ligand) or free folic acid (see FIGS. 38B, C) reversed the effect EC0565 on these cells. More importantly, despite the lower FR expression in TG-macs and AIA-macs than in RAW264.7 cells, these results suggested that the amount of FRs on these ex-vivo isolated macrophages were sufficient to deliver a FR-specific target inhibition of the mTOR-signaling pathway.

Example

Subcutaneously Dosed EC0565 and Everolimus were Similarly Active

Figure 39:
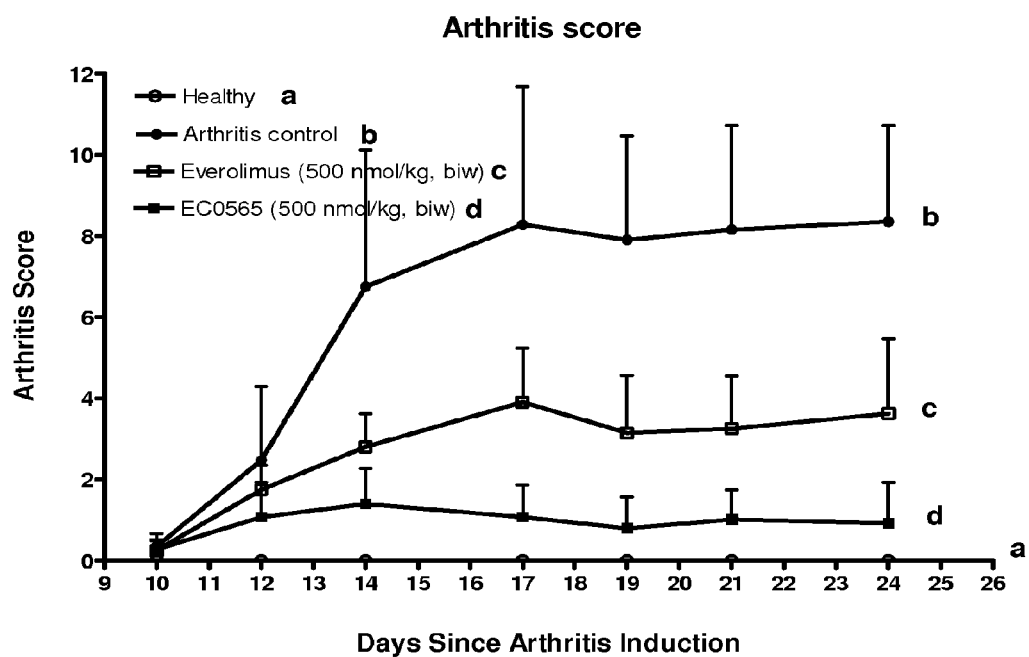
FIG. 39 compares the arthritis score of animals treated with biweekly injections of 500 nmol/kg of EC0565 (d) and biweekly injections of 500 nmol/kg of unconjugated everolimus (c) with healthy controls (a) and untreated animals (b).
Figure 40:
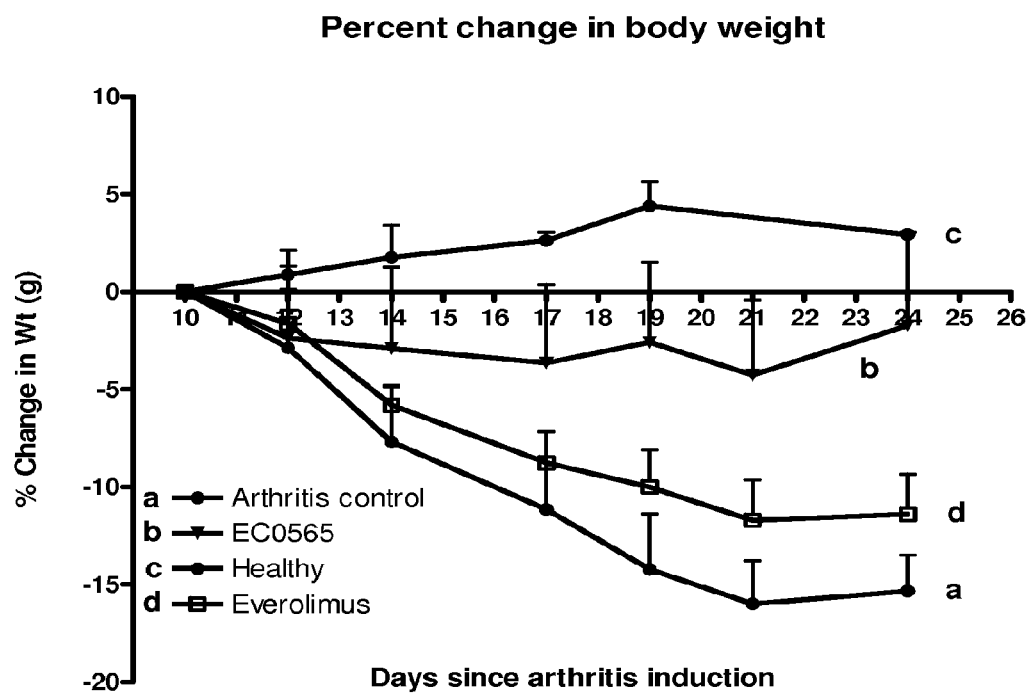
FIG. 40 shows the percentage weight change observed for the same animals used to generate the data shown in FIG. 39. (a) Untreated animals, (b) treated with biweekly injections of 500 nmol/kg of EC0565, (c) untreated healthy control animals, and (d) treated with biweekly injections of 500 nmol/kg of unconjugated everolimus.
Figure 41:
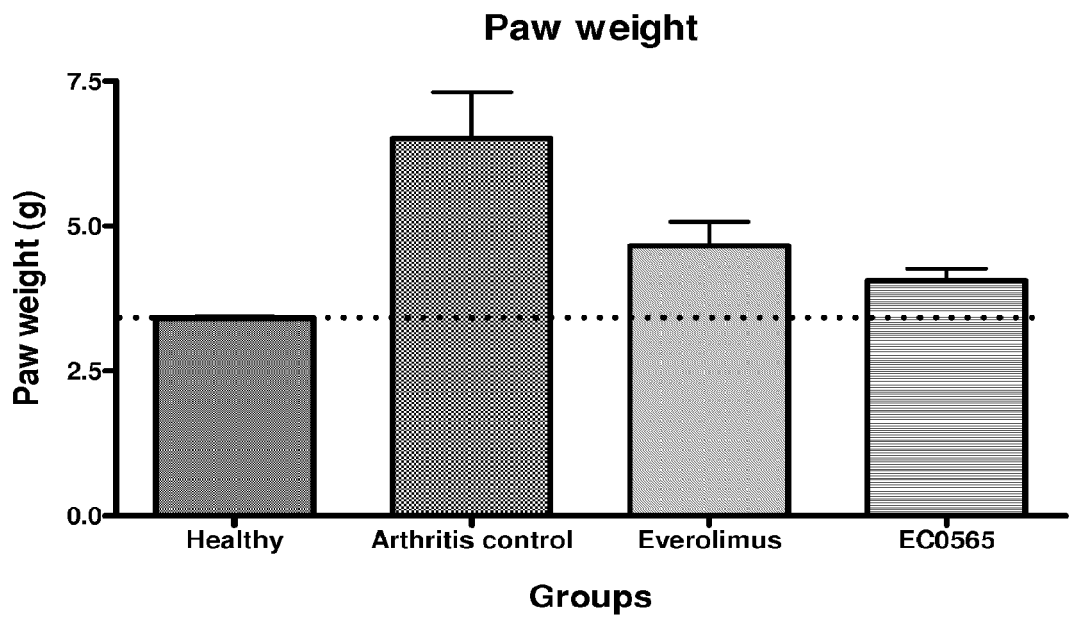
FIG. 41 shows the paw weight data (localized disease) for the animals at the end of the treatment period for each of the treatment groups described in FIGS. 39 and 40.
Figure 42:
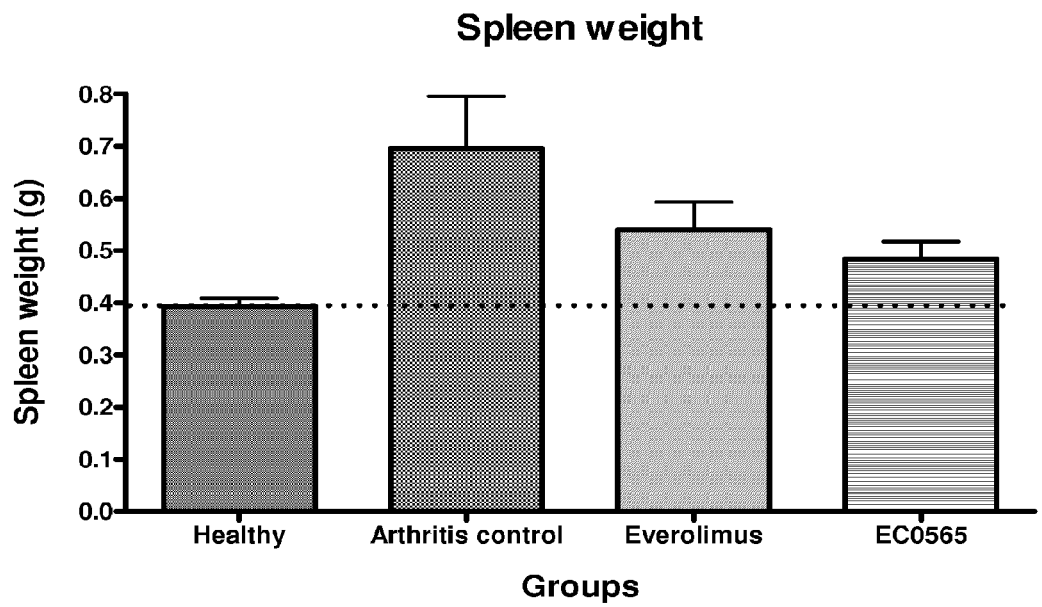
FIG. 42 shows the spleen weight data (systemic disease) for the animals at the end of the treatment period for each of the treatment groups described in FIGS. 39 and 40.

AIA rats were treated subcutaneously (twice a week) with EC0565 (500 nmol/kg) and everolimus (500 nmol/kg) on days 10, 13, 17, and 20. The animals in the healthy and arthritis control groups were left untreated. The arthritis scores (see FIG. 39) and animal body weights (see FIG. 40) were recorded three times a week. At the completion of study (day 24), the rats were euthanized by $CO_2$ asphyxiation and processed for paw and spleen weights (see FIGS. 41 and 42, respectively). Without being bound be theory, it is believed that, given its low water solubility, the bioavailability of everolimus after subcutaneous administration was lower than that of EC0565. In this study, EC0565 was shown to be as active or more active as everolimus against adjuvant-induced arthritis.

Example

Figure 43:
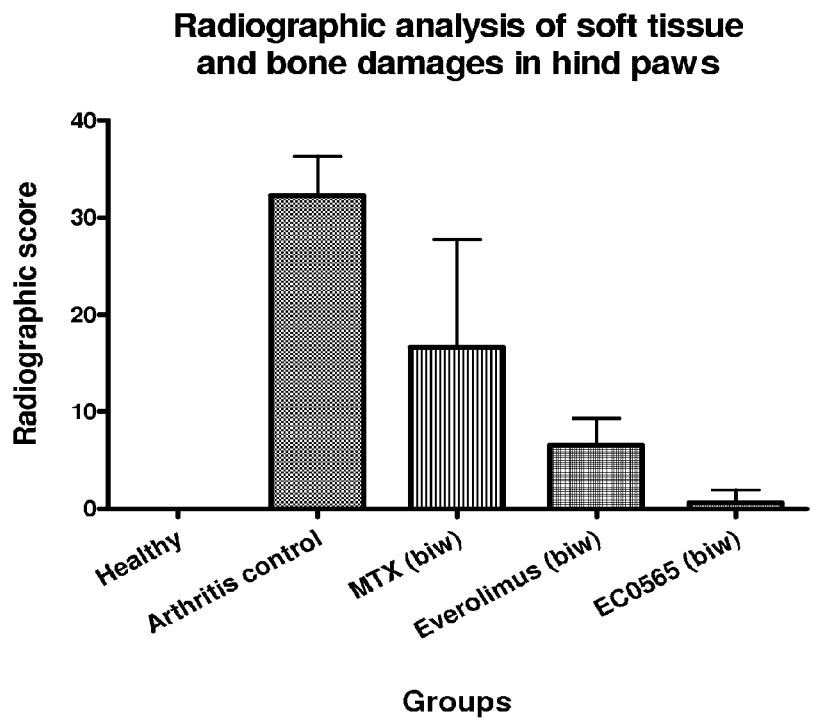
FIG. 43 shows the radiographic analysis of soft tissue and bone damage in the hind paws of animals treated with EC0565 (500nmol/kg), Everolimus (500 nmol/kg), methotrexate (MTX, 190 nmol/kg), untreated animals with adjuvant induced arthritis, and untreated, healthy control animals.

RadiographicAnalysis Confirmed Less Tissue/Bone Damage in EC0565-Treated Arthritic Paws AIA rats were treated subcutaneously (twice a week) with EC0565 (500 nmol/kg), everolimus (500 nmol/kg), and methotrexate (190 nmol/kg) on days 10,13,17, and 20. The animals in the healthy and arthritis control groups were left untreated. At the completion of study (day 24), the rats were euthanized by $CO_2$ asphyxiation and the hind paws were fixed in 10% PBS-buffered formalin and subjected to radiographic analysis. All radiographs were evaluated by a board-certified radiologist without knowledge of the assignment of treatment groups. The following radiographic changes were graded numerically according to severity: increased soft tissue volume (0-4), narrowing or widening of joint spaces (0-5), subchondral erosion (0-3), periosteal reaction (0-4), osteolysis (0-4), subluxation (0-3) and degenerative joint changes (0-3). The maximum possible score per foot was 26. In this study, EC0565-treated rats showed minimal tissue and bone damage in their hind paws when compared to arthritis control, everolimus-treated, and methotrexate-treated animals (see FIG. 43).

Example

Figure 44B:
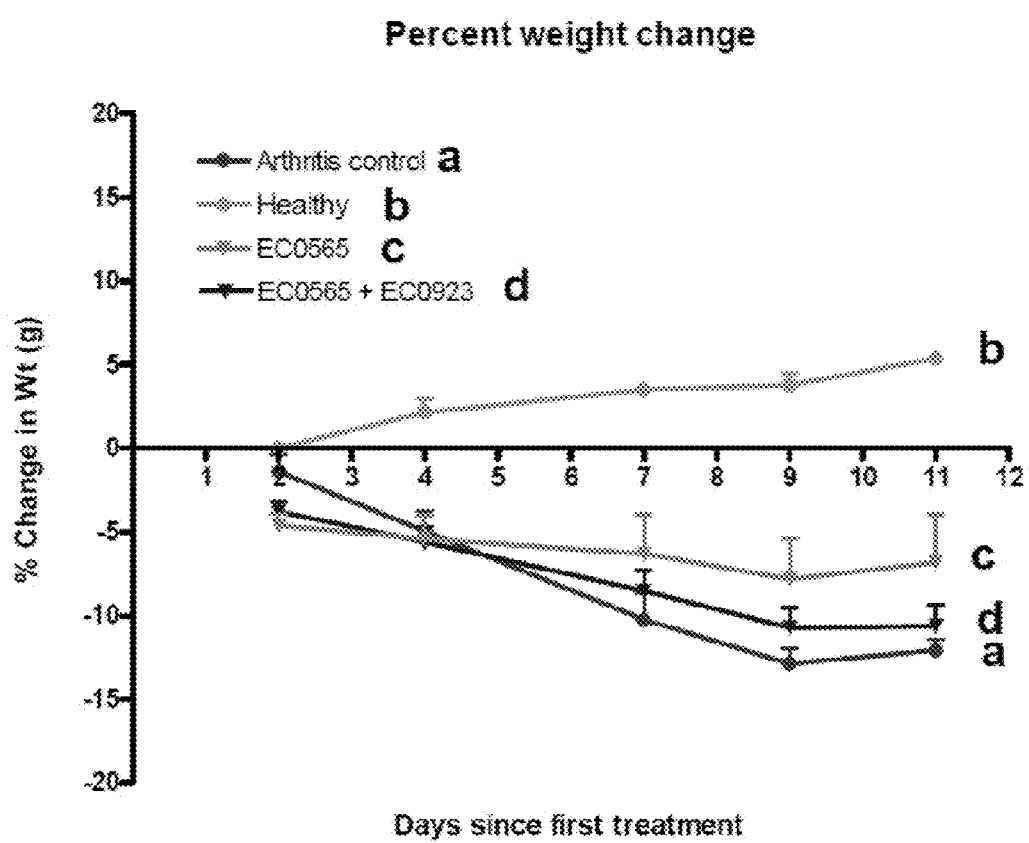
FIG. 44B shows the percentage weight change observed for the the treatment groups shown in FIG. 44A.
Figure 44C:
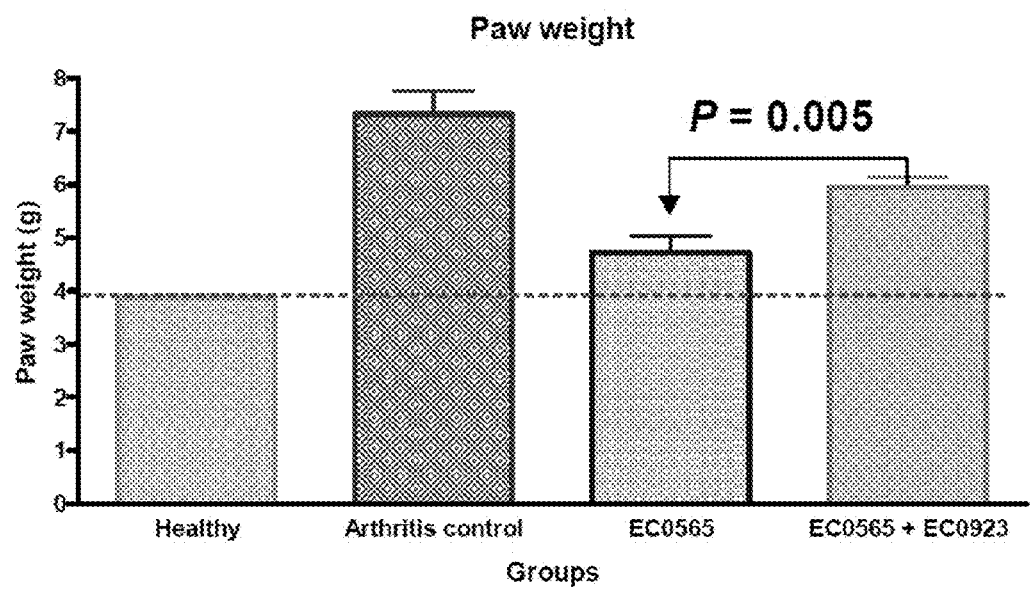
FIG. 44C shows the paw weight data (localized disease) for the animals at the end of the treatment period for each of the treatment groups described in FIGS. 44A, B.
Figure 44D:
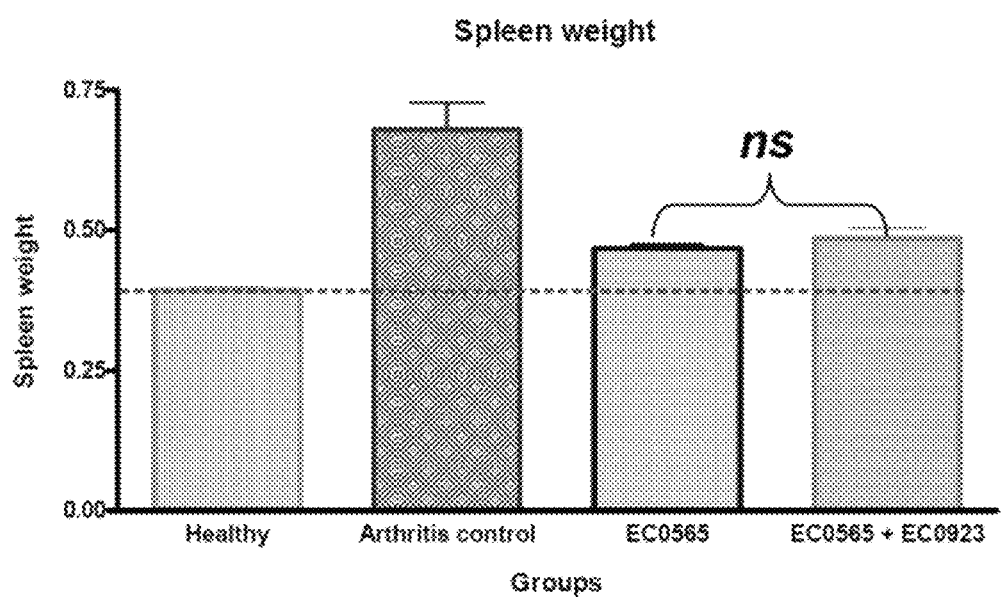
FIG. 44D shows the spleen weight data (systemic disease) for the animals at the end of the treatment period for each of the treatment groups described in FIGS. 44A, B.

Anti-Arthritis Activity of EC0565 Could be Partially Blocked a Folate Competitor The AIA rats were treated subcutaneously with EC0565 (500 nmol/kg) in the absence (c) or presence (d) of 500-fold excess of EC0923 (250 μmol/kg) on days 10,13, and 17. The animals in the healthy (b) and arthritis control (a) groups were left untreated. The arthritis scores (see FIG. 44A) and animal body weights (see FIG. 44B) were recorded three times a week. At the completion of study (day 24), the rats were euthanized by $CO_2$ asphyxiation and processed for paw (see FIG. 44C) and spleen (see FIG. 44D) weights. In this study, the anti-arthritis activity of EC0565 was partially blocked by EC0923, a folate competitor with similar affinity as free folic acid.

Example mTor Knockdown

Figure 45:
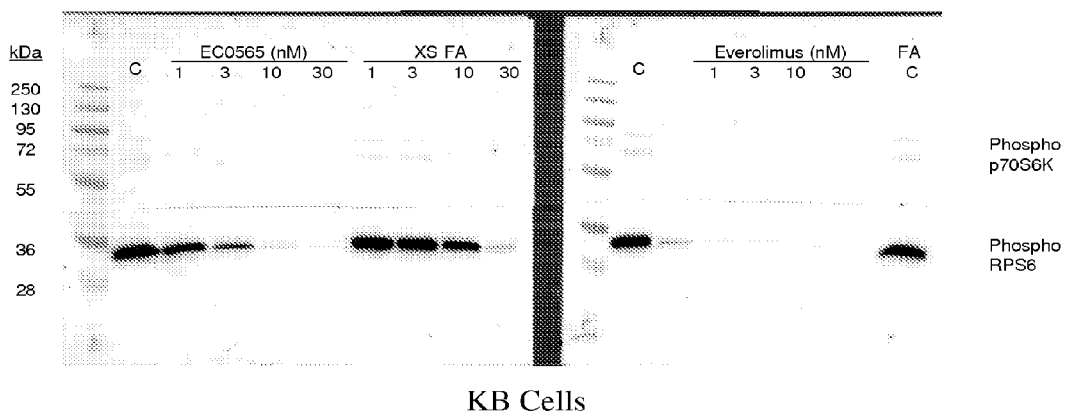
FIG. 45 shows that EC0565 induces dose-responsive inhibition of the production of pRPS6 and p70S6K in KB cells (1 h pulse/4 h chase) using a 30 min camera exposure, where C=Control (untreated cells); FAC=Folic acid control (100 μM).
Figure 46A:
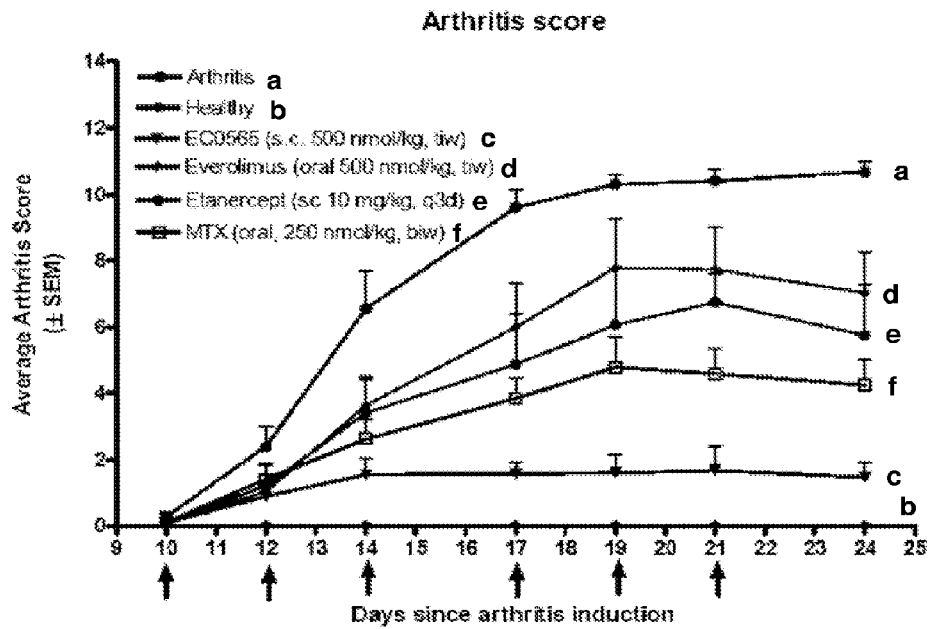
FIG. 46A. Arthritis scores for AIA rats. a) untreated animals; b) healthy animals; c) EC0565, subcutaneously (s.c.), 500 nmol/kg, tiw; d) everolimus, oral, 500 nmol/kg, tiw; e) etanercept, s.c. 10 mg/kg, q3d; and e) methotrexate (MTX), oral, 250 nmol/kg, biw).
Figure 46B:
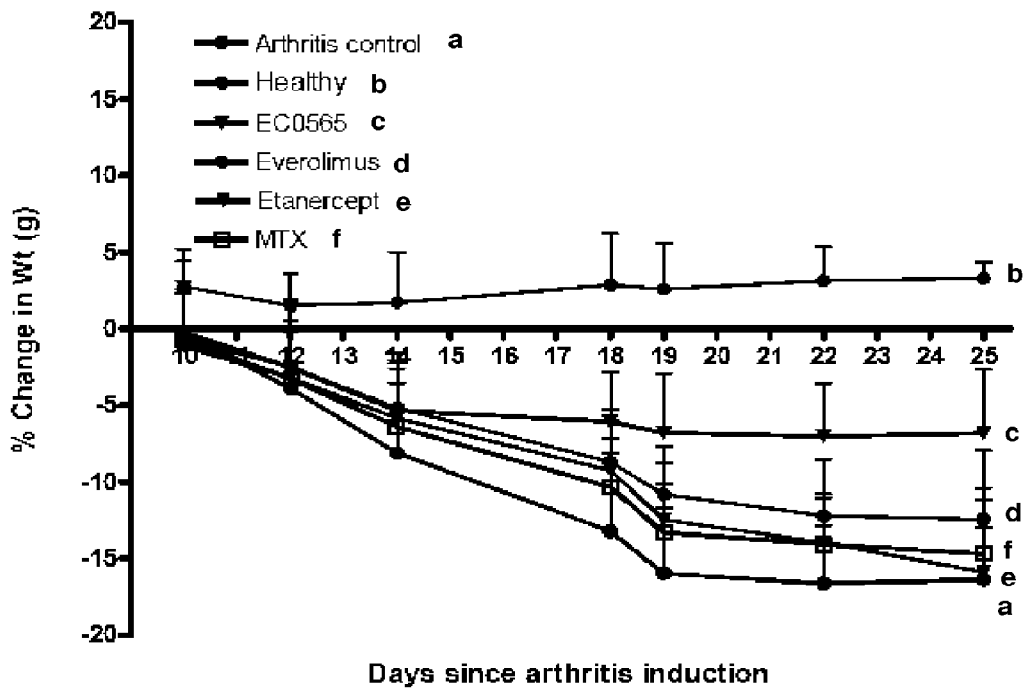
FIG. 46B. Weight change for AIA rats. a) untreated animals; b) healthy animals; c) EC0565, subcutaneously (s.c.), 500 nmol/kg, tiw; d) everolimus, oral, 500 nmol/kg, tiw; e) etanercept, s.c. 10 mg/kg, q3d; and e) methotrexate (MTX), oral, 250 nmol/kg, biw).
Figure 46C:
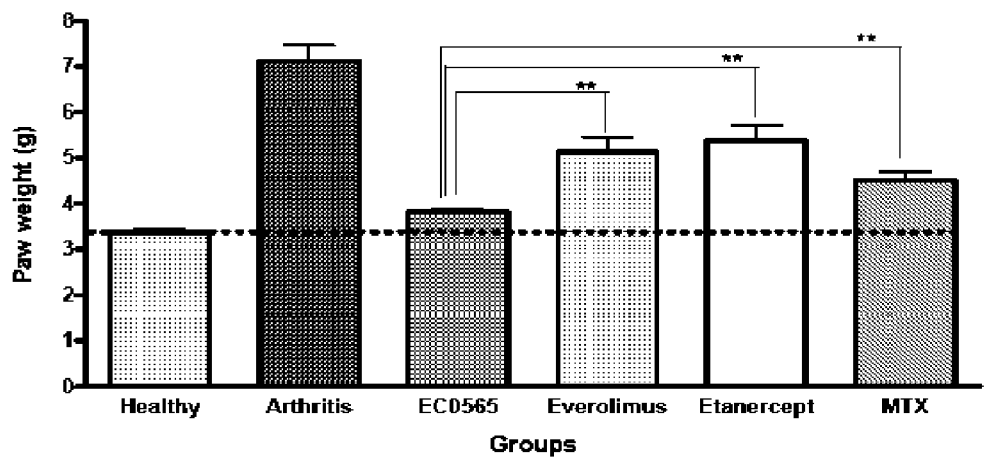
FIG. 46C. Paw Weights (a measure of swelling) for AIA rats. healthy animals; untreated controls; EC0565, subcutaneously (s.c.), 500 nmol/kg, tiw; everolimus, oral, 500 nmol/kg, tiw; etanercept, s.c. 10 mg/kg, q3d; and methotrexate (MTX), oral, 250 nmol/kg, biw).
Figure 46D:
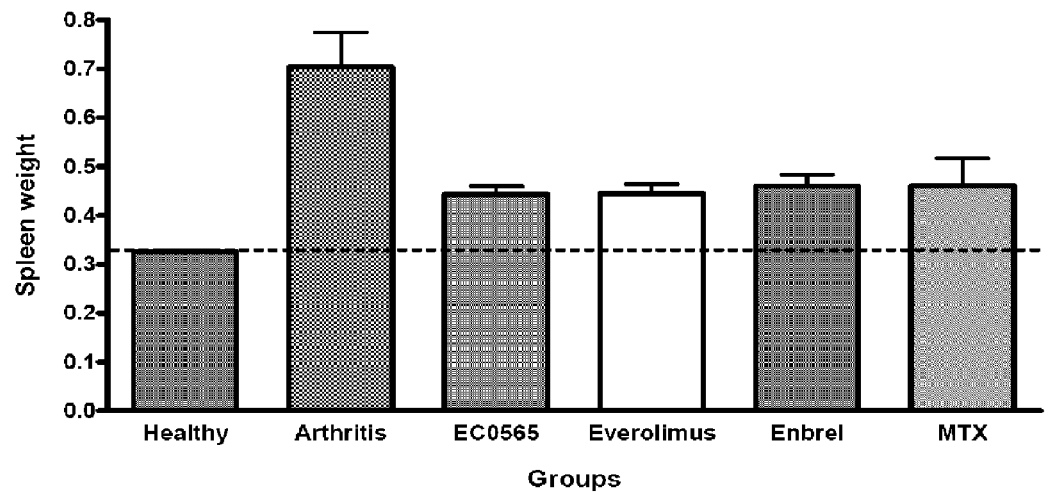
FIG. 46D. Spleen Weights for AIA rats. Healthy animals; untreated controls; EC0565, subcutaneously (s.c.), 500 nmol/kg, tiw; everolimus, oral, 500 nmol/kg, tiw; Enbrel (etanercept), s.c. 10 mg/kg, q3d; and methotrexate (MTX), oral, 250 nmol/kg, biw).

Western Blot Analysis. The data shown in FIG. 45 indicate that EC0565 (folate-sugar-everolimus) can cause a dose-dependent, and specific knockdown of the downstream targets of mTOR (intracellular target for everolimus). Without being bound by theory, in it believed that folate delivers everolimus inside the cell where everolimus inhibits mTOR, which is the mammalian target of rapamycin and a ser/thr kinase Inhibition of mTOR's downstream targets (P70 S6-kinase and Ribosomal S6) results, as shown on the Western blot.

Example

Comparison of EC0565 with Oral Everolimus and Subcutaneous Etanercept in AIA Rats Methotrexate (MTX) and etanercept (Enbrel®) are part of the current standard of care for RA. Treatment with EC0565 was compared to treatment with its base drug everolimus, MTX, and etanercept in rats with adjuvant arthritis using clinically relevant dosing routes. AIA rats were treated 3 times a week with subcutaneous EC0565 (500 nmo/kg) and oral everolimus (500 nmol/kg) on days 10, 12, 14, 17, 19, and 21 post arthritis induction. Biweekly oral MTX (250 nmol/kg) was given on days 10, 13, 17, and 20. Etanercept was given subcutaneously at 10 mg/kg once every 3 days starting on day 10. At the completion of each study (day 24), rats were euthanized by $CO_2$ asphyxiation and processed for paw weight (cut at the hairline) and spleen weight. The removed hind paws were immersion-fixed in 10% buffered formalin and subjected to radiographic and histopathological analyses.

As shown in FIGS. 46A-46D, subcutaneously administered EC0565 (500 nmol/kg/dose, 6 doses in 2 weeks) was more efficacious than oral everolimus on an equimolar basis in the following clinical parameters assessed: arthritis score, percent change in body weight, and paw weight. EC0565 and everolimus-treated arthritic animals had significantly decreased spleen weight compared to arthritic controls. The difference between treatment with EC0565 and treatment with erverolimus on spleen weight was not statistically different. EC0565 was found to be more effective than oral MTX and subcutaneous etanercept in all parameters assessed except for the effect on spleen weight.

Figure 47:
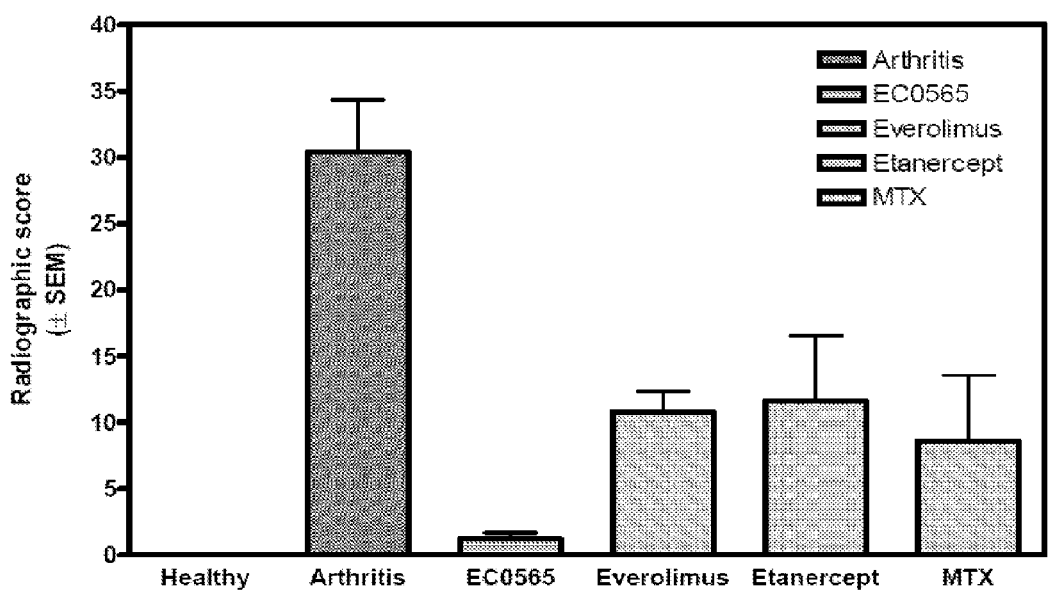
FIG. 47. Radiographic analysis of hind paws of AIA rats. Healthy animals; untreated controls; EC0565, subcutaneously (s.c.), 500 nmol/kg, tiw; everolimus, oral, 500 nmol/kg, tiw; Enbrel (etanercept), s.c. 10 mg/kg, q3d; and methotrexate (MTX), oral, 250 nmol/kg, biw.

Radiographic analysis of hind paws FIG. 47 revealed that EC0565-treated rats had minimal tissue and bone damage in their hind paws when compared to arthritis control, oral everolimus-treated, etanercept-treated, and oral MTX treated animals.

Figure 48A:
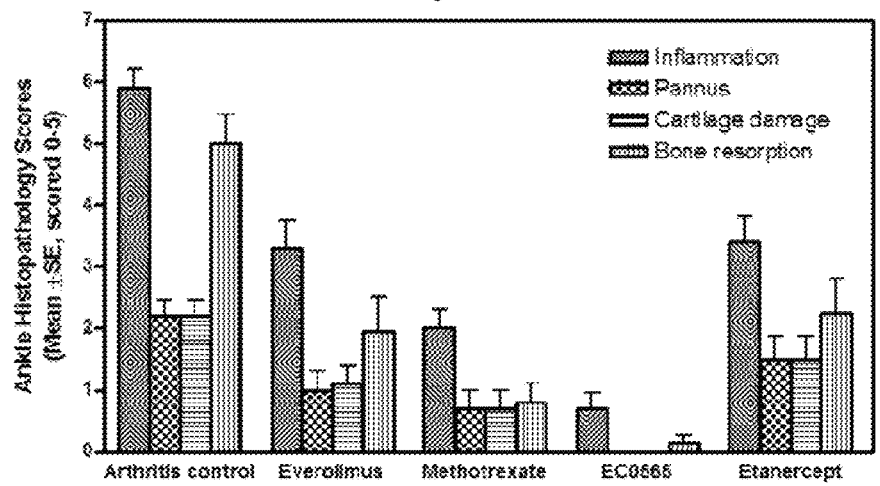
FIG. 48A—Histological study of AIA rats. Scores for inflammation, pannus formation, cartilage damage, and bone resorption are shown for untreated animals (untreated control); everolimus, oral, 500 nmol/kg, tiw; methotrexate (MTX), oral, 250 nmol/kg, biw; EC0565, subcutaneously (s.c.), 500 nmol/kg, tiw; and etanercept, s.c. 10 mg/kg, q3d.
Figure 48B:
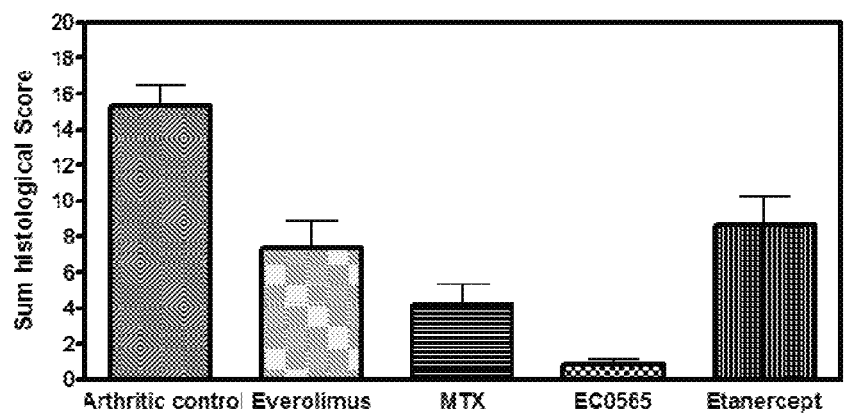
FIG. 48B—The sum of the scores shown in panel a for each treatment.
Figure 48C:
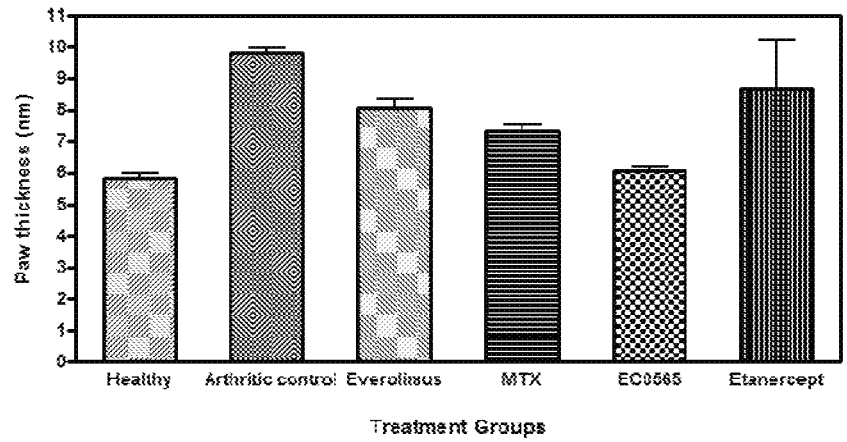
FIG. 48C—The measured paw thickness for each treatment shown in FIG. 48A.
Figure 49:
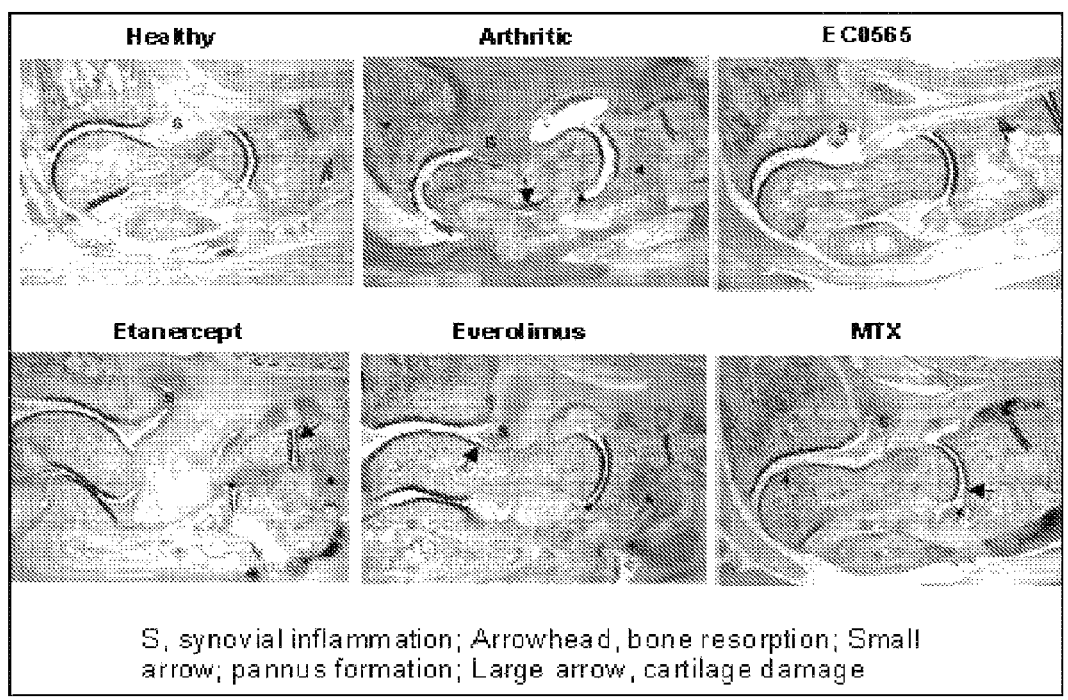
FIG. 49 shows representative photomicrographs (16×) of the ankle closest to the mean summed score for each treatment group.

Histological grading of arthritis compared to the untreated controls showed oral everolimus-treated animals had significant reductions (44-61%) in all scored parameters (i.e. ankle inflammation, bone resorption, pannus formation, and cartilage damage) (FIG. 48A). There was a 52% significant decrease in the summed histological score (FIG. 48B). Dorsal to ventral paw thickness was significantly decreased by 44% (FIG. 48C). While etanercept was not as effective as oral MTX, animals treated with etanercept also had significant reductions in inflammation (42%) and bone resorption (55%), which contributed to a significant 43% decrease in the summed score (FIG. 48B) The dorsal to ventral paw thicknesses in both MTX and etanercept-treated rats were significantly decreased by 63% and 40%, respectively (FIG. 48C). Animals treated with EC0565 had significant 88-100% decreases in all scored parameters (FIG. 48A), with an overall 94% significant decrease in summed scores (FIG. 48B). Dorsal to ventral paw thickness was significantly decreased by 94% (FIG. 48C). Overall, EC0565 consistently outperformed everolimus, MTX, and etanercept in all histological parameters assessed with further decreases in the summed scores and dorsal to ventral paw thicknesses. The representative photomicrographs (16×) of the ankle closest to the mean summed score for each group are shown in FIG. 49.

Example 2

EC0565 Anti-arthritic Activity is Dose and Schedule-dependent

Figure 50A:
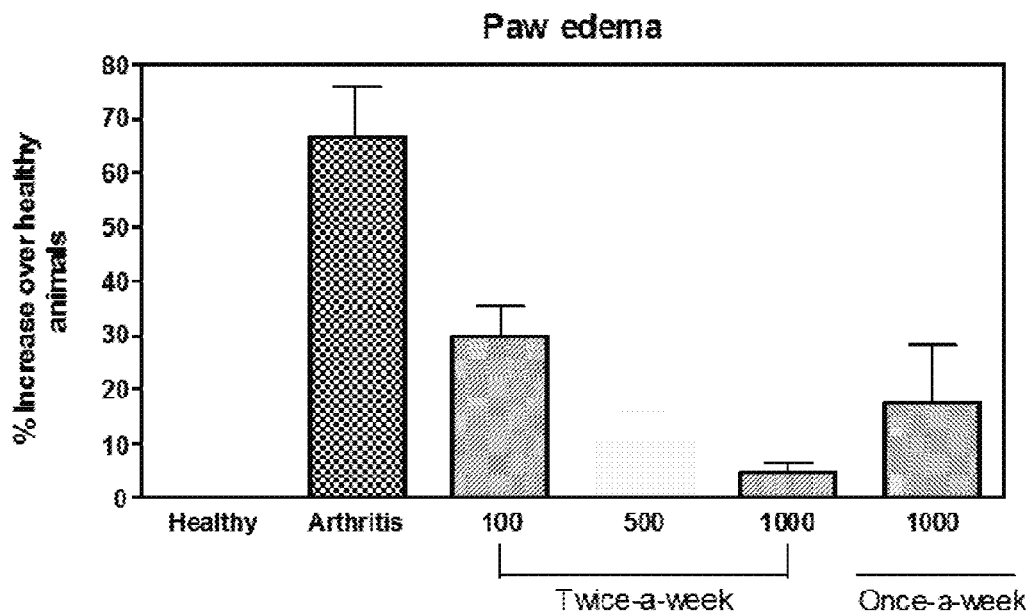
FIG. 50A shows the amount of paw edema for healthy or AIA rats. Healthy rats, no induces arthritis; arthritis (untreated AIA rats); treated with EC0565 100 nmol/kg/dose, twice/week; 500 nmol/kg/dose, twice/week; 1000 nmol/kg, twice/week; and 1000 nmol/kg/dose, once/week.
Figure 50B:
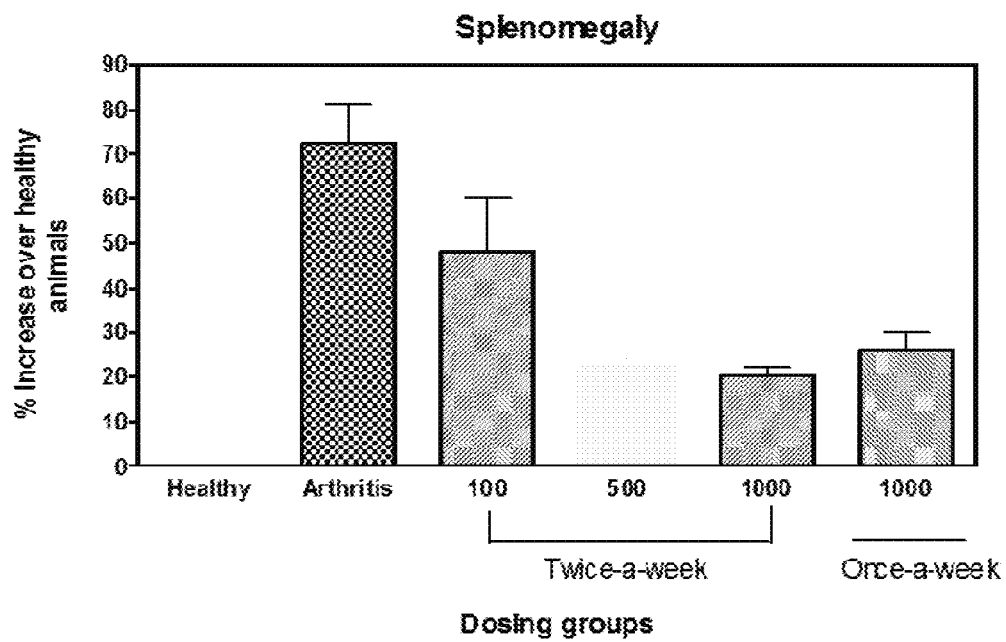
FIG. 50B shows the change in spleen weight of for healthy or AIA rats. Healthy rats, no induces arthritis; arthritis (untreated AIA rats); treated with EC0565 100 nmol/kg/dose, twice/week; 500 nmol/kg/dose, twice/week; 1000 nmol/kg, twice/week; and 1000 nmol/kg/dose, once/week.

To further investigate dose-response relationship and schedule-dependency, EC0565 was administered to rats with developing AIA (day 10) at 100, 500, and 1000 nmol/kg/dose (biweekly) or 1000 nmol/kg/dose (once weekly). At completion of the study (day 24), rats were euthanized by $CO_2$ asphyxiation and processed for paw weight (cut at the hairline) and spleen weight. The differences in total paw weight between arthritic rats after treatment and that of healthy rats were used as a measure of the extent of paw edema (FIG. 50A) Similarly, the differences in spleen weight between arthritic rats after treatment and that of healthy rats were used as a measure of the extent of splenomegaly (FIG. 50B). As shown in FIG. 50A, EC0565 dosed for 2 weeks displayed a linear dose response in inhibiting paw edema from 100 to 1000 nmol/kg/dose with an R-squared value of 0.862. As shown in FIG. 50B, biweekly EC0565 treatment displayed a linear dose response in inhibiting splenomegaly from 0 to 500 nmol/kg/dose with an R-squared value of 0.909 and no statistical difference between 500 and 1000 nmol/kg was seen. When dosed once weekly for 2 weeks, EC0565 at 1000 nmol/kg/dose remained highly effective, but this schedule did not control the fast progressing AIA to the same degree as the biweekly regimen at 500-1000 nmol/kg/dose (FIGS. 50A, B). Overall, EC0565 was found very effective against AIA and capable of controlling local (joints) and systemic (spleen) inflammation and halting the progression of arthritis.

Example 3

Collagen-Induced Arthritis (CIA) Model

Figure 51A:
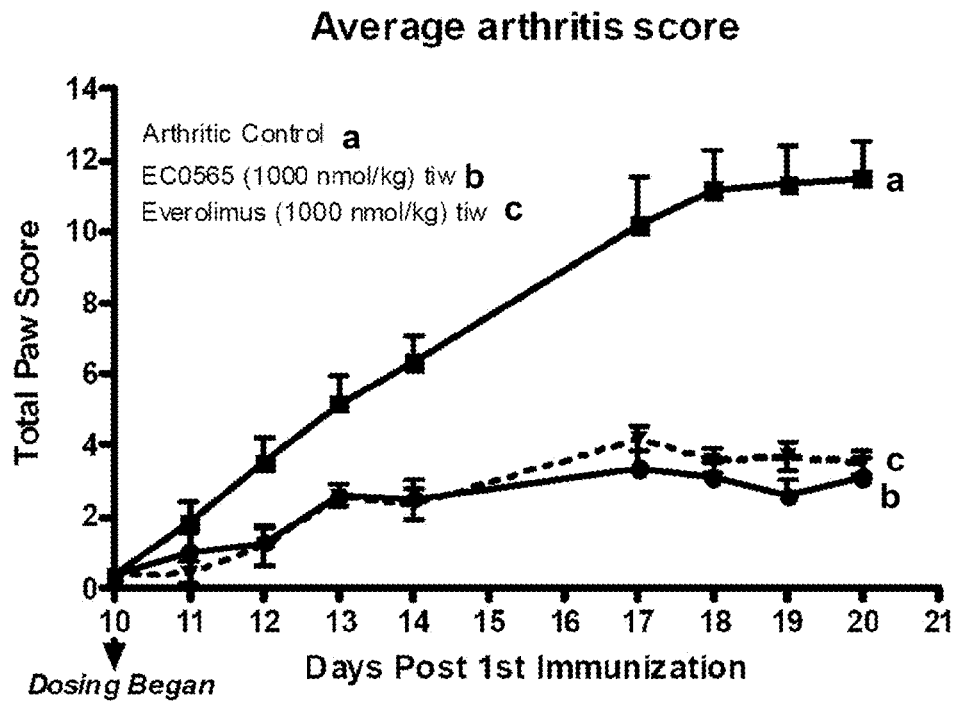
FIG. 51A shows the average arthritis score for treated rats with collagen-induced arthritis (CIA). a) untreated CIA animals; b) EC0565, 1000 nmol/kg/dose, tiw; and c) everolimus, 1000 nmol/kg/dose, tiw.

Collagen-induced arthritis (CIA) was induced in female Lewis rats on folate-deficient diet (Harlan Teklad, Indianapolis, Ind.). On Day 0, rats were immunized with 500 μg of bovine collagen Type II (Chondrex, Redmond, Wash.) formulated with Freund's complete adjuvant. A booster immunization was given on day 7 with 250 μg of the bovine collagen formulated with Freund's incomplete adjuvant. Arthritis disease was assessed by a qualitative clinical score system described by the manufacturer (Chondrex, Redmond, Wash.): 0=normal, 1=Mild, but definite redness and swelling of the ankle or wrist, or apparent redness and swelling limited to individual digits, regardless of the number of affected digits, 2=Moderate redness and swelling of ankle of wrist, 3=Severe redness and swelling of the entire paw including digits, and 4=Maximally inflamed limb with involvement of multiple joints. On Day 10 post first immunization, rats were distributed evenly (according to the arthritis score) across the control and treatment groups. The CIA rats were given subcutaneous doses of EC0565 and everolimus at 1000 nmol/kg 3 times a week. The animals in the arthritis control group were left untreated. The arthritis score and animal body weight were recorded daily during weekdays. As shown in FIGS. 51A and 51B, EC0565 was also effective in rats with collagen-induced arthritis.

Example 4

Figure 52A:
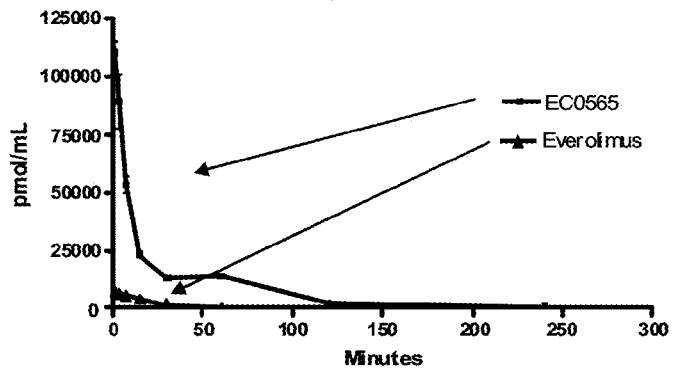
FIG. 52A shows the plasma concentration of EC0565 and everolimus over time after a 2 mmol/kg intravenous dose of EC0565.
Figure 52B:
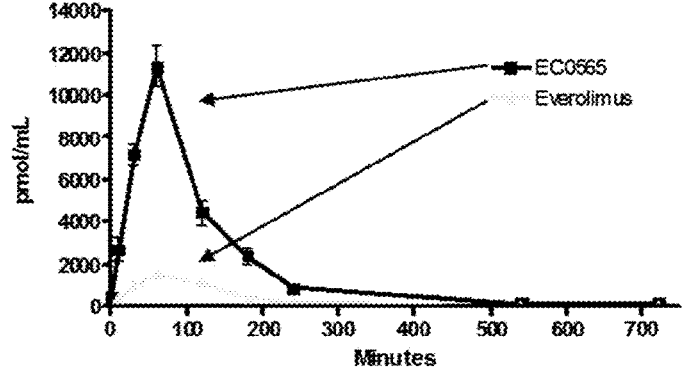
FIG. 52B shows the plasma concentration of EC0565 and everolimus over time after a 2 mmol/kg subcutaneous dose of EC0565.
Figure 52C:
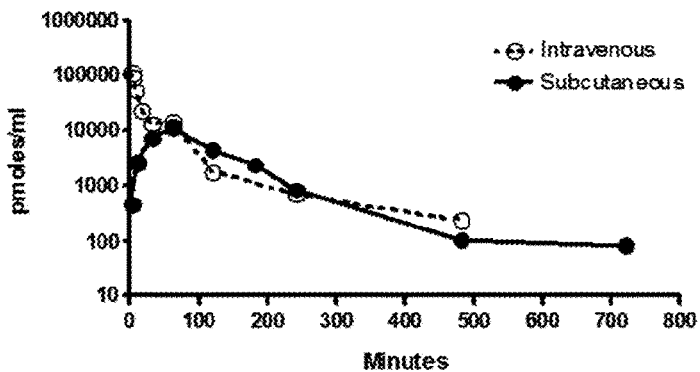
FIG. 52C shows a comparison of the plasma concentration of EC0565 given subcutaneously or intravenously.

EC0565 Shows Higher Water Solubility and Bioavailability than Everolimus in Rats Everolimus, the base drug of EC0565 has poor water solubility (1-10 μM) and low and variable oral bioavailability (~12% in rats, *Journal of Pharmacokinetics and Pharmacodynamics*, Vol. 34, No. 3, June 2007). These limitations render formulation of this drug difficult and contribute to a relatively narrow therapeutic index. In contrast, EC0565 displays a improved water solubility at >1 mM in phosphate-buffered saline (pH 7.4). The bioavailability of EC0565 after subcutaneous injection was measured. Female Lewis rats with rounded tip jugular vein catheters (Harlan) were fed regular rodent diet. The treated animals were given a single intravenous or subcutaneous dose of EC0565 at 2 μmol/kg. For intravenous administration (FIG. 52A), whole blood samples (300 μl) were collected from the animals at 1 min, 3 min, 7 min, 15 min, 30 mM, 1 h, 2 h, 4 h, and 8 h post injection. For subcutaneous administration (FIG. 52B), whole blood samples (300 μl) were collected from the animals at 1 min, 10 min, 30 min, 1 h, 2 h, 3 h, 4 h, 8 h, and 12 h post injection. The blood samples were placed into anti-coagulant tubes containing 1.7 mg/mL of K3-EDTA and 0.35 mg/mL of N-maleoyl-beta-alanine (0.35 mg/mL). Plasma samples were obtained by centrifugation for 3 min at ~2,000 g and stored at −80° C. The amount of EC0565 and its released base drug (everolimus) were determined by HPLC using the EC0565 injection solution as the standard. The results (based on the area under the curve) showed that approximately 18% and 17% of free drug exposure/release were detected in the plasma after a single intravenous or subcutaneous dose of EC0565, respectively (FIGS. 52A, B). The Tmax for EC0565 and everolimus after subcutaneous injection were observed at ~1 h (FIG. 52B). Based on the area under the curve, the bioavailablity of EC0565 after subcutaneous administration (compared to intravenous administration) was calculated to be ~128% (FIG. 52C).

Example 5

EC0565 Inhibits Proliferating Cell Nuclear Antigen in Raw264.7 Cells

Figure 53A:
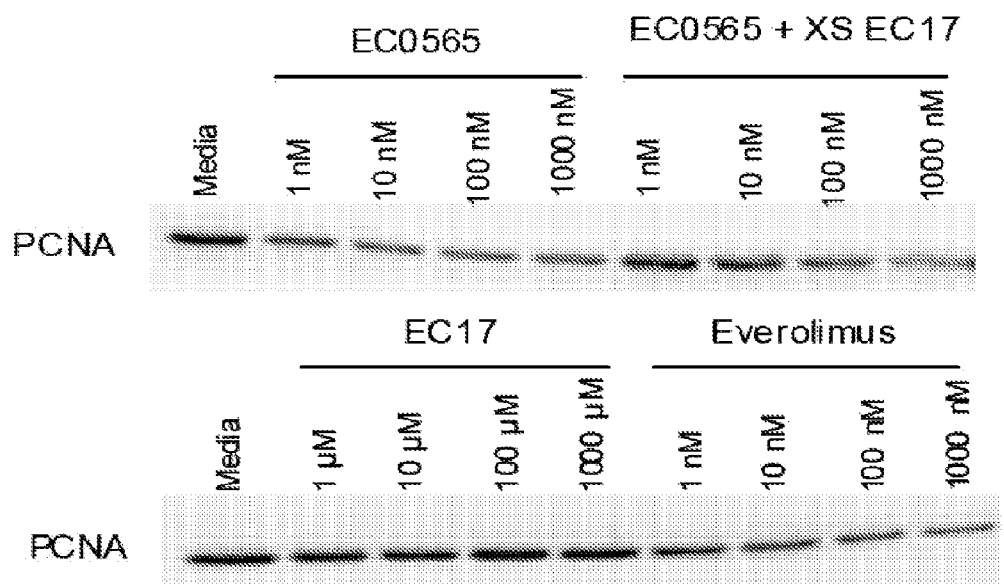
FIG. 53A shows the effect on Proliferating Cell Nuclear Antigen (PCNA) in synchronized FR-positive murine macrophage-like RAW264.7 cells treated with media as measured by Western blot analysis on whole cell lysates using a monoclonal antibody specific for PCNA, a) EC0565 (1 nM, 10 nM, 100 nM, and 1000 nM); b) EC0565 (1 nM, 10 nM, 100 nM, and 1000 nM) in the presence of XS EC17 (a folate receptor binding competitor); c) EC17 alone (1 nM, 10 nM, 100 nM, and 1000 nM); and d) everolimus (1 nM, 10 nM, 100 nM, and 1000 nM).
Figure 53B:
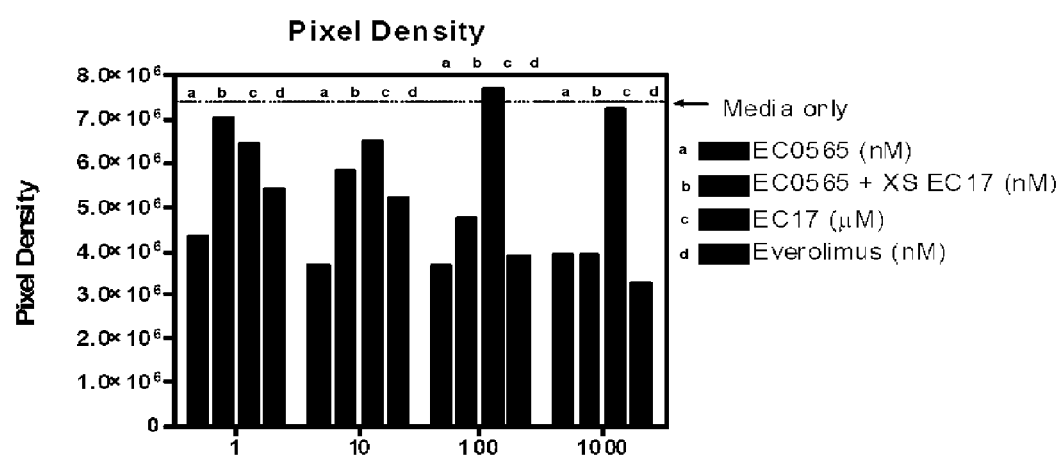
FIG. 53B shows the pixel density measurements for the images shown in FIG. 53A a) EC0565 (1 nM, 10 nM, 100 nM, and 1000 nM); b) EC0565 (1 nM, 10 nM, 100 nM, and 1000 nM) in the presence of XS EC17 (a folate receptor binding competitor); c) EC17 alone (1 nM, 10 nM, 100 nM, and 1000 nM); and d) everolimus (1 nM, 10 nM, 100 nM, and 1000 nM).
Figure 53C:
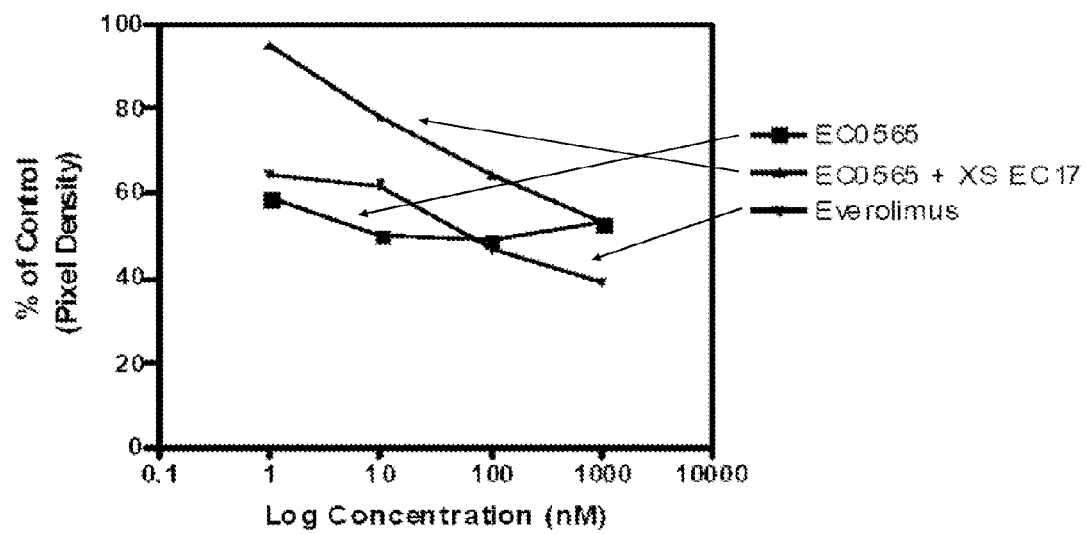
FIG. 53C shows a plot of percent control of PCNA data shown in FIG. 53B for EC0565 (1 nM, 10 nM, 100 nM, and 1000 nM); EC0565 (1 nM, 10 nM, 100 nM, and 1000 nM) in the presence of XS EC17 and for everolimus (1 nM, 10 nM, 100 nM, and 1000 nM).

Proliferating Cell Nuclear Antigen (PCNA) is a cell-cycle regulated nuclear protein that is often used to evaluate cellular proliferative activity. To study anti-proliferative effect of EC0565, FR-positive murine macrophage-like RAW264.7 cells (serum deprived for 36 h for synchronization) were given a 2 h treatment of EC0565 (1, 10, 100, and 1000 nM) without or with 1000× excess of EC17 (as a folate competitor) followed by a 48-h chase in drug-free medium. For comparison, the cells were also treated for 48 h with everolimus (1, 10, 100, and 1000 nM). All media contained 1% DMSO due to the low water solubility of everolimus. Western blot analysis was carried out on whole cell lysates using a monoclonal antibody specific for PCNA (PC10, Cell Signaling, Danvers, Mass.). After incubation with a peroxidase-conjugated secondary antibody, the signals were visualized using SuperSignal West Pico Chemiluminescent Substrate system (ThermoScientific, Waltham, Mass.) following the manufacturer's instructions. The images were acquired using a G:BOX Chemi HR 16 gel imaging system (Syngene, Frederick, Md.). As shown in FIG. 53A, both everolimus and EC0565 inhibited PCNA activities in the synchronized RAW264.7 cells. The inhibitory activity of EC0565 at 1 nM was 100% blocked by the presence of excess EC17, while EC17 alone was benign (FIGS. 53B-C). As the EC0565 concentration was increased from 10, 100, to 1000 nM, EC0565 showed both FR-specific and non FR-specific anti-PCNA effects. This data indicates that EC0565 reduces PCNA activity in RAW264.7 cells in a FR-dependent manner, especially at lower concentrations.

Compound Examples

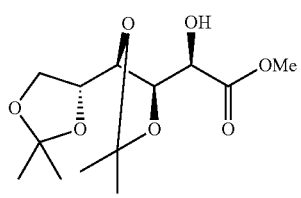

EXAMPLE. (3,4), (5,6)-Bisacetonide-D-Gluconic Acid Methyl Ester. In a dry 250 mL round bottom flask, under argon δ-gluconolactone (4.14 g, 23.24 mmol) was suspended in acetone-methanol (50 mL). To this suspension dimethoxypropane (17.15 mL, 139.44 mmol) followed by catalytic amount of p-toulenesulfonic acid (200 mg) were added. This solution was stirred at room temperature for 16 h. TLC (50% EtOAc in petroleum ether) showed that all of the starting material had been consumed and product had been formed. Acetone-methanol was removed under reduced pressure. The residue of the reaction was dissolved in EtOAc and washed with water. The organic layer was washed with brine, dried over $Na_2SO_4$, and concentrated to dryness. This material was then loaded onto a $SiO_2$ column and chromatographed (30% EtOAc in petroleum ether) to yield pure (3,4), (5,6)-bisacetonide-D-gluconic acid methyl ester (3.8 g, 56%) and regio-isomer (2,3), (5,6)-bisacetonide-D-gluconic acid methyl ester (0.71 g, 10%). $^1$H NMR data was in accordance with the required products. $C_{13}H_{22}O_7$; MW 290.31; Exact Mass: 290.14.

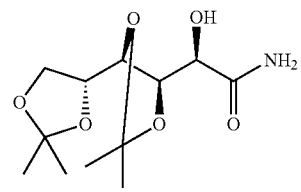

EXAMPLE. (3,4), (5,6)-Bisacetonide-D-Gluconic Amide. 20 g of the methyl ester was dissolved in 100 mL methanol, cooled the high-pressure reaction vessel with dry ice/acetone, charged with 100 mL liquid ammonia, warmed up to room temperature and heated to 160° C./850 PSI for 2 hours. The reaction vessel was cooled to room temperature and released the pressure. Evaporation of the solvent gave brownish syrup, and minimum amount of isopropyl alcohol was added to make the homogeneous solution with reflux. The solution was cooled to −20° C. and the resulting solid was filtered to give 8.3 g of solid. The mother liquid was evaporated, and to the resulting residue, ether was added and refluxed until homogeneous solution was achieved. The solution was then cooled to −20° C. and the resulting solid was filtered to give 4.0 g product. The solid was combined and recrystallized in isopropyl alcohol to give 11.2 g (59%) of the white amide product. $C_{12}H_{21}NO_6$; MW 275.30; Exact Mass: 275.14.

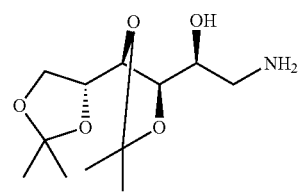

EXAMPLE. (3,4), (5,6)-Bisacetonide-1-Deoxy-1-Amino-D-Glucitol. In a dry 100 mL round bottom flask, under argon, $LiAlH_4$ (450 mg, 11.86 momol)) was dissolved in THF (10 mL) and cooled to 0° C. To this suspension (3,4), (5,6)-bisacetonide-D-gluconic amide (1.09 g, 3.96 mmol) in THF (30 mL) was added very slowly over 15 min. This mixture was refluxed for 5 h. TLC (10% MeOH in methylene chloride) showed that all of the starting material had been consumed and product had been formed. The reaction mixture was cooled to room temperature, and then cooled to ice-bath temperature, diluted with diethyl ether (40 mL), slowly added 0.5 mL of water, 0.5 mL of 15% aq. NaOH, and then added 1.5 mL of water. The reaction mixture was warmed to room temperature and stirred for 30 min $MgSO_4$ was added and stirred for additional 15 min and filtered. The organic layer was concentrated to dryness to yield (3,4), (5,6)-bisacetonide-1-deoxy-1-amino-D-glucitol. $^1$H NMR data was in accordance with the product. $C_{12}H_{23}NO_5$; MW 261.31; Exact Mass: 261.16.

(silica gel, 1% MeOH/CHCl$_3$ followed by 3.5% MeOH/CHCl$_3$) to give 1.3 g (81%) EC0475 as a solid material. MW 612.67; Exact Mass: 612.27.

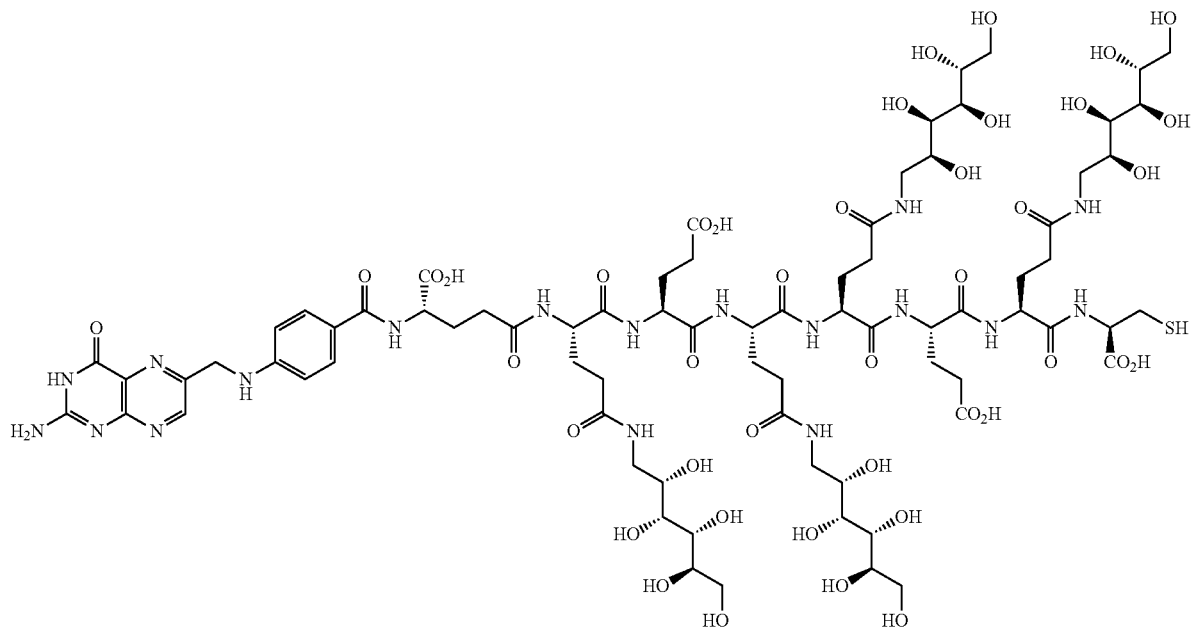

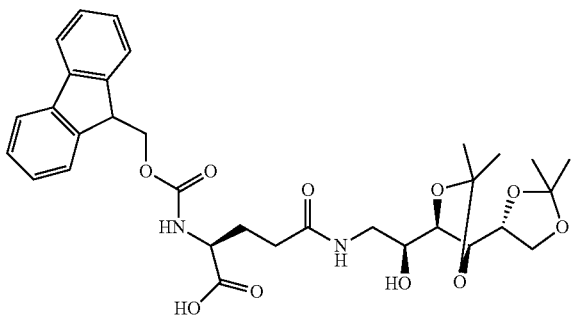

EXAMPLE. EC0475. O-Allyl protected Fmoc-Glu (2.17 g, 1 eq), PyBOP (2.88 g, 1 eq), and DIPEA (1.83 mL, 2 eq) were added to a solution of (3,4),(5,6)-bisacetonide-1-deoxy-1-amino-D-glucitol (1.4 g, 5 3 mmol) in dry DMF (6 mL) and the mixture was stirred at RT under Ar for 2 h. The solution was diluted with EtOAc (50 mL), washed with brine (10 mL×3), organic layer separated, dried (MgSO$_4$), filtered and concentrated to give a residue, which was purified by a flash column (silica gel, 60% EtOAc/petroether) to afford 1.72 g (50%) allyl-protected EC0475 as a solid. Pd(Ph$_3$)$_4$ (300 mg, 0.1 eq) was added to a solution of allyl-protected EC0475 (1.72 g, 2.81 mmol) in NMM/AcOH/CHCl$_3$ (2 mL/4 mL/74 mL). The resulting yellow solution was stirred at RT under Ar for 1 h, to which was added a second portion of Pd(Ph$_3$)$_4$ (300 mg, 0.1 eq). After stirring for an additional 1 h, the mixture was washed with 1 N HCl (50 mL×3) and brine (50 mL), organic layer separated, dried (MgSO4), filtered, and concentrated to give a yellow foamy solid, which was subject to chromatography EXAMPLE. Tetra-Saccharoglutamate-Bis-aGlu-Folate Spacer EC0491. EC0491 was synthesized by SPPS in eight steps according to the general peptide synthesis procedure described herein starting from H-Cys(4-methoxytrityl)-2-chlorotrityl-Resin, and the following SPPS reagents:

| Reagents | Mmol | equivalent | MW | Amount |
|---|---|---|---|---|
| H-Cys(4-methoxytrityl)-2-chlorotrityl-Resin (loading 0.56 mmol/g) | 0.1 | | | 0.167 g |
| EC0475 | 0.13 | 1.3 | 612.67 | 0.080 g |
| Fmoc-Glu(OtBu)—OH | 0.2 | 2 | 425.5 | 0.085 g |
| EC0475 | 0.13 | 1.3 | 612.67 | 0.080 g |
| EC0475 | 0.13 | 1.3 | 612.67 | 0.080 g |
| Fmoc-Glu(OtBu)—OH | 0.2 | 2 | 425.5 | 0.085 g |
| EC0475 | 0.13 | 1.3 | 612.67 | 0.080 g |
| Fmoc-Glu-OtBu | 0.2 | 2 | 425.5 | 0.085 g |
| N$^{10}$TFA-Pteroic Acid•TFA (dissolve in 10 ml DMSO) | 0.2 | 2 | 408 | 0.105 g |
| DIPEA | 0.4 | 4 | 129.25 (d = 0.742) | 0.070 mL |
| PyBOP | 0.2 | 2 | 520 | 0.104 g |

The Coupling steps, Cleavage step, and Cleavage Reagent were identical to those described above. HPLC Purification step: Column: Waters NovaPak C$_{18}$ 300×19 mm; Buffer A=10 mM ammonium acetate, pH 5; B=ACN; Method: 100% A for 5 min then 0% B to 20% B in 20 minutes at 26 ml/min; yield ~100 mg, 51%. $C_{76}H_{118}N_{18}O_{41}S$; MW 1971.91; Exact Mass: 1970.74.

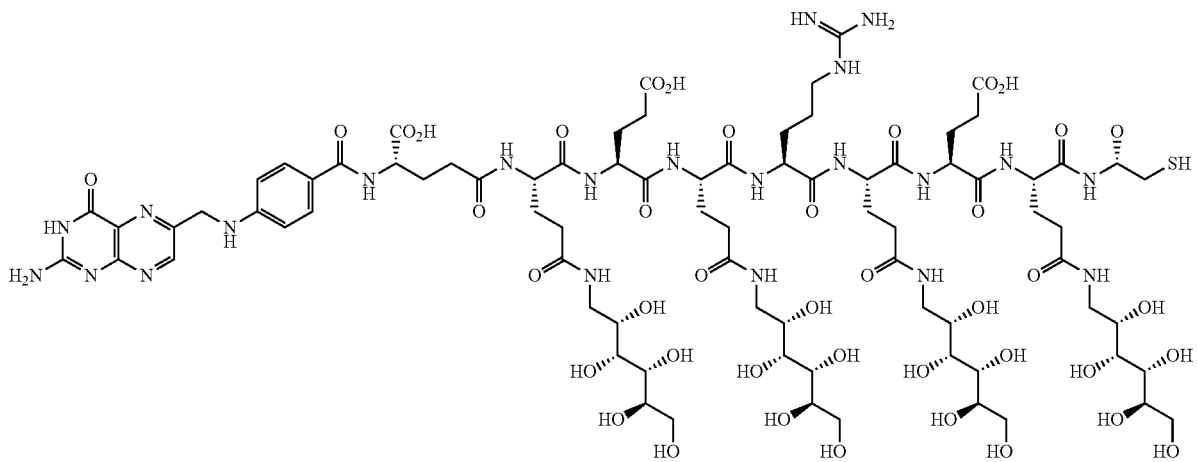 [SMILES: N=C(N)NCCC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c1ccc(NCc2cnc3nc(N)[nH]c(=O)c3n2)cc1)C(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@H](O)CS]

EXAMPLE. EC0479 was synthesized by SPPS according to the general peptide synthesis procedure described herein starting from H-Cys(4-methoxytrityl)-2-chlorotrityl-Resin, and the following SPPS reagents:

| Reagents | mmol | equivalent | MW | Amount |
|---|---|---|---|---|
| H-Cys(4-methoxytrityl)-2-chlorotrityl-Resin (loading 0.6 mmol/g) | 0.094 | | | 0.16 g |
| EC0475 | 0.13 | 1.4 | 612.67 | 0.082 g |
| Fmoc-Glu(OtBu)—OH | 0.19 | 2.0 | 425.47 | 0.080 g |
| EC0475 | 0.13 | 1.4 | 612.67 | 0.082 g |
| Fmoc-Arg(Pbf)-OH | 0.19 | 2.0 | 648.77 | 0.12 g |
| EC0475 | 0.13 | 1.4 | 612.67 | 0.082 g |
| Fmoc-Glu(OtBu)—OH | 0.19 | 2.0 | 425.47 | 0.080 g |
| EC0475 | 0.13 | 1.4 | 612.67 | 0.082 g |
| Fmoc-Glu-OtBu | 0.19 | 2.0 | 425.47 | 0.080 g |
| $N^{10}$TFA-Pteroic Acid (dissolve in 10 ml DMSO) | 0.16 | 1.7 | 408.29 | 0.066 g |
| DIPEA | | 2.0 eq of AA | | 41 µL or 49 µL |
| PyBOP | | 1.0 eq of AA | | 122 mg or 147 mg |

Coupling steps. In a peptide synthesis vessel add the resin, add the amino acid solution, DIPEA, and PyBOP. Bubble argon for 1hr. and wash 3× with DMF and IPA. Use 20% piperidine in DMF for Fmoc deprotection, 3× (10 min), before each amino acid coupling. Continue to complete all 9 coupling steps. At the end treat the resin with 2% hydrazine in DMF 3× (5 min) to cleave TFA protecting group on Pteroic acid, wash the resin with DMF (3×), IPA (3×), MeOH (3×), and bubble the resin with argon for 30 min.

Cleavage step. Reagent: 92.5% TFA, 2.5% $H_2O$, 2.5% triisopropylsilane, 2.5% ethanedithiol. Treat the resin with cleavage reagent for 15 min with argon bubbling, drain, wash the resin once with cleavage reagent, and combine the solution. Rotavap until 5 ml remains and precipitate in diethyl ether (35 mL). Centrifuge, wash with diethyl ether, and dry. The crude solid was purified by HPLC.

HPLC Purification step. Column: Waters Atlantis Prep T3 10 µm OBD 19×250 mm; Solvent A: 10 mM ammonium acetate, pH 5; Solvent B: ACN; Method: 5 min 0% B to 20 min 20% B 26 mL/min Fractions containing the product was collected and freeze-dried to give ~70 mg EC0479 (35% yield). $^1$H NMR and LC/MS were consistent with the product. MW 2128.10; Exact Mass: 2126.84.

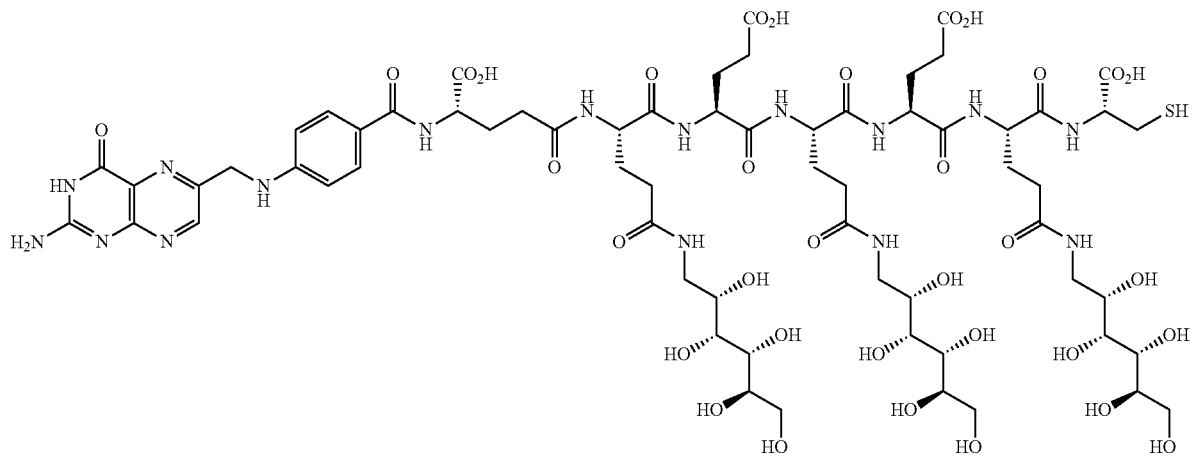 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)O)C(=O)O)cc3)nc2c(=O)[nH]1]

EC0488. This compound was prepared by SPPS according to the general peptide synthesis procedure described herein starting from H-Cys(4-methoxytrityl)-2-chlorotrityl-Resin, and the following SPPS reagents:

| Reagents | mmol | equivalent | MW | amount |
|---|---|---|---|---|
| H-Cys(4-methoxytrityl)-2-chlorotrityl-Resin (loading 0.6 mmol/g) | 0.10 | | | 0.17 g |
| EC0475 | 0.13 | 1.3 | 612.67 | 0.082 g |
| Fmoc-Glu(OtBu)—OH | 0.19 | 1.9 | 425.47 | 0.080 g |
| EC0475 | 0.13 | 1.3 | 612.67 | 0.082 g |
| Fmoc-Glu(OtBu)—OH | 0.19 | 1.9 | 425.47 | 0.080 g |
| EC0475 | 0.13 | 1.3 | 612.67 | 0.082 g |
| Fmoc-Glu-OtBu | 0.19 | 1.9 | 425.47 | 0.080 g |
| $N^{10}$TFA-Pteroic Acid (dissolve in 10 ml DMSO) | 0.16 | 1.6 | 408.29 | 0.066 g |
| DIPEA | | 2.0 eq of AA | | |
| PyBOP | | 1.0 eq of AA | | |

Coupling steps. In a peptide synthesis vessel add the resin, add the amino acid solution, DIPEA, and PyBOP. Bubble argon for 1 hr. and wash 3× with DMF and IPA. Use 20% piperidine in DMF for Fmoc deprotection, 3× (10 min), before each amino acid coupling. Continue to complete all 9 coupling steps. At the end treat the resin with 2% hydrazine in DMF 3× (5 min) to cleave TFA protecting group on Pteroic acid, wash the resin with DMF (3×), IPA (3×), MeOH (3×), and bubble the resin with argon for 30 min.

Cleavage step. Reagent: 92.5% TFA, 2.5% $H_2O$, 2.5% triisopropylsilane, 2.5% ethanedithiol. Treat the resin with cleavage reagent 3× (10 min, 5 min, 5 min) with argon bubbling, drain, wash the resin once with cleavage reagent, and combine the solution. Rotavap until 5 ml remains and precipitate in diethyl ether (35 mL). Centrifuge, wash with diethyl ether, and dry. About half of the crude solid (~100 mg) was purified by HPLC.

HPLC Purification step. Column: Waters Xterra Prep MS C18 10 μm 19×250 mm; Solvent A: 10 mM ammonium acetate, pH 5; Solvent B: ACN; Method: 5 min 0% B to 25 min 20% B 26mL/min Fractions containing the product was collected and freeze-dried to give 43 mg EC0488 (51% yield). $^1$H NMR and LC/MS (exact mass 1678.62) were consistent with the product. MW 1679.63; Exact Mass: 1678.62.

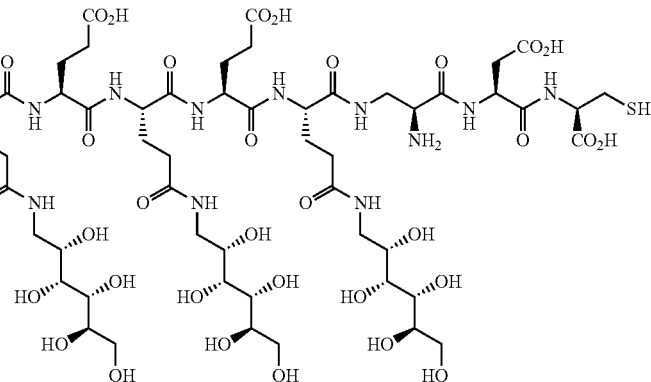

EC0536 Conjugate Intermediate

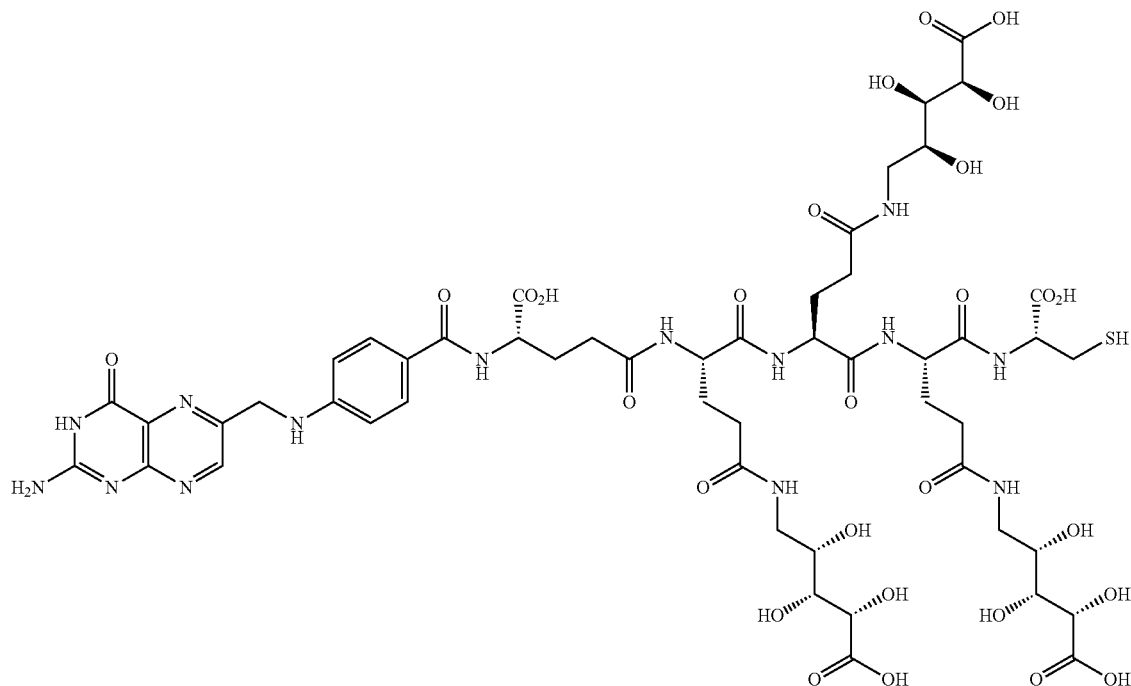 [SMILES: Nc1nc2ncc(CNc3ccc(C(=O)N[C@@H](CCC(=O)N[C@@H](CCC(=O)NC[C@H](O)[C@@H](O)[C@H](O)C(=O)O)C(=O)N[C@@H](CCC(=O)NC[C@H](O)[C@@H](O)[C@H](O)C(=O)O)C(=O)N[C@@H](CCC(=O)NC[C@H](O)[C@@H](O)[C@H](O)C(=O)O)C(=O)N[C@@H](CS)C(=O)O)C(=O)O)cc3)nc2c(=O)[nH]1]

EC0632 Conjugate intermediate. C52H72N14O28S, MW 1373.27, Exact Mass: 1372.44, prepared from the corresponding tert-butyl protected carboxylates.

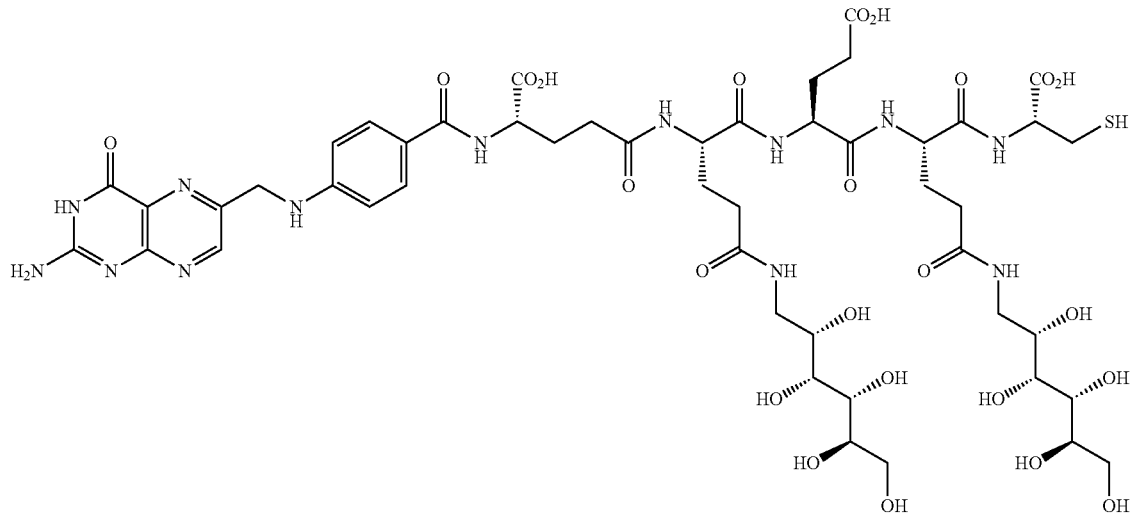 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)O)C(=O)O)cc3)nc2c(=O)[nH]1]

EC0669 Conjugate intermediate. C49H71N13O24S, MW 1258.23, Exact Mass: 1257.45

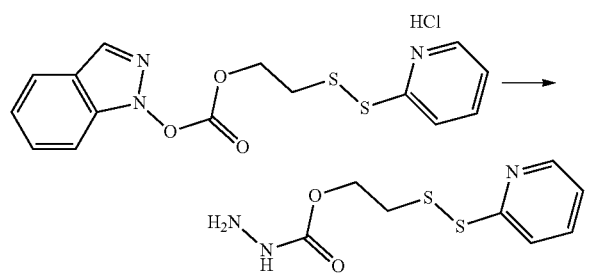

EXAMPLE. Synthesis of Coupling Reagent EC0311. DIPEA (0.60 mL) was added to a suspension of HOBt-OCO$_2$—(CH$_2$)$_2$—SS-2-pyridine HCl (685 mg, 91%) in anhydrous DCM (5.0 mL) at 0° C., stirred under argon for 2 minutes, and to which was added anhydrous hydrazine (0.10 mL). The reaction mixture was stirred under argon at 0° C. for 10 minutes and room temperature for an additional 30 minutes, filtered, and the filtrate was purified by flash chromatography (silica gel, 2% MeOH in DCM) to afford EC0311 as a clear thick oil (371 mg), solidified upon standing.

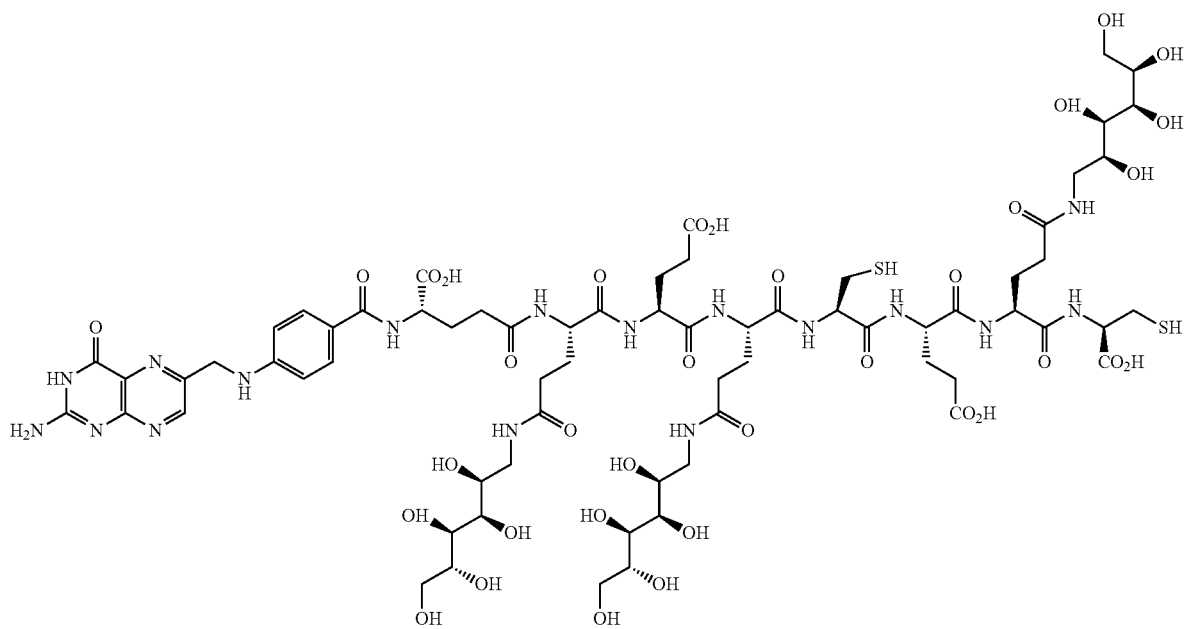 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)O)C(=O)O)cc3)nc2c(=O)[nH]1]

EC0593 Multidrug intermediate for two drugs. C68H103N17O35S2, MW 1782.77, Exact Mass: 1781.62

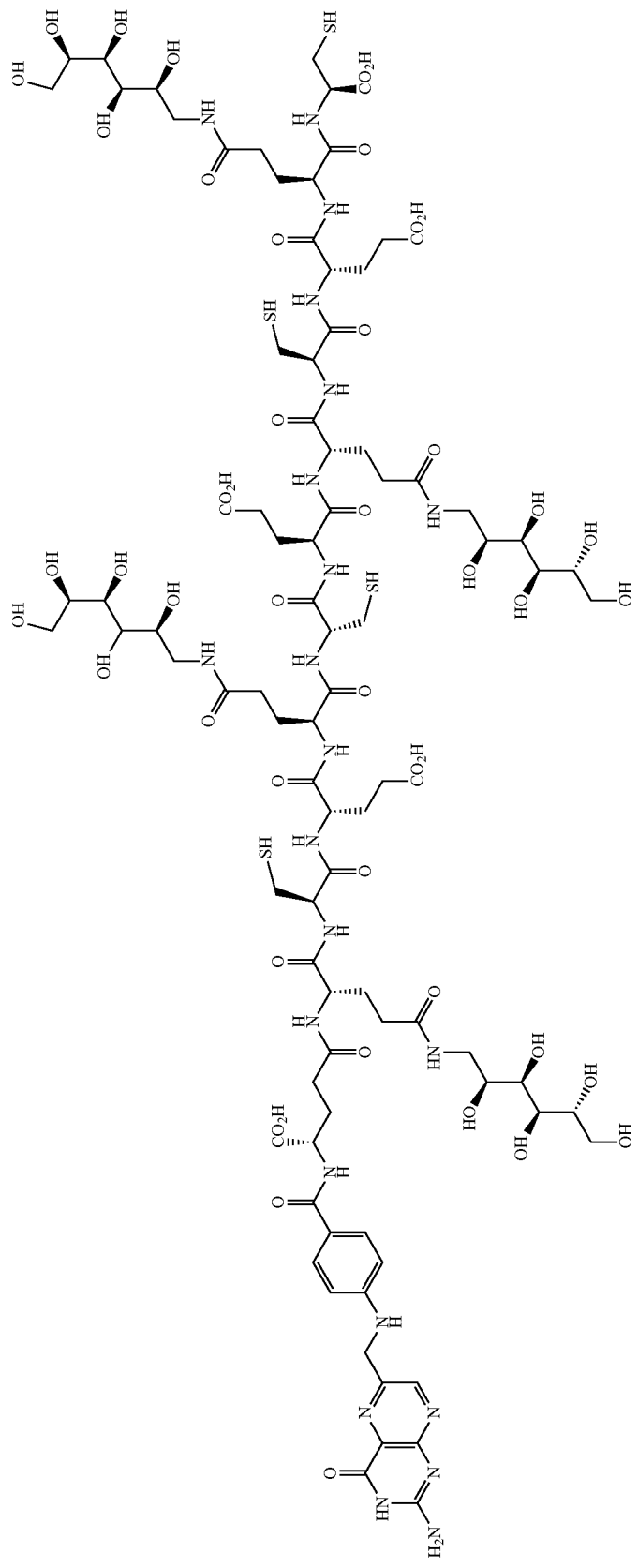

EC0613 Multidrug intermediate for three drugs. C90H140N22O47S4, MW 2410.45, Exact Mass: 2408.81
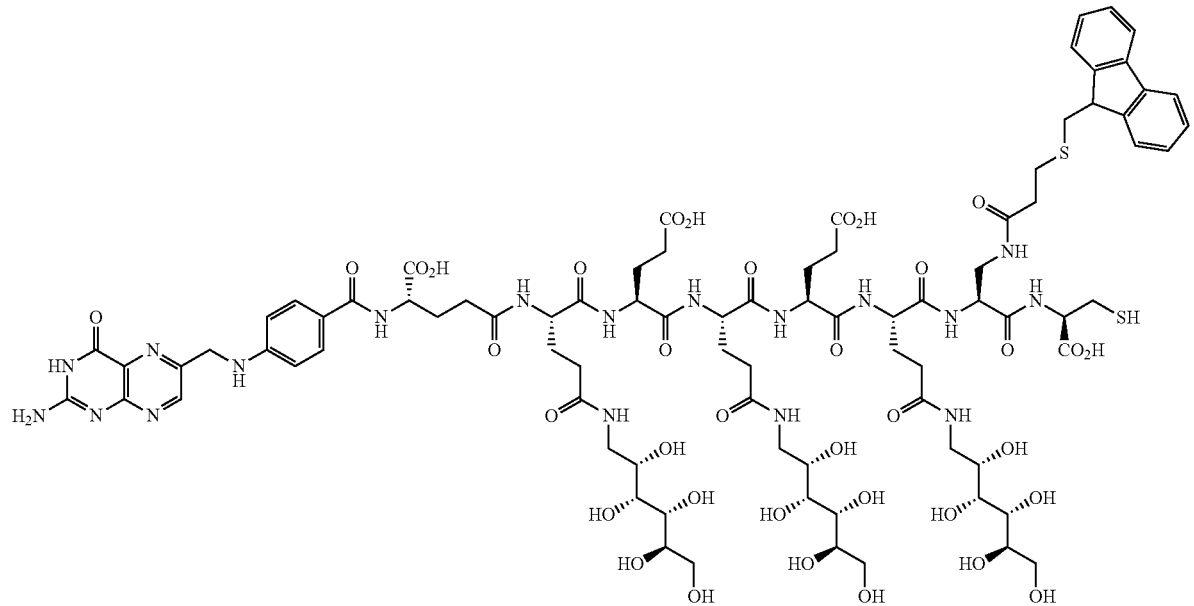 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CNC(=O)CCSCC4c5ccccc5-c5ccccc54)C(=O)N[C@@H](CS)C(=O)O)C(=O)O)cc3)nc2c(=O)[nH]1]
EC0542 Optionally selective multidrug intermediate for two drugs. C85H118N18O36S2, C, 50.24; H, 5.85; N, 12.41; O, 28.34; S, 3.16, MW 2032.08, Exact Mass: 2030.74
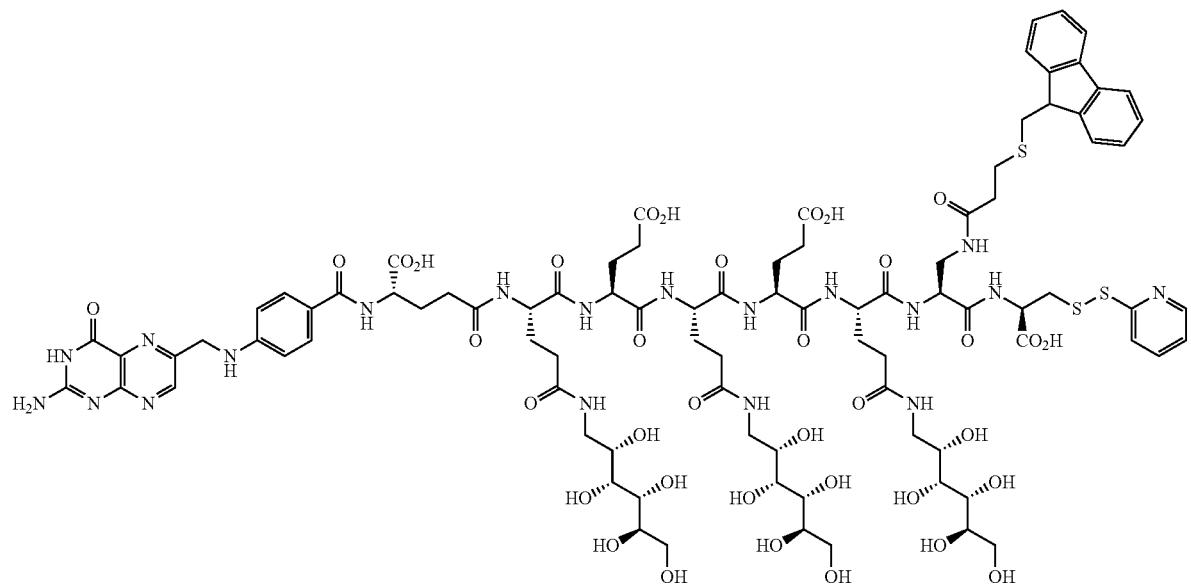 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CNC(=O)CCSCC4c5ccccc5-c5ccccc54)C(=O)N[C@@H](CSSc4ccccn4)C(=O)O)C(=O)O)cc3)nc2c(=O)[nH]1]
EC0559 Optionally selective multidrug intermediate for two drugs. C90H121N19O36S3, MW 2141.22, Exact Mass: 2139.74

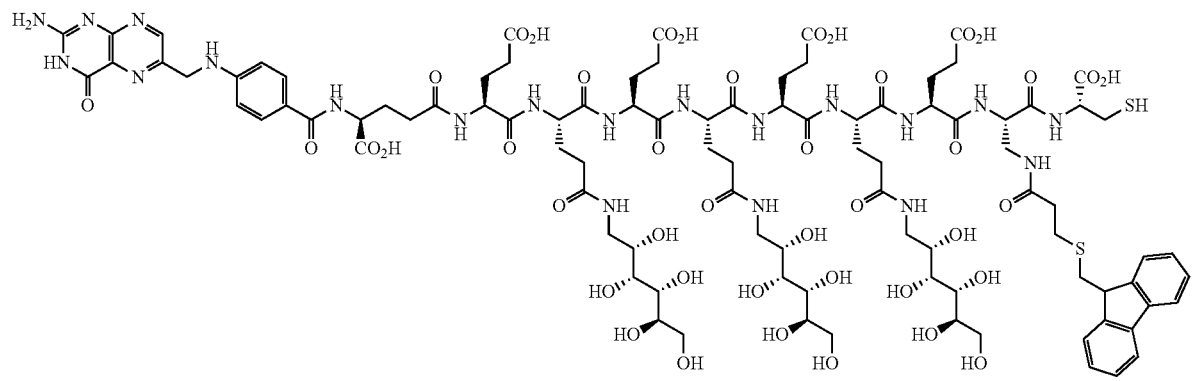 [SMILES: Nc1nc2ncc(CNc3ccc(C(=O)N[C@@H](CCC(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CNC(=O)CCSCC4c5ccccc5-c5ccccc54)C(=O)N[C@@H](CS)C(=O)O)C(=O)O)cc3)nc2c(=O)[nH]1]
EC0682 Optionally selective multidrug intermediate for two drugs. C95H132N20O42S2, MW 2290.30, Exact Mass: 2288.82

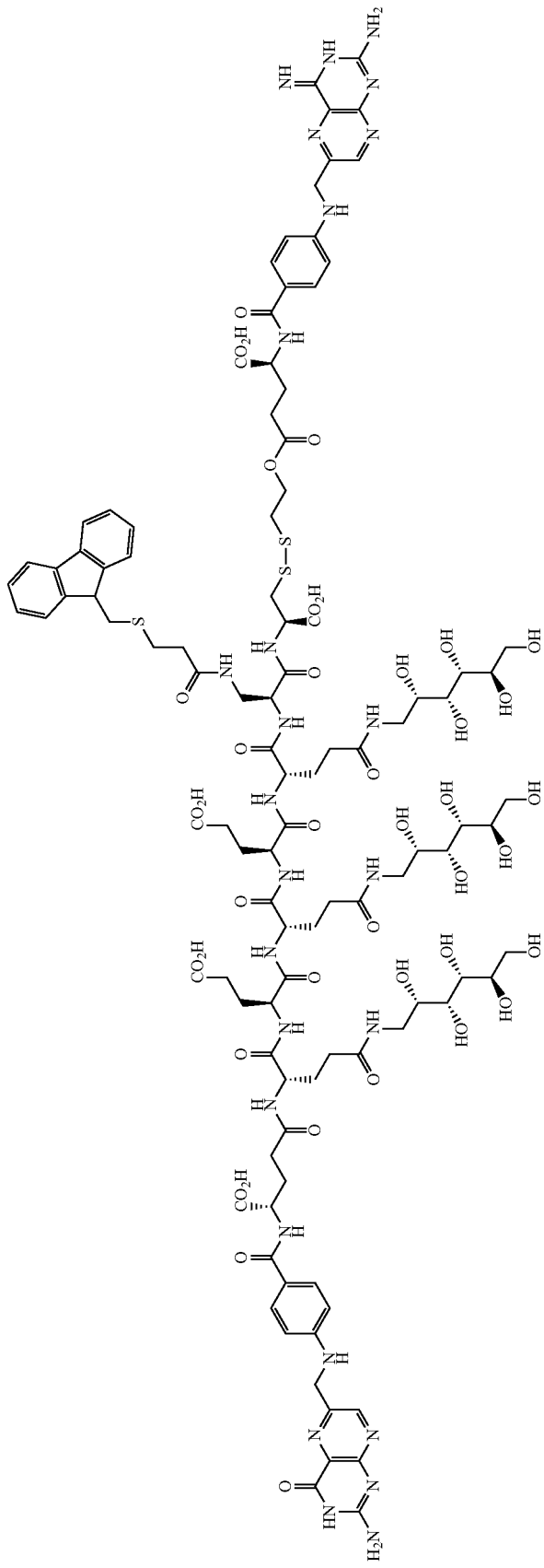

EC0646 Conjugate of Aminopterin and intermediate for multidrug conjugate. C106H140N26O41S3, MW 2530.59, Exact Mass: 2528.88

Example 5

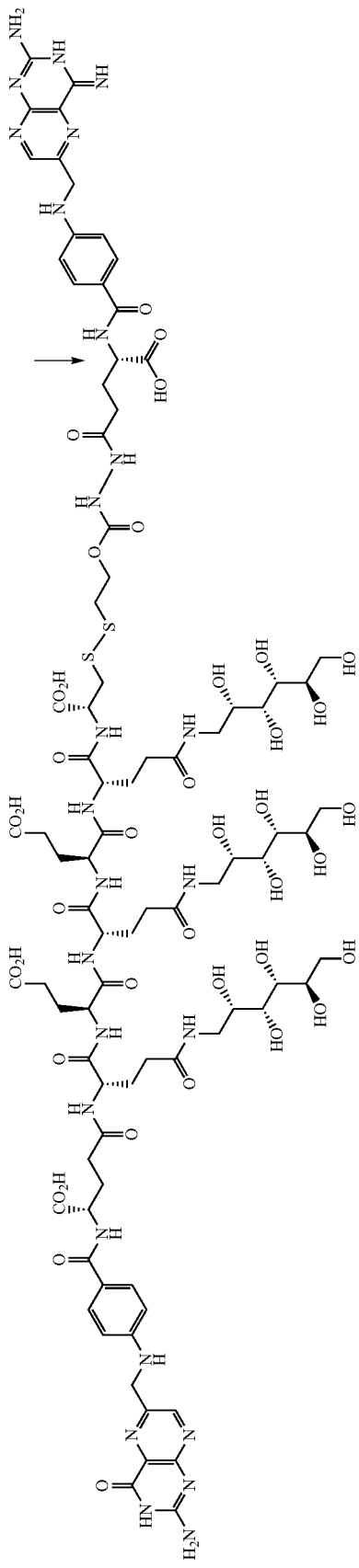

EC0746 Conjugate of aminopterin. $C_{87}H_{122}N_{26}O_{40}S_2$; C, 46.73; H, 5.50; N, 16.29; O, 28.62; S, 2.87; MW 2236.180, Exact Mass: 2234.775.
Reaction of mixed carbonate 101 with t-butyl-carbazate in the presence of diisopropylethylamine (DIPEA) gave the corresponding t-butyl-carbazate 102. Trifluoroacetic acid
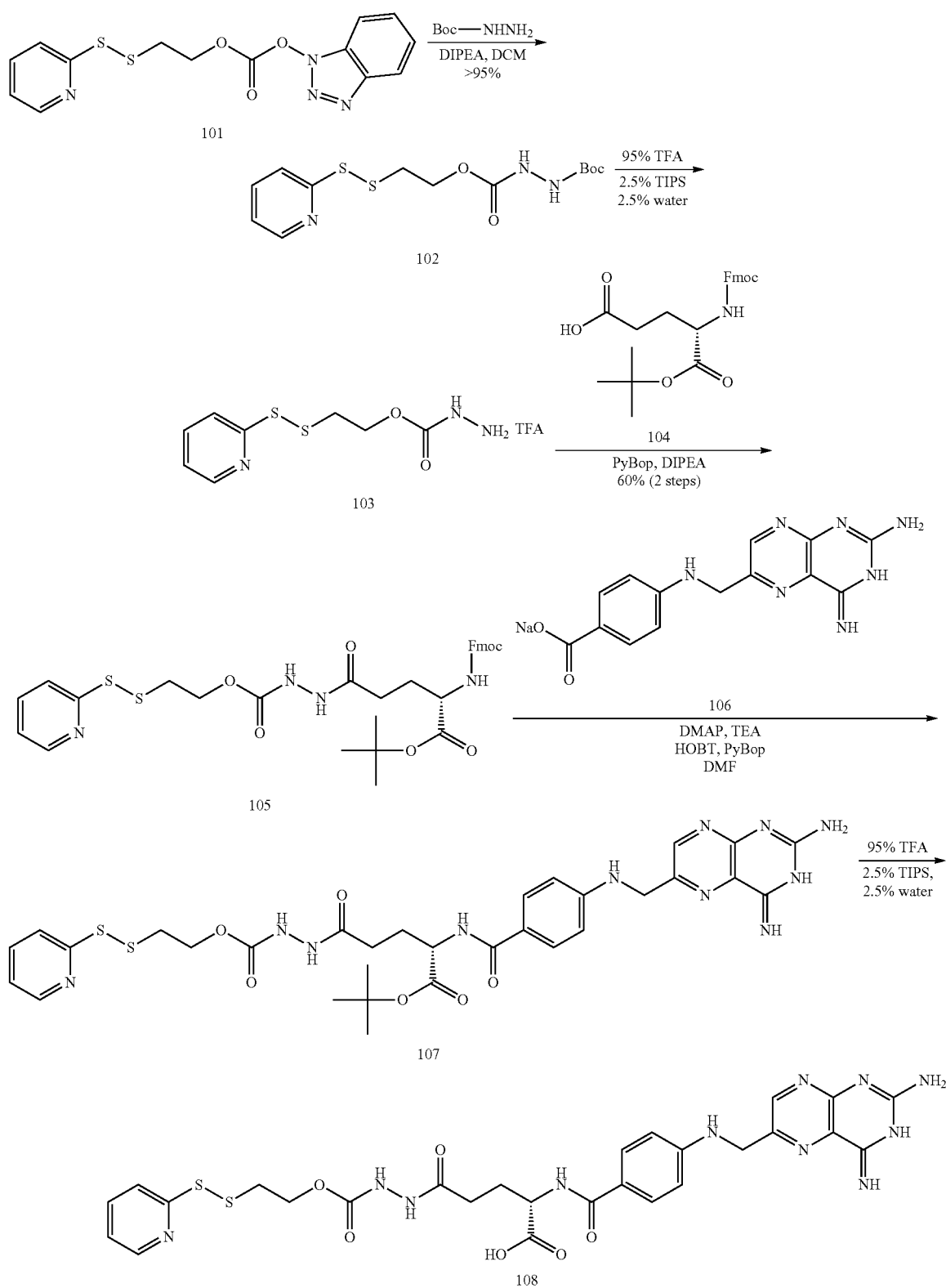
Scheme 2.

(TFA) mediated Boc deprotection of 102 in the presence of triisopropylsilane (TIPS) resulted in pyridyldisulfanylethyl carbazate 103 as a TFA salt. Coupling of carbazate 103 with protected glutamic acid 104, using benzotriazol-1-yl-oxytripyrrolidinophosphonium hexafluorophosphate (PyBop) and DIPEA, yielded glutamic acid derivative 105. 4-dimethylaminopyridine (DMAP) mediated Fmoc deprotection of 105 followed by in situ coupling with commercially available 4-[(2-amino-4-imino-3,4-dihydro-pteridin-6-yl-methyl)-amino]-benzoic acid 106 using PyBop and hydroxybenzotriazol (HOBt) resulted in protected aminopterin hydrazide 107. Treatment of 107 with TFA removed the t-butyl moiety to yield pyridinedisulfanyl-activated aminopterin hydrazide 108. $^1$H NMR (DMSO-$d_6$ & $D_2O$) δ 8.82 (s, 1H), 8.44 (d, J=4.7 Hz, 1H), 7.80 (m, 2H), 7.71 (d, J=8.8 Hz, 2H), 7.24 (t, J=4.6 Hz, 1H), 6.74 (d, J=8.8 Hz, 2H), 4.60 (s, 2H), 4.32 (dd, J=5.0 Hz, 1H), 4.20 (t, J=6.0 Hz, 2H), 3.07 (t, J=6.0 Hz, 2H), 2.22 (t, J=7.8 Hz, 2H), 2.15-1.94 (m, 2H). ESI-MS: $(M+H)^+$=Calculated 668.2; found 668.2. Treatment of a suspension of EC0488 in phosphate buffer under argon with $NaHCO_3$ resulted in a clear yellow solution. A dimethylsulfoxide (DMSO) solution of 108 was added to this mixture at once under vigorous stirring to yield EC0746. $^1$H NMR (DMSO-$d_6$ & $D_2O$) δ 8.67 (s, 1H) 8.60 (s, 1H), 7.62 (d, J=9 Hz, 2H), 7.59 (d, J=9 Hz, 2H), 6.71 (d, J=8.7 Hz, 2H), 6.62 (d, J=8.1 Hz, 2H), 4.47 (m, 4H), 4.26-4.04 (m, 10H), 3.70-3.30 (m, 22H), 3.30-3.10 (m, 6H), 3.10-2.76 (m, 9H), 2.40-2.04 (m, 15H), 2.04-1.60 (m, 4H). ESI-MS: $[(M+2H)^{2+}]/2$=Calculated 1119.09; found 1119.10.

EC0808 is an isomer of EC0746 having the opposite configuration at the stereogenic carbon indicated with the arrow.

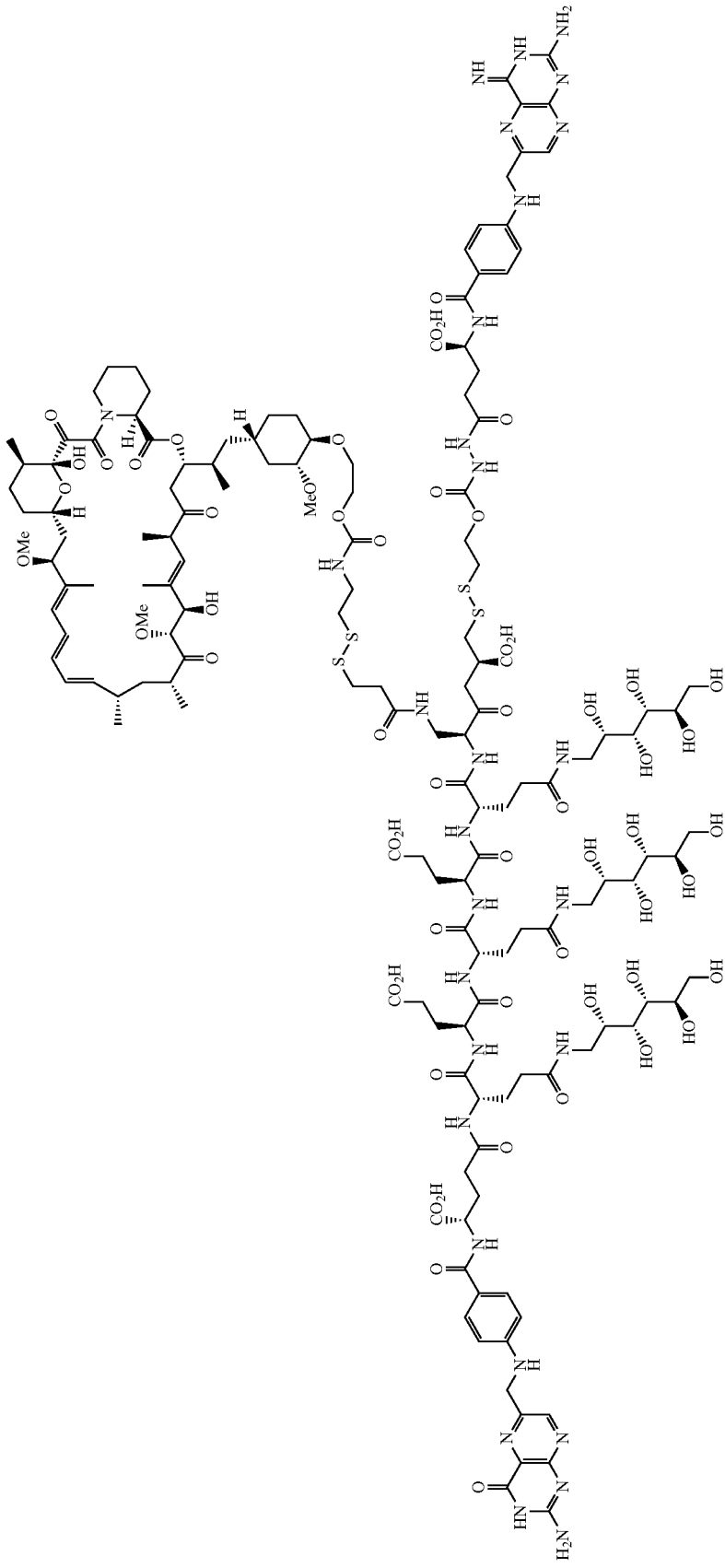

EC0932, everolimus-aminopterin hydrazide conjugate C149H218N30O57S4; C, 51.58; H, 6.33; N, 12.11; O, 26.28; S, 3.70; MW 3469.752; Exact Mass: 3467.396.

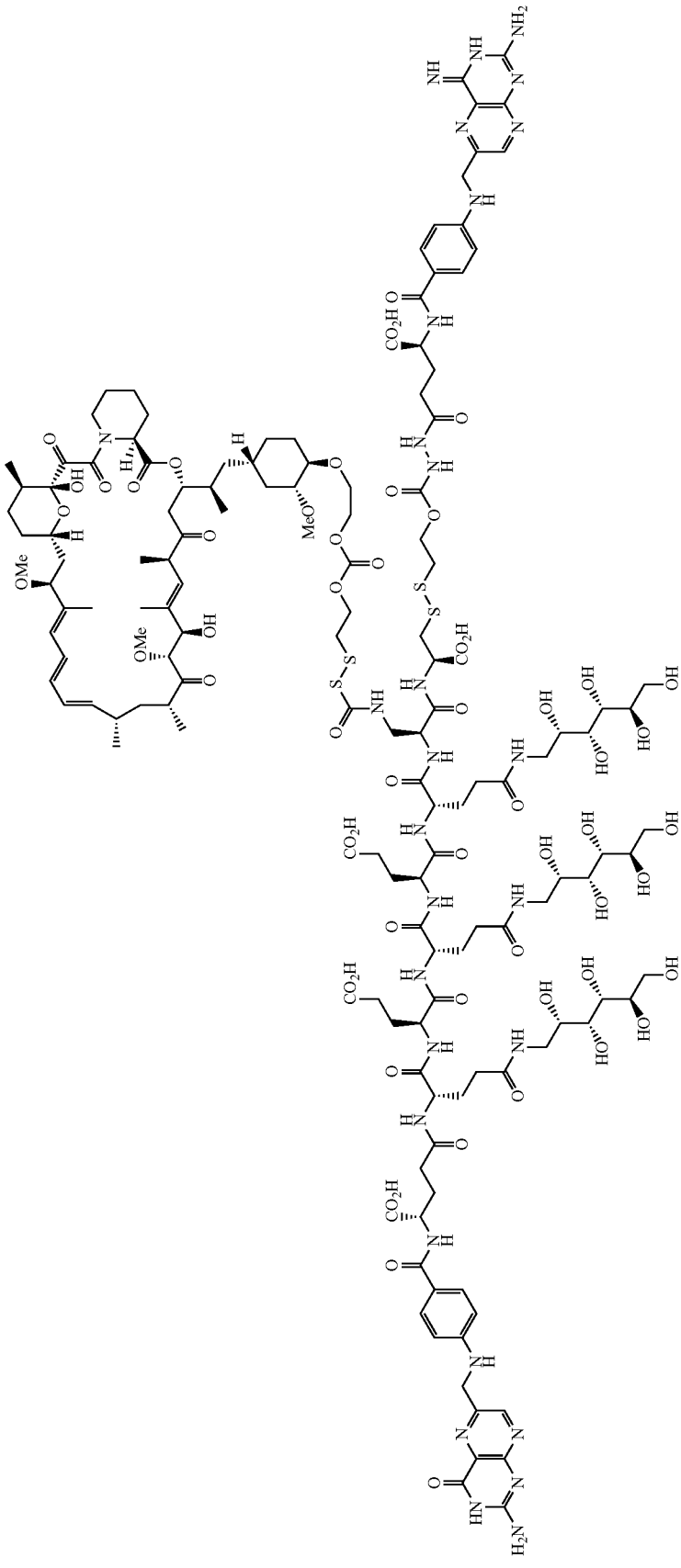

EC0828 everolimus-aminopterin hydrazide conjugate. C149H217N29O58S4; C, 51.56; H, 6.30; N, 11.70; O, 26.74; S, 3.70; MW: 3470.737; Exact Mass: 3468.381.

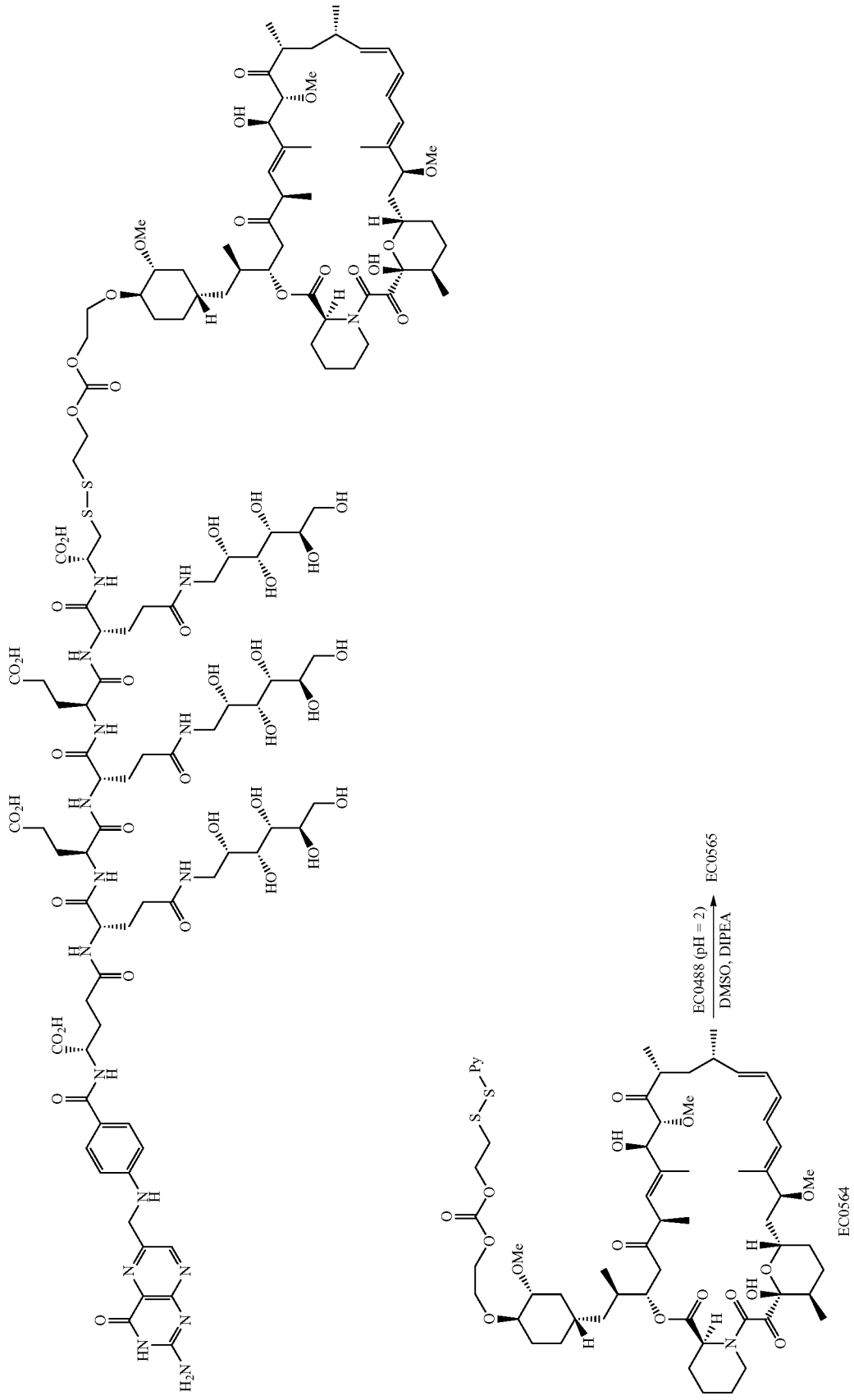

EXAMPLE. Everolimus (2'-pyridyldisulfanyl)ethyl carbonate (EC0564). In a 10 mL round bottom flask, under argon atmosphere, everolimus (130 mg, 0.136 mmol) was dissolved in 2.0 mL of $CH_2Cl_2$. 2-[Benzotriazole-1-yl-(oxycarbonyloxy)-ethyldisulfanyl]-pyridine (104.4 mg, 0.271 mmol) followed by DMAP (49.85 mg, 0.41 mmol) were added. The reaction mixture was stirred for 30 min Progress of the reaction was monitored by analytical HPLC (0.1% TFA in water, pH=2.0 and acetonitrile). The reaction mixture was diluted with $CH_2Cl_2$ and washed with sat. $NH_4Cl$. The organic layer was dried over $Na_2SO_4$ and concentrated to yield everolimus (2'-pyridyldisulfanyl)ethyl carbonate, EC0564.

EXAMPLE. Everolimus-EC0488 conjugate (EC0565). In a 25 mL round bottom flask, folate linker (EC0488, 104 mg, 0.06 mmol) was dissolved in 2.0 mL of DMSO, and 0.13 mL of DIPEA (20 equiv) were added. The everolimus carbonate derivative (EC0564, 38 mg, 1.0 eq) in 1.0 mL of DMSO was added quickly to the above solution. The resulting clear solution was stirred under argon. Progress of the reaction was monitored by analytical HPLC (20 mM $NH_4OAc$ buffer, pH=5.0 and acetonitrile). After 20 min, reaction mixture was injected on a prep-HPLC. HPLC purification conditions—column: Waters X-Bridge Prep MS $C_{18}$ 10 μm 19×100 mm; solvent A: 20 mM ammonium acetate, pH 5; solvent B: acetonitrile; method: 5 min 10% B to 25 min 80% B 25 mL/min. Fractions containing EC0565 were collected and freeze-dried to afford 68 mg (50% yield, over 2 steps from everolimus) of fluffy yellow solid. $C_{121}H_{183}N_{17}O_{50}S_2$; C, 53.04; H, 6.73; N, 8.69; O, 29.20; S, 2.34; MW 2739.96; Exact Mass: 2738.17.

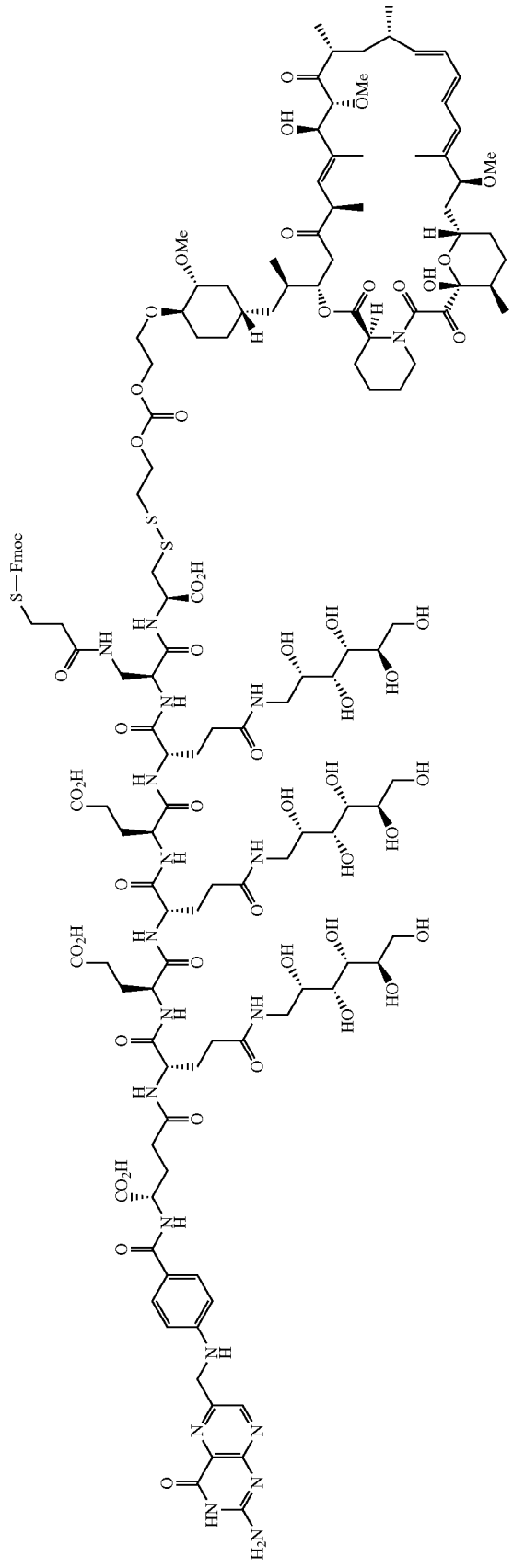

EC0606 Conjugate of Everolimus and intermediate for multidrug conjugate. C141H203N19O52S3, C, 54.76; H, 6.62; N, 8.61; O, 26.90; S, 3.11, MW 3092.42, Exact Mass: 3090.30
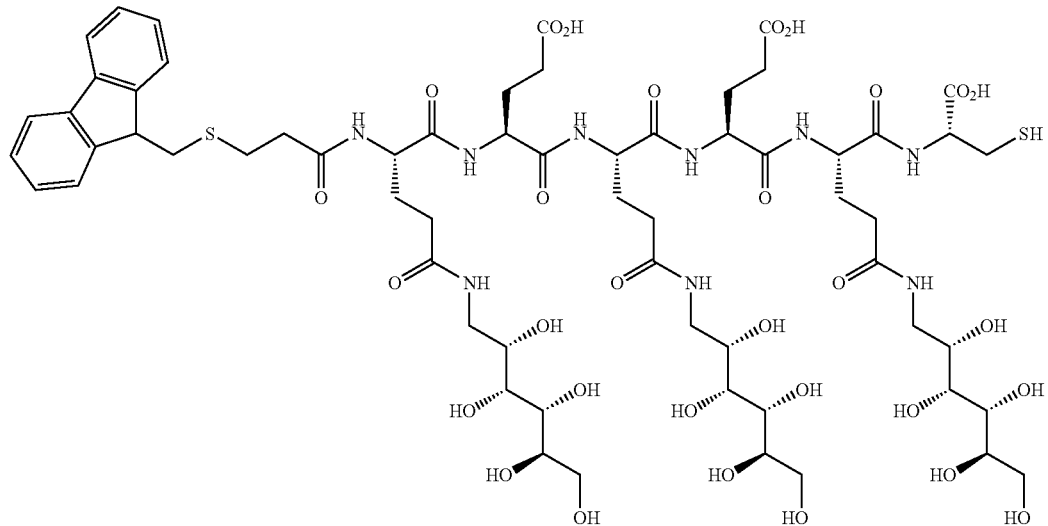 [SMILES: O=C(O)CC[C@H](NC(=O)[C@H](CCC(=O)NC[C@H](O)[C@@H](O)[C@H](O)[C@H](O)CO)NC(=O)CCSCC1c2ccccc2-c2ccccc21)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)O]
EC0634 Intermediate for optional non-targeted delivery.
C63H95N9O30S2, MW 1522.60, Exact Mass: 1521.56
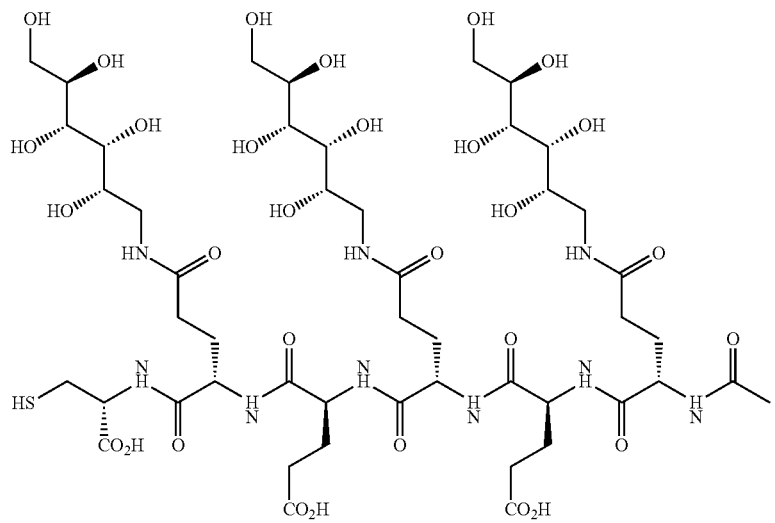 [SMILES: CC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)O]
EC0586 Intermediate for optional non-target delivery.
C48H83N9O30S, MW 1298.28, Exact Mass: 1297.50

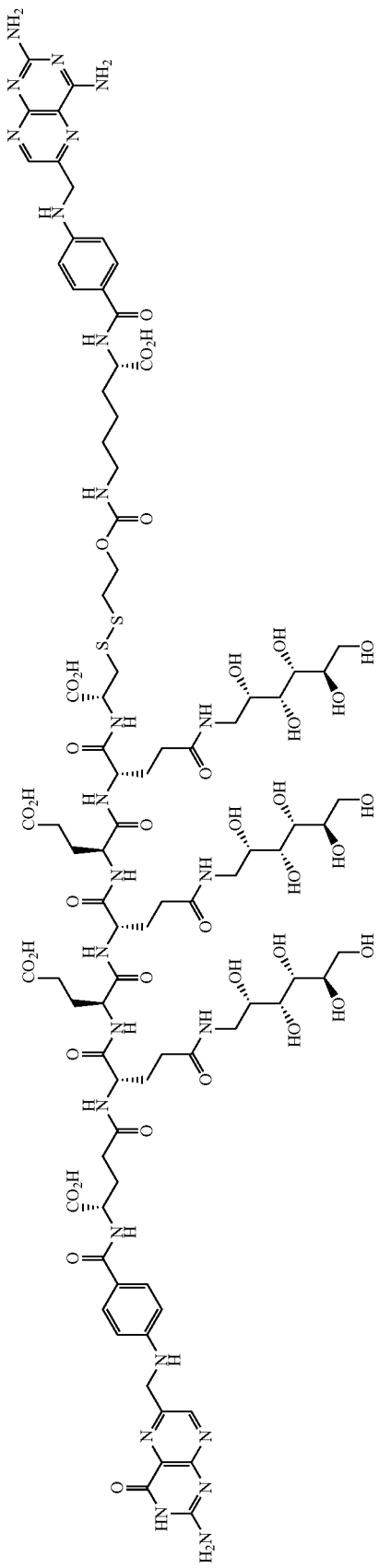

EC0539 Conjugate of lysine analog of aminopterin.

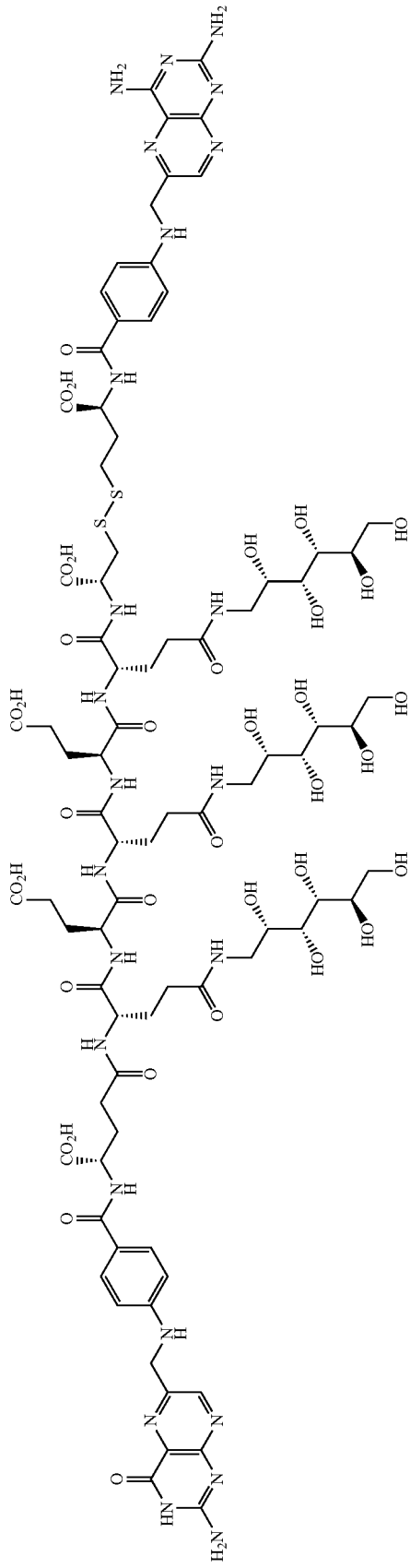

EC0544 Conjugate of cysteine analog of aminopterin. C83H116N24O37S2, C, 47.33; H, 5.55; N, 15.96; O, 28.11; S, 3.05, MW 2106.08, Exact Mass: 2104.74

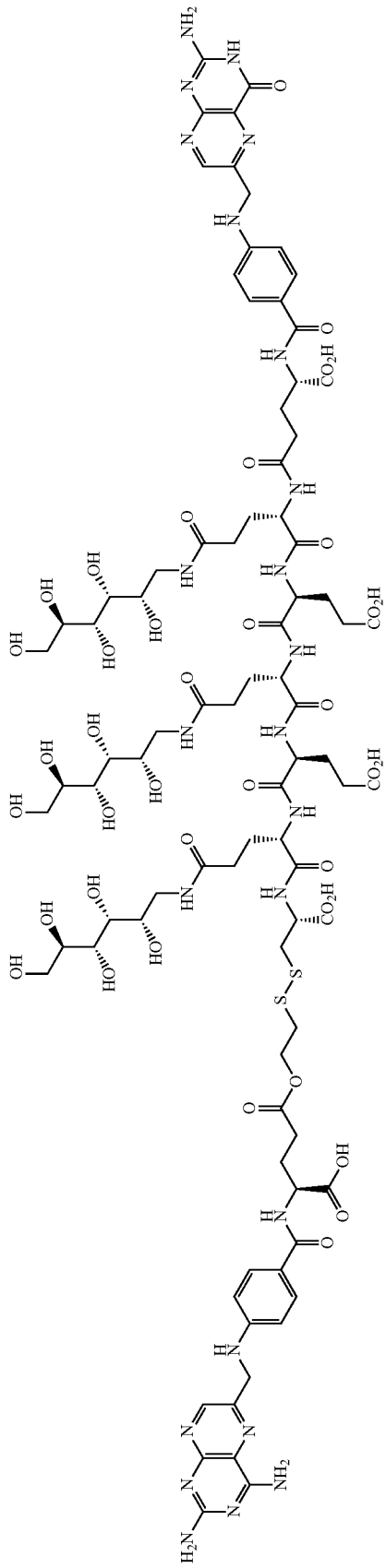

EC0551 Conjugate of aminopterin. C86H120N24O39S2, C, 47.42; H, 5.55; N, 15.43; O, 28.65; S, 2.94, MW 2178.14, Exact Mass: 2176.76

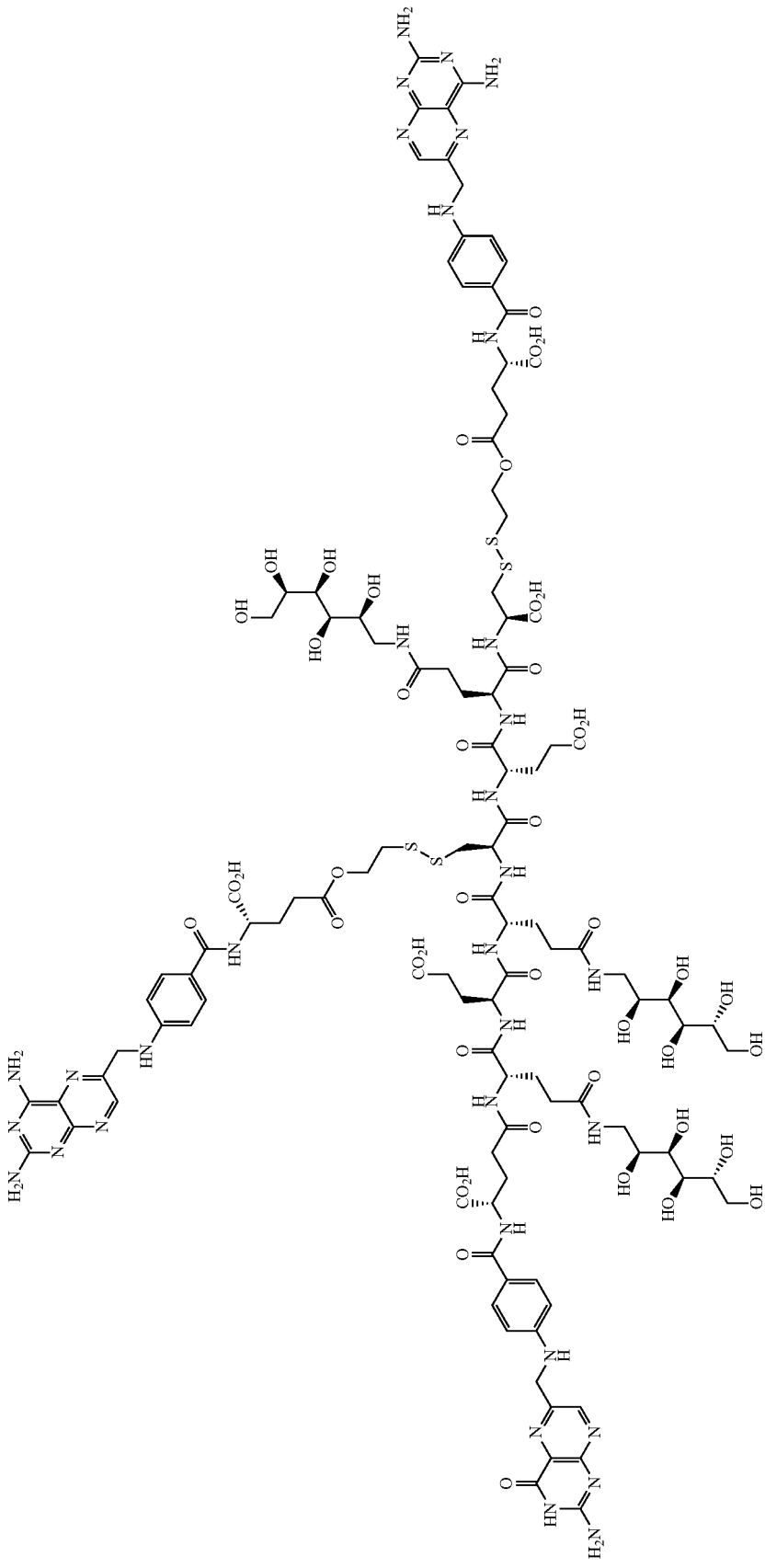

EC0647 Bis aminopterin conjugate. C110H147N33O45S4, MW, 2779.80, Exact Mass: 2777.9112, m/z: 2778.91 (100.0%), 2777.91 (74.4%), 2779.92 (62.2%).

What is claimed is:

1. A compound of the formula

BLA or a pharmaceutically acceptable salt thereof; wherein
B is a vitamin receptor binding ligand;
L is a linker that comprises one or more hydrophilic spacer linkers selected from the group consisting of

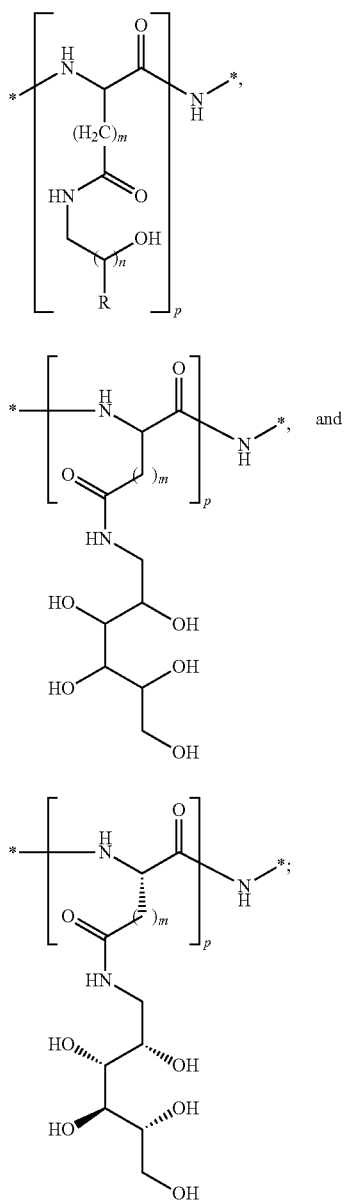

wherein
R is selected from the group consisting of H, alkyl, cycloalkyl, and arylalkyl; m is an integer from 1 to about 3; n is an integer from 1 to about 6; p is an integer from 1 to about 5; and (*) indicates the point of attachment to the rest of the compound and
a fragment of the formula

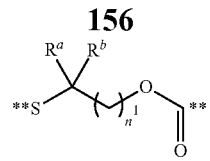

wherein
each $R^a$ and $R^b$ is independently hydrogen or alkyl; or $R^a$ and $R^b$ are taken together with the attached carbon atom to form a carbocyclic ring;
$n^1$ is an integer selected from 1 to 4; and
(**) indicates points of attachment for other parts of the conjugate; and
A is an anti-inflammatory agent.

2. The compound of claim 1 or a pharmaceutically acceptable salt thereof, wherein the anti-inflammatory agent is an antifolate.

3. The compound of claim 1 or a pharmaceutically acceptable salt thereof, wherein the linker comprises three hydrophilic spacer linkers.

4. The compound of claim 1 or a pharmaceutically acceptable salt thereof, wherein the one or more hydrophilic spacer linkers each comprise five hydroxyl groups.

5. The compound of claim 1 or a pharmaceutically acceptable salt thereof, wherein the linker further comprises one or more amino acids selected from the group consisting of the naturally occurring amino acids and stereoisomers thereof.

6. The compound of claim 5 or a pharmaceutically acceptable salt thereof, wherein the linker further comprises one or more amino acids selected from the group consisting of asparagine, aspartic acid, cysteine, glutamic acid, lysine, glutamine, arginine, serine, ornithine, threonine, and stereoisomers thereof.

7. The compound of claim 1 or a pharmaceutically acceptable salt thereof, wherein the linker further comprises a releasable linker.

8. The compound of claim 7 or a pharmaceutically acceptable salt thereof, wherein the linker further comprises a disulfide group.

9. The compound of claim 1 or a pharmaceutically acceptable salt thereof, wherein the purity of the compound is at least 98%.

10. The compound of claim 1 or a pharmaceutically acceptable salt thereof, wherein the vitamin receptor binding ligand is a folate.

11. The compound of claim 10 or a pharmaceutically acceptable salt thereof, wherein the vitamin receptor binding ligand is of the formula

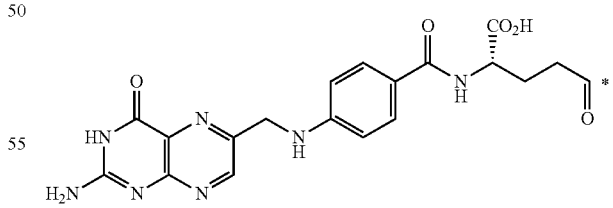

wherein * indicates the point of attachment to the linker.

12. A pharmaceutical composition comprising a compound of the formula

BLA or a pharmaceutically acceptable salt thereof; wherein
B is a vitamin receptor binding ligand;
L is a linker that comprises one or more hydrophilic spacer linkers selected from the group consisting of

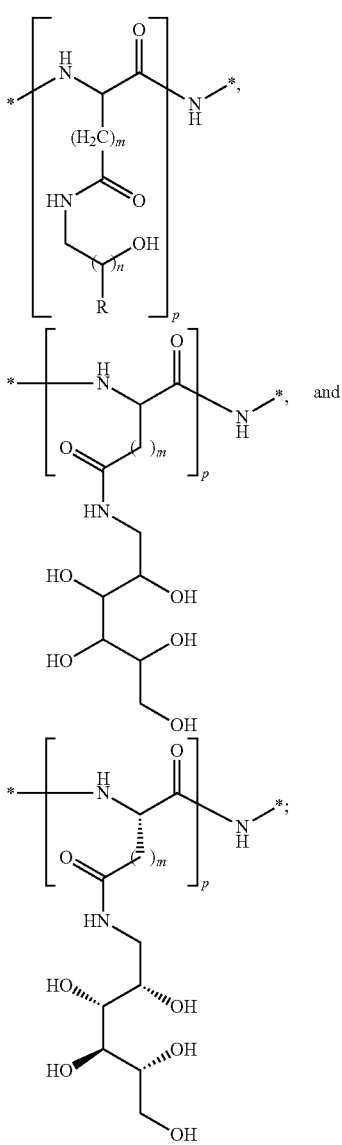

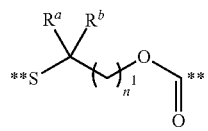

wherein

R is selected from the group consisting of H, alkyl, cycloalkyl, and arylalkyl; m is an integer from 1 to about 3; n is an integer from 1 to about 6; p is an integer from 1 to about 5; and (*) indicates the point of attachment to the rest of the compound and a fragment of the formula wherein each $R^a$ and $R^b$ is independently hydrogen or alkyl; or $R^a$ and $R^b$ are taken together with the attached carbon atom to form a carbocyclic ring;

$n^1$ is an integer selected from 1 to 4; and (**) indicates points of attachment for other parts of the conjugate; and A is an anti-inflammatory agent.

13. The pharmaceutical composition of claim 12, wherein, in the compound, or the pharmaceutically acceptable salt thereof, the vitamin receptor binding ligand is a folate and the anti-inflammatory agent is an antifolate.

14. The pharmaceutical composition of claim 12, further comprising one or more carriers, diluents, or excipients, or a combination thereof.

15. The compound of claim 2 or a pharmaceutically acceptable salt thereof, wherein the antifolate is aminopterin, or an analogue or derivative thereof.

16. The compound of claim 1, wherein the compound is

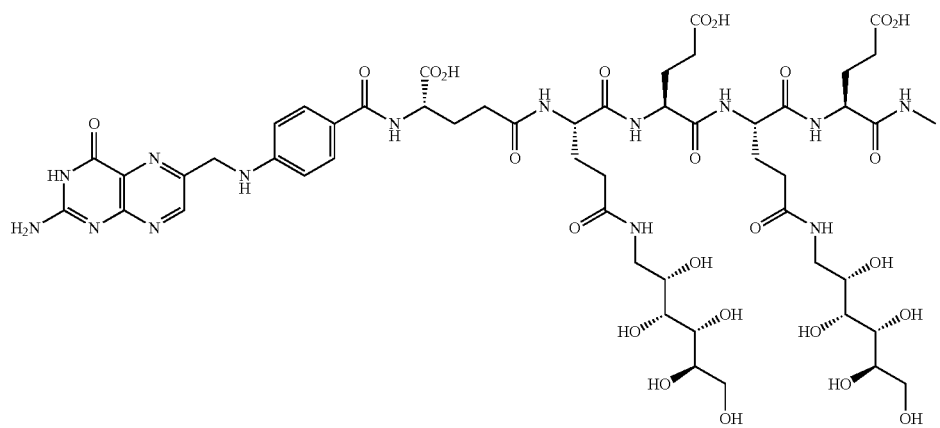

-continued
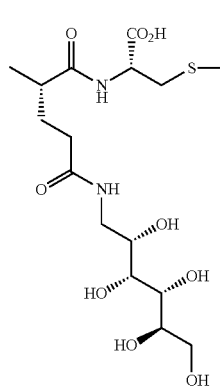
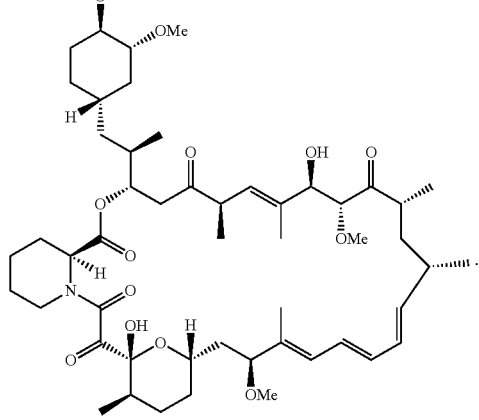
* * * * *